US012721914B2

(12) United States Patent
Kelly et al.

(10) Patent No.: US 12,721,914 B2
(45) **Date of Patent: *Sep. 1, 2026**

(54) RADIOLABELED ANTI-LAG3 ANTIBODIES FOR IMMUNO-PET IMAGING

(71) Applicant: REGENERON PHARMACEUTICALS, INC., Tarrytown, NY (US)

(72) Inventors: Marcus Kelly, New York, NY (US); Dangshe Ma, Pleasantville, NY (US); William Olson, Yorktown Heights, NY (US); Gavin Thurston, Millerton, NY (US); Richard Tavare, Salt Lake City, UT (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 526 days.

This patent is subject to a terminal disclaimer.

(21) Appl. No.: 18/049,609

(22) Filed: Oct. 25, 2022

(65) Prior Publication Data

US 2023/0270894 A1 Aug. 31, 2023

Related U.S. Application Data

(60) Continuation of application No. 17/127,618, filed on Dec. 18, 2020, now Pat. No. 11,511,001, which is a division of application No. 15/892,440, filed on Feb. 9, 2018, now Pat. No. 10,905,784.

(60) Provisional application No. 62/457,287, filed on Feb. 10, 2017.

(51) Int. Cl.

| | |
|---|---|
| ***A61K 51/10*** | (2006.01) |
| ***A61K 39/00*** | (2006.01) |
| ***C07C 259/00*** | (2006.01) |
| ***C07K 16/28*** | (2006.01) |

(52) U.S. Cl.

CPC .......... *A61K 51/1027* (2013.01); *A61K 39/00* (2013.01); *A61K 51/1039* (2013.01); *C07C 259/00* (2013.01); *C07K 16/2803* (2013.01); *C07K 2317/21* (2013.01)

(58) Field of Classification Search

CPC .... A61K 51/00; A61K 51/1027; A61K 39/00; A61K 51/1039; A61K 45/00; A61K 45/06; A61K 2039/505; A61K 2300/00; A61K 51/1093; A61K 39/395; A61K 51/10; C07K 16/28; C07K 16/2803; C07K 2317/21; C07C 259/00

See application file for complete search history.

(56) References Cited

U.S. PATENT DOCUMENTS

| | | | | |
|---|---|---|---|---|
| 4,680,338 | A | 7/1987 | Sundoro | |
| 5,332,567 | A | 7/1994 | Goldenberg | |
| 5,639,879 | A | 6/1997 | Mease et al. | |
| 5,976,877 | A | 11/1999 | Hercend et al. | |
| 6,143,273 | A | 11/2000 | Faure et al. | |
| 6,197,524 | B1 | 3/2001 | Romagnani | |
| 6,524,802 | B1 | 2/2003 | Lee et al. | |
| 6,596,541 | B2 | 7/2003 | Murphy et al. | |
| 7,087,411 | B2 | 8/2006 | Daly et al. | |
| 7,582,298 | B2 | 9/2009 | Stevens et al. | |
| 8,246,995 | B2 | 8/2012 | Dai et al. | |
| 8,257,740 | B1 | 9/2012 | Sung et al. | |
| 8,502,018 | B2 | 8/2013 | Murphy et al. | |
| 8,551,481 | B2 | 10/2013 | Pardoll et al. | |
| 8,771,966 | B2 | 7/2014 | Dennis et al. | |
| 9,321,832 | B2 | 4/2016 | Tomlinson et al. | |
| 9,429,584 | B2 | 8/2016 | Matsumura et al. | |
| 9,475,874 | B2 | 10/2016 | Sawada et al. | |
| 9,475,875 | B2 | 10/2016 | Kirshner et al. | |
| 9,546,206 | B2 | 1/2017 | Ring et al. | |
| 10,358,495 | B2 * | 7/2019 | Ullman | C07K 16/2803 |
| 10,730,944 | B2 | 8/2020 | Giurleo et al. | |
| 10,736,976 | B2 | 8/2020 | Kelly et al. | |
| 10,738,124 | B2 | 8/2020 | Kirshner et al. | |
| 10,738,130 | B2 | 8/2020 | Haber et al. | |
| 10,905,784 | B2 * | 2/2021 | Kelly | A61K 39/00 |
| 10,925,971 | B2 | 2/2021 | Kelly et al. | |
| 11,511,001 | B2 * | 11/2022 | Kelly | C07K 16/2803 |
| 11,525,001 | B2 | 12/2022 | Giurleo et al. | |
| 11,640,848 | B2 | 5/2023 | Lim et al. | |
| 11,692,032 | B2 * | 7/2023 | Ullman | A61P 37/02<br>424/142.1 |
| 11,896,682 | B2 | 2/2024 | Kelly et al. | |
| 12,053,534 | B2 | 8/2024 | Kelly et al. | |
| 12,077,587 | B2 | 9/2024 | Giurleo et al. | |
| 12,230,364 | B2 * | 2/2025 | Lim | G16B 5/00 |
| 12,564,651 | B2 | 3/2026 | Kelly et al. | |

(Continued)

FOREIGN PATENT DOCUMENTS

| | | |
|---|---|---|
| EP | 0510079 B1 | 5/1999 |
| EP | 0758383 B1 | 1/2007 |

(Continued)

OTHER PUBLICATIONS

Martin et al. (1989) "Modeling antibody hypervariable loops: A combined algorithm," PNAS 86:9268-9272.

Matsuzaki et al. (2010) "Tumor-infiltrating NY-ESO-1-specific CD8+ T cells are negatively regulated by LAG-3 and PD-1 in human ovarian cancer," PNAS 107(17):7875-7880.

Maute et al. (2015) "Engineering high-affinity PD-1 variants for optimized immunotherapy and immuno-PET imaging", Proc Natl Acad Sci U S A, 112(47):E6506-E6514.

Mindt et al. (2014) "Octadetante bifuntional chelating agent for Zr-89 based Imagining probes", Technology Opportunity, Ref. No. UZ-15/736, 1 page.

(Continued)

*Primary Examiner* — D. L. Jones

(74) *Attorney, Agent, or Firm* — FisherBroyles, LLP; Cara L. Crowley-Weber; Casey Donahoe

(57) ABSTRACT

Radiolabeled anti-LAG3 antibodies and their use in immuno-PET imaging are provided herein. Included are methods of detecting the presence of LAG3 proteins in a patient or sample.

16 Claims, 13 Drawing Sheets

Specification includes a Sequence Listing.

(56) References Cited

U.S. PATENT DOCUMENTS

2004/0018557 A1 1/2004 Qu et al.
2004/0101920 A1 5/2004 Radziejewski et al.
2008/0193376 A1 8/2008 Tawakol et al.
2008/0260650 A1 10/2008 Tawakol et al.
2009/0297439 A1 12/2009 Comoglio et al.
2010/0111856 A1 5/2010 Gill et al.
2010/0233183 A1 9/2010 Triebel et al.
2010/0331527 A1 12/2010 Davis et al.
2011/0070238 A1 3/2011 Triebel et al.
2011/0150892 A1 6/2011 Thudium et al.
2011/0195454 A1 8/2011 Mcwhirter
2013/0022759 A1 1/2013 Okumura et al.
2013/0095114 A1 4/2013 Pardoll et al.
2014/0088295 A1 3/2014 Smith et al.
2014/0093511 A1 4/2014 Lonberg et al.
2014/0127226 A1 5/2014 Pardoll et al.
2014/0243504 A1 8/2014 Davis et al.
2014/0286935 A1 9/2014 Hamblin et al.
2014/0377174 A1 12/2014 Houthoff et al.
2015/0191543 A1 7/2015 Wu et al.
2015/0203579 A1 7/2015 Papadopoulos et al.
2015/0203580 A1 7/2015 Papadopoulos et al.
2015/0299133 A1 10/2015 Osterkamp et al.
2016/0000946 A1 1/2016 Cheng et al.
2016/0151515 A1 6/2016 Joubert et al.
2016/0222116 A1 8/2016 Korman et al.
2016/0310570 A1 10/2016 Triebel et al.
2017/0022273 A1 1/2017 Zhou et al.
2017/0029507 A1 2/2017 Ho et al.
2017/0097333 A1 4/2017 Bhagwat et al.
2017/0119913 A1 5/2017 Osterkamp et al.
2017/0137517 A1 5/2017 Bowman et al.
2017/0258948 A1 9/2017 Morin et al.
2017/0267759 A1 9/2017 Liang et al.
2017/0283442 A1 10/2017 D'Souza et al.
2017/0290914 A1 10/2017 Liang et al.
2017/0334995 A1 11/2017 Zettl et al.
2018/0015154 A1 1/2018 Weichert et al.
2018/0043041 A1 2/2018 Bansal et al.
2018/0055947 A1 3/2018 Van Dongen et al.
2018/0078662 A1 3/2018 Agnew et al.
2018/0126012 A1 5/2018 Weichert et al.
2018/0201991 A1 7/2018 Zhang et al.
2018/0228926 A1 8/2018 Kelly et al.
2019/0087538 A1 3/2019 Lim
2021/0138096 A1 5/2021 Kelly et al.
2022/0249659 A1 8/2022 Kroog et al.
2023/0051304 A1 2/2023 Chang et al.
2023/0357446 A1 11/2023 Smith et al.
2024/0166740 A1 5/2024 Ullman et al.
2024/0299601 A1 9/2024 Cheung et al.
2024/0307563 A1 9/2024 Kelly et al.
2024/0335572 A1 10/2024 Kelly et al.
2024/0376229 A1 11/2024 Garg et al.
2024/0409637 A1 12/2024 Giurleo et al.
2025/0179177 A1 6/2025 Tang et al.
2025/0218540 A1 7/2025 Lim et al.

FOREIGN PATENT DOCUMENTS

EP 1897548 B1 8/2013
EP 2320940 B1 3/2015
EP 2954933 A1 12/2015
EP 3266465 A1 7/2016
EP 2142210 B1 8/2016
WO 1995/30750 A2 11/1995
WO 1997/03695 A1 2/1997
WO 1998/58059 A1 12/1998
WO 2004/078928 A2 9/2004
WO 2005/103081 A2 11/2005
WO 2008/124467 A1 10/2008
WO 2008/132601 A1 11/2008
WO 2010/019570 A2 2/2010
WO 2011/056983 A1 5/2011
WO 2011/153346 A1 12/2011
WO 2012/087962 A2 6/2012
WO 2013/022782 A1 2/2013
WO 2013/138696 A1 9/2013
WO 2013/149159 A1 10/2013
WO 2013/165940 A1 11/2013
WO 2013/177055 A2 11/2013
WO 2014/008218 A1 1/2014
WO 2014/140180 A1 9/2014
WO 2014/159087 A1 10/2014
WO 2014/159835 A1 10/2014
WO 2014/200969 A2 12/2014
WO 2014/210064 A1 12/2014
WO 2015/042246 A1 3/2015
WO 2015/048312 A1 4/2015
WO 2015/053871 A2 4/2015
WO 2015/061209 A1 4/2015
WO 2015/075445 A1 5/2015
WO 2015/089344 A1 6/2015
WO 2015/132602 A1 9/2015
WO 2015/138920 A1 9/2015
WO 2015/140212 A1 9/2015
WO 2015/179658 A2 11/2015
WO 2015/191715 A1 12/2015
WO 2015/200119 12/2015
WO 2016/020502 A1 2/2016
WO 2016/028672 A1 2/2016
WO 2016/040723 A1 3/2016
WO 2016/040724 A1 3/2016
WO 2016/040868 A1 3/2016
WO 2016/058056 A1 4/2016
WO 2016/126858 8/2016
WO 2016/144873 A2 9/2016
WO 2016/172010 A1 10/2016
WO 2016/200782 12/2016
WO 2017/015560 A2 1/2017
WO 2017/016497 2/2017
WO 2017/059397 A1 4/2017
WO 2017/062888 A1 4/2017
WO 2017/087589 5/2017
WO 2017/087826 A1 5/2017
WO 2017/087901 5/2017
WO 2017/106129 6/2017
WO 2017/149143 9/2017
WO 2017/198741 11/2017
WO 2017/201111 A1 11/2017
WO 2017/213494 A1 12/2017
WO 2017/219995 12/2017
WO 2017/220569 12/2017
WO 2017/223565 A1 12/2017
WO 2018/049083 A1 3/2018
WO 2018/058125 A1 3/2018
WO 2018/083705 A1 5/2018
WO 2018/128664 A2 7/2018
WO 2018/148476 8/2018
WO 2018222718 A1 12/2018

OTHER PUBLICATIONS

Miyazaki et al. (1996) "Independent Modes of Natural Killing Distinguished in Mice Lacking Lag3," Science 272:405-408.
Natarajan et al. (2015) "Novel Radiotracer for ImmunoPET Imaging of PD-1 Checkpoint Expression on Tumor Infiltrating Lymphocytes", Bioconjug Chem, 26(10):2062-2069.
NCT01968109 on Sep. 3, 2015, ClinicalTrials.gov Archive, Sep. 3, 2015, pp. 1-6, XP055328270, retrieved from the Internet: URL:https://clinicaltrials.gov/archive/NCT01968109/2015_09_03.
NCT03780725 on Dec. 19, 2018, ClinicalTrials.gov Archive, "This Study Tests How BI 754111 is Distributed in Patients With Advanced Non-small Cell Lung Cancer or Patients With Head and Neck Cancer Who Are Treated With BI754091", https://clinicaltrials.gov/ct2/show/NCT03780725.
Needleman and Wunsch (1970) "A general method applicable to the search for similarities in the amino acid sequence of two proteins," J. Mol. Biol. 48:443-453.
Nguyen, et al. (2014) "Clinical blockade of PD1 and LAG3—potential mechanisms of action", Nature Reviews Immunology, 15(1):45-56.

(56) References Cited

OTHER PUBLICATIONS

Nijland et al. (2019) "Molecular Imaging Using Radiolabeled Atezolizumab to Assess Atezolizumab Biodistribution in Lymphoma Patients", University Medical Center Groningen, ClinicalTrials.gov Identifier: NCT03850028, 11 pages.
Nishino et al. (2013) "Developing a Common Language for Tumor Response to Immunotherapy: Immune-Related Response Criteria Using Unidimensional Measurements," Clin. Cancer Res. 19:3936-3943.
Norde et al. (2012) "Coinhibitory molecules in hematologic malignancies: targets for therapeutic intervention," Blood 120(4):728-736.
Okamura et al. (2009) "CD4+ CD25− LAG3+ regulatory T cells controlled by the transcription factor Egr-2," PNAS 106(33):13974-13979.
Okamura et al. (2012) "Roles of LAG3 and EGR2 in regulatory T cells," Ann. Rheum. Dis. 71: 196-i100. doi:10.1136/annrheumdis-2011-200588.
Okamura et al. (2015) "TGF-b3-expressing CD4+ CD25− LAG3+ regulatory T cells control humoral immune responses," Nature Communications 6:6329.
Okazaki (2010) "PD-1 and LAG-3 inhibitory co-receptors act synergistically to prevent autoimmunity in mice," J. Exp. Med. 208(2):395-407.
Oosting et al. (2015) "89Zr-Bevacizumab PET Visualizes Heterogeneous Tracer Accumulation in Tumor Lesions of Renal Cell Carcinoma Patients and Differential Effects of Antiangiogenic Treatment", The Journal of Nuclear Medicine, 56(1):63-69.
Padlan et al. (1995) "Identification of specificity-determining residues in antibodies," The FASEB Journal 9:133-139.
Pandya et al. (2015) "Di-macrocyclic terephthalamide ligands as chelators for the PET radionuclide zirconium-89", Chem Commun (Camb), 51(12):2301-2303.
Pardol (2012) "Regulating the Regulators for Cancer Immunotherapy: LAG-3 Finally Catches Up," LAG-3 Presentation.
Pardoll (2012) "The blockade of immune checkpointsin cancer immunotherapy," Nature Reviews Cancer 12:252-264.
Patra, et al. (2014) "An octadentate bifunctional chelating agent for the development of stable zirconium-89 based molecular imaging probes", Chem. Commun. 50:11523-11525.
Pearson (1994) "Using the FASTA Program to Search Protein and DNA Sequence Databases," Methods in Molecular Biology 24:307-331.
Perez-Garcia (2014) "Orchestrating immune check-point blockade for cancerimmunotherapy in combinations," Current Opinion in Immunology, Tumour Immunology 27:89-97.
Perk et al. (2009) "p-Isothiocyanatobenzyl-desferrioxamine: a new bifunctional chelate for facile radiolabeling of monoclonal antibodies with zirconium-89 for immuno-PET imaging", Eur. J. Nucl. Med. Mol Imaging, 37(2):250-259.
Perk, et al. (2010) "p-Isothiocyanatobezyl desferrioxamine: a new bifunctional chelate for facile radiolabeling of monoclonal antibodies with zirconium-89 for immuno-PET imaging", European Journal of Nuclear Medicine and Molecular Imagining, Springer, Berlin, DE, 37(2):250-259.
Petrik, et al. (2016) "In Vitro and In Vivo Comparison of SelectedGa-68 and Zr-89 Labelled Siderophores", Mol. Imaging Biol., 18:344-352.
Poirier, et al. (2011) "Antibody-mediated depletion of lymphocyte-activation gene-3 (LAG-3+)-activated T lymphocytes prevents delayed-type hypersensitivity in non-human primates," British Society for Immunology, Clinical and Experimental Immunology 164: 265-274.
Powell et al. (1998) "Compendium of excipients for parenteral formulations," J. Pharm. Sci. Technol. 52:238-311.
Price et al. (2014) "H6phospa-trastuzumab: bifunctional methylenephosphonate-based chelator with 89Zr, 111In and 177Lu", Dalton Trans., 43(1):119-131.
Reddy et al. (2000) "Elimination of Fc Receptor-Dependent Effector Functions of a Modified IgG4 Monoclonal Antibody to Human CD4," J. Immunol. 164:1925-1933.
Reineke (2004) "Antibody Epitope Mapping Using Arrays of Synthetic Peptides," Methods Mol. Biol. 248:443-463.
Roncarolo et al. (2014) "Tr1 Cells and the Counter-Regulation of Immunity: Natural Mechanisms and Therapeutic Applications," Curr. Top. Microbiol. Immunol. 380: 39-68.
Rouhani et al. (2015) "Roles of lymphatic endothelial cells expressing peripheral tissue antigens in CD4 T-cell tolerance induction," Nature Communications 6:6771.
Rudikoff, et al. (1982) "Single amino acid substitution altering antigen-binding specificity," Proc. Natl. Acad. Sci. 79:1979-1983.
Schumacher, et al. (2016) "Current Status: Site-Specific Antibody Drug Conjugates", J. Clin. Immunol. 36(Suppl1):S100-S107.
Sega et al. (2014) "Role of Lymphocyte Activation Gene-3 (Lag-3) in Conventional and Regulatory T Cell Function in Allogeneic Transplantation," PLoS One 9(1):e86551.
Shield et al. (2002) "Lack of Fucose on Human IgG1 N-Linked Oligosaccharide Improves Binding to Human Fc RIII and Antibody-dependent Cellular Toxicity," J. of Biol. Chem. 277(30):26733-26740.
Shin and Ribas (2015) "The evolution of checkpoint blockade as a cancer therapy: what's here, what's next?" Current Opinion in Immunology, Tumour Immunology 33:23-35.
Sierro et al. (2011) "The CD4-like molecule LAG-3, biology and therapeutic applications," Expert Opin. Ther. Targets 15(1):91-101.
Sittig et al. (2013) "Clonal expansion of renal cell carcinoma-infiltrating T lymphocytes," Landes Bioscience, OncoImmunology 2:9, e26014-1-10.
Slizys and Widnersson (2016) "The new "Pet" on the block: radio imaging with Zirconium-89", FPA Patent Attorneys, 5 pages.
Smith and Waterman (1981) "Identification of common molecular subsequences," J. Mol. Biol. 147:195-197.
Sun et al. (2014) "Expression regulation of co-inhibitory molecules on human natural killer cells in response to cytokine stimulations," Cytokine 65:33-41.
Taube et al. (2015) "Differential expression of immune-regulatory genes associated with PD-L1 display in melanoma: Implications for PD-L1 pathway blockade," Clin Cancer Res Published Online First May 5, 2015.
Tavare et al. (2016) "An Effective Immuno-PET Imaging Method to Monitor CD8-Dependent Responses to Immunotherapy", Cancer Research , 76(1):73-82.
Thaventhiran et al. (2012) "T Cell Co-inhibitory Receptors: Functions and Signalling Mechanisms," J. Clin. Cell Immunol. S12:004. doi:10.4172/2155-9899.S12-004.
Tian et al. (2015) "The Upregulation of LAG-3 on T Cells Defines a Subpopulation with Functional Exhaustion and Correlates with Disease Progression in HIV-Infected Subjects," J. Immunol. 194:3873-3882.
Triebel (2003) "LAG-3: a regulator of T-cell and DC responses and its use in therapeutic vaccination," Trends in Immunology 24(12): 619-622.
Gagliani et al. (2013) "Coexpression of CD49b and LAG-3 identifies human and mouse T regulatory type 1 cells," Nature Medicine 19(6):739-746.
Gautron, et al. (2014) "Enhanced suppressor function of TIM-3+ FoxP3+ regulatory T cells," Eur. J. Immunol. 44:2703-2711.
Gebhart et al. (2015) "Molecular imaging as a tool to investigate heterogeneity of advanced HER2-positive breast cancer and to predict patient outcome under trastuzumab emtansine (T-DM1); the Zephir trial", Annals of Oncology Advance Access, 22 pages.
GenBank Accession NP_002277.4.
GenBank Accession NP_005182.1.
Goldberg and Drake (2011) "LAG-3 in Cancer Immunotherapy," LAG-3 Biology Review, 269-278.
Goldrath et al. (1999) "Selecting and maintaining a diverse T-cell repertoire," Nature 402:255-262.
Gonnet et al. (1992) "Exhaustive Matching of the Entire Protein Sequence Database," Science 256:1443-1445.

(56) References Cited

OTHER PUBLICATIONS

Gros et al. (2014) "PD-1 identifies the patient-specific CD8+ tumor-reactive repertoire infiltrating human tumors," J. of Clinical Investigation 125(5):2246-2259.
Grosso (2009) "Functionally Distinct LAG-3 and PD-1 Subsets on Activated and Chronically Stimulated CD8 T Cells1," J. Immunol. 182:6659-6669.
Grosso et al. (2007) "LAG-3 regulates CD8+ T cell accumulation and effector function in murine self-and tumor-tolerance systems," J. of Clinical Investigation 117(11):3383-3392.
Hemon et al. (2011) "MHC Class II Engagement by Its Ligand LAG-3 (CD223) Contributes to Melanoma Resistance to Apoptosis," J. Immunol. 186:5173-5183.
Herbst et al. (2014) "Predictive correlates of response to the anti-PD-L1 antibody MPDL3280A in cancer patients" Nature 515(7528):563-567.
Heskamp et al. (2015) "Noninvasive Imaging of Tumor PD-L1 Expression Using Radiolabeled Anti-PD-L1 Antibodies", Cancer Res, 75(14):2928-2936.
Higashikawa et al. (2014) "64Cu-DOTA-Anti-CTLA-4 mAb Enabled PET Visualization of CTLA-4 on the T-Cell Infiltrating Tumor Tissues", PLoS One, 9(11):e109866, 8 pages.
Hochleitner et al. (2000) "Characterization of a discontinuous epitope of the human immunodeficiency virus (HIV) core protein p24 by epitope excision and differential chemical modification followed by mass spectrometric peptide mapping analysis" Protein Sci. 9:487-496.
Huang et al. (2004) "Role of LAG-3 in Regulatory T Cells," Immunity 21:503-513.
Huang et al. (2015) "LAG3 and PD1 co-inhibitory molecules collaborate to limit CD8+ T cell signaling and dampen antitumor immunity in a murine ovarian cancer model," Oncotarget, 6(29):27359-27377.
Huard et al. (1994) "Cellular expression and tissue distribution of the humanLAG-3-encoded protein, an MHC class II ligand," Immunogenetics 39: 213-217.
Huard et al. (1996) "T cell major histocompatibility complex class II molecules down-regulate CD4+ T cell clone responses following LAG-3 binding," Eur. J. Immunol. 26:1180-1186.
Huard et al. (1997) "Characterization of the major histocompatibility complex class II binding site on LAG-3 protein," PNAS 94:5744-5749.
Huard, et al. (1995) "CD4/major histocompatibility complex class II interaction analyzed with CD4– and lymphocyte activation gene-3 (LAG-3)-Ig fusion proteins," Eur. J. Immunol. 25:2718-2721.
International Search Report and Written Opinion, PCT/US2018/017525, mailed Apr. 17, 2018, 14 pages.
International Search Report and Written Opinion, received for PCT/US2016/056156, on Mar. 10, 2017, 23 pages.
Invitation to Pay Additional Fees and, Where Applicable, Protest Fee, received for PCT/US2016/056156, on Jan. 10, 2017, 10pgs.
Jackson, et al. (1995) "In Vitro Antibody Maturation Improvement of a High Affinity, Neutralizing Antibody Against IL-1 beta," The Journal of Immunology 154:3310-3319.
Jauw et al. (2016) "Immuno-PositronEmissionRob'sographywithZirconium-89-Labeled Monoclonal Antibodies in Oncology: What Can We Learn from Initial Clinical Trials?" Frontiers in Pharmacology, vol. 7, Article 131, 15 pages.
Jing et al. (2015) "Combined immune checkpoint protein blockade and low dose whole body irradiation as immunotherapy for myeloma," J. for Immuno. Therapy of Cancer 3:2 pp. 1-15.
Junghans et al. (1990) "Anti-Tac-H, a Humanized Antibody to the Interleukin 2 Receptor with New Features for Immunotherapy in Malignant and Immune Disorders," Cancer Research 50:1495-1502.
Juno et al. (2015) "Elevated expression of LAG-3, but not PD-1, is associated with impaired iNKT cytokine production during chronic HIV-1 infection and treatment," Retrovirology 12:17.
Kabat (1991) "Sequences of Proteins of Immunological Interest" National Institutes of Health, Bethesda, Md. 147:1709-1719.
Kazane, et al. (2013) "Self-Assembled Antibody Multimers through Peptide Nucleic Acid Conjugation," Journal of the American Chemical Society, 135(1):340-346.
Kelly et al. (2018) "Immuno-PET detection of LAG-3 expressing intratumoral lymphocytes using the zirconium-89 radiolabeled fully human anti-LAG-3 antibody REGN3767", Abstract in Proceedings AACR Cancer Res., 78(Suppl): Abstract No. 3033, 4pgs.
Klein, et al. (2012) "Progress in overcoming the chain association issue in bispecific heterodimeric IgG antibodies," mAbs 4(6):653-663.
Kouo et al. (2015) "Galectin-3 shapes antitumor immune responses by suppressing CD8+ T cells via LAG-3 and inhibiting expansion of plasmacytoid dendritic cells," Cancer Immunol. Res. Published Online First Feb. 17, 2015, 42 pages.
Kufer et al. (2004) "A revival of bispecific antibodies," Trends in Biotech. 22(5):238-244.
LAG3 protein [*Homo sapiens*] AAH52589, GenBank: AAH52589.1 dated Jul. 10, 2003.
Lamberts et al., (2015) "ImmunoPET with Anti-Mesothelin Antibody in Patients with Pancreatic and Ovarian Cancer Before Anti-Mesothelin Antibody-Drug Conjugate Treatment", Clinical Cancer Research, 22(7):1642-1652.
Langer (1990) "New methods of drug delivery," Science 249:1527-1533.
Lecocq et al. (2019) "Noninvasive Imaging of the Immune CheckpointLAG-3 Using Nanobodies, from Development to Pre-Clinical Use", Biomolecules, 9(10):1-19.
Lederman et al. (1991) "A Single Amino Acid Substitution in a Common African Allele of the CD4 Molecule Ablates Binding of the Monoclonal Antibody, OKT4" Molecular Immunology 28:1171-1181.
Legat et al. (2013) "Inhibitory receptor expression depends more dominantly on differentiation and activation than "exhaustion" of human CD8 T cells," Frontiers in Immunol., Tumor Immunity 4:455.
Lerner (1982) "Tapping the immunological repertoire to produce antibodies of predetermined specificity" Nature 299:592-596.
Li and Zhu (2016) "Immuno-PET imagining using 89Zr labeled PD-L1 antibody in non-small cell lung cancer Kenograft", Journal of Nuclear Medicine, 57(Suppl. 2):337.
Li et al. (2007) "Metalloproteases regulate T-cell proliferation and effector function via LAG-3," The EMBO Journal 26 (2) 494-504.
Liang et al. (2008) "Regulatory T Cells Inhibit Dendritic Cells by LymphocyteActivation Gene-3 Engagement of MHC Class II 1," J. Immunol. 180:5916-5926.
Llosa et al. (2014) "The Vigorous Immune Microenvironment of Microsatellite Instable Colon Cancer Is Balanced by Multiple Counter-Inhibitory Checkpoints," Cancer Discov. 5(1):43-51.
Lloyd (1999) "The Art, Science and Technology of Pharmaceutical Compounding," 8 pages.
Macon-Lemaitre and Triebel (2005) "The negative regulatory function of the lymphocyte-activation gene-3 co-receptor (CD223) on human T cells," Immunology 115:170-178.
Mao et al. (2016) "Pathological a-synuclein transmission initiated by binding lymphocyte-activation gene 3," Science 353:6307.
Iyer et al. (2011) "Antibody Drug Conjugates—Trojan Horses in the War on Cancer", Journal of Pharmacological and Toxicological Methods, 64(3): 207-212.
Sugyo et al. (2013) "Evaluation of 89Zr-Labeled Human Anti-CD147 Monoclonal Antibody as a Positron Emission Tomography Probe in a Mouse Model of Pancreatic Cancer", PLOS One, 8(4): e61230, 9 pages.
Abaza and Atassi (1992) "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin" Journal of Protein Chemistry 11(5):433-444.
Al-Lazikani et al. (1997) "Standard Conformations for the Canonical Structures of Immunoglobulins," J. Mol. Biol. 273:927-948.
Altschul et al. (1990) "Basic Local Alignment Search Tool," J. Mol. Biol. 215:403-410.

(56) References Cited

OTHER PUBLICATIONS

Altschul et al. (1997) "Gapped BLAST and PSI-BLAST: a new generation of protein database search programs," Nucleic Acids Research, 25(17):3389-3402.
Alzimami et al., "Comparison of Zr-89, I-124, and F-18 Imaging Characteristics in PET Using Gate Monte Carlo Simulations: Imaging" International Journal of Radiation Oncology, 2014, 88:502.
Anderson et al. (2016) "Lag-3, Tim-3, and TIGIT: Co-inhibitory Receptorswith Specialized Functions in Immune Regulation," Immunity 44:989-1004.
Andreae et al. (2002) "Maturation and Activation of Dendritic Cells Induced by Lymphocyte Activation Gene-3 (CD223)," J. Immunol. 168:3874-3880.
Andreae et al. (2003) "MHC class II signal transduction in human dendritic cells induced by a natural ligand, the LAG-3 protein (CD223)," Blood 102(6):2130-2137.
Arruebo et al. (2009) "Antibody-conjugated nanoparticles for biomedical applications," J. of Nanomaterials, vol. 2009, Article ID 439389, 24 pgs, doi: 10.1155/2009/439389.
Bae et al. (2014) "Trafficking of LAG-3 to the Surface on Activated T Cells vialts Cytoplasmic Domain and Protein Kinase C Signaling," J. Immunol. 2014; 193:3101-3112.
Barber et al. (2006) "Restoring function in exhausted CD8 T cells during chronic viral infection," Nature 439:682-687.
Blackburn et al. (2009) "Coregulation of CD8+ T cell exhaustion by multipleinhibitory receptors during chronic viral Infection," Nature Immunology 10(1):29-37.
Boerman and Oyen (2011) "Immuno-PET of Cancer: A Revival of Antibody Imaging", Journal of Nuclear Medicine, 52(8): 1171.
Brignone et al (2010) "First-line chemoimmunotherapy in metastatic breast carcinoma: combination of paclitaxel and IMP321 (LAG-3Ig) enhances immune responses and antitumor activity," J. of Translational Medicine 8:71.
Brignone et al. (2007) "A Soluble Form of Lymphocyte Activation Gene-3 (IMP321)Induces Activation of a Large Range of Human Effector Cytotoxic Cells," J. Immunol. 179:4202-4211.
Brignone et al. (2007) "IMP321 (sLAG-3) safety and T cell response potentiation using an influenza vaccine as a model antigen: A single-blind phase I study," Vaccine 25:4641-4650.
Brignone et al. (2007) "IMP321 (sLAG-3), an immunopotentiator for T cell responses against a HBsAg antigen in healthy adults: a single blind randomised controlled phase I study," Journal of Immune Based Therapies and Vaccines 5:1-15.
Brignone et al. (2009) "A Phase I Pharmacokinetic and Biological Correlative Study of IMP321, a Novel MHC Class II Agonist, in Patients with Advanced Renal Cell Carcinoma," Clin. Cancer Res. 15(19):6225-6231.
Brown, et al. (1996) "Tolerance to Single, but Not Multiple, Amino Acid Replacements in Antibody V, CDR2", The Journal of Immunology, 156: 3285-3291.
Buisson and Triebel (2005) "LAG-3 (CD223) reduces macrophage and dendritic cell differentiation from monocyte precursors," Immunology 114:369-374.
Camisaschi et al. (2010) "LAG-3 Expression Defines a Subset of CD4+CD25highFoxp3+ Regulatory T Cells That Are Expanded at Tumor Sites," J. Immunol. 184:6545-6551.
Camisaschi et al. (2014) "Alternative Activation of Human Plasmacytoid DCs In Vitro and in Melanoma Lesions: Involvement of LAG-3," J. of Investigative Dermatology 134:1893-1902.
Casati et al. (2006) "Soluble Human LAG-3 Molecule Amplifies the In vitro Generation of Type 1 Tumor-Specific Immunity," Cancer Res. 66(8):4450-4460.
Casati et al. (2008) "Human Lymphocyte Activation Gene-3 Molecules Expressed by Activated T Cells Deliver Costimulation Signal for Dendritic Cell Activation1," J. Immunol. 180:3782-3788.
Chang et al. (2015) "Metabolic Competition in the Tumor Microenvironment Is a Driver of Cancer Progression", Cell, 162:1229-1241.
Chatterjee et al. (2016) "A humanized antibody for imaging immune checkpoint ligand PD-L1 expression in tumors", Oncotarget 7(9):10215-10227.
Chen and Chen (2014) "The effect of immune microenvironment on the progressionand prognosis of colorectal cancer," Med. Oncol. 31:82.
Chen and Flies (2013) "Molecular mechanisms of T cell co-stimulation and co-inhibition," Nature Rev. Immunol. 13:227-242.
Chen et al. (2015) "LAG-3 Negatively Regulates the Function of Intrahepatic HCV-specific CD8+ T Cells," doi: 10.1111/jgh.13017.
Cheson et al. (2014) "Recommendations for Initial Evaluation, Staging, and Response Assessment of Hodgkin and Non-Hodgkin Lymphoma: The Lugano Classification," J. Clin. Oncol. 32(27):3059-3068.
Chun et al. (2004) "The effect of soluble LAG-3 (CD223) treatment in fetal thymic organ culture," Biotechnology Letters 26: 1371-1377.
Colman, et al. (1994) "Effects of amino acid sequence changes on antibody-antigen interactions", Research in Immunology 145(1):33-36.
Crawford et al. (2014) Molecular and Transcriptional Basis of CD4+ T Cell Dysfunction during Chronic Infection, Immunity 40:289-302.
Creelan (2015) "Update on Immune Checkpoint Inhibitors in Lung Cancer," Cancer Control, J. of Moffitt Cancer Center 21(1):80-89.
De Vries "Antibody immunotherapy imaging." Department of Medical Oncology University Medical Center Groningen, The Netherlands, 16 pages.
De Vries (2015) "MPDL3280A-imaging-IST-UMCG", ClinicalTrials.gov Identifier: NCT02453984, University Medical Center Groningen, 10 pages.
Demeure et al. (2001) "T Lymphocytes infiltrating various tumour types express the MHC class II ligand lymphocyte activation gene-3 (LAG-3): role of LAG-3/MHC class II interactions in cell-cell contacts," Eur. J. of Cancer 37:1709-1718.
Deng et al. (2016) "Preclinical pharmacokinetics, pharmacodynamics, tissue distribution, and tumor penetration of anti-PD-L1 monoclonal antibody, an immune checkpoint inhibitor", mAbs, 8(3):593-603.
Deri et al. (2015) "p-SCN-Bn-HOPO: A Superior Bifunctional Chelator for (89)Zr ImmunoPET", Bioconjugate Chem., 26(12) 2579-2591.
Dijkers et al. (2010) "Biodistribution of 89Zr-trastuzumab and PETImaging of HER2-Positive Lesions in Patients With Metastatic Breast Cancer", Clinical Pharmacology and Therapeutics, 87(5):586-592.
Domizio et al. (2014) "Plasmacytoid Dendritic Cells in Melanoma: Can We Revert Bad into Good?" J. of Investigative Dermatology 134, 1797-1800.
Edwards, et al. (2003) "The Remarkable Flexibility of the Human Antibody Repertoire; Isolation of Over One Thousand Different Antibodies to a Single Protein, BLyS" J. Mol. Biol. 334:103-118.
Ehring (1999) "Hydrogen Exchange/Electrospray Ionization Mass Spectrometry Studies of Structural Features of Proteins and Protein/Protein Interactions," Analytical Biochem. 267:252-259.
Eisenhauer et al. (2009) "New response evaluation criteria in solid tumours: Revised RECIST guideline (version 1.1), " Eur. J. Cancer 45:228-247.
Engen and Smith (2001) "The Basics of Ion Chromatography," Anal. Chem. 73:256A-265A.
Ferrara, et al. (2015) "Recombinant renewable polyclonal antibodies" mAbs 7(1):32-41.
Ferris et al. (2014) "Too Much of a Good Thing? Tim-3 and TCR Signaling in T Cell Exhaustion," J. Immunol. 193:1525-1530.
Flies et al (2011) "Blockade of the B7-H1/PD-1 Pathway for Cancer Immunotherapy," Yale J. Biol. Med. 84(4):409-421.
Foote et al. (1992) "Antibody Framework Residues Affecting the Conformation of the Hypervariable Loops," J. Mol. Biol. 224: 487-499.
Fougeray et al. (2006) "A soluble LAG-3 protein as an immunopotentiator for therapeutic vaccines: Preclinical evaluation of IMP321," Vaccine 24:5426-5433.
Triebel et al. (2006) "A soluble lymphocyte activation gene-3 (sLAG-3) protein as a prognostic factor in human breast cancer expressing estrogen or progesterone receptors," Cancer Letters 235:147-153.

(56) References Cited

OTHER PUBLICATIONS

Turnis et al. (2012) "Combinatorial immunotherapy PD-1 may not be LAG-ing behind any more," Oncolmmunology 1(7):1172-1174.
Turnis et al. (2015) "Inhibitory receptors as targets for cancer immunotherapy," Eur. J. Immunol. 45:1892-1905.
Tutt et al. (1991) "Trispecific F(ab')3 derivatives that use cooperative signaling via the TCR/CD3 complex and CD2 to activate and redirect resting cytotoxic T cells," J. Immunol. 147:60-69.
Vajdos et al. (2002) "Comprehensive Functional Maps of the Antigen-binding Site of an Anti-ErbB2 Antibody Obtained with Shotgun Scanning Mutagenesis," J. Mol. Biol. 320:415-428.
Van De Watering et al. (2014) "Zirconium-89 Labeled Antibodies: A New Tool for Molecular Imaging in Cancer Patients", Biomed Research international, Article ID 203601, 2014:1-13.
Van Dongen, et al. (2007) "Immuno-PET: A Navigator in Monoclonal Antibody Development and Applications", The Oncologist, 12:1379-1389.
Vosjan, et al. (2010) "Conjugation and radiolabeling of monoclonal antibodies with zirconium-89 for PET imaging using the bifunctional chelate p-isothiocyanatobenzyl-desferrioxamine" Nature Protocols, 5(4):739-743.
Vugts, et al. (2017) "Comparison of the octadentate bifunctional chelatorDFO*-pPhe-NCS and the clinically used hexadentate bifunctional chelator DFO-pPhe-NCS for 89Zr-immuno-PET", Eur J Nucl Med Mol Imaging, 44: 286-295.
Wang-Gillam et al. (2013) "A phase I study of IMP321 and gemcitabine as the front-line therapy in patients with advanced pancreatic adenocarcinoma," Invest New Drugs 31:707-713.
Williams et al. (2015) "LAG-3 and 4-1BB identify dysfunctional antigen specificT cells in the tumor microenvironment and combinatorial LAG-3/4-1BB targeting gives synergistic tumor control," Journal for Immuno Therapy of Cancer; 3 (Suppl 2):P328.
Wolchok et al. (2009) "Guidelines for the Evaluation of Immune Therapy Activity in Solid Tumors: Immune-Related Response Criteria," Clin. Cancer Res. 15:7412-7420.
Wong, et al. (1998) "Structural Requirements for a Specificity Switch and for Maintenance of Affinity Using Mutational Analysis of a Phage-Displayed Anti-Arsonate Antibody of Fab Heavy Chain First Complementarity-Determining Region," The Journal of Immunology, 160:5990-5997.
Woo et al. (2010) "Differential subcellular localization of the regulatory T-cell protein LAG-3 and the coreceptor CD4," Eur J Immunol; 40(6): 1768-1777.
Woo et al. (2012) "Immune Inhibitory Molecules LAG-3 and PD-1 Synergistically Regulate T-cell Function to Promote Tumoral Immune Escape," Cancer Res. 72:917-927.
Workman et al. (2002) "Cutting Edge: Molecular Analysis of the Negative Regulatory Function of Lymphocyte Activation Gene-31," J. Immunol. 169:5392-5395.
Workman et al. (2009) "LAG-3 Regulates Plasmacytoid Dendritic Cell Homeostasis1," J. Immunol. 182(4):1885-1891.
Wu et al. (1987) "Receptor-mediated in vitro gene transformation by a soluble DNA carrier system," J. Biol. Chem. 262:4429-4432.
Xiao and Freeman (2015) "The Microsatellite Instable Subset of Colorectal Cancer Is a Particularly Good Candidate for Checkpoint Blockade Immunotherapy," Cancer Discovery 5:16-18.
Xu et al. (2014) "LSECtin Expressed on Melanoma Cells Promotes TumorProgression by Inhibiting Antitumor T-cell Responses," Cancer Res. 74(13):3418-3428.
Yan et al. (2015) "Targeting C-type lectin receptors for cancer immunity," Frontiers in Immunology 6:408.
Zhai, et al. (2015) "Novel Bifunctional Cyclic Chelator for 89Zr Labeling-Radiolabeling and Targeting Properties of RGD Conjugates", Mol. Pharmaceutics, 12:2142.
Knight et al. (2016) "Scaling-down Antibody Radiolabeling Reactions With Zirconium-89", Dalton Trans., 45:6343-6347.
Josefsson et al. (2016) "Imaging Biodistribution, and Dosimetry of Radionuclide-Labeled PD-L1 Antibody in an Immunocompetent Mouse Model of Breast Cancer," Cancer Research, 76(2):472-479.

* cited by examiner

Statistic analysis was performed using Unpaired Mann-Whitney nonparametric T test

Sample information of melanoma tissues

| Sample ID | Sex | Age | Ethnicity | Sample type | Matrix | Diagnosis | Histological diagnosis | TNM | Stage | Clark's level of invasion | Breslow microstaging, cm | Tumor size, cm | Metastases | Date of surgery | Tumor content % | Weight, g |
|---|---|---|---|---|---|---|---|---|---|---|---|---|---|---|---|---|
| 131815T2(3) | M | 45 | Caucasian | FF | skin | melanoma | epithelioid cell melanoma | T4bN3M0 | IIIC | V | 1 | 1.8x1x1 | 9/9 lymph nodes | 03/16/2015 | 95 | 0.9 |
| 131719T2(3) | M | 58 | Caucasian | FF | skin | melanoma | spindle cell melanoma | T4bN0M0 | IIC | V | 1 | 6x5x1 | no | 09/23/2014 | 100 | 0.8 |
| 13841T2(1) | F | 51 | Caucasian | FF | skin | melanoma | mixed cell melanoma | T4aN0M0 | IIB | IV | 1.3 | 3.5x3.5x1.3 | no | 02/08/2010 | 100 | 0.8 |
| 13788T2(4) | F | 63 | Caucasian | FF | skin | melanoma | spindle cell melanoma | T4bN1bM0 | IIIC | III | 2.5 | 7 cm | 1/1 lymph nodes | 10/23/2009 | 100 | 0.7 |
| 13765T2(2) | M | 56 | Caucasian | FF | skin | melanoma | epithelioid cell melanoma | T4bN3M0 | IIIC | III | 0.7 | 2.5x1.5 | 6/6 lymph nodes | 08/26/2009 | 90 | 0.8 |
| 131778T2(5) | M | 58 | Caucasian | FF | skin | melanoma | epithelioid cell melanoma | T4bN3M0 | IIIC | V | 30 mm | 5x3x3 | 11/17 lymph nodes | 12/15/2014 | 100 | 0.7 |
| 131291T2(1) | F | 33 | Caucasian | FF | skin | melanoma | nevoid cell melanoma | T4bN3M0 | IIIC | III | 15 mm | 3x1.5 | 6/6 lymph nodes | 03/15/2012 | 100 | 1 |
| 131086T6(1) | M | 59 | Caucasian | FF | skin | melanoma | epithelioid cell melanoma | T4aN0M0 | IIB | V | 10 mm | 2.5 cm | no | 05/12/2011 | 75 | 0.6 |
| 13547T2(1) | M | 73 | Caucasian | FF | skin and adipose tissue | melanoma | epithelioid cell melanoma | recurrent | recurrent | III | 15 mm | N/A | 1/18 lymph nodes | 05/21/2008 | 100 | 0.9 |
| 13524T2(7) | F | 44 | Caucasian | FF | skin | melanoma | epithelioid cell melanoma | T4bN2aM0 | IIIC | III | 22 mm | 2 cm | 2/12 lymph nodes | 01/24/2008 | 100 | 0.65 |

FIGURE 12

RADIOLABELED ANTI-LAG3 ANTIBODIES FOR IMMUNO-PET IMAGING

CROSS-REFERENCE TO RELATED APPLICATIONS

This application is a continuation of U.S. patent application Ser. No. 17/127,618 filed Dec. 18, 2020, which is a divisional of U.S. patent application Ser. No. 15/892,440, filed Feb. 9, 2018, which claims the benefit under 34 U.S.C. § 119(e) of U.S. Provisional Application No. 62/457,287, filed Feb. 10, 2017, which is herein specifically incorporated by reference in its entirety.

FIELD

This disclosure relates to radiolabeled anti-LAG3 antibodies and their use in immuno-PET imaging.

SEQUENCE LISTING

An official copy of the sequence listing is submitted concurrently with the specification electronically via Patent Center. The contents of the electronic sequence listing (10329US03-US_Sequence_Listing.xml; Size: 707.351 bytes; and Date of Creation: Oct. 25, 2022) is herein incorporated by reference in its entirety.

BACKGROUND

T cell co-stimulatory and co-inhibitory molecules (collectively named co-signaling molecules) play a crucial role in regulating T cell activation, subset differentiation, effector function and survival (Chen et al 2013, Nature Rev. Immunol. 13: 227-242). Following recognition of cognate peptide-MHC complexes on antigen-presenting cells by the T cell receptor (TCR), co-signaling receptors co-localize with T cell receptors at the immune synapse, where they synergize with TCR signaling to promote or inhibit T cell activation and function (Flies et al 2011, Yale J. Biol. Med. 84: 409-421). The ultimate immune response is regulated by a balance between co-stimulatory and co-inhibitory signals ("immune checkpoints") (Pardoll 2012, Nature Reviews Cancer 12: 252-264). Lymphocyte activation gene-3 (LAG3) functions as one such 'immune checkpoint' in mediating peripheral T cell tolerance.

LAG3 (also called CD223) is a 503 amino acid transmembrane protein receptor expressed on activated CD4 and CD8 T cells, γδ T cells, natural killer T cells, B-cells, natural killer cells, plasmacytoid dendritic cells and regulatory T cells. LAG3 is a member of the immunoglobulin (Ig) superfamily. The primary function of LAG3 is to attenuate the immune response. LAG3 binding to MHC class II molecules results in delivery of a negative signal to LAG3-expressing cells and down-regulates antigen-dependent CD4 and CD8 T cell responses. LAG3 negatively regulates the ability of T cells to proliferate, produce cytokines and lyse target cells, termed as 'exhaustion' of T cells. LAG3 is also reported to play a role in enhancing T regulatory (Treg) cell function (Pardoll 2012, Nature Reviews Cancer 12: 252-264).

Immuno-positron emission tomography (PET) is a diagnostic imaging tool that utilizes monoclonal antibodies labeled with positron emitters, combining the targeting properties of an antibody with the sensitivity of positron emission tomography cameras. See, e.g., *The Oncologist,* 12: 1379 (2007); *Journal of Nuclear Medicine,* 52(8): 1171 (2011). Immuno-PET enables the visualization and quantification of antigen and antibody accumulation in vivo and, as such, can serve as an important tool for diagnostics and complementing therapy. For example, immuno-PET can aid in the selection of potential patient candidates for a particular therapy, as well as in the monitoring of treatment.

As LAG3 has emerged as a target for tumor immunotherapy and infectious immunotherapy, there is need for diagnostic tools for anti-LAG3 therapy, including, inter alia, diagnostic tools that enable the detection of suitable patient candidates for said therapy.

BRIEF SUMMARY

Included in this disclosure are radiolabeled anti-LAG3 antibody conjugates for use in immuno-PET imaging.

In one aspect, the conjugate comprises an anti-LAG3 antibody or antigen-binding fragment thereof, a chelating moiety, and a positron emitter.

Provided herein are also processes for synthesizing said conjugates and synthetic intermediates useful for the same.

Provided herein are also methods of imaging a tissue that expresses LAG3, the methods comprising administering a radiolabeled anti-LAG3 antibody conjugate described herein to the tissue; and visualizing the LAG3 expression by positron emission tomography (PET) imaging.

Provided herein are also methods of imaging a tissue comprising LAG3-expressing cells, for example, LAG3-expressing intratumoral lymphocytes, the methods comprising administering a radiolabeled anti-LAG3 antibody conjugate described herein to the tissue, and visualizing the LAG3 expression by PET imaging.

Provided herein are also methods for detecting LAG3 in a tissue, the methods comprising administering a radiolabeled anti-LAG3 antibody conjugate described herein to the tissue; and visualizing the LAG3 expression by PET imaging. In one embodiment, the tissue is present in a human subject. In certain embodiments, the subject is a non-human mammal. In certain embodiments, the subject has a disease or disorder such as cancer, an inflammatory disease, or an infection.

Provided herein are also methods for identifying a patient to be suitable for anti-tumor therapy comprising an inhibitor of LAG3, the methods comprising selecting a patient with a solid tumor, administering a radiolabeled antibody conjugate described herein, and visualizing the administered radiolabeled antibody conjugate in the tumor by PET imaging wherein presence of the radiolabeled antibody conjugate in the tumor identifies the patient as suitable for anti-tumor therapy comprising an inhibitor of LAG3.

Provided herein are also methods of treating a tumor, the methods comprising selecting a subject with a solid tumor; determining that the solid tumor is LAG3-positive; and administering an anti-tumor therapy to the subject in need thereof. In certain embodiments, the anti-tumor therapy comprises an inhibitor of LAG3. In certain embodiments, the anti-tumor therapy comprises an inhibitor of the PD-1/PD-L1 signaling axis (e.g., an anti-PD-1 antibody or an anti-PD-L1 antibody). In certain embodiments, the anti-tumor therapy comprises an inhibitor of LAG3 and/or an inhibitor of the PD-1/PD-L1 signaling axis. In certain embodiments, the subject is administered a radiolabeled anti-LAG3 antibody conjugate described herein, and localization of the radiolabeled antibody conjugate is imaged via positron emission tomography (PET) imaging to determine if the tumor is LAG3-positive. In certain embodiments, the subject is further administered a radiolabeled anti-PD-1 antibody conjugate, and localization of the radiolabeled antibody conjugate is imaged via positron emission tomography (PET) imaging to determine if the tumor is PD-1-positive.

Provided herein are also methods for monitoring the efficacy of an anti-tumor therapy in a subject, wherein the methods comprise selecting a subject with a solid tumor wherein the subject is being treated with an anti-tumor therapy; administering a radiolabeled anti-LAG3 conjugate described herein to the subject; imaging the localization of the administered radiolabeled conjugate in the tumor by PET imaging; and determining tumor growth, wherein a decrease from the baseline in uptake of the conjugate or radiolabeled signal indicates efficacy of the anti-tumor therapy. In certain embodiments, the anti-tumor therapy comprises an inhibitor of LAG3 (e.g., an anti-LAG3 antibody). In certain embodiments, the anti-tumor therapy comprises an inhibitor of LAG3 and an inhibitor of the PD-1/PD-L1 signaling axis. In certain embodiments, the anti-tumor therapy comprises a PD-1 inhibitor (e.g., REGN2810, BGB-A317, nivolumab, pidilizumab, and pembrolizumab), a PD-L1 inhibitor (e.g., atezolizumab, avelumab, durvalumab, MDX-1105, and REGN3504, as well as those disclosed in Patent Publication No. US 2015-0203580), CTLA-4 inhibitor (e.g., ipilimumab), a TIM3 inhibitor, a BTLA inhibitor, a TIGIT inhibitor, a CD47 inhibitor, a GITR inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., *Bacillus* Calmette-Guerin, a cancer vaccine), an adjuvant to increase antigen presentation (e.g., granulocyte-macrophage colony-stimulating factor), a bispecific antibody (e.g., CD3×CD20 bispecific antibody, or PSMA×CD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, and an antibody-drug conjugate (ADC) (e.g., anti-CD19-DM4 ADC, and anti-DS6-DM4 ADC).

Provided herein are also methods for predicting response of a patient to an anti-tumor therapy, the methods comprising selecting a patient with a solid tumor; and determining if the tumor is LAG3-positive, wherein if the tumor is LAG3-positive it predicts a positive response of the patient to an anti-tumor therapy. In certain embodiments, the tumor is determined positive by administering a radiolabeled anti-LAG3 antibody conjugate of the present disclosure and localizing the radiolabeled antibody conjugate in the tumor by PET imaging wherein presence of the radiolabeled antibody conjugate in the tumor indicates that the tumor is LAG3-positive. In some embodiments, the anti-tumor therapy is selected from a PD-1 inhibitor (e.g., REGN2810, BGB-A317, nivolumab, pidilizumab, and pembrolizumab), a PD-L1 inhibitor (e.g., atezolizumab, avelumab, durvalumab, MDX-1105, and REGN3504), CTLA-4 inhibitor (e.g., ipilimumab), a TIM3 inhibitor, a BTLA inhibitor, a TIGIT inhibitor, a CD47 inhibitor, a GITR inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., *Bacillus* Calmette-Guerin, a cancer vaccine), an adjuvant to increase antigen presentation (e.g., granulocyte-macrophage colony-stimulating factor), a bispecific antibody (e.g., CD3×CD20 bispecific antibody, or PSMA×CD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, and an antibody-drug conjugate (ADC) (e.g., anti-CD19-DM4 ADC, and anti-DS6-DM4 ADC).

Provided herein are also methods for predicting response of a patient to an anti-tumor therapy comprising an inhibitor LAG3, the methods comprising selecting a patient with a solid tumor; and determining if the tumor is LAG3-positive, wherein if the tumor is LAG3-positive it indicates a positive response of the patient to an anti-tumor therapy comprising an inhibitor of LAG3. In certain embodiments, the tumor is determined positive by administering a radiolabeled anti-LAG3 antibody conjugate of the present disclosure and localizing the radiolabeled antibody conjugate in the tumor by PET imaging wherein presence of the radiolabeled antibody conjugate in the tumor indicates that the tumor is LAG3-positive.

BRIEF DESCRIPTION OF THE FIGURES

FIG. 12 provides characteristics of the melanoma samples studied in Example 7.

DETAILED DESCRIPTION

I. Definitions

Figure 1:
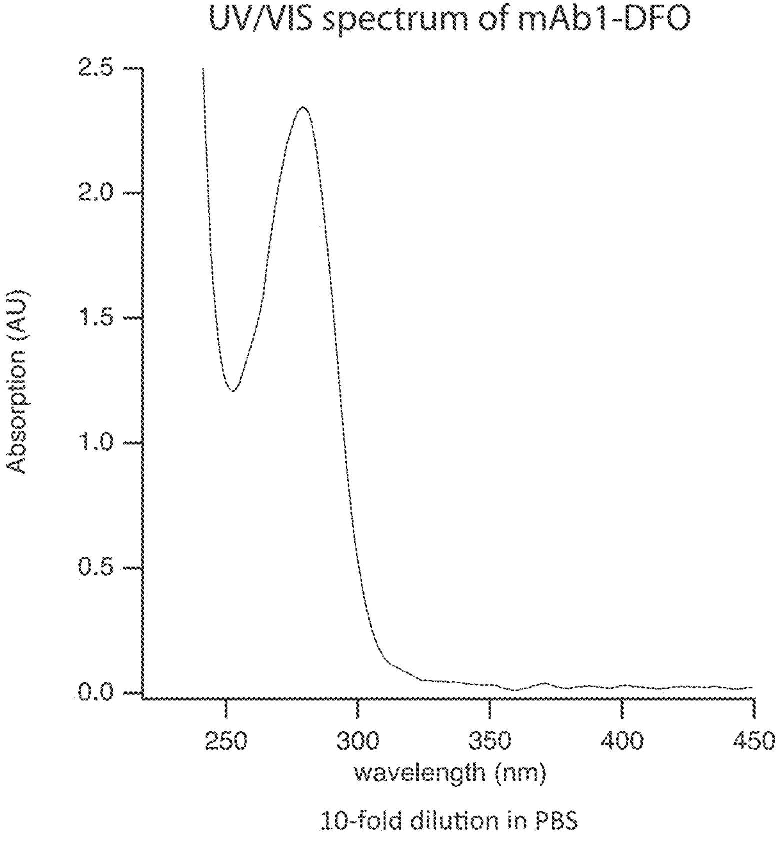
FIG. 1 depicts UV/VIS spectrum of DFO modified anti-LAG3 antibody (mAb1-DFO).

Unless defined otherwise herein, all technical and scientific terms used herein have the same meaning as commonly understood by one of ordinary skill in the art to which the disclosed subject matter belongs.

The term "LAG3" refers to the lymphocyte activation gene-3 protein, an immune checkpoint receptor or T cell co-inhibitor, also known as CD223. The amino acid sequence of full-length LAG3 is provided in GenBank as accession number NP_002277.4 and is also referred to herein as SEQ ID NO: 582. The term "LAG3" also includes protein variants of LAG3 having the amino acid sequence of SEQ ID NOs: 574, 575 or 576. The term "LAG3" includes recombinant LAG3 or a fragment thereof. The term also encompasses LAG3 or a fragment thereof coupled to, for example, histidine tag, mouse or human Fc, or a signal sequence such as the signal sequence of ROR1. For example, the term includes sequences exemplified by SEQ ID NO: 575, comprising a mouse Fc (mIgG2a) at the C-terminal, coupled to amino acid residues 29-450 of full-length ectodomain LAG3. Protein variants as exemplified by SEQ ID NO: 574 comprise a histidine tag at the C-terminal, coupled to amino acid residues 29-450 of full length ectodomain LAG3. Unless specified as being from a non-human species, the term "LAG3" means human LAG3.

LAG3 is a member of the immunoglobulin (Ig) superfamily. LAG3 is a type-1 transmembrane protein with four extracellular Ig-like domains D1 to D4 and is expressed on intratumoral lymphocytes including activated T cells, natural killer cells, B cells, plasmacytoid dendritic cells, and regulatory T cells. The LAG3 receptor binds to MHC class II molecules present on antigen presenting cells (APCs).

The term "B7-1" refers to the T-lymphocyte activation antigen, also known as costimulatory factor CD80. B7-1 is a 288 amino acid membrane receptor with an extracellular N-terminal domain which comprises IgV-like (aa 37-138) and IgC-like (aa 154-232) regions, a transmembrane domain (aa 243-263) and a C-terminal intracellular region (aa 263-288). The amino acid sequence of full-length B7-1 is provided in GenBank as accession number NP_005182.1.

As used herein, the term "T-cell co-inhibitor" refers to a ligand and/or receptor which modulates the immune response via T-cell activation or suppression. The term "T-cell co-inhibitor", also known as T-cell co-signaling molecule, includes, but is not limited to, lymphocyte activation gene 3 protein (LAG-3, also known as CD223), programmed death-1 (PD-1), cytotoxic T-lymphocyte antigen-4 (CTLA-4), B and T lymphocyte attenuator (BTLA), CD-28, 2B4, LY108, T-cell immunoglobulin and mucin-3 (TIM3), T-cell immunoreceptor with immunoglobulin and ITIM domains (TIGIT; also known as VSIG9), leucocyte associated immunoglobulin-like receptor 1 (LAIR1; also known as CD305), inducible T-cell costimulator (ICOS; also known as CD278), B7-1 (CD80), and CD160.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order FR1, CDR1, FR2, CDR2, FR3, CDR3, FR4. In certain embodiments, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The anti-LAG3 monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The present disclosure also includes anti-LAG3 monoclonal antibodies comprising variants of any of the HCVR, LCVR, and/or CDR amino acid sequences disclosed herein having one or more conservative substitutions. For example, the present disclosure includes anti-LAG3 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The term "multi-specific antigen-binding molecules", as used herein refers to bispecific, tri-specific or multi-specific antigen-binding molecules, and antigen-binding fragments thereof. Multi-specific antigen-binding molecules may be specific for different epitopes of one target polypeptide or may contain antigen-binding domains specific for epitopes of more than one target polypeptide. A multi-specific antigen-binding molecule can be a single multifunctional polypeptide, or it can be a multimeric complex of two or more polypeptides that are covalently or non-covalently associated with one another. The term "multi-specific antigen-binding molecules" includes antibodies of the present disclosure that may be linked to or co-expressed with another functional molecule, e.g., another peptide or protein. For example, an antibody or fragment thereof can be functionally linked (e.g., by chemical coupling, genetic fusion, non-covalent association or otherwise) to one or more other molecular entities, such as a protein or fragment thereof to produce a bi-specific or a multi-specific antigen-binding molecule with a second binding specificity. According to the present disclosure, the term "multi-specific antigen-binding molecules" also includes bi-specific, tri-specific or multi-specific antibodies or antigen-binding fragments thereof. In certain embodiments, an antibody of the present disclosure is functionally linked to another antibody or antigen-binding fragment thereof to produce a bispecific antibody with a second binding specificity. Bispecific and multi-specific antibodies of the present disclosure are described elsewhere herein.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1\times10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to LAG3. Moreover, multi-specific antibodies that bind to one domain in LAG3 and one or more additional antigens or a bi-specific that binds to two different regions of LAG3 are nonetheless considered antibodies that "specifically bind", as used herein.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to LAG3.

An "isolated antibody", as used herein, is intended to refer to an antibody that is substantially free of other antibodies (Abs) having different antigenic specificities (e.g., an isolated antibody that specifically binds LAG3, or a fragment thereof, is substantially free of Abs that specifically bind antigens other than LAG3.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix. Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, in need of amelioration, prevention and/or treatment of a disease or disorder such as chronic viral infection, cancer or autoimmune disease.

II. Radiolabeled Immunoconjugates of LAG3 Antibodies for Immuno-PET Imaging

Provided herein are radiolabeled antigen-binding proteins that bind LAG3. In some embodiments, the radiolabeled antigen-binding proteins comprise an antigen-binding protein covalently linked to a positron emitter. In some embodiments, the radiolabeled antigen-binding proteins comprise an antigen-binding protein covalently linked to one or more chelating moieties, which are chemical moieties that are capable of chelating a positron emitter.

In some embodiments, antigen-binding proteins that bind LAG3, e.g., antibodies, are provided, wherein said antigen-binding proteins that bind LAG3 are covalently bonded to one or more moieties having the following structure:

$-L-M_Z$ wherein L is a chelating moiety; M is a positron emitter; and z, independently at each occurrence, is 0 or 1; and wherein at least one of z is 1.

In some embodiments, the radiolabeled antigen-binding protein is a compound of Formula (I):

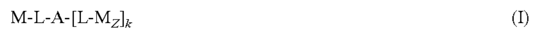

$$M-L-A-[L-M_Z]_k \quad (I)$$

A is a protein that binds LAG3; L is a chelating moiety; M is a positron emitter; z is 0 or 1; and k is an integer from 0-30. In some embodiments, k is 1.

In certain embodiments, the radiolabeled antigen-binding protein is a compound of Formula (II):

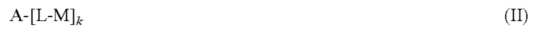

$A\text{-}[L\text{-}M]_k$ (II)

wherein A is a protein that binds LAG3; L is a chelating moiety; M is a positron emitter; and k is an integer from 1-30.

In some embodiments, provided herein are compositions comprising a conjugate having the following structure:

$A\text{-}L_k$ wherein A is a protein that binds LAG3; L is a chelating moiety; and k is an integer from 1-30; wherein the conjugate is chelated with a positron emitter in an amount sufficient to provide a specific activity suitable for clinical PET imaging.

Suitable binding proteins, chelating moieties, and positron emitters are provided below.

A. LAG3 Binding Proteins

Suitable LAG3 binding protein are proteins that specifically bind to LAG3, including those described in PCT/US16/56156, incorporated herein by reference in its entirety. Exemplary anti-LAG3 antibodies of the present disclosure are listed in Table 1 of PCT/US16/56156, also presented below.

TABLE 1

| Amino Acid Sequence Identifiers | | | | | | | | |
|---|---|---|---|---|---|---|---|---|
| | SEQ ID NOs: | | | | | | | |
| Antibody Designation | HCVR | HCDR1 | HCDR2 | HCDR3 | LCVR | LCDR1 | LCDR2 | LCDR3 |
| H1M14985N | 2 | 4 | 6 | 8 | 10 | 12 | 14 | 16 |
| H1M14987N | 18 | 20 | 22 | 24 | 26 | 28 | 30 | 32 |
| H2M14811N | 34 | 36 | 38 | 40 | 42 | 44 | 46 | 48 |
| H2M14885N | 50 | 52 | 54 | 56 | 58 | 60 | 62 | 64 |
| H2M14926N | 66 | 68 | 70 | 72 | 74 | 76 | 78 | 80 |
| H2M14927N | 82 | 84 | 86 | 88 | 90 | 92 | 94 | 96 |
| H2M14931N | 98 | 100 | 102 | 104 | 106 | 108 | 110 | 112 |
| H2M18336N | 114 | 116 | 118 | 120 | 122 | 124 | 126 | 128 |
| H2M18337N | 130 | 132 | 134 | 136 | 138 | 140 | 142 | 144 |
| H4H15477P | 146 | 148 | 150 | 152 | 154 | 156 | 158 | 160 |
| H4H15483P | 162 | 164 | 166 | 168 | 170 | 172 | 174 | 176 |
| H4H15484P | 178 | 180 | 182 | 184 | 186 | 188 | 190 | 192 |
| H4H15491P | 194 | 196 | 198 | 200 | 202 | 204 | 206 | 208 |
| H4H17823P | 210 | 212 | 214 | 216 | 218 | 220 | 222 | 224 |
| H4H17826P2 | 226 | 228 | 230 | 232 | 234 | 236 | 238 | 240 |
| H4H17828P2 | 242 | 244 | 246 | 248 | 250 | 252 | 254 | 256 |
| H4sH15460P | 258 | 260 | 262 | 264 | 266 | 268 | 270 | 272 |
| H4sH15462P | 274 | 276 | 278 | 280 | 282 | 284 | 286 | 288 |
| H4sH15463P | 290 | 292 | 294 | 296 | 298 | 300 | 302 | 304 |
| H4sH15464P | 306 | 308 | 310 | 312 | 314 | 316 | 318 | 320 |
| H4sH15466P | 322 | 324 | 326 | 328 | 330 | 332 | 334 | 336 |
| H4sH15467P | 338 | 340 | 342 | 344 | 346 | 348 | 350 | 352 |
| H4sH15470P | 354 | 356 | 358 | 360 | 362 | 364 | 366 | 368 |
| H4sH15475P | 370 | 372 | 374 | 376 | 378 | 380 | 382 | 384 |
| H4sH15479P | 386 | 388 | 390 | 392 | 394 | 396 | 398 | 400 |
| H4sH15480P | 402 | 404 | 406 | 408 | 410 | 412 | 414 | 416 |
| H4sH15482P | 418 | 420 | 422 | 424 | 426 | 428 | 430 | 432 |
| H4sH15488P | 434 | 436 | 438 | 440 | 442 | 444 | 446 | 448 |
| H4sH15496P2 | 450 | 452 | 454 | 456 | 522 | 524 | 526 | 528 |
| H4sH15498P2 | 458 | 460 | 462 | 464 | 522 | 524 | 526 | 528 |
| H4sH15505P2 | 466 | 468 | 470 | 472 | 522 | 524 | 526 | 528 |
| H4sH15518P2 | 474 | 476 | 478 | 480 | 522 | 524 | 526 | 528 |
| H4sH15523P2 | 482 | 484 | 486 | 488 | 522 | 524 | 526 | 528 |
| H4sH15530P2 | 490 | 492 | 494 | 496 | 522 | 524 | 526 | 528 |
| H4sH15555P2 | 498 | 500 | 502 | 504 | 530 | 532 | 534 | 536 |
| H4sH15558P2 | 506 | 508 | 510 | 512 | 530 | 532 | 534 | 536 |
| H4sH15567P2 | 514 | 516 | 518 | 520 | 530 | 532 | 534 | 536 |
| H4H14813N | 538 | 540 | 542 | 544 | 546 | 548 | 550 | 552 |
| H4H17819P | 554 | 556 | 558 | 560 | 562 | 564 | 566 | 568 |

Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-LAG3 antibodies.

In some embodiments, the binding protein is an antibody or antigen binding fragment comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

In some embodiments, the binding protein is an antibody or antigen binding fragment comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

In some embodiments, the binding protein is an antibody or antigen binding fragment comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present disclosure provides antibodies, or antigen-binding fragments thereof, comprising an HCVR/LCVR amino acid sequence pair contained within any of the exemplary anti-LAG3 antibodies listed in Table 1. In certain embodiments, the HCVR/LCVR amino acid sequence pair is selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/394, 402/410, 418/426, 434/442, 450/522, 458/522, 466/522, 474/522, 482/522, 490/522, 498/530, 506/530, 514/530, 538/546, and 554/562. In certain embodiments, the HCVR/LCVR amino acid sequence pair is selected from one of SEQ ID NOs: 386/394 (e.g., H4sH15479P), 418/426 (e.g., H4sH15482P) or 538/546 (e.g., H4sH14813N). In certain other embodiments, the HCVR/LCVR amino acid sequence pair is selected from one of SEQ ID NOs: 458/464 (e.g., H4sH15498P2), 162/170 (e.g., H4H15483P), and 579/578 (e.g., H4H15482P).

In some embodiments, the binding protein is an antibody or antigen binding fragment comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

In some embodiments, the binding protein is an antibody or antigen binding fragment comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present disclosure provides antibodies, or antigen-binding fragments thereof, comprising an HCDR3/LCDR3 amino acid sequence pair contained within any of the exemplary anti-LAG3 antibodies listed in Table 1. In certain embodiments, the HCDR3/LCDR3 amino acid sequence pair is selected from the group consisting of SEQ ID NOs: 392/400 (e.g., H4sH15479P), 424/432 (e.g., H4sH15482P), and 544/552 (e.g., H4sH14813N).

In some embodiments, the binding protein is an antibody or antigen binding fragment comprising a set of six CDRs (i.e., HCDR1-HCDR2-HCDR3-LCDR1-LCDR2-LCDR3) contained within any of the exemplary anti-LAG3 antibodies listed in Table 1. In certain embodiments, the HCDR1-HCDR2-HCDR3-LCDR1-LCDR2-LCDR3 amino acid sequence set is selected from the group consisting of SEQ ID NOs: 388-390-392-396-398-400 (e.g., H4sH15479P), 420-422-424-428-430-432 (e.g., H4sH15482P), and 540-542-544-548-550-552 (e.g., H4sH14813N).

In some embodiments, the binding protein is an antibody or antigen binding fragment comprising a set of six CDRs (i.e., HCDR1-HCDR2-HCDR3-LCDR1-LCDR2-LCDR3) contained within an HCVR/LCVR amino acid sequence pair as defined by any of the exemplary anti-LAG3 antibodies listed in Table 1. For example, in some embodiments, the binding protein is an antibody or antigen binding fragment comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 386/394 (e.g., H4sH15479P), 418/426 (e.g., H4sH15482P) and 538/546 (e.g., H4sH14813N). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In some embodiments, binding proteins are antibodies and antigen-binding fragments thereof that compete for specific binding to LAG3 with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

Additional exemplary anti-LAG3 antibodies useful herein include LAG525 (and other LAG3 antibodies disclosed in U.S. 20100233183), relatlimab (and other LAG3 antibodies disclosed in U.S. 20110150892), GSK2831781 (and other LAG3 antibodies disclosed in U.S. 20140286935), MGD013 (and other LAG3 antibodies disclosed in WO2015200119) and LAG3 antibodies disclosed in U.S. 20160222116, U.S. 20170022273, U.S. 20170097333, U.S. 20170137517, U.S. 20170267759, U.S. 20170290914, U.S. 20170334995, WO2016126858, WO2016200782, WO2017087589, WO2017087901, WO2017106129, WO2017149143, WO2017198741, WO2017219995, and WO2017220569.

Also provided herein are isolated antibodies and antigen-binding fragments thereof that block LAG3 binding to MHC class II. In some embodiments, the antibody or antigen-binding fragment thereof that blocks LAG3 binding may bind to the same epitope on LAG3 as MHC class II or may bind to a different epitope on LAG3 as MHC class II. In certain embodiments, the antibodies of the disclosure that block LAG3 binding to MHC class II comprise the CDRs of an HCVR having an amino acid sequence selected from the group consisting of HCVR sequences listed in Table 1; and the CDRs of a LCVR having an amino acid sequence selected from the group consisting of LCVR sequences listed in Table 1.

In alternate embodiments, the present disclosure provides antibodies and antigen-binding fragments thereof that do not block LAG3 binding to MHC class II.

In some embodiments, the binding proteins are antibodies and antigen-binding fragments thereof that bind specifically to LAG3 from human or other species. In certain embodiments, the antibodies may bind to human LAG3 and/or to cynomolgus LAG3.

In some embodiments, the binding proteins are antibodies and antigen-binding fragments thereof that cross-compete for binding to LAG3 with a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

In one embodiment, the binding protein is an isolated antibody or antigen-binding fragment that has one or more of the following characteristics: (a) blocks the binding of LAG3 or to MHC class II; (b) binds specifically to human LAG3 and/or cynomolgus LAG3; (c) blocks LAG3-induced impairment of T cell activation and rescues T cell signaling; and (d) suppresses tumor growth and increases survival in a subject with cancer.

In some embodiments, the antibody or antigen binding fragment thereof may bind specifically to LAG3 in an agonist manner, i.e., it may enhance or stimulate LAG3 binding and/or activity; in other embodiments, the antibody may bind specifically to LAG3 in an antagonist manner, i.e., it may block LAG3 from binding to its ligand.

In some embodiments, the antibody or antigen binding fragment thereof may bind specifically to LAG3 in an neutral manner, i.e., it binds but does not block or enhance or stimulate LAG3 binding and/or activity.

In certain embodiments, the antibodies or antigen-binding fragments are bispecific comprising a first binding specificity to LAG3 and a second binding specificity for a second target epitope. The second target epitope may be another epitope on LAG3 or on a different protein. In certain embodiments, the second target epitope may be on a different cell including a different T cell, a B-cell, a tumor cell or a virally infected cell.

In certain embodiments, an isolated antibody or antigen-binding fragment thereof is provided that binds specifically to human lymphocyte activation gene 3 (LAG3) protein, wherein the antibody or antigen-binding fragment thereof has a property selected from the group consisting of: (a) binds monomeric human LAG3 with a binding dissociation equilibrium constant ($K_D$) of less than about 10 nM as measured in a surface plasmon resonance assay at 25° C. (using the assay format as defined in Example 3 of PCT/US16/56156, or a substantially similar assay); (b) binds monomeric human LAG3 with a $K_D$ less than about 8 nM as measured in a surface plasmon resonance assay at 37° C.; (c) binds dimeric human LAG3 with a $K_D$ less than about 1.1 nM as measured in a surface plasmon resonance assay at 25° C.; (d) binds dimeric human LAG3 with a $K_D$ less than about 1 nM as measured in a surface plasmon resonance assay at 37° C.; (e) binds to a hLAG3-expressing cell with an $EC_{50}$ less than about 8 nM as measured in a flow cytometry assay; (f) binds to a mfLAG3-expressing cell with a $EC_{50}$ less than about 2.3 nM as measured in a flow cytometry assay; (g) blocks binding of hLAG3 to human MHC class II with $IC_{50}$ less than about 32 nM as determined by a cell adherence assay; (h) blocks binding of hLAG3 to mouse MHC class II with $IC_{50}$ less than about 30 nM as determined by a cell adherence assay; (i) blocks binding of hLAG3 to MHC class II by more than 90% as determined by a cell adherence assay; (j) rescues LAG3-mediated inhibition of T cell activity with $EC_{50}$ less than about 9 nM as determined in a luciferase reporter assay; and (k) binds to activated CD4+ and CD8+ T cells with $EC_{50}$ less than about 1.2 nM, as determined in a fluorescence assay.

In some embodiments, the antibodies and antigen-binding fragments thereof bind LAG3 with a dissociative half-life (t½) of greater than about 1.6 minutes as measured by surface plasmon resonance at 25° C. or 37° C., e.g., using an assay format as defined in Example 3 of PCT/US16/56156, or a substantially similar assay. In certain embodiments, the antibodies or antigen-binding fragments bind LAG3 with a t½ of greater than about 5 minutes, greater than about 10 minutes, greater than about 30 minutes, greater than about 50 minutes, greater than about 60 minutes, greater than about 70 minutes, greater than about 80 minutes, greater than about 90 minutes, greater than about 100 minutes, greater than about 200 minutes, greater than about 300 minutes, greater than about 400 minutes, greater than about 500 minutes, greater than about 600 minutes, greater than about 700 minutes, greater than about 800 minutes, greater than about 900 minutes, greater than about 1000 minutes, or greater than about 1100 minutes, as measured by surface plasmon resonance at 25° C. or 37° C., e.g., using an assay format as defined in Example 3 of PCT/US16/56156 (e.g., mAb-capture or antigen-capture format), or a substantially similar assay.

In some embodiments, antibodies or antigen-binding fragments thereof bind to a human LAG3-expressing cell with an $EC_{50}$ less than about 8 nM as measured by a flow cytometry assay as defined in Example 5 of PCT/US16/56156, or a substantially similar assay. In certain embodiments, the antibodies or antigen-binding fragments thereof bind to a hLAG3-expressing cell with an $EC_{50}$ less than about 5 nM, less than about 2 nM, less than about 1 nM, or less than about 0.5 nM, as measured by a flow cytometry assay, e.g., using the assay format in Example 5 of PCT/US16/56156, or a substantially similar assay.

In some embodiments, antibodies or antigen-binding fragments thereof bind to a cynomolgus monkey LAG3-expressing cell with an $EC_{50}$ less than about 2.5 nM as measured by a flow cytometry assay as defined in Example 5 of PCT/US16/56156, or a substantially similar assay. In certain embodiments, the antibodies or antigen-binding fragments thereof bind to a mfLAG3-expressing cell with an $EC_{50}$ less than about 2 nM, or less than about 1 nM, as measured by a flow cytometry assay, e.g., using the assay format as defined in Example 5 of PCT/US16/56156, or a substantially similar assay.

In some embodiments, antibodies or antigen-binding fragments thereof block LAG3 binding to MHC class II (e.g., human HLA-DR2) with an $IC_{50}$ of less than about 32 nM as determined using a cell adherence assay, e.g., as shown in Example 7 of PCT/US16/56156, or a substantially similar assay. In certain embodiments, the antibodies or antigen-binding fragments thereof block LAG3 binding to human MHC class II with an $IC_{50}$ less than about 25 nM, less than about 20 nM, less than about 10 nM, or less than about 5 nM, as measured by a cell adherence assay, e.g., using the assay format as defined in Example 7 of PCT/US16/56156, or a substantially similar assay.

In some embodiments, the antibodies or antigen-binding fragments thereof block LAG3 binding to MHC class II with an $IC_{50}$ of less than about 30 nM as determined using a cell adherence assay, e.g., as shown in Example 7 of PCT/US16/56156, or a substantially similar assay. In certain embodiments, the antibodies or antigen-binding fragments thereof block mouse LAG3 binding to human MHC class II with an $IC_{50}$ less than about 25 nM, less than about 20 nM, less than about 10 nM, or less than about 5 nM, as measured by a cell adherence assay, e.g., using the assay format as defined in Example 7 of PCT/US16/56156, or a substantially similar assay.

In some embodiments, the antibodies or antigen-binding fragments thereof block binding of LAG3 to human or mouse MHC class II by more than 90% as measured by a cell adherence assay as defined in Example 7 of PCT/US16/56156, or a substantially similar assay.

In some embodiments, the antibodies or antigen-binding fragments thereof block LAG-induced T cell down-regulation with an $EC_{50}$ less than 9 nM as measured by a T cell/APC luciferase reporter assay as defined in Example 8 of PCT/US16/56156, or a substantially similar assay. In certain embodiments, the antibodies or antigen-binding fragments thereof block LAG3-induced T cell down-regulation with an $EC_{50}$ less than about 5 nM, less than about 1 nM, less than about 0.5 nM, or less than about 0.1 nM, as measured by a T cell/APC luciferase reporter assay, e.g., using the assay format as defined in Example 8 of PCT/US16/56156, or a substantially similar assay.

In some embodiments, the antibodies or antigen-binding fragments thereof bind to cynomolgus activated CD4+ and CD8+ T cells with an $EC_{50}$ less than about 1.2 nM as measured by a fluorescence assay as defined in Example 9 of PCT/US16/56156, or a substantially similar assay. In certain embodiments, the antibodies or antigen-binding fragments thereof bind to cynomolgus activated CD4+ and CD8+ T cells with an $EC_{50}$ less than about 1.1 nM, less than about 1 nM, less than about 0.5 nM, less than about 0.2 nM, or less than about 0.1 nM, as measured by a fluorescence assay, e.g., using the assay format as defined in Example 9 of PCT/US16/56156, or a substantially similar assay.

In one embodiment, the antibody or fragment thereof is a monoclonal antibody or antigen-binding fragment thereof that binds to LAG3, wherein the antibody or fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354, 370, 386, 402, 418, 434, 450, 458, 466, 474, 482, 490, 498, 506, 514, 538, and 554, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 186, 202, 218, 234, 250, 266, 282, 298, 314, 330, 346, 362, 378, 394, 410, 426, 442, 522, 530, 546, and 562, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 200, 216, 232, 248, 264, 280, 296, 312, 328, 344, 360, 376, 392, 408, 424, 440, 456, 464, 472, 480, 488, 496, 504, 512, 520, 544, and 560, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, 288, 304, 320, 336, 352, 368, 384, 400, 416, 432, 448, 528, 536, 552, and 568, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 196, 212, 228, 244, 260, 276, 292, 308, 324, 340, 356, 372, 388, 404, 420, 436, 452, 460, 468, 476, 484, 492, 500, 508, 516, 540, and 556, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 198, 214, 230, 246, 262, 278, 294, 310, 326, 342, 358, 374, 390, 406, 422, 438, 454, 462, 470, 478, 486, 494, 502, 510, 518, 542, and 558, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, 204, 220, 236, 252, 268, 284, 300, 316, 332, 348, 364, 380, 396, 412, 428, 444, 524, 532, 548, and 564, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 190, 206, 222, 238, 254, 270, 286, 302, 318, 334, 350, 366, 382, 398, 414, 430, 446, 526, 534, 550, and 566, or a substantially similar sequence thereof having at least 90%, at least 95%, at least 98% or at least 99% sequence identity; (v) binds monomeric human LAG3 with a binding dissociation equilibrium constant ($K_D$) of less than about 10 nM as measured in a surface plasmon resonance assay at 25° C.; (vi) binds monomeric human LAG3 with a $K_D$ less than about 8 nM as measured in a surface plasmon resonance assay at 37° C.; (vii) binds dimeric human LAG3 with a $K_D$ less than about 1.1 nM as measured in a surface plasmon resonance assay at 25° C.; (viii) binds dimeric human LAG3 with a $K_D$ less than about 1 nM as measured in a surface plasmon resonance assay at 37° C.; (ix) binds to a hLAG3-expressing cell with an $EC_{50}$ less than about 8 nM as measured in a flow cytometry assay; (x) binds to a mfLAG3-expressing cell with a $EC_{50}$ less than about 2.3 nM as measured in a flow cytometry assay; (xi) blocks binding of hLAG3 to human MHC class II with $IC_{50}$ less than about 32 nM as determined by a cell adherence assay; (xii) blocks binding of hLAG3 to mouse MHC class II with $IC_{50}$ less than about 30 nM as determined by a cell adherence assay; (xiii) blocks binding of hLAG3 to MHC class II by more than 90% as determined by a cell adherence assay; (xiv) rescues LAG3-mediated inhibition of T cell activity with $EC_{50}$ less than about 9 nM as determined in a luciferase reporter assay; (xv) binds to activated CD4+ and CD8+ T cells with $EC_{50}$ less than about 1.2 nM, as determined in a fluorescence assay; and (xvi) suppresses tumor growth and increases survival in a subject with cancer.

In one embodiment, the antibody or fragment thereof is a monoclonal antibody or antigen-binding fragment thereof that blocks LAG3 binding to MHC class II, wherein the antibody or fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354, 370, 386, 402, 418, 434, 450, 458, 466, 474, 482, 490, 498, 506, 514, 538, and 554, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 186, 202, 218, 234, 250, 266, 282, 298, 314, 330, 346, 362, 378, 394, 410, 426, 442, 522, 530, 546, and 562, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 200, 216, 232, 248, 264, 280, 296, 312, 328, 344, 360, 376, 392, 408, 424, 440, 456, 464, 472, 480, 488, 496, 504, 512, 520, 544, and 560, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, 288, 304, 320, 336, 352, 368, 384, 400, 416, 432, 448, 528, 536, 552, and 568, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 196, 212, 228, 244, 260, 276, 292, 308, 324, 340, 356, 372, 388, 404, 420, 436, 452, 460, 468, 476, 484, 492, 500, 508, 516, 540, and 556, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 198, 214, 230, 246, 262, 278, 294, 310, 326, 342, 358, 374, 390, 406, 422, 438, 454, 462, 470, 478, 486, 494, 502, 510, 518, 542, and 558, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, 204, 220, 236, 252, 268, 284, 300, 316, 332, 348, 364, 380, 396, 412, 428, 444, 524, 532, 548, and 564, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 190, 206, 222, 238, 254, 270, 286, 302, 318, 334, 350, 366, 382, 398, 414, 430, 446, 526, 534, 550, and 566, or a substantially similar sequence thereof having at least 90%, at least 95%, at least 98% or at least 99% sequence identity; (v) binds monomeric human LAG3 with a binding dissociation equilibrium constant ($K_D$) of less than about 10 nM as measured in a surface plasmon resonance assay at 25° C.; (vi) binds monomeric human LAG3 with a $K_D$ less than about 8 nM as measured in a surface plasmon resonance assay at 37° C.; (vii) binds dimeric human LAG3 with a $K_D$ less than about 1.1 nM as measured in a surface plasmon resonance assay at 25° C.; (viii) binds dimeric human LAG3 with a $K_D$ less than about 1 nM as measured in a surface plasmon resonance assay at 37° C.; (ix) binds to a hLAG3-expressing cell with an $EC_{50}$ less than about 8 nM as measured in a flow cytometry assay; (x) binds to a mfLAG3-expressing cell with a $EC_{50}$ less than about 2.3 nM as measured in a flow cytometry assay; (xi) blocks binding of hLAG3 to human MHC class II with $IC_{50}$ less than about 32 nM as determined by a cell adherence assay; (xii) blocks binding of hLAG3 to mouse MHC class II with $IC_{50}$ less than about 30 nM as determined by a cell adherence assay; (xiii) blocks binding of hLAG3 to MHC class II by more than 90% as determined by a cell adherence assay; (xiv) rescues LAG3-mediated inhibition of T cell activity with $EC_{50}$ less than about 9 nM as determined in a luciferase reporter assay; (xv) binds to activated CD4+ and CD8+ T cells with $EC_{50}$ less than about 1.2 nM, as determined in a fluorescence assay; and (xvi) suppresses tumor growth and increases survival in a subject with cancer.

In certain embodiments, the antibodies may function by blocking or inhibiting the MHC class II-binding activity associated with LAG3 by binding to any other region or fragment of the full length protein, the amino acid sequence of which is shown in SEQ ID NO: 582.

In certain embodiments, the antibodies are bi-specific antibodies. The bi-specific antibodies can bind one epitope in one domain and can also bind a second epitope in a different domain of LAG3. In certain embodiments, the bi-specific antibodies bind two different epitopes in the same domain. In one embodiment, the multi-specific antigen-binding molecule comprises a first antigen-binding specificity wherein the first binding specificity comprises the extracellular domain or fragment thereof of LAG3; and a second antigen-binding specificity to another epitope of LAG3.

In certain embodiments, the anti-LAG3 antibodies or antigen-binding fragments thereof bind an epitope within any one or more of the regions exemplified in LAG3, either in natural form, as exemplified in SEQ ID NO: 582, or recombinantly produced, as exemplified in SEQ ID NOS: 574-576, or to a fragment thereof. In some embodiments, the antibodies bind to an extracellular region comprising one or more amino acids selected from the group consisting of amino acid residues 29-450 of LAG3. In some embodiments, the antibodies bind to an extracellular region comprising one or more amino acids selected from the group consisting of amino acid residues 1-533 of cynomolgus LAG3, as exemplified by SEQ ID NO: 576.

In certain embodiments, anti-LAG3 antibodies and antigen-binding fragments thereof interact with one or more epitopes found within the extracellular region of LAG3 (SEQ ID NO: 588). The epitope(s) may consist of one or more contiguous sequences of 3 or more (e.g., 3, 4, 5, 6, 7, 8, 9, 10, 11, 12, 13, 14, 15, 16, 17, 18, 19, 20 or more) amino acids located within the extracellular region of LAG3. Alternatively, the epitope may consist of a plurality of non-contiguous amino acids (or amino acid sequences) located within the extracellular region of LAG3. The epitope of LAG3 with which the exemplary antibody H4sH15482P interacts is defined by the amino acid sequence LRRAGVTWQHQPDSGPPAAAPGHPLAPGPHPAAPSSWGPRPRRY (SEQ ID NO: 589), which corresponds to amino acids 28 to 71 of SEQ ID NO: 588. Accordingly, also included are anti-LAG3 antibodies that interact with one or more amino acids contained within the region consisting of amino acids 28 to 71 of SEQ ID NO: 588 (i.e., the sequence LRRAGVTWQHQPDSGPPAAAPGHPLAPGPHPAAPSSWGPRPRRY [SEQ ID NO: 589]).

The present disclosure includes anti-LAG3 antibodies that bind to the same epitope, or a portion of the epitope, as any of the specific exemplary antibodies described herein in Table 1, or an antibody having the CDR sequences of any of the exemplary antibodies described in Table 1. Likewise, also included are anti-LAG3 antibodies that compete for binding to LAG3 or a LAG3 fragment with any of the specific exemplary antibodies described herein in Table 1, or an antibody having the CDR sequences of any of the exemplary antibodies described in Table 1. For example, the present disclosure includes anti-LAG3 antibodies that cross-compete for binding to LAG3 with one or more antibodies provided herein (e.g., H4sH15482P, H4sH15479P, H4sH14813N, H4H14813N, H4H15479P, H4H15482P, H4H15483P, H4sH15498P, H4H15498P, H4H17828P2, H4H17819P, and H4H17823P).

The antibodies and antigen-binding fragments described herein specifically bind to LAG3 and modulate the interaction of LAG3 with MHC class II. The anti-LAG3 antibodies may bind to LAG3 with high affinity or with low affinity. In certain embodiments, the antibodies are blocking antibodies wherein the antibodies bind to LAG3 and block the interaction of LAG3 with MHC class II. In some embodiments, the blocking antibodies of the disclosure block the binding of LAG3 to MHC class II and/or stimulate or enhance T-cell activation. In some embodiments, the blocking antibodies are useful for stimulating or enhancing the immune response and/or for treating a subject suffering from cancer, or a chronic viral infection. The antibodies when administered to a subject in need thereof may reduce the chronic infection by a virus such as human immunodeficiency virus (HIV), hepatitis B virus (HBV), hepatitis C virus (HCV), human papilloma virus (HPV), lymphocytic choriomeningitis virus (LCMV), and simian immunodeficiency virus (SIV) in the subject. They may be used to inhibit the growth of tumor cells in a subject. They may be used alone or as adjunct therapy with other therapeutic moieties or modalities known in the art for treating cancer, or viral infection. In certain embodiments, the anti-LAG3 antibodies that bind to LAG3 with a low affinity are used as multi-specific antigen-binding molecules wherein the first binding specificity binds to LAG3 with a low affinity and the second binding specificity binds to an antigen selected from the group consisting of a different epitope of LAG3 and another T-cell co-inhibitor.

In some embodiments, the antibodies bind to LAG3 and reverse the anergic state of exhausted T cells. In certain embodiments, the antibodies bind to LAG3 and inhibit regulatory T cell activity. In some embodiments, the antibodies may be useful for stimulating or enhancing the immune response and/or for treating a subject suffering from cancer, a viral infection, a bacterial infection, a fungal infection, or a parasitic infection. The antibodies when administered to a subject in need thereof may reduce chronic infection by a virus such as HIV, LCMV or HBV in the subject. They may be used to inhibit the growth of tumor cells in a subject. They may be used alone or as adjunct therapy with other therapeutic moieties or modalities known in the art for treating cancer, or viral infection.

In certain embodiments, the antibodies of the present disclosure are agonist antibodies, wherein the antibodies bind to LAG3 and enhance the interaction of LAG3 and MHC class II. In some embodiments, the activating antibodies enhance binding of LAG3 to MHC class II and/or inhibit or suppress T-cell activation. The activating antibodies of the present disclosure may be useful for inhibiting the immune response in a subject and/or for treating autoimmune disease.

Certain anti-LAG3 antibodies are able to bind to and neutralize the activity of LAG3, as determined by in vitro or in vivo assays. The ability of the antibodies to bind to and neutralize the activity of LAG3 may be measured using any standard method known to those skilled in the art, including binding assays, or activity assays, as described herein.

Non-limiting, exemplary in vitro assays for measuring binding activity are illustrated in Examples provided in PCT/US16/56156: in Example 3, the binding affinities and kinetic constants of human anti-LAG3 antibodies for human LAG3 were determined by surface plasmon resonance and the measurements were conducted on a Biacore 4000 or T200 instrument; in Example 4, blocking assays were used to determine cross-competition between anti-LAG3 antibodies; Examples 5 and 6 describe the binding of the antibodies to cells overexpressing LAG3; in Example 7, binding assays were used to determine the ability of the anti-LAG3 antibodies to block MHC class II-binding ability of LAG3 in vitro; in Example 8, a luciferase assay was used to determine the ability of anti-LAG3 antibodies to antagonize LAG3 signaling in T cells; and in Example 9, a fluorescence assay was used to determine the ability of anti-LAG3 antibodies to bind to activated monkey CD4+ and CD8+ T cells.

Unless specifically indicated otherwise, the term “antibody,” as used herein, shall be understood to encompass antibody molecules comprising two immunoglobulin heavy chains and two immunoglobulin light chains (i.e., “full antibody molecules”) as well as antigen-binding fragments thereof. The terms “antigen-binding portion” of an antibody, “antigen-binding fragment” of an antibody, and the like, as used herein, include any naturally occurring, enzymatically obtainable, synthetic, or genetically engineered polypeptide or glycoprotein that specifically binds an antigen to form a complex. The terms “antigen-binding fragment” of an antibody, or “antibody fragment”, as used herein, refers to one or more fragments of an antibody that retain the ability to specifically bind to LAG3. An antibody fragment may include a Fab fragment, a $F(ab')_2$ fragment, a Fv fragment, a dAb fragment, a fragment containing a CDR, or an isolated CDR. In certain embodiments, the term “antigen-binding fragment” refers to a polypeptide or fragment thereof of a multi-specific antigen-binding molecule. In such embodiments, the term “antigen-binding fragment” includes, e.g., MHC class II molecule which binds specifically to LAG3. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present disclosure using routine techniques available in the art.

The anti-LAG3 antibodies and antibody fragments of the present disclosure encompass proteins having amino acid sequences that vary from those of the described antibodies, but that retain the ability to bind LAG3. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present disclosure encompass sequences that comprise one or more additions, deletions, or substitutions of nucleotides when compared to the disclosed sequence, but that encode an antibody or antibody fragment that is essentially bioequivalent to an antibody or antibody fragment of the disclosure.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the disclosure may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

According to certain embodiments of the present disclosure, anti-LAG3 antibodies comprise an Fc domain comprising one or more mutations which enhance or diminish antibody binding to the FcRn receptor, e.g., at acidic pH as compared to neutral pH. For example, the present disclosure includes anti-LAG3 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present disclosure includes anti-LAG3 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). In one embodiment, the present disclosure includes anti-LAG3 antibodies comprising an Fc domain comprising a S108P mutation in the hinge region of IgG4 to promote dimer stabilization. All possible combinations of the foregoing Fc domain mutations, and other mutations within the antibody variable domains disclosed herein, are contemplated within the scope of the present disclosure.

The present disclosure also includes anti-LAG3 antibodies comprising a chimeric heavy chain constant ($C_H$) region, wherein the chimeric $C_H$ region comprises segments derived from the $C_H$ regions of more than one immunoglobulin isotype. For example, the antibodies of the disclosure may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the disclosure comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., US Patent Publication No. 20140243504, the disclosure of which is hereby incorporated by reference in its entirety). In certain embodiments, the Fc region comprises a sequence selected from the group consisting of SEQ ID NOs: 569, 570, 571, 572 and 573.

B. Positron Emitters and Chelating Moieties

Suitable positron emitters include, but are not limited to, those that form stable complexes with the chelating moiety and have physical half-lives suitable for immuno-PET imaging purposes. Illustrative positron emitters include, but are not limited to, $^{89}Zr$, $^{68}Ga$, $^{64}Cu$, $^{44}Sc$, and $^{86}Y$. Suitable positron emitters also include those that directly bond with the LAG3 binding protein, including, but not limited to, $^{76}Br$ and $^{124}I$, and those that are introduced via prosthetic group, e.g., $^{18}F$.

The chelating moieties described herein are chemical moieties that are covalently linked to the LAG3 binding protein, e.g., anti-LAG3 antibody and comprise a portion capable of chelating a positron emitter, i.e., capable of reacting with a positron emitter to form a coordinated chelate complex. Suitable moieties include those that allow efficient loading of the particular metal and form metal-chelator complexes that are sufficiently stable in vivo for diagnostic uses, e.g., immuno-PET imaging. Illustrative chelating moieties include those that minimize dissociation of the positron emitter and accumulation in mineral bone, plasma proteins, and/or bone marrow depositing to an extent suitable for diagnostic uses.

Examples of chelating moieties include, but are not limited to, those that form stable complexes with positron emitters $^{89}Zr$, $^{68}Ga$, $^{64}Cu$, $^{44}Sc$, and/or $^{86}Y$. Illustrative chelating moieties include, but are not limited to, those described in *Nature Protocols,* 5(4): 739, 2010; *Bioconjugate Chem.,* 26(12): 2579 (2015); *Chem Commun* (*Camb*), 51(12): 2301 (2015); *Mol. Pharmaceutics,* 12: 2142 (2015); *Mol. Imaging Biol.,* 18: 344 (2015); *Eur. J. Nucl. Med. Mol. Imaging,* 37:250 (2010); *Eur. J. Nucl. Med. Mol. Imaging* (2016). doi:10.1007/s00259-016-3499-x; Bioconjugate Chem., 26(12): 2579 (2015); WO 2015/140212A1; and U.S. Pat. No. 5,639,879, incorporated by reference in their entireties.

Illustrative chelating moieties also include, but are not limited to, those that comprise desferrioxamine (DFO), 1,4,7,10-tetraacetic acid (DOTA), diethylenetriaminepentaacetic acid (DTPA), ethylenediaminetetraacetic acid (EDTA), (1,4,7,10-Tetraazacyclododecane-1,4,7,10-tetra (methylene phosphonic) acid (DOTP), 1R, 4R, 7R, 10R)-α'α"α'"-Tetramethyl-1,4,7,10-tetraazacyclododecane-1,4,7,10-tetraacetic acid (DOTMA), 1,4,8,11-Tetraazacyclotetradecane-1,4,8,11-tetraacetic acid (TETA), $H_4$octapa, $H_6$phospa, $H_2$dedpa, $H_5$decapa, $H_2$azapa, HOPO, DO2A, 1,4,7,10-Tetrakis(carbamoylmethyl)-1,4,7,10-tetraazacyclododecane (DOTAM), 1,4,7-triazacyclononane-N,N',N"-triacetic acid (NOTA), 1,4,7,10-Tetrakis(carbamoylmethyl)-1,4,7,10-tetraazacyclododecane (DOTAM), 1,4,8,11-tetraazabicyclo[6.6.2]hexadecane-4,11-diacetic acid (CB-TE2A), 1,4,7,10-Tetraazacyclododecane (Cyclen), 1,4,8,11-Tetraazacyclotetradecane (Cyclam), octadentate chelators, e.g., DFO*, which can be conjugated to the antibody via DFO*-pPhe-NCS (See Vugt et al., Eur J Nucl Med Mol Imaging (2017) 44: 286-295), hexadentate chelators, phosphonate-based chelators, macrocyclic chelators, chelators comprising macrocyclic terephthalamide ligands, bifunctional chelators, fusarinine C and fusarinine C derivative chelators, triacetylfusarinine C (TAFC), ferrioxamine E (FOXE), ferrioxamine B (FOXB), ferrochrome A (FCHA), and the like.

In some embodiments, the chelating moieties are covalently bonded to the LAG3 binding protein, e.g., antibody or antigen binding fragment thereof, via a linker moiety, which covalently attaches the chelating portion of the chelating moiety to the binding protein. In some embodiments, these linker moieties are formed from a reaction between a reactive moiety of the LAG3 binding protein, e.g., cysteine or lysine of an antibody, and reactive moiety that is attached to a chelator, including, for example, a p-isothiocyanatobenzyl group and the reactive moieties provided in the conjugation methods below. In addition, such linker moieties optionally comprise chemical groups used for purposes of adjusting polarity, solubility, steric interactions, rigidity, and/or the length between the chelating portion and the LAG3 binding protein.

C. Preparation of Radiolabeled Anti-LAG3 Conjugates

The radiolabeled anti-LAG3 protein conjugates can be prepared by (1) reacting a LAG3 binding protein, e.g., antibody, with a molecule comprising a positron emitter chelator and a moiety reactive to the desirable conjugation site of the LAG3 binding protein and (2) loading the desirable positron emitter.

Suitable conjugation sites include, but are not limited to, lysine and cysteine, both of which can be, for example, native or engineered, and can be, for example, present on the heavy or light chain of an antibody. Cysteine conjugation sites include, but are not limited to, those obtained from mutation, insertion, or reduction of antibody disulfide bonds. Methods for making cysteine engineered antibodies include, but are not limited to, those disclosed in WO2011/056983. Site-specific conjugation methods can also be used to direct the conjugation reaction to specific sites of an antibody, achieve desirable stoichiometry, and/or achieve desirable chelator-to-antibody ratios. Such conjugation methods are known to those of ordinary skill in the art and include, but are not limited to cysteine engineering and enzymatic and chemo-enzymatic methods, including, but not limited to, glutamine conjugation, Q295 conjugation, and transglutaminase-mediated conjugation, as well as those described in *J. Clin. Immunol.,* 36: 100 (2016), incorporated herein by reference in its entirety. Suitable moieties reactive to the desirable conjugation site generally enable efficient and facile coupling of the LAG3 binding protein, e.g., antibody and positron emitter chelator. Moieties reactive to lysine and cysteine sites include electrophilic groups, which are known to those of ordinary skill. In certain aspects, when the desired conjugation site is lysine, the reactive moiety is an isothiocyanate, e.g., p-isothiocyanatobenzyl group or reactive ester. In certain aspects, when the desired conjugation site is cysteine, the reactive moiety is a maleimide.

When the chelator is desferrioxamine (DFO), suitable reactive moieties include, but are not limited to, an isothiocyanatobenzyl group, an n-hydroxysuccinimide ester, 2,3,5,6 tetrafluorophenol ester, n-succinimidyl-S-acetylthioacetate, and those described in *BioMed Research International*, Vol 2014, Article ID 203601, incorporated herein by reference in its entirety. In certain embodiments, the LAG3 binding protein is an antibody and the molecule comprising a positron emitter chelator and moiety reactive to the conjugation site is p-isothiocyanatobenzyl-desferrioxamine (p-SCN-Bn-DFO):

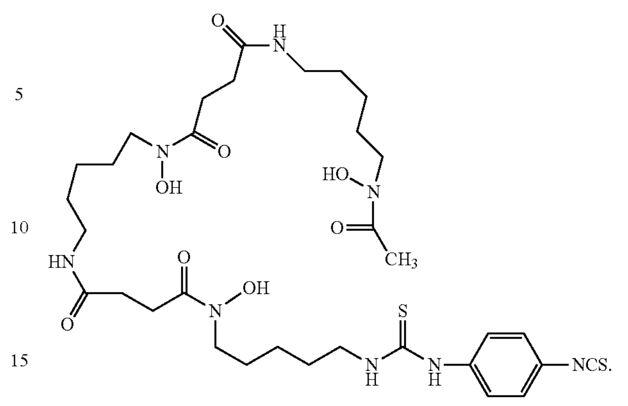

Positron emitter loading is accomplished by incubating the LAG3 binding protein chelator conjugate with the positron emitter for a time sufficient to allow coordination of said positron emitter to the chelator, e.g., by performing the methods described in the examples provided herein, or substantially similar method.

D. Illustrative Embodiments of Conjugates

Included in the instant disclosure are radiolabeled antibody conjugates comprising an antibody or antigen binding fragment thereof that binds human LAG3 and a positron emitter. Also included in the instant disclosure are radiolabeled antibody conjugates comprising an antibody or antigen binding fragment thereof that binds human LAG3, a chelating moiety, and a positron emitter.

In some embodiments, the chelating moiety comprises a chelator capable of forming a complex with $^{89}$Zr. In certain embodiments, the chelating moiety comprises desferrioxamine. In certain embodiments, the chelating moiety is p-isothiocyanatobenzyl-desferrioxamine.

In some embodiments, the positron emitter is $^{89}$Zr. In some embodiments, less than 1.0% of the anti-LAG3 antibody is conjugated with the positron emitter, less than 0.9% of the anti-LAG3 antibody is conjugated with the positron emitter, less than 0.8% of the anti-LAG3 antibody is conjugated with the positron emitter, less than 0.7% of the anti-LAG3 antibody is conjugated with the positron emitter, less than 0.6% of the anti-LAG3 antibody is conjugated with the positron emitter, less than 0.5% of the anti-LAG3 antibody is conjugated with the positron emitter, less than 0.4% of the anti-LAG3 antibody is conjugated with the positron emitter, less than 0.3% of the anti-LAG3 antibody is conjugated with the positron emitter, less than 0.2% of the anti-LAG3 antibody is conjugated with the positron emitter, or less than 0.1% of the anti-LAG3 antibody is conjugated with the positron emitter.

In some embodiments, the chelating moiety-to-antibody ratio of the conjugate is from 1 to 2.

In a particular embodiment, chelating moiety is p-isothiocyanatobenzyl-desferrioxamine and the positron emitter is $^{89}$Zr. In another particular embodiment, the chelating moiety is p-isothiocyanatobenzyl-desferrioxamine and the positron emitter is $^{89}$Zr, and the chelating moiety-to-antibody ratio of the conjugate is from 1 to 2.

In some embodiments, provided herein are antigen-binding proteins that bind LAG3, wherein said antigen-binding proteins that bind LAG3 are covalently bonded to one or more moieties having the following structure:

wherein L is a chelating moiety; M is a positron emitter; and z, independently at each occurrence, is 0 or 1; and wherein at least one of z is 1. In certain embodiments, the radiolabeled antigen-binding protein is a compound of Formula (I):

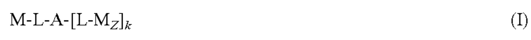

A is a protein that binds LAG3; L is a chelating moiety; M is a positron emitter z is 0 or 1; and k is an integer from 0-30. In some embodiments, k is 1.

In some embodiments, L is:

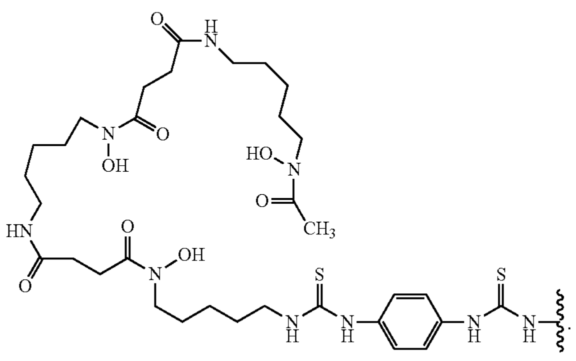 [SMILES: *NC(=S)Nc1ccc(NC(=S)NCCCCCN(O)C(=O)CCC(=O)NCCCCCN(O)C(=O)CCC(=O)NCCCCCN(O)C(C)=O)cc1]

In some embodiments, M is $^{89}Zr$.

In some embodiments, k is an integer from 1 to 2. In some embodiments, k is 1.

In some embodiments, -L-M is

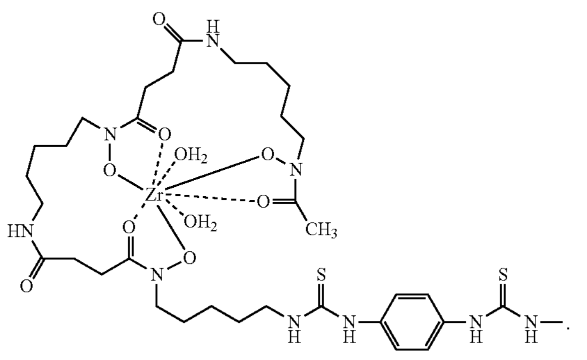

Included in the instant disclosure are also methods of synthesizing a radiolabeled antibody conjugates comprising contacting a compound of Formula (III):

(III)

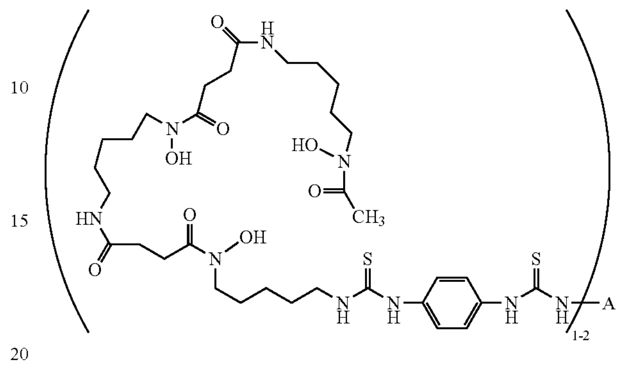

with $^{89}Zr$, wherein A is an antibody or antigen-binding fragment thereof that binds LAG3. In certain embodiments, the compound of Formula (III) is synthesized by contacting an antibody, or antigen binding fragment thereof, that binds LAG3, with p-SCN-Bn-DFO.

Provided herein is also the product of the reaction between a compound of Formula (III) with $^{89}Zr$.

Provided herein are compounds of Formula (III):

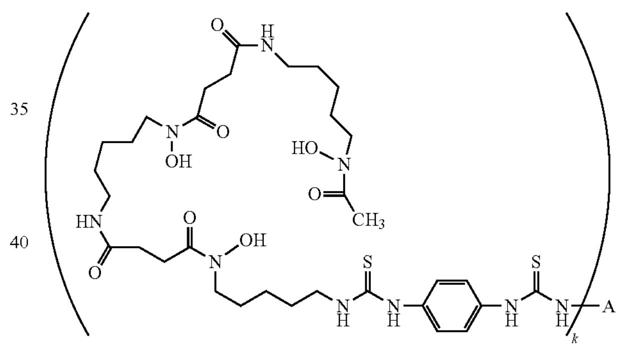

wherein A is an antibody or antigen binding fragment thereof that binds LAG3 and k is an integer from 1-30. In some embodiments, k is 1 or 2.

In some embodiments, provided herein are compositions comprising a conjugate having the following structure:

wherein A is a protein that binds LAG3; L is a chelating moiety; and k is an integer from 1-30; wherein the conjugate is chelated with a positron emitter in an amount sufficient to provide a specific activity suitable for clinical PET imaging. In some embodiments, the amount of chelated positron emitter is an amount sufficient to provide a specific activity of about 1 to about 20 mCi per 1-50 mg of the protein that binds LAG3. In some embodiments, the amount of chelated positron emitter is an amount sufficient to provide a specific activity of up to 20 mCi, up to 15 mCi, or up to 10 mCi per 1-50 mg of the protein that binds LAG3, for example, in a range of about 3 to about 20 mCi, about 5 to about 20 mCi, about 1 to about 15 mCi, about 3 to about 15 mCi, about 5 to about 15 mCi, about 1 to about 10 mCi, or about 3 to about 10 mCi.

In some embodiments, the antibody or antigen-binding fragment thereof binds monomeric human LAG3 with a binding dissociation equilibrium constant ($K_D$) of less than about 2 nM as measured in a surface plasmon resonance assay at 37° C.

In some embodiments, the antibody or antigen-binding fragment thereof binds monomeric human LAG3 with a $K_D$ less than about 1.5 nM in a surface plasmon resonance assay at 25° C.

In some embodiments, the antibody or antigen-binding fragment thereof binds dimeric human LAG3 with a $K_D$ of less than about 90 pM as measured in a surface plasmon resonance assay at 37° C.

In some embodiments, the antibody or antigen-binding fragment thereof that binds dimeric human LAG3 with a $K_D$ less than about 20 pM in a surface plasmon resonance assay at 25° C.

In some embodiments, the antibody or antigen-binding fragment thereof competes for binding to human LAG3 with a reference antibody comprising the complementarity determining regions (CDRs) of a HCVR, wherein the HCVR has an amino acid sequence selected from the group consisting of HCVR sequences listed in Table 1; and the CDRs of a LCVR, wherein the LCVR has an amino acid sequence selected from the group consisting of LCVR sequences listed in Table 1. In some embodiments, the reference antibody or antigen-binding fragment thereof comprises an HCVR/LCVR amino acid sequence pair as set forth in Table 1. In some embodiments, the reference antibody comprises an HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/394, 402/410, 418/426, 434/442, 450/522, 458/522, 466/522, 474/522, 482/522, 490/522, 498/530, 506/530, 514/530, 538/546, and 554/562.

In some embodiments, the antibody or antigen-binding fragment thereof enhances LAG3 binding to MHC class II. In some embodiments, the antibody or antigen binding fragment thereof blocks LAG3 binding to MHC class II. In some embodiments, the antibody or antigen binding fragment thereof do not increase or decrease LAG3 binding to its ligands.

In some embodiments, the antibody or antigen-binding fragment thereof comprises the complementarity determining regions (CDRs) of a HCVR, wherein the HCVR has an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338, 354, 370, 386, 402, 418, 434, 450, 458, 466, 474, 482, 490, 498, 506, 514, 538, and 554; and the CDRs of a LCVR, wherein the LCVR has an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 378, 394, 410, 426, 442, 522, 530, 546, and 562. In certain embodiments, the isolated antibody comprises an HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/394, 402/410, 418/426, 434/442, 450/522, 458/522, 466/522, 474/522, 482/522, 490/522, 498/530, 506/530, 514/530, 538/546, and 554/562. In certain embodiments, the isolated antibody comprises an HCVR/LCVR amino acid sequence pair selected from the group consisting of SEQ ID NOs: 386/394, 418/426, 538/546, 577/578, 579/578, and 580/581.

In some embodiments, the antibody is a human monoclonal antibody or antigen-binding fragment thereof that binds specifically to human LAG3, wherein the antibody or antigen-binding fragment thereof comprises a heavy chain variable region (HCVR) having an amino acid sequence selected from the group consisting of HCVR sequences listed in Table 1.

In some embodiments, the antibody is a human monoclonal antibody or antigen-binding fragment thereof that binds specifically to human LAG3, wherein the antibody or antigen-binding fragment thereof comprises a light chain variable region (LCVR) having an amino acid sequence selected from the group consisting of LCVR sequences listed in Table 1.

In some embodiments, the antibody a human monoclonal antibody or antigen-binding fragment thereof that binds specifically to human LAG3, wherein the antibody or antigen-binding fragment thereof comprises (a) a HCVR having an amino acid sequence selected from the group consisting of HCVR sequences listed in Table 1; and (b) a LCVR having an amino acid sequence selected from the group consisting of LCVR sequences listed in Table 1.

In some embodiments, the antibody or antigen-binding fragment thereof comprises three heavy chain complementarity determining regions (CDRs) (HCDR1, HCDR2 and HCDR3) contained within any one of the heavy chain variable region (HCVR) sequences listed in Table 1; and three light chain CDRs (LCDR1, LCDR2 and LCDR3) contained within any one of the light chain variable region (LCVR) sequences listed in Table 1.

In Some Embodiments, the Antibody or Antigen-Binding Fragment Thereof Comprises:

(a) a HCDR1 domain having an amino acid sequence selected from the group consisting of SEQ ID NOs: 4, 20, 36, 52, 68, 84, 100, 116, 132, 148, 164, 180, 196, 212, 228, 244, 260, 276, 292, 308, 324, 340, 356, 372, 388, 404, 420, 436, 452, 460, 468, 476, 484, 492, 500, 508, 516, 540, and 556;

(b) a HCDR2 domain having an amino acid sequence selected from the group consisting of SEQ ID NOs: 6, 22, 38, 54, 70, 86, 102, 118, 134, 150, 166, 182, 198, 214, 230, 246, 262, 278, 294, 310, 326, 342, 358, 374, 390, 406, 422, 438, 454, 462, 470, 478, 486, 494, 502, 510, 518, 542, and 558;

(c) a HCDR3 domain having an amino acid sequence selected from the group consisting of SEQ ID NOs: 8, 24, 40, 56, 72, 88, 104, 120, 136, 152, 168, 184, 200, 216, 232, 248, 264, 280, 296, 312, 328, 344, 360, 376, 392, 408, 424, 440, 456, 464, 472, 480, 488, 496, 504, 512, 520, 544, and 560;

(d) a LCDR1 domain having an amino acid sequence selected from the group consisting of SEQ ID NOs: 12, 28, 44, 60, 76, 92, 108, 124, 140, 156, 172, 188, 204, 220, 236, 252, 268, 284, 300, 316, 332, 348, 364, 380, 396, 412, 428, 444, 524, 532, 548, and 564;

(e) a LCDR2 domain having an amino acid sequence selected from the group consisting of SEQ ID NOs: 14, 30, 46, 62, 78, 94, 110, 126, 142, 158, 174, 190, 206, 222, 238, 254, 270, 286, 302, 318, 334, 350, 366, 382, 398, 414, 430, 446, 526, 534, 550, and 566; and (f) a LCDR3 domain having an amino acid sequence selected from the group consisting of SEQ ID NOs: 16, 32, 48, 64, 80, 96, 112, 128, 144, 160, 176, 192, 208, 224, 240, 256, 272, 288, 304, 320, 336, 352, 368, 384, 400, 416, 432, 448, 528, 536, 552, and 568.

In some embodiments, the antibody or antigen-binding fragment comprises a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/394, 402/410, 418/426, 434/442, 450/522, 458/522, 466/522, 474/522, 482/522, 490/522, 498/530, 506/530, 514/530, 538/546, and 554/562. In some embodiments, the antibody or antigen-binding fragment comprises a HCVR/LCVR amino acid sequence pair selected from the group consisting of SEQ ID NOs: 386/394, 418/426, and 538/546.

E. Scaled Manufacturing for Production of Anti-LAG3 Antibody-Chelator Conjugates Included in the present disclosure are scaled-up manufacturing processes for producing anti-LAG3 antibodies conjugated to a chelator. The anti-LAG3 antibody-chelator conjugates are in a form suitable for radiolabeling.

Good manufacturing processes are adhered to in all aspects of production, including maintaining a sterile environment, practicing aseptic procedures, keeping records of all processes, and documenting product quality, purity, strength, and identity, and any deviations therefrom.

The scaled-up manufacturing process is, in some embodiments, much faster than the manufacturing process for research and development. In some embodiments, the scaled-up manufacturing process can take less than 12 hours, or less than 10 hours, or less than 8 hours, or less than 6 hours, or less than 4 hours, or less than or about 2 hours.

In some embodiments, a first step comprises ultrafiltration and diafiltration (UFDF), using a 30-50 kDa membrane, of the anti-LAG3 antibody to remove excipients, conjugation interfering species, and salts that inhibit the conjugation process. Exemplary membrane polymers include polyethersulfone (PES), cellulose acetate (CA), and regenerated cellulose (RC). In this step, the antibody is buffer exchanged in a low ionic strength and non-interfering buffer solution. The buffer pH can be between about 4.5 to about 6, or about 5 to about 6, or about 5.3 to about 5.7, or about 5.5. Buffer systems contemplated herein include any buffer system lacking a primary amine. Exemplary buffers include acetate, phosphate, or citrate buffers. The buffer provides protein stability during pre-conjugation processing. The process volume can be further reduced to concentrate the antibody, then sterile filtered.

Following the pre-conjugation UFDF, the concentrated and filtered antibody can be transferred into an amine free carbonate buffer system. The carbonate buffer system can have a pH in a range from about 8.5 to about 9.6, or from about 9.0 to about 9.6, or from about 9.2 to about 9.4, or from about 9.4 to about 9.6, or a pH of about 9.4.

A chelator, for example, DFO, in solvent is added to a target concentration into the buffer system containing the antibody, and additional solvent can be added to the solution to a desired percentage. The chelator can be added in molar excess of the antibody, for example, 3.5-5:1 chelator to antibody. The total reaction volume can be up to 5 L.

The reaction temperature and the reaction time are inversely related. For example, if the reaction temperature is higher, the reaction time is lower. If the reaction temperature is lower, the reaction time is higher. Illustratively, at a temperature above about 18° C., the reaction may take less than 2 hours; at a temperature below 18° C., the reaction may take more than 2 hours.

The conjugation reaction can be terminated by quenching, for example, by the addition of acetic acid.

In some embodiments, conjugation of the antibody with deferoxamine is performed to produce DFO-mAb conjugates. In some embodiments, conjugation of the antibody with p-SCN-Bn-deferoxamine is performed to produce DFO-mAb conjugates.

Exemplary solvents for the chelator include DMSO and DMA. Subsequent UFDF steps utilize membranes, and the membrane is chosen based on the solvent system used in the conjugation step. For example, DMA dissolves PES membranes, so the two could not be used in the same system.

Carbonate buffers are not preferred for stability of the conjugate during long term storage. Thus, once the antibody-chelator conjugates have been formed, they can be buffer exchanged into a buffer chosen specifically for long term storage and stability. Exemplary buffers include citrate, acetate, phosphate, arginine, and histidine buffers. A further UFDF step can be performed to remove residual salts and to provide a suitable concentration, excipient level, and pH of the conjugated monoclonal antibody. The resulting antibody-chelator conjugates can be sterile filtered and stored for subsequent formulation.

III. Methods of Using Radiolabeled Immunoconjugates

In certain aspects, the present disclosure provides diagnostic and therapeutic methods of use of the radiolabeled antibody conjugates of the present disclosure.

According to one aspect, the present disclosure provides methods of detecting LAG3 in a tissue, the methods comprising administering a radiolabeled anti-LAG3 antibody conjugate of the provided herein to the tissue; and visualizing the LAG3 expression by positron emission tomography (PET) imaging. In certain embodiments, the tissue comprises cells or cell lines. In certain embodiments, the tissue is present in a subject, wherein the subject is a mammal. In certain embodiments, the subject is a human subject. In certain embodiments, the subject has a disease or disorder selected from the group consisting of cancer, infectious disease and inflammatory disease. In one embodiment, the subject has cancer. In certain embodiments, the infectious disease is a bacterial infection caused by, for example, rickettsial bacteria, bacilli, *Klebsiella*, meningococci and gonococci, *Proteus*, pneumonococci, *Pseudomonas*, streptococci, staphylococci, *Serratia, Borriella, Bacillus anthricis, Chlamydia, Clostridium, Corynebacterium diphtheriae, Legionella, Mycobacterium leprae, Mycobacterium lepromatosis, Salmonella, Vibrio cholerae*, and *Yersinia pestis*. In certain embodiments, the infectious disease is a viral infection caused by, for example, human immunodeficiency virus (HIV), hepatitis C virus (HCV), hepatitis B virus (HBV), herpes virus (e.g., VZV, HSV-1, HAV-6, HSV-II, CMV, and Epstein Barr virus), human papilloma virus (HPV), lymphocytic choriomeningitis virus (LCMV), and simian immunodeficiency virus (SIV). In certain embodiments, the infectious disease is a parasitic infection caused by, for example, *Entamoeba* spp., *Enterobius vermicularis, Leishmania* spp., *Toxocara* spp., *Plasmodium* spp., *Schistosoma* spp., *Taenia solium, Toxoplasma gondii*, and *Trypanosoma cruzi*. In certain embodiments, the infectious disease is a fungal infection caused by, for example, *Aspergillus* (*fumigatus, niger*, etc.), *Blastomyces dermatitidis, Candida* (*albicans, krusei, glabrata, tropicalis*, etc.), *Coccidioides immitis, Cryptococcus neoformans*, Genus *Mucorales* (*mucor, absidia, rhizopus*, etc.), *Histoplasma capsulatum, Paracoccidioides brasiliensis*, and *Sporothrix schenkii*.

According to one aspect, the present disclosure provides methods of imaging a tissue that expresses LAG3 comprising administering a radiolabeled anti-LAG3 antibody conjugate of the present disclosure to the tissue; and visualizing the LAG3 expression by positron emission tomography (PET) imaging. In one embodiment, the tissue is comprised in a tumor. In one embodiment, the tissue is comprised in a tumor cell culture or tumor cell line. In one embodiment, the tissue is comprised in a tumor lesion in a subject. In one embodiment, the tissue is intratumoral lymphocytes in a tissue. In one embodiment, the tissue comprises LAG3-expressing cells.

According to one aspect, the present disclosure provides methods for measuring response to a therapy, wherein the response to a therapy is measured by measuring inflammation. The methods, according to this aspect, comprise administering a radiolabeled antibody conjugate provided herein to a subject in need thereof and visualizing the LAG3 expression by positron emission tomography (PET) imaging. In certain embodiments, the inflammation is present in a tumor in the subject. In certain embodiments, an increase in LAG3 expression correlates to increase in inflammation in a tumor. In certain embodiments, the inflammation is present in an infected tissue in the subject. In certain embodiments, an decrease in LAG3 expression correlates to a decrease in inflammation in an infected tissue.

According to one aspect, the present disclosure provides methods for measuring response to a therapy, wherein the response to a therapy is measured by measuring inflammation. The methods, according to this aspect, comprise (i) administering a radiolabeled antibody conjugate provided herein to a subject in need thereof and visualizing the LAG3 expression by positron emission tomography (PET) imaging, and (ii) repeating step (i) one or more times after initiation of therapy. In certain embodiments, the inflammation is present in a tissue in the subject. In certain embodiments, an increase in LAG3 expression correlates to increase in inflammation in the tissue. In certain embodiments, a decrease in LAG3 expression correlates to a decrease in inflammation in the tissue. In certain embodiments, LAG3 expression visualized in step (i) is compared to LAG3 expression visualized in step (ii).

According to one aspect, the present disclosure provides methods for determining if a patient is suitable for anti-tumor therapy comprising an inhibitor of LAG3, the methods comprising selecting a patient with a solid tumor, administering a radiolabeled antibody conjugate of the present disclosure, and localizing the administered radiolabeled antibody conjugate in the tumor by PET imaging wherein presence of the radiolabeled antibody conjugate in the tumor identifies the patient as suitable for anti-tumor therapy comprising an inhibitor of LAG3.

According to one aspect, the present disclosure provides methods for identifying a candidate for anti-tumor therapy comprising an inhibitor of LAG3 and an inhibitor of the PD-1/PD-L1 signaling axis, the methods comprising selecting a patient with a solid tumor, administering a radiolabeled antibody conjugate of the present disclosure, and localizing the administered radiolabeled antibody conjugate in the tumor by PET imaging wherein presence of the radiolabeled antibody conjugate in the tumor identifies the patient as suitable for anti-tumor therapy comprising an inhibitor of LAG3. In some embodiments, the patient is further administered a radiolabeled anti-PD-1 conjugate and the administered radiolabeled anti-PD-1 conjugate is localized in the tumor by PET imaging, wherein presence of the radiolabeled antibody conjugate in the tumor identifies the patient as suitable for anti-tumor therapy comprising an inhibitor of the PD-1/PD-L1 signaling axis.

Provided herein are also methods for predicting response of a patient to an anti-tumor therapy, the methods comprising selecting a patient with a solid tumor; and determining if the tumor is LAG3-positive, wherein if the tumor is LAG3-positive it predicts a positive response of the patient to an anti-tumor therapy. In certain embodiments, the tumor is determined positive by administering a radiolabeled anti-LAG3 antibody conjugate of the present disclosure and localizing the radiolabeled antibody conjugate in the tumor by PET imaging wherein presence of the radiolabeled antibody conjugate in the tumor indicates that the tumor is LAG3-positive.

In some embodiments, the anti-tumor therapy is selected from a PD-1 inhibitor (e.g., REGN2810, BGB-A317, nivolumab, pidilizumab, and pembrolizumab), a PD-L1 inhibitor (e.g., atezolizumab, avelumab, durvalumab, MDX-1105, and REGN3504, as well as those disclosed in Patent Publication No. US 2015-0203580), CTLA-4 inhibitor (e.g., ipilimumab), a TIM3 inhibitor, a BTLA inhibitor, a TIGIT inhibitor, a CD47 inhibitor, a GITR inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., *Bacillus* Calmette-Guerin, a cancer vaccine), an adjuvant to increase antigen presentation (e.g., granulocyte-macrophage colony-stimulating factor), a bispecific antibody (e.g., CD3×CD20 bispecific antibody, or PSMA×CD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, and an antibody-drug conjugate (ADC) (e.g., anti-CD19-DM4 ADC, and anti-DS6-DM4 ADC).

In some embodiments, the anti-tumor therapy is selected from the following: nivolumab, ipilimumab, pembrolizumab, and combinations thereof.

According to one aspect, the present disclosure provides methods for predicting response of a patient to an anti-tumor therapy comprising an inhibitor of LAG3, the methods comprising selecting a patient with a solid tumor, determining if the tumor is LAG3-positive, wherein a positive response of the patient is predicted if the tumor is LAG3-positive. In certain embodiments, the tumor is determined positive by administering a radiolabeled antibody conjugate of the present disclosure and localizing the radiolabeled antibody conjugate in the tumor by PET imaging wherein presence of the radiolabeled antibody conjugate in the tumor indicates that the tumor is LAG3-positive.

According to one aspect, the present disclosure provides methods for predicting response of a patient to an anti-tumor therapy comprising an inhibitor of LAG3 in combination with an inhibitor of the PD-1/PD-L1 signaling axis, the methods comprising selecting a patient with a solid tumor, determining if the tumor is LAG3 positive and PD-1-positive, wherein a positive response of the patient is predicted if the tumor is LAG3 positive and PD-1-positive. In certain embodiments, the tumor is determined LAG3 positive by administering a radiolabeled anti-LAG3 conjugate and localizing the radiolabeled antibody conjugate in the tumor by PET imaging wherein presence of the radiolabeled antibody conjugate in the tumor indicates that the tumor is LAG3-positive. In certain embodiments, the tumor is determined PD-1 positive by further administering a radiolabeled anti-PD-1 conjugate and localizing the radiolabeled anti-PD-1 conjugate in the tumor by PET imaging wherein presence of the radiolabeled antibody conjugate in the tumor indicates that the tumor is PD-1-positive.

According to one aspect, the present disclosure provides methods for detecting a LAG3-positive tumor in a subject. The methods, according to this aspect, comprise selecting a subject with a solid tumor; administering a radiolabeled antibody conjugate of the present disclosure to the subject; and determining localization of the radiolabeled antibody conjugate by PET imaging, wherein presence of the radiolabeled antibody conjugate in a tumor indicates that the tumor is LAG3-positive.

In some aspects, the subject in need thereof is administered a dose of about 20 mg or less, a dose of about 15 mg or less, a dose of about 10 mg or less, for example, a dose of 2 mg, or 5 mg, or 10 mg, of a radiolabeled anti-LAG3 antibody conjugate.

As used herein, the expression "a subject in need thereof" means a human or non-human mammal that exhibits one or more symptoms or indications of cancer, and/or who has been diagnosed with cancer, including a solid tumor and who needs treatment for the same. In many embodiments, the term "subject" may be interchangeably used with the term "patient". For example, a human subject may be diagnosed with a primary or a metastatic tumor and/or with one or more symptoms or indications including, but not limited to, unexplained weight loss, general weakness, persistent fatigue, loss of appetite, fever, night sweats, bone pain, shortness of breath, swollen abdomen, chest pain/pressure, enlargement of spleen, and elevation in the level of a cancer-related biomarker (e.g., CA125). The expression includes subjects with primary or established tumors. In specific embodiments, the expression includes human subjects that have and/or need treatment for a solid tumor, e.g., colon cancer, breast cancer, lung cancer, prostate cancer, skin cancer, liver cancer, bone cancer, ovarian cancer, cervical cancer, pancreatic cancer, head and neck cancer, and brain cancer. The term includes subjects with primary or metastatic tumors (advanced malignancies). In certain embodiments, the expression "a subject in need thereof" includes patients with a solid tumor that is resistant to or refractory to or is inadequately controlled by prior therapy (e.g., treatment with an anti-cancer agent). For example, the expression includes subjects who have been treated with one or more lines of prior therapy such as treatment with chemotherapy (e.g., carboplatin or docetaxel). In certain embodiments, the expression "a subject in need thereof" includes patients with a solid tumor which has been treated with one or more lines of prior therapy but which has subsequently relapsed or metastasized. In certain embodiments, the term includes subjects having an inflammatory disease or disorder including, but not limited to, cancer, rheumatoid arthritis, atherosclerosis, periodontitis, hay fever, heart disease, coronary artery disease, infectious disease, bronchitis, dermatitis, meningitis, asthma, tuberculosis, ulcerative colitis, Crohn's disease, inflammatory bowel disease, hepatitis, sinusitis, psoriasis, allergy, fibrosis, lupus, vasculitis, ankylosing spondylitis, Graves' disease, Celiac disease, fibromyalgia, and transplant rejection.

In certain embodiments, the methods of the present disclosure are used in a subject with a solid tumor. The terms "tumor", "cancer" and "malignancy" are interchangeably used herein. As used herein, the term "solid tumor" refers to an abnormal mass of tissue that usually does not contain cysts or liquid areas. Solid tumors may be benign (not cancer) or malignant (cancer). In some embodiments, the tumor is metastatic. For the purposes of the present disclosure, the term "solid tumor" means malignant solid tumors. The term includes different types of solid tumors named for the cell types that form them, viz. sarcomas, carcinomas and lymphomas. In certain embodiments, the term "solid tumor" includes cancers including, but not limited to, colorectal cancer, ovarian cancer, prostate cancer, breast cancer, brain cancer, cervical cancer, bladder cancer, anal cancer, uterine cancer, colon cancer, liver cancer, melanoma, metastatic melanoma, pancreatic cancer, lung cancer, endometrial cancer, bone cancer, testicular cancer, skin cancer, kidney cancer, stomach cancer, esophageal cancer, head and neck cancer, salivary gland cancer, and myeloma.

In some embodiments, the methods disclosed herein can be used in a subject with cancer, for example, a subject having blood cancer, brain cancer, renal cell cancer, ovarian cancer, bladder cancer, prostate cancer, breast cancer, hepatic cell carcinoma, bone cancer, colon cancer, non-small-cell lung cancer, squamous cell carcinoma of head and neck, colorectal cancer, mesothelioma, B cell lymphoma, and melanoma. In some aspects, the cancer is metastatic, for example, metastatic melanoma.

According to one aspect, the present disclosure provides methods of treating a tumor in a subject. The methods, according to this aspect, comprise selecting a subject with a solid tumor, determining that the tumor is LAG3-positive; and administering one or more doses of an inhibitor of LAG3. In certain embodiments, the tumor is determined to be LAG3-positive by administering a radiolabeled antibody conjugate of the present disclosure to the subject; and visualizing the radiolabeled antibody conjugate in the tumor by PET imaging, wherein presence of the radiolabeled antibody conjugate in the tumor indicates that the tumor is LAG3-positive.

In a further aspect, the methods of treating comprise administering one or more doses of an inhibitor of LAG3 in combination with a CTLA-4 inhibitor (e.g., ipilimumab), a TIM3 inhibitor, a BTLA inhibitor, a TIGIT inhibitor, a CD47 inhibitor, a GITR inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., *Bacillus* Calmette-Guerin, a cancer vaccine), an adjuvant to increase antigen presentation (e.g., granulocyte-macrophage colony-stimulating factor), a bispecific antibody (e.g., CD3×CD20 bispecific antibody, or PSMA×CD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, an antibody-drug conjugate (ADC) (e.g., anti-CD19-DM4 ADC, and anti-DS6-DM4 ADC), an anti-inflammatory drug (e.g., corticosteroids, and non-steroidal anti-inflammatory drugs), a dietary supplement such as anti-oxidants or any other therapy care to treat cancer. In certain embodiments, an inhibitor of LAG3 may be used in combination with cancer vaccines including dendritic cell vaccines, oncolytic viruses, tumor cell vaccines, etc. to augment the anti-tumor response. Examples of cancer vaccines that can be used in combination with an inhibitor of LAG3 include MAGE3 vaccine for melanoma and bladder cancer, MUC1 vaccine for breast cancer, EGFRv3 (e.g., Rindopepimut) for brain cancer (including glioblastoma multiforme), or ALVAC-CEA (for CEA+ cancers).

In certain embodiments, an inhibitor of LAG3 may be used in combination with radiation therapy in methods to generate long-term durable anti-tumor responses and/or enhance survival of patients with cancer. In some embodiments, the inhibitor of LAG3, e.g. an anti-LAG3 antibody, may be administered prior to, concomitantly or after administering radiation therapy to a cancer patient. For example, radiation therapy may be administered in one or more doses to tumor lesions followed by administration of one or more doses of anti-LAG3 antibodies. In some embodiments, radiation therapy may be administered locally to a tumor lesion to enhance the local immunogenicity of a patient's tumor (adjuvanting radiation) and/or to kill tumor cells (ablative radiation) followed by systemic administration of an anti-LAG3 antibody. For example, intracranial radiation may be administered to a patient with brain cancer (e.g., glioblastoma multiforme) in combination with systemic administration of an anti-LAG3 antibody. In certain embodiments, the anti-LAG3 antibodies may be administered in combination with radiation therapy and a chemotherapeutic agent (e.g., temozolomide) or a VEGF antagonist (e.g., aflibercept).

In certain embodiments, an inhibitor of LAG3 may be administered in combination with one or more anti-viral drugs to treat viral infection caused by, for example, LCMV, HIV, HPV, HBV or HCV. Examples of anti-viral drugs include, but are not limited to, zidovudine, lamivudine, abacavir, ribavirin, lopinavir, efavirenz, cobicistat, tenofovir, rilpivirine and corticosteroids.

In certain embodiments, an inhibitor of LAG3 may be administered in combination with one or more anti-bacterial drugs to treat bacterial infection caused by, for example, rickettsial bacteria, bacilli, *Klebsiella*, meningococci and gonococci, *Proteus*, pneumonococci, *Pseudomonas*, streptococci, staphylococci, *Serratia, Borriella, Bacillus anthricis, Chlamydia, Clostridium, Corynebacterium diphtheriae, Legionella, Mycobacterium leprae, Mycobacterium lepromatosis, Salmonella, Vibrio cholerae*, and *Yersinia pestis*. Examples of anti-bacterial drugs include, but are not limited to, penicillins, tetracyclines, cephalosporins, quinolones, lincomycins, macrolides, ketolides, sulfonamides, glycopeptides, aminoglycosides, and carbapenems.

In certain embodiments, an inhibitor of LAG3 may be administered in combination with one or more anti-fungal drugs to treat fungal infection caused by, for example, *Aspergillus* (*fumigatus, niger*, etc.), *Blastomyces dermatitidis, Candida* (*albicans, krusei, glabrata, tropicalis*, etc.), *Coccidioides immitis, Cryptococcus neoformans*, Genus *Mucorales* (*mucor, absidia, rhizopus*, etc.), *Histoplasma capsulatum, Paracoccidioides brasiliensis*, and *Sporothrix schenkii*. Examples of anti-fungal drugs include, but are not limited to, amphotericin B, fluconazole, vorixonazole, posaconazole, itraconazole, voriconazole, anidulafungin, caspofungin, micafungin, and flucytosine.

In certain embodiments, an inhibitor of LAG3 may be administered in combination with one or more anti-parasitic drugs to treat parasitic infection caused by, for example, *Entamoeba* spp., *Enterobius vermicularis, Leishmania* spp., *Toxocara* spp., *Plasmodium* spp., *Schistosoma* spp., *Taenia solium, Toxoplasma gondii*, and *Trypanosoma cruzi*. Examples of anti-parasitic drugs include, but are not limited to, praziquantel, oxamniquine, metronidazole, tinidazole, nitazoxanide, dehydroemetine or chloroquine, diloxanide furoate, iodoquinoline, chloroquine, paromomycin, pyrantel pamoate, albendazole, nifurtimox, and benznidazole.

The additional therapeutically active agent(s)/component(s) may be administered prior to, concurrent with, or after the administration of the inhibitor of LAG3. For purposes of the present disclosure, such administration regimens are considered the administration of a LAG3 inhibitor "in combination with" a second therapeutically active component.

In some aspects, the methods of treating comprise selecting a subject with a bacterial infection, a viral infection, a fungal infection, or a parasitic infection; determining that an affected tissue in the subject is LAG3-positive; and administering one or more doses of a therapeutic agent appropriate to the infection. In certain embodiments, the affected tissue is determined to be LAG3-positive by administering a radiolabeled anti-LAG3 conjugate of the present disclosure to the subject; and visualizing the radiolabeled antibody conjugate in the subject by PET imaging, wherein presence of the radiolabeled antibody conjugate in a tissue indicates that the tissue is LAG3-positive. In certain embodiments, the steps of administering and visualizing are performed one or more times in order to monitor the effectiveness of the therapeutic agent in treating the infection.

In some aspects, the methods of treating comprise selecting a subject with a solid tumor, determining that the tumor is LAG3-positive and PD-1-positive; and administering one or more doses of an inhibitor of LAG3 and/or one or more doses of an inhibitor of the PD-1/PD-L1 signaling axis (e.g., an anti-PD-1 antibody or an anti-PD-L1 antibody). In certain embodiments, the tumor is determined to be LAG3-positive by administering a radiolabeled anti-LAG3 conjugate of the present disclosure to the subject; and visualizing the radiolabeled antibody conjugate in the tumor by PET imaging, wherein presence of the radiolabeled antibody conjugate in the tumor indicates that the tumor is LAG3-positive. In certain embodiments, the tumor is determined to be PD-1-positive by administering a radiolabeled anti-PD-1 conjugate of the present disclosure to the subject; and visualizing the radiolabeled anti-PD-1 conjugate in the tumor by PET imaging, wherein presence of the radiolabeled anti-PD-1 conjugate in the tumor indicates that the tumor is PD-1-positive.

Exemplary anti-PD-1 antibodies include REGN2810, BGB-A317, nivolumab, pidilizumab, and pembrolizumab.

Exemplary anti-PD-L1 antibodies include atezolizumab, avelumab, durvalumab, MDX-1105, and REGN3504, as well as those disclosed in Patent Publication No. US 2015-0203580.

The inhibitor of the PD-1/PD-L1 signaling axis may be administered prior to, concurrent with, or after the administration of the inhibitor of LAG3. For purposes of the present disclosure, such administration regimens are considered the administration of a LAG3 inhibitor "in combination with" an inhibitor of the PD-1/PD-L1 signaling axis.

As used herein, the terms "treat", "treating", or the like, mean to alleviate symptoms, eliminate the causation of symptoms either on a temporary or permanent basis, to delay or inhibit tumor growth, to reduce tumor cell load or tumor burden, to promote tumor regression, to cause tumor shrinkage, necrosis and/or disappearance, to prevent tumor recurrence, to prevent or inhibit metastasis, to inhibit metastatic tumor growth, and/or to increase duration of survival of the subject.

According to one aspect, the present disclosure provides methods for monitoring the efficacy of an anti-tumor therapy in a subject, wherein the methods comprise selecting a subject with a solid tumor wherein the subject is being treated with an anti-tumor therapy; administering a radiolabeled anti-LAG3 conjugate of the present disclosure to the subject; imaging the localization of the administered radiolabeled conjugate in the tumor by PET imaging; and determining tumor growth, wherein a decrease from the baseline in radiolabeled signal indicates efficacy of the anti-tumor therapy. In certain embodiments, the anti-tumor therapy comprises an inhibitor of LAG3. In certain embodiments, the anti-tumor therapy further comprises an inhibitor of the PD-1/PD-L1 signaling axis (e.g., an anti-PD-1 antibody or an anti-PD-L1 antibody).

In certain embodiments, the present disclosure provides methods to assess changes in the inflammatory state of a tumor, the methods comprising selecting a subject with a solid tumor wherein the subject is being treated with an anti-tumor therapy; administering a radiolabeled anti-LAG3 conjugate provided herein to the subject; and imaging the localization of the administered radiolabeled conjugate in the tumor by PET imaging, wherein an increase from the baseline in radiolabeled signal indicates increase in inflammation and efficacy of the anti-tumor therapy. In certain embodiments, the anti-tumor therapy comprises an inhibitor of LAG3 and/or an inhibitor of the PD-1/PD-L1 signaling axis (e.g., an anti-PD-1 antibody or an anti-PD-L1 antibody). In certain embodiments, the anti-tumor therapy comprises a PD-1 inhibitor (e.g., REGN2810, BGB-A317, nivolumab, pidilizumab, and pembrolizumab), a PD-L1 inhibitor (e.g., atezolizumab, avelumab, durvalumab, MDX-1105, and REGN3504), CTLA-4 inhibitor (e.g., ipilimumab), a TIM3 inhibitor, a BTLA inhibitor, a TIGIT inhibitor, a CD47 inhibitor, a GITR inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., *Bacillus* Calmette-Guerin, a cancer vaccine), an adjuvant to increase antigen presentation (e.g., granulocyte-macrophage colony-stimulating factor), a bispecific antibody (e.g., CD3×CD20 bispecific antibody, or PSMA×CD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, and an antibody-drug conjugate (ADC) (e.g., anti-CD19-DM4 ADC, and anti-DS6-DM4 ADC).

As used herein, the term "baseline," with respect to LAG3 expression in the tumor, means the numerical value of uptake of the radiolabeled conjugate for a subject prior to or at the time of administration of a dose of anti-tumor therapy. The uptake of the radiolabeled conjugate is determined using methods known in the art (see, for example, Oosting et al 2015, J. Nucl. Med. 56: 63-69). In certain embodiments, the anti-tumor therapy comprises an inhibitor of LAG3.

In some embodiments, sequential iPET scanning and tumor biopsies are performed before and after treatment with standard of care immunotherapies. Such immunotherapies can be selected from the following: nivolumab, ipilimumab, pembrolizumab, and combinations thereof.

To determine whether there is efficacy in anti-tumor therapy, the uptake of the radiolabeled conjugate is quantified at baseline and at one or more time points after administration of the LAG3 inhibitor. For example, the uptake of the administered radiolabeled antibody conjugate (e.g., radiolabeled anti-LAG3 antibody conjugate) may be measured at day 2, day 3, day 4, day 5, day 6, day 7, day 8, day 9, day 10, day 11, day 12, day 14, day 15, day 22, day 25, day 29, day 36, day 43, day 50, day 57, day 64, day 71, day 85; or at the end of week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with the LAG3 inhibitor (e.g., an anti-LAG3 antibody). The difference between the value of the uptake at a particular time point following initiation of treatment and the value of the uptake at baseline is used to establish whether anti-tumor therapy is efficacious (tumor regression or progression).

In certain embodiments, the radiolabeled antibody conjugate is administered intravenously or subcutaneously to the subject. In certain embodiments, the radiolabeled antibody conjugate is administered intra-tumorally. Upon administration, the radiolabeled antibody conjugate is localized in the tumor. The localized radiolabeled antibody conjugate is imaged by PET imaging and the uptake of the radiolabeled antibody conjugate by the tumor is measured by methods known in the art. In certain embodiments, the imaging is carried out 1, 2, 3, 4, 5, 6 or 7 days after administration of the radiolabeled conjugate. In certain embodiments, the imaging is carried out on the same day upon administration of the radiolabeled antibody conjugate.

In certain embodiments, the antibody or antigen-binding fragment thereof that binds specifically to LAG3. In certain embodiments, the anti-LAG3 antibody comprises the CDRs of a HCVR, wherein the HCVR has an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338, 354, 370, 386, 402, 418, 434, 450, 458, 466, 474, 482, 490, 498, 506, 514, 538, and 554; and the CDRs of a LCVR, wherein the LCVR has an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 378, 394, 410, 426, 442, 522, 530, 546, and 562.

In certain embodiments, the LAG3 inhibitor comprises an antibody or antigen-binding fragment thereof that binds specifically to LAG3. In certain embodiments, the anti-LAG3 antibody is BMS986016. In certain other embodiments, the LAG3 inhibitor comprises an antibody or antigen-binding fragment thereof that binds specifically to LAG3. In one embodiment, the anti-LAG3 antibody comprises an HCVR of SEQ ID NO: 418 and a LCVR of SEQ ID NO: 426.

IV. EXAMPLES

Certain embodiments of the disclosure are illustrated by the following non-limiting examples.

Example 1: Generation of Human Antibodies to LAG3

Human antibodies to LAG3 were generated using a fragment of LAG3 that ranges from about amino acids 29-450 of GenBank Accession NP_002277.4 (SEQ ID NO: 582) genetically fused to a mouse Fc region. The immunogen was administered directly, with an adjuvant to stimulate the immune response, to a VELOCIMMUNE® mouse (i.e., an engineered mouse comprising DNA encoding human Immunoglobulin heavy and kappa light chain variable regions), as described in U.S. Pat. No. 8,502,018 B2, or to a humanized Universal Light Chain (ULC) VelocImmune® mouse, as described in WO 2013022782. The antibody immune response was monitored by a LAG3-specific immunoassay. When a desired immune response was achieved splenocytes were harvested and fused with mouse myeloma cells to preserve their viability and form hybridoma cell lines. The hybridoma cell lines were screened and selected to identify cell lines that produce LAG3-specific antibodies. Using this technique, and the immunogen described above, several anti-LAG3 chimeric antibodies (i.e., antibodies possessing human variable domains and mouse constant domains) were obtained. Fully human versions of the antibodies can be made by replacing the mouse constant region with a human constant region. Exemplary antibodies generated in this manner from the VELOCIMMUNE® mice were designated as H1 M14985N, H1 M14987N, H2 M14811N, H2 M14885N, H2 M14926N, H2 M14927N, H2 M14931N, H2 M18336N, H2 M18337N and H4H14813N.

Anti-LAG3 antibodies were also isolated directly from antigen-positive B cells (from either of the immunized mice) without fusion to myeloma cells, as described in U.S. Pat. No. 7,582,298, herein specifically incorporated by reference in its entirety. Using this method, several anti-LAG3 antibodies (i.e., antibodies possessing human variable domains and human constant domains) were obtained; exemplary antibodies generated in this manner were designated as follows: H4H15477P, H4H15483P, H4H15484P, H4H15491P, H4H17823P, H4H17826P2, H4H17828P2, H4sH15460P, H4sH15462P, H4sH15463P, H4sH15464P, H4sH15466P, H4sH15467P, H4sH15470P, H4sH15475P, H4sH15479P, H4sH15480P, H4sH15482P, H4sH15488P, H4sH15496P2, H4sH15498P2, H4sH15505P2, H4sH15518P2, H4sH15523P2, H4sH15530P2, H4sH15555P2, H4sH15558P2, H4sH15567P2, and H4H17819P.

Exemplary antibodies H4sH15496P2, H4sH15498P2, H4sH15505P2, H4sH15518P2, H4sH15523P2, H4sH15530P2, H4sH15555P2, H4sH15558P2, and H4sH15567P2 were generated from B-cells from the ULC VELOCIMMUNE® mice.

The biological properties of the exemplary antibodies generated in accordance with the methods of this Example are described in detail in the Examples set forth below.

Example 2: Conjugation of Anti-LAG3 Antibody H4sH15482P with p-SCN-Bn-DFO

In order to modify the parental anti-LAG3 antibody, H4sH15482P (having an HCVR/LCVR sequence pair of SEQ ID NOs: 418/426; hereinafter referred to as mAb1), and an isotype control antibody to be suitable for ImmunoPET studies with radiolabeling, a chelator, p-SCN-bn-Deferoxamine (DFO; Macrocyclics, Cat #: B-705), was attached to the antibodies.

For the modification, mAb1, was first buffer exchanged into PBS, pH 7.2 from histidine buffer by dialysis at 4° C. overnight (Slide-A-Lyzer Dialysis Cassette G2 10 k MWCO; ThermoScientific) then buffer exchanged again using a PD-10 column (GE Healthcare, Cat. #: 17-0851-01) into a buffer composed of 50 mM carbonate buffer, 150 mM NaCl, pH 9.0 (conjugation buffer). To determine the concentration following the buffer exchanges, the samples were measured on a Nanodrop 2000 UV/VIS spectrometer (Thermo Scientific) using the MacVector sequence based extinction coefficient of 223400 $M^{-1}$ $cm^{-1}$ and molecular weight 145709 g/mol (see Table 2). In 15 a mL polypropylene tube, 1485.24 uL of mAb1 (70 mg) was added to 5374.8 uL of conjugation buffer. A 139 μL solution of DFO in DMSO was added in one-quarter increments to the mAb1 solution, each time gently being mixed by pipetting up-and-down. The final solution was 10 mg/mL mAb1 in conjugation buffer, 2% DMSO with 3-fold mole-to-mole excess of DFO. This solution was allowed to incubate in a 37° C. water bath with no additional stirring.

After 30 minutes at 37° C., the solution was promptly passed through a PD-10 desalting column (GE Healthcare, Cat. #: 17-0851-01), pre-equilibrated with a buffer containing 250 mM NaAcO at pH 5.4 (formulation buffer). The volume of the solution was reduced by approximately 50% with a 10K MWCO concentrator (Amicon Ultra-15 Centrifugal Filter Unit, EMD Millipore, Cat #: UFC901024). The final solution was sterile-filtered via a syringe filter (Acrodisc 13 mm syringe filter, Pall Corporation, Cat #: 4602). The concentration and DFO-to-Antibody Ratio (DAR) was subsequently measured by UV/VIS spectroscopy. See FIG. 1. For the absorbance measurement, the DFO-conjugated antibody was measured against the formulation buffer at 252 nm (A252), 280 nm (A280) and 600 nm (A600). For the calculation, the background was corrected at each absorbance value using the equation:

$$A'_{\lambda}=A_{\lambda}-A_{600}$$

Figure 2:
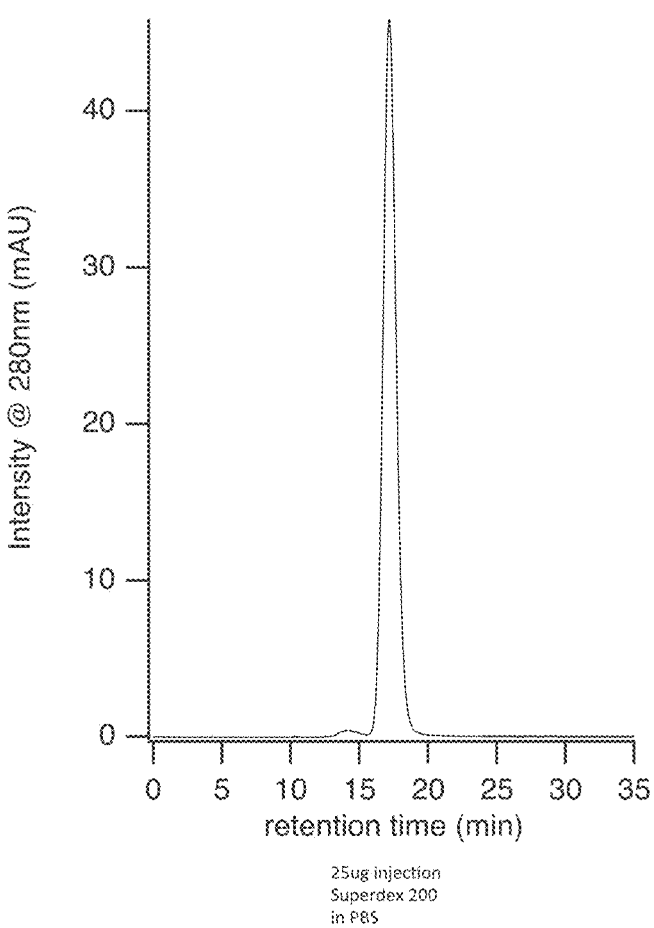
FIG. 2 depicts HPLC-SEC of DFO modified anti-LAG3 antibody.

The antibody conjugate was tested for aggregation using SEC chromatography, with 25 ug of the sample injected onto a Superdex 200 column (GE Healthcare, Cat. No. 17-5175-01) monitored at 280 nm with a PBS mobile phase (0.75 mL/min). See FIG. 2. The antibody integrity was evaluated by SDS-PAGE 4-20% Tris/Gly pre-cast gel (Novex) with 2 ug of the sample loaded. The antibody concentration, conjugate concentration, and DAR were calculated using the equations below:

Antibody Concentration Calculation $$Conc\ mAb\ (\text{mg/mL}) = \frac{A'_{280}}{\epsilon_{280}} * \text{MW}$$

Conjugate Concentration Calculation $$Conc\ \text{conjugate}\ (\text{mg/mL}) = \frac{A'_{252} - 1.53A'_{280}}{\epsilon_{252} - 1.53\epsilon_{280}} * \text{MW}$$

DAR Calculation $$DAR = \frac{\epsilon_{252}A'_{280} - \epsilon_{280}A'_{252}}{18800A'_{252} - 28700A'_{280}}$$

TABLE 2

| Molar extinction coefficients and molecular weight | | | |
|---|---|---|---|
| mAb | MW ($gmol^{-1}$) | $\epsilon_{280}$ ($M^{-1}cm^{-1}$) | $\epsilon_{252}$ ($M^{-1}cm^{-1}$) |
| mAb1 | 145709 | 223400 | 87077 |

TABLE 3

| UV DAR, percent aggregate and concentration post DFO-attachment | | | |
|---|---|---|---|
| Antibody | UV DAR | Concentration (mg/mL) | % aggregate |
| mAb1 | 1.48 | 13.58 | 1.4% |

Example 3: $^{89}$Zr Chelation of DFO Conjugated Monoclonal Antibodies

For usage in ImmunoPET in vivo studies, the DFO-conjugated anti-LAG3 antibody, mAb1, and a DFO-conjugated isotype control antibody were radiolabeled with $^{89}$Zr.

DFO-conjugated antibody was first brought to 1.25 mg/mL in 1 M HEPES, pH 7.2. The composition of the DFO-Ab conjugate solutions for each study is listed in Table 4. Separately, $^{89}$Zr solution was prepared using the compositions for each corresponding study shown in Table 5. Stock $^{89}$Zr-oxalic acid solution was obtained from 3D Imaging. The final radioactivity of the solution was first confirmed using a Capintec CRC-25R dose calibrator (Capintec #520), then immediately combined with the DFO-Ab conjugate solution, gently mixed (pipetting up-and-down) and subsequently incubated for 45 minutes at room temperature.

After the incubation, the mixtures were transferred to desalting columns, either PD-10 (GE Healthcare, Cat. #: 17-0851-01) for study 1 or NAP-5 (GE Healthcare, Cat. #17-0853-02) for study 2, pre-equilibrated with 250 mM sodium acetate at pH 5.4 for gravity-fed desalting. For study 1, the reaction mixture was added to a PD-10 column. After the contents of the reaction entered the column bed, the flow through was discarded. The product was eluted with 250 mM sodium acetate at pH 5.4 (formulation buffer) and eluate was collected as per manufacturer's instructions. For study 2, the mixture was transferred to a NAP-5 column, and the flow through was discarded. The product was eluted with 250 mM sodium acetate at pH 5.4 (formulation buffer) and eluate was collected per the manufacturer's instructions. The Ab concentration was subsequently measured by UV/VIS spectroscopy, calculated using the appropriate extinction coefficient and the absorption at 280 nm using the equation:

Concentration in mg/mL=Absorption at 280 nm÷Extinction coefficient at 280 nm(found in Table 6)

The final mass measured in grams was recorded in Table 7. The radioactivity was then measured using the dose calibrator and reported in Table 7. The final material (5 ug) was analyzed using a SEC-HPLC with UV 280 and radioisotope detector connected in series (Agilent 1260 with Lablogic Radio-TLC/HPLC Detector, SCAN-RAM) using a Superdex 200 Increase column with PBS mobile phase at a flow rate of 0.75 mL/min. The radiotrace was used for determining radiochemical purity (100%—percent of unlabeled $^{89}$Zr) by comparing the integration of the total protein peak (~10 to 16 min) and unlabeled $^{89}$Zr peak (~25 min). The percent monomeric purity was determined by the UV 280 trace by comparing the integration of the high molecular weight (HMW) species peak (10 min to ~15 min) to the monomer (~16 min).

The specific activity and protein recovery (%) of each radiolabeled conjugate was determined using the following equations:

Mass of conjugate in mg=concentration in mg/mL× mass of solution in grams a.

Specific activity in mCi/mg=activity of vial in mCi÷mass of conjugate in mg b.

Protein recovery=starting conjugate mass (mg)÷Mass of conjugate in mg c.

Figure 3:
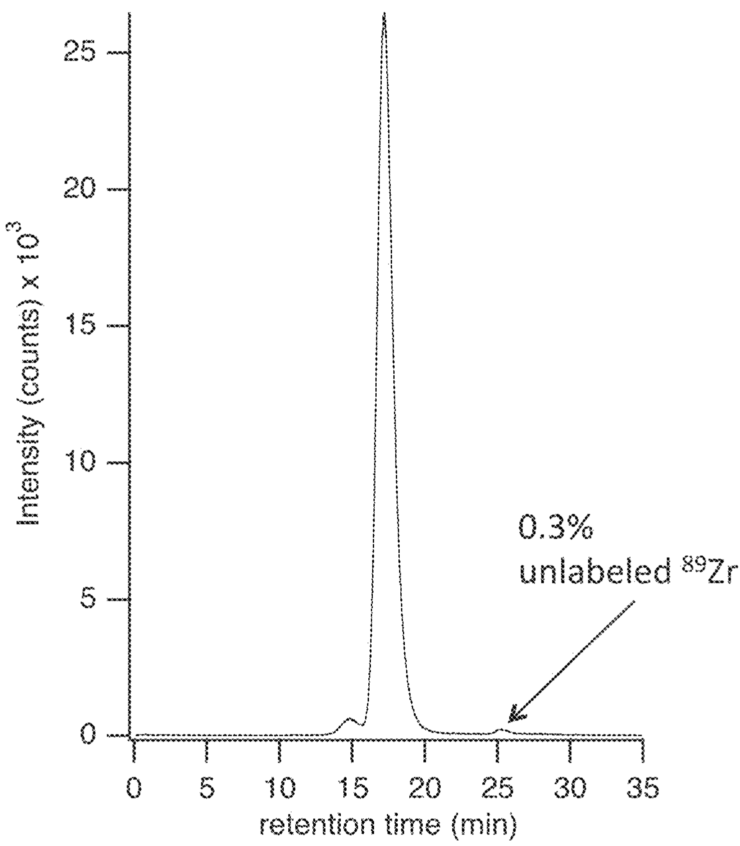
FIG. 3 depicts radio-SEC-HPLC of isotype-DFO-conjugate after $^{89}$Zr radiolabeling for Study 1.
Figure 4:
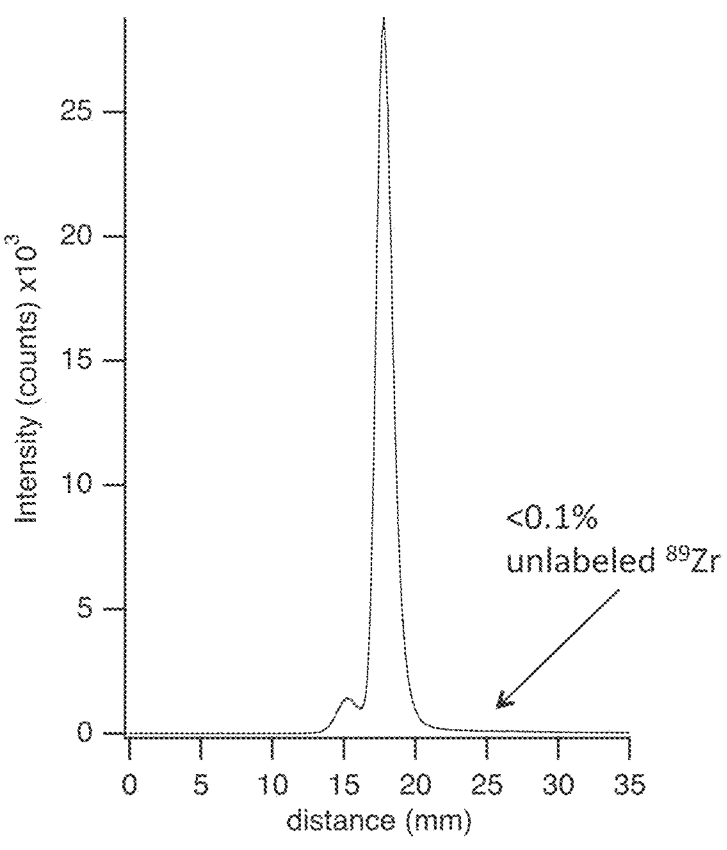
FIG. 4 depicts radio-SEC-HPLC of anti-LAG3-DFO-conjugate after $^{89}$Zr radiolabeling for Study 1.
Figure 5:
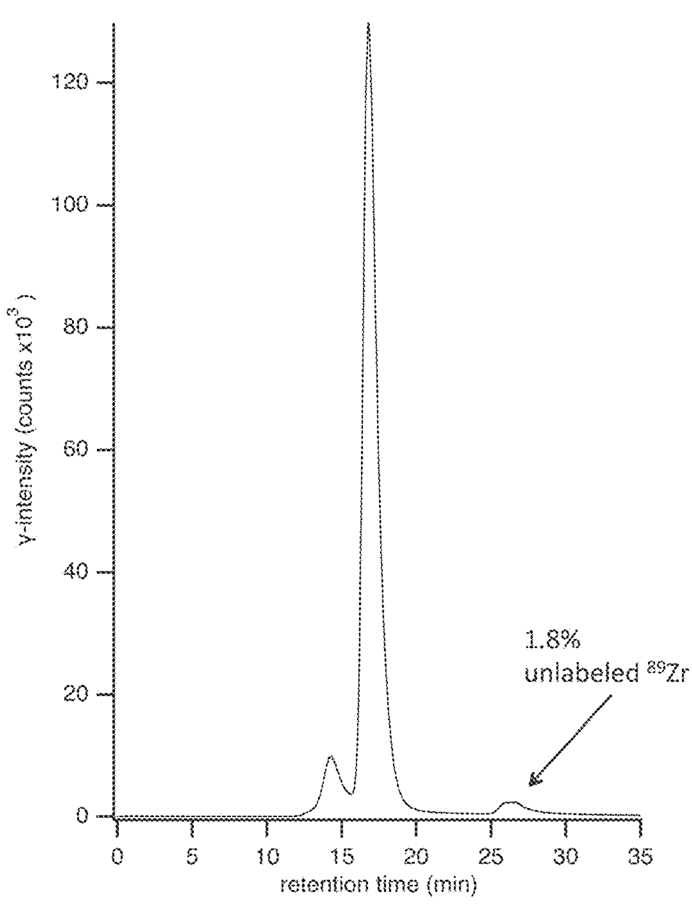
FIG. 5 depicts radio-SEC-HPLC of anti-LAG3-DFO-conjugate after $^{89}$Zr radiolabeling for Study 2.
Figure 6:
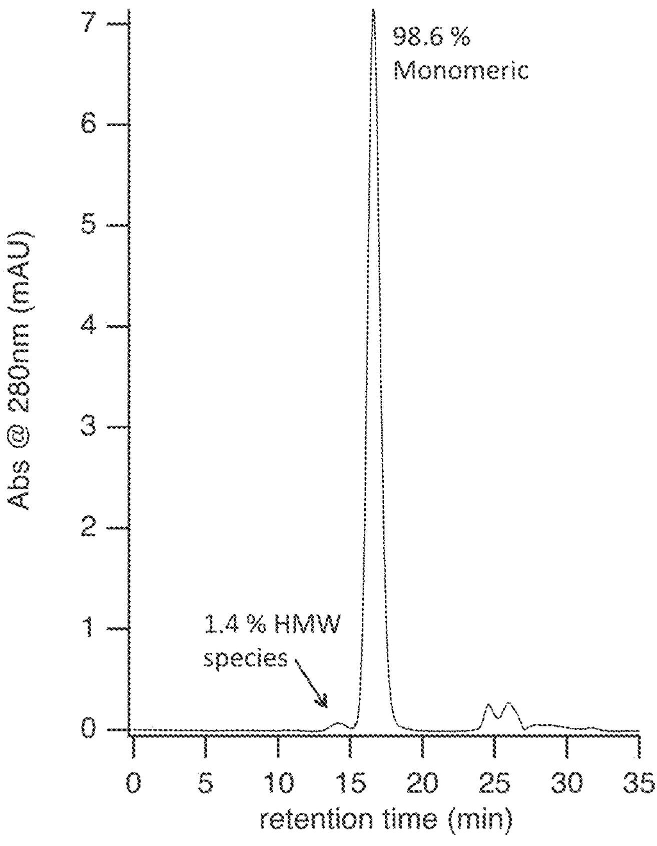
FIG. 6 depicts UV280-SEC-HPLC chromatogram and radio-iTLC trace of isotype-DFO-conjugate after $^{89}Zr$ radiolabeling for Study 1.
Figure 7:
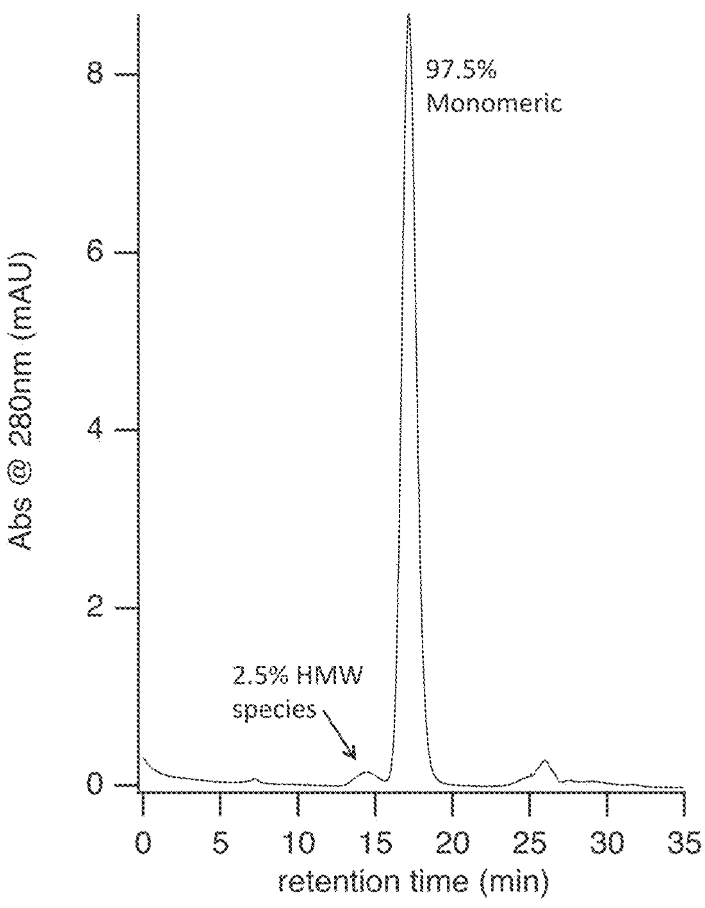
FIG. 7 depicts UV280-SEC-HPLC chromatogram and radio-iTLC trace of anti-LAG3-DFO-conjugate after $^{89}Zr$ radiolabeling for Study 1.
Figure 8:
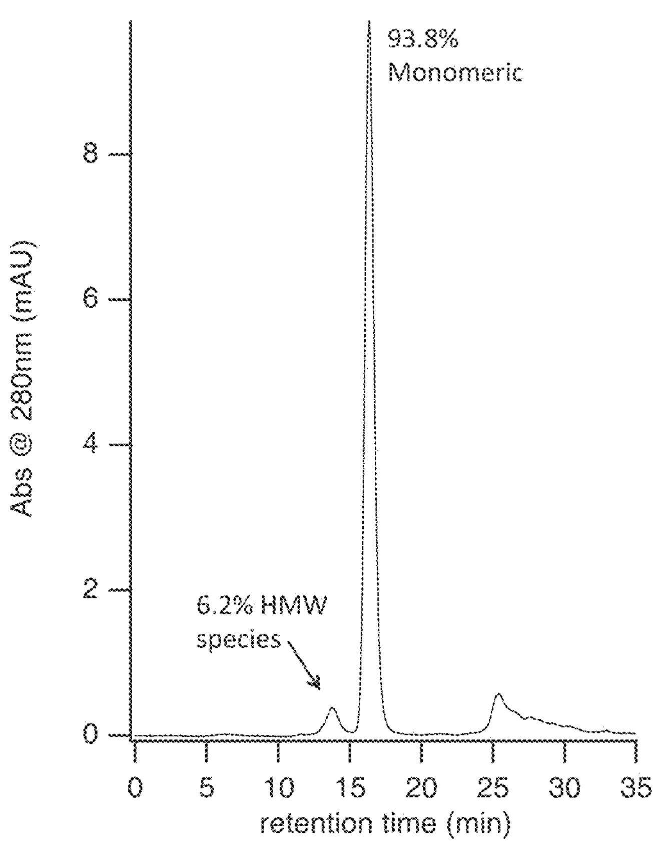
FIG. 8 depicts UV280-SEC-HPLC chromatogram and radio-iTLC trace of anti-LAG3-DFO-conjugate after $^{89}Zr$ radiolabeling for Study 2.

Finally the appearance was noted and recorded in Table 7. The results are consolidated in Table 7. The radio-SEC-HPLC chromatograms, shown in FIGS. 3-5, confirm at least 98% radiochemical purity. The UV280-HPLC SEC chromatograms shown in FIGS. 6-8 confirm the highly monomeric product (>90%).

TABLE 4

| DFO-antibody conjugate preparation for radiolabeling | | | | | | | |
|---|---|---|---|---|---|---|---|
| Radio-labeling # | Study # | Radio-labeling Lots | Concen-tration (mg/mL) | DAR* | Conjugate mass (mg) | Total volume (uL) | Final Concentration (mg/mL) |
| 1 | 1 | Isotype-DFO-$^{89}$Zr | 15.4 | 1.53 | 250 | 200 | 1.25 |
| 2 | 1 | mAb1-DFO-$^{89}$Zr | 13.6 | 1.48 | 500 | 400 | 1.25 |
| 3 | 2 | mAb1-DFO-$^{89}$Zr | 13.6 | 1.48 | 100 | 80 | 1.25 |

*DAR is defined as the DFO to Antibody Ratio

TABLE 5

| $^{89}$Zr reaction solution preparation for radiolabeling | | | | | | | |
|---|---|---|---|---|---|---|---|
| Radio-labeling | Study # | Radio-labeling Lots | $^{89}$Zr-oxalate (uL) | 1M HEPES, pH 7.2 (uL) | Final Vol (uL) | Final Activity (uCi) | Specific Activity (uCi/uL) |
| 1 | 1 | Isotype-DFO-$^{89}$Zr | ~3 | 500 | 1000 | 995 | 1.0 |
| 2 | 1 | mAb1-DFO-$^{89}$Zr | ~5 | 500 | 2000 | 2060 | 1.0 |
| 3 | 2 | mAb1-DFO-$^{89}$Zr | ~6 | 394 | 400 | 2010 | 5.0 |

TABLE 6

| Extinction coefficients for conjugate lots | |
|---|---|
| Radiolabeling Lot | $\varepsilon_{280}$ (AU ml mg$^{-1}$ cm$^{-1}$) |
| Isotype-DFO-$^{89}$Zr | 1.70 |
| mAb1-DFO-$^{89}$Zr | 1.72 |

TABLE 7

| Summary of $^{89}$Zr labeled DFO-Ab conjugates for in vivo imaging and biodistribution studies | | | | | | | | |
|---|---|---|---|---|---|---|---|---|
| Radio-label-ing | Study # | Conjugate Lots | Appear-ance | Radio-chemical Purity* (%) | Mono-meric Purity** (%) | Protein Recovery (%) | Conc. (mg/mL) | Specific Activity (mCi/mg) |
| 1 | 1 | Isotype-DFO-$^{89}$Zr | Clear | 99.7% | 98.6% | 70% | 0.108 | 3.41 |
| 2 | 1 | mAb1-DFO-$^{89}$Zr | Clear | >99.9% | 97.5% | 70% | 0.133 | 3.58 |
| 3 | 2 | mAb1-DFO-$^{89}$Zr | Clear | 98.2% | 93.8% | 57% | 0.121 | 14.7 |

*by radio-SEC-HPLC,
**by UV-SEC-HPLC

Example 4: Immunoreactivity

The immunoreactivity (IR) of the radiolabeled anti-LAG3 antibody and isotype control antibody was measured as follows. In these assays, 20 ng of the respective $^{89}$Zr labeled antibodies were added to $15\times10^6$ MC38-cOVA/eGFP-mLAG3$^{-/-}$hLAG3$^{Tg}$ cells in a final volume of 1 mL. Samples were incubated for 45 minutes (at 37° C., 5% $CO_2$) with continuous mixing before undergoing 2 washes with media to remove any unbound antibody. The radioactivity of the test cell pellets was then counted in an automatic gamma counter (2470 Wizard2, Perkin Elmer) against 2 reference standards containing the same 20 ng of $^{89}$Zr labeled antibody. The percentage immunoreactivity was determined for the samples using the average of the standards as a measure of total activity.

As seen in Table 8, $^{89}$Zr labeled anti-LAG3 antibody retained immunoreactivity following conjugation and radiolabeling, with 86% IR.

TABLE 8

| Immunoreactivity of $^{89}$Zr chelated DFO-conjugates | |
|---|---|
| Samples | Zr89 CPM |
| Standard 1 | 39643 |
| Standard 2 | 40134 |
| Average of Standards | 39889 |
| Cells | 34261 |
| IR | 86% |

Example 5: Selective Localization of Radiolabeled Anti-LAG3 Antibody to LAG3 Positive Tumors in Mice Implantation of Tumors and Allocation of Dosing Groups:

For in vivo imaging studies, a LAG3 positive tumor line was used. First, a murine colon carcinoma cell-line MC38-cOVA/eGFP-mLAG3$^{-/-}$hLAG3$^{Tg}$ was used. Here, cells over-express human LAG3 and full-length chicken ovalbumin fused with eGFP that was introduced by lentiviral transduction (pLVX EF1a and pLKO SSFV, respectively). For MC38-cOVA/eGFP-mLAG3$^{-/-}$hLAG3$^{Tg}$ tumor allografts, $1\times10^6$ cells were implanted subcutaneously into the left flank of male NCr nude (Taconic, Hudson NY). Once tumors had reached an average volume of 100-150 mm$^3$ (~Day 7 post implantation), mice were randomized into groups of 5 and dosed with test or control $^{89}$Zr radiolabeled antibodies.

Dosing and Biodistribution of $^{89}$Zr-DFO-mAb1:

For the initial study in nude mice bearing MC38/ova/LAG3 tumors, mice received 50±1 μCi of $^{89}$Zr labeled antibody with a protein dose ~0.6 mg/kg. For the biodistribution studies, mice were euthanized 6 days post-dosing and blood was collected via cardiac puncture. Tumors and normal tissues were then excised and placed in counting tubes. Count data for $^{89}$Zr in CPM was then collected by measuring samples on an automatic gamma counter (Wizard 2470, Perkin Elmer). All tissues were also weighed and the percent-injected dose per gram (% ID/g) was calculated for each sample using standards prepared from the injected material.

Results, Summary, and Conclusion:

In this example, the NCr mice bearing MC38/ova/hLAG3 tumors received $^{89}$Zr conjugated anti-LAG3 mAb1 or non-binding antibody at a final dose of 50 μCi/mouse. Mice were subsequently left for 6 days until blood, tumor and tissues were taken and the % ID/g for the samples was calculated for all samples. The average % ID/g for each antibody is presented in Table 9. From this, the clear high uptake in MC38/ova/hLAG3 tumors is apparent over other normal tissues, with tumor uptake of 43.1% being significantly higher than the next highest uptake of 6.6% ID/g observed in the thymus. The specificity of anti-LAG3 mAb1 uptake into tumor is apparent in the significantly reduced tumor uptake of 7.8% observed for the non-binding antibody.

TABLE 9

| | $^{89}$Zr- mAb1 | | $^{89}$Zr-non-binding Ab | |
|---|---|---|---|---|
| SAMPLE | AVERAGE % ID/G | STDEV % ID/G | AVERAGE % ID/G | STDEV % ID/G |
| LIVER | 0.5 | 6.2 | 3.9 | 0.3 |
| SPLEEN | 4.2 | 0.8 | 6.7 | 0.8 |
| KIDNEY | 5.1 | 0.8 | 6.2 | 1.2 |
| BONE | 4.3 | 2.1 | 4.9 | 1.0 |
| LUNG | 3.1 | 2.3 | 9.3 | 2.1 |
| HEART | 2.6 | 0.9 | 6.5 | 2.4 |
| BLOOD | 5.9 | 3.1 | 15.7 | 2.6 |
| THYMUS | 6.7 | 1.7 | 12.1 | 1.8 |
| MC38/ova/LAG3 | 43.1 | 9.5 | 7.8 | 0.4 |
| S. BOWEL | 1.7 | 0.5 | 2.8 | 0.5 |

Example 6: Selective Localization of Radiolabeled Anti-LAG3 Antibody to Raji/PBMC Tumors in Mice This Example describes the in vivo imaging and ex vivo biodistribution of a Zirconium-89 labeled DFO-anti-LAG3 antibody conjugate in NSG mice co-implanted with Raji cells and human PBMC.

The exemplary antibody used in this Example was MAb1, comprising HCVR/LCVR of SEQ ID NOs: 418/426.

Implantation of Tumors and Allocation of Dosing Groups:

To demonstrate specificity of the radiolabeled antibody for LAG3 targeting, $2\times10^6$ Raji cells and $5\times10^5$ human PBMC (Lot 0151029, ReachBio Research Labs) were co-implanted into the right flank of female NSG mice (8-10 weeks old, Jackson Labs). 14 days post-tumor implantation, mice were randomized into groups of 4 and injected intravenously with varying protein doses of $^{89}$Zr-DFO-mAb1.

Dosing and PET/CT Imaging of $^{89}$Zr-DFO-mAb1:

Mice bearing Raji/hPBMC tumors were injected with 5, 0.3, 0.1, or 0.03 mg/kg $^{89}$Zr-DFO-mAb1 at day 14 post-tumor implantation. Mice who received 0.1 and 0.03 mg/kg doses received ~30 or ~9 μCi of radiolabeled $^{89}$Zr-DFO-mAb1, respectively. The mice who received 5 or 0.3 mg/kg protein doses received ~30 μCi of radiolabeled $^{89}$Zr-DFO-mAb1 and additional non-DFO conjugated mAb1 (L5) as supplement to yield the final injected total protein dose.

PET imaging of antibody localization was assessed 6 days after administration of $^{89}$Zr-DFO-mAb1. A Sofie Biosciences G8 PET/CT was used to acquire PET/CT images (Sofie Biosciences and Perkin Elmer). The instrument was pre-calibrated for detection of $^{89}$Zr prior to image acquisition. The energy window ranged from 150 to 650 keV with a reconstructed resolution of 1.4 mm at the center of the field of view. Mice underwent induction anesthesia using isoflurane and were kept under continuous flow of isoflurane during imaging. Static 10-minute images were acquired using the G8 acquisition software and subsequently reconstructed using the pre-configured settings. Image data was corrected for decay and other parameters. CT images were acquired following PET acquisition and subsequently co-registered with the PET images. Images were prepared using VivoQuant post-processing software (inviCRO Imaging Services).

Biodistribution of $^{89}$Zr-DFO-mAb1:

For biodistribution studies, mice were euthanized at the final time-point (6 days post-$^{89}$Zr-DFO-mAb1 administration) and blood was collected via cardiac puncture. Raji/hPBMC tumors and normal tissues were then excised, placed in counting tubes, and weighed. Count data for $^{89}$Zr in CPM was then collected by measuring samples on an automatic gamma counter (Wizard 2470, Perkin Elmer). The percent-injected dose per gram (% ID/g) was calculated for each sample using standards prepared from the injected material.

Figure 9:
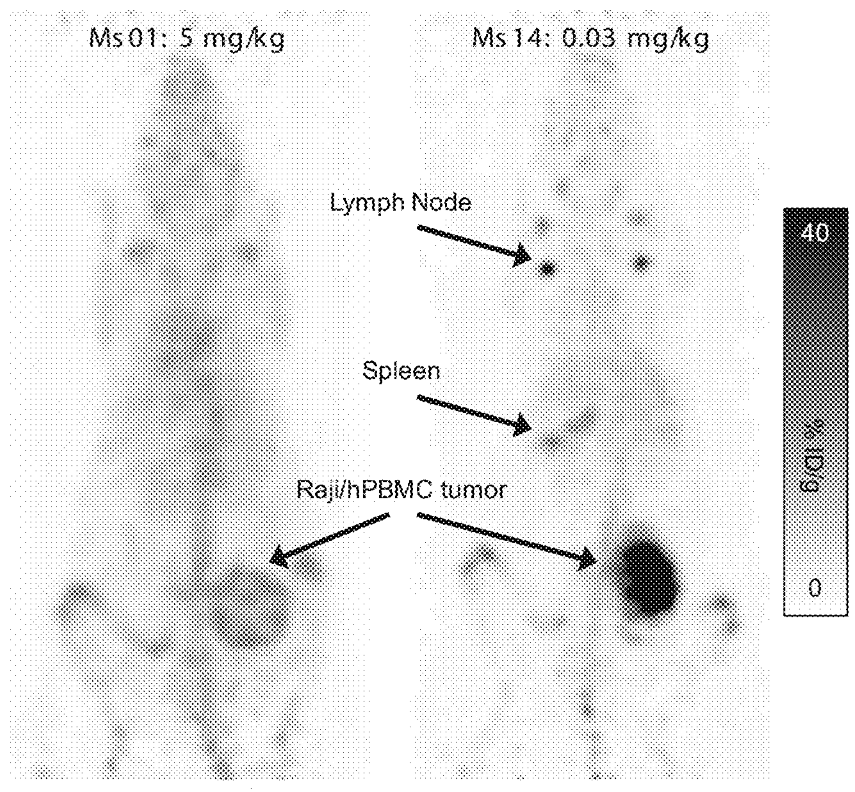
FIG. 9 provides representative images of $^{89}Zr$-DFO-mAb1 injected at a protein dose of 5 mg/kg (Ms01) or 0.03 mg/kg (Ms14) demonstrating specific targeting of $^{89}Zr$-DFO-mAb1 to Raji/hPBMC tumors using 0.03 mg/kg of $^{89}Zr$-DFO-mAb1 and blocking at 5 mg/kg of $^{89}Zr$-DFO-mAb1. Specific uptake in the spleen and lymph nodes is seen at the lower dose of 0.03 mg/kg $^{89}Zr$-DFO-mAb1.

Results, Summary, and Conclusions:

This study demonstrates antigen-specific targeting of $^{89}$Zr-DFO-mAb1 to LAG3 expressed on human lymphocytes in subcutaneous Raji/hPBMC tumors grown in NSG mice. The blocking dose of 5 mg/kg $^{89}$Zr-DFO-mAb1 showed increased blood uptake (% ID/g) and lower tumor uptake (% ID/g) in Raji/hPBMC tumors compared to the lower doses of 0.3, 0.1, and 0.03 mg/kg $^{89}$Zr-DFO-mAb1 (Table 10). Furthermore, as the protein dose decreased, the average tumor-to-blood ratio increased demonstrating specificity to Lag-3 in vivo (Table 10). In addition to targeting Lag-3 expressed in the Raji/hPBMC tumors, the lower doses of 0.3, 0.1, and 0.03 mg/kg $^{89}$Zr-DFO-mAb1 demonstrated targeting to the spleen and axillary lymph nodes of tumor bearing mice. Representative PET images (FIG. 9) at day 6 post $^{89}$Zr-DFO-mAb1 administration demonstrate higher targeting of $^{89}$Zr-DFO-mAb1 to the tumor, spleen, and axillary lymph nodes at 0.03 mg/kg compared 5 mg/kg.

TABLE 10

Ex vivo biodistribution at day 6 after administration of $^{89}$Zr-DFO-mAb1 injected at protein doses of 5. 0.3, 0.1, or 0.03 mg/kg in NSG mice bearing Raji/hPBMC tumors. Values are shown as average and standard deviations of % ID/g and tumor-to-blood ratios

| | $^{89}$Zr-DFO-mAb1 5 mg/kg | | $^{89}$Zr-DFO-mAb1 0.3 mg/kg | | $^{89}$Zr-DFO-mAb1 0.1 mg/kg | | $^{89}$Zr-DFO-mAb1 0.03 mg/kg | |
|---|---|---|---|---|---|---|---|---|
| SAMPLE | Average % ID/g | STDEV % ID/g | Average % ID/g | STDEV % ID/g | Average % ID/g | STDEV % ID/g | Average % ID/g | STDEV % ID/g |
| Blood | 18.45 | 1.69 | 12.17 | 3.20 | 8.13 | 4.28 | 7.81 | 5.37 |
| Tumor | 20.52 | 5.34 | 40.43 | 8.09 | 33.26 | 10.81 | 48.92 | 28.53 |
| Thymus | 7.78 | 0.64 | 6.57 | 2.04 | 7.98 | 4.71 | 3.22 | 2.43 |
| Heart | 5.5 | 0.45 | 3.74 | 0.57 | 2.79 | 1.14 | 2.39 | 1.47 |
| Lungs | 10.14 | 0.54 | 8.30 | 2.40 | 9.72 | 1.63 | 8.14 | 1.08 |
| Spleen | 7.74 | 0.17 | 22.32 | 13.82 | 103.68 | 126.79 | 59.20 | 40.84 |
| Intestine | 1.82 | 0.23 | 1.43 | 0.20 | 0.80 | 0.44 | 1.19 | 0.23 |
| Liver | 4.51 | 0.26 | 5.56 | 1.16 | 9.75 | 3.87 | 10.75 | 5.58 |
| Kidney | 6.73 | 0.99 | 6.17 | 1.28 | 5.77 | 1.59 | 5.49 | 1.56 |
| Bone | 8.78 | 1.75 | 8.39 | 3.10 | 8.87 | 2.64 | 9.83 | 1.54 |
| Tumor-to-blood ratio | 1.10 | 0.21 | 3.46 | 1.05 | 5.44 | 3.60 | 9.71 | 8.27 |

Example 7: LC-PRM-MS Quantitation of LAG3 in Raji/PBMC Xenografts and Clinical Samples Frozen tissue samples (Raji/PBMC tumors, mouse spleens, and melanoma tissue; see FIG. 12 for source and characteristics of melanoma tissues) were lysed with lysis buffer (8 M urea in 50 mM $NH_4HCO_3$ with 1% RapiGest). Tissues were cut into small pieces and were homogenized with 1 mL lysis buffer in a tight fitting dounce homogenizer. The lysate was incubated on ice for 30 mins with sonication for 30 sec every 10 mins to achieve complete protein extraction. The lysate was centrifuged at 14,000 g for 10 mins. Protein concentration was measured by BCA assay. Each sample was diluted to 1 mg/mL then was centrifuged at 14,000 g for 10 mins and was stored in aliquots at −80° C.

Unimplanted NSG mouse spleen lysate was used as the surrogate matrices to generate the standard curve for LAG3 quantitation. LAG3.Fc was spiked into each of 100 µg of mouse spleen lysate at a final concentration ranging from 0.39 to 50 ng/mg protein (1:2 serial dilution). Standards, xenografts and clinical melanoma lysates were precipitated in 900 µL of cold acetone overnight and then denatured in 90 µL of 8 M Urea/TCEP buffer at 37° C. for 1 hr. Heavy labeled human LAG3 peptide (FVWSSLDTPSQR$^{13}$C6$^{15}$N4) was added to all samples as internal standard. The standards and test samples were alkylated with IAA at room temperature for 30 min and digested by lys-C (1:100 w/w) for 4 hrs then by trypsin (1:20 w/w) overnight at 37° C. Samples were quenched with 10% FA to reach a final Vol. of 100 µL.

Each processed sample (2 µL) was injected onto a pre-equilibrated nano C18 trap column and was separated by an easy nano C18 separation column. The flow rate was 250 nL/min (Mobile Phase A: water:formic acid/100:0.1 [V:V] and Mobile Phase B: acetonitrile:formic acid/100:0.1 [V:V]). Retention time and peak area were determined using Skyline software. The calibration curve was generated by plotting the peak area ratio of LAG3.Fc reference standard (unlabeled LAG3 peptide FVWSSLDTPSQR$^{12}C_6{}^{14}N_4$ generated by tryptic digest of hLAG3) to the internal standard (stable isotope-labeled LAG3 peptide). The concentration of LAG3 in each sample was calculated using linear regression. The lowest concentration of LAG3 reference standard (0.39 ng/mg protein) was within the dynamic range of the assay and was defined as the assay's lower limit of quantification.

Results Summary and Conclusions:

LAG3 quantitation was performed on tissue samples from 4 of PBMC/Raji xenografts from 27 days, 5 xenografts from 15 days after tumor implantation and 10 melanoma clinical samples. The tissue weights, protein amounts, extraction yield and LAG3 expression were listed in Table 11. Bmax was calculated based on the following equation with an estimation of tumor density at 1 g/mL.

$$Bmax\ (nM) = \frac{LAG3\ (ng/\text{mg protein}) \times \text{Total Protein Amount (mg)} \times 10E6}{5.74 * 10E4 \times \text{Tumor Weight (mg)}}$$

Figure 10:
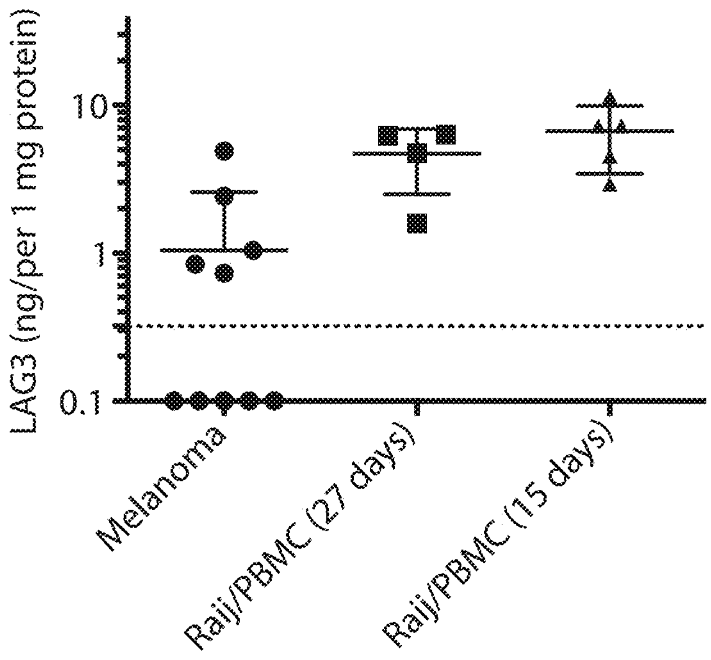
FIG. 10 shows LAG3 expression in tissue samples from PBMC/Raji xenografts (obtained at 27 days and 15 days after tumor implantation) and in melanoma clinical samples.

Five of 10 melanoma tissue samples were detected as LAG3 positive with an average expression level of 2.52±1.87 nM. This expression level is similar to Raji/PBMC model at 27 days (3.79±1.93 nM) and at 15 days (6.06±4.04 nM). See Table 11 and also FIG. 10.

TABLE 11

| | | Tissue Weight (mg) | Total Protein Amount (mg) | % protein | Lag3 (ng/mg protein) | Bmax (nM) |
|---|---|---|---|---|---|---|
| Melanoma Tissue | 131815T2(3) | 290 | 9.1 | 3.14% | BLQ | BLQ |
| | 131719T2(3) | 230 | 17.6 | 7.65% | BLQ | BLQ |
| | 13841T2(1) | 220 | 20.1 | 9.14% | 0.73 | 1.16 |
| | 13788T2(4) | 250 | 24.1 | 9.64% | 1.04 | 1.75 |
| | 13765T2(2) | 250 | 19.4 | 7.76% | BLQ | BLQ |
| | 131778T2(5) | 180 | 9.2 | 5.11% | BLQ | BLQ |
| | 131291T2(1) | 240 | 17.4 | 7.25% | 0.84 | 1.06 |
| | 131086T6(1) | 180 | 9.32 | 5.18% | BLQ | BLQ |
| | 13547T2(1) | 220 | 16.1 | 7.32% | 2.42 | 3.08 |
| | 13524T2(7) | 200 | 13 | 6.50% | 4.90 | 5.53 |

TABLE 11-continued

| | | Tissue Weight (mg) | Total Protein Amount (mg) | % protein | Lag3 (ng/mg protein) | Bmax (nM) |
|---|---|---|---|---|---|---|
| | Mean | 226 | 15.5 | 6.87% | 1.99 | 2.52 |
| | SD | 34 | 5.2 | 1.96% | 1.76 | 1.87 |
| Raji/PBMC | 85100_0 | 419.5 | 20.9 | 4.98% | 4.74 | 4.10 |
| Xenograft | 85101_8 | 248.9 | 10.3 | 4.14% | 1.58 | 1.14 |
| (27 Days) | 85104_23 | 256.5 | 9.74 | 3.80% | 6.24 | 4.12 |
| | 85103_19 | 112.5 | 5.92 | 5.26% | 6.32 | 5.78 |
| | Mean | 259 | 11.72 | 4.54% | 4.72 | 3.79 |
| | SD | 126 | 6.43 | 0.69% | 2.21 | 1.93 |
| Raji/PBMC | 213_1 | 140 | 8.8 | 6.29% | 11.46 | 12.5 |
| Xenograft | 213_2 | 260 | 10.14 | 3.90% | 4.54 | 3.08 |
| (15 Days) | 213_3 | 230 | 9.3 | 4.04% | 7.22 | 5.09 |
| | 213_4 | 160 | 7.9 | 4.94% | 2.95 | 2.54 |
| | 213_5 | 50 | 2.8 | 5.60% | 7.23 | 7.05 |
| | Mean | 168 | 7.8 | 4.95% | 6.68 | 6.06 |
| | SD | 82 | 6.43 | 0.69% | 2.21 | 1.93 |

Example 8: Up-Regulation of Human LAG-3 and PD-1 Expression on T Cells in the Tumor Microenvironment by Therapy with REGN2810 (Anti-Human PD-1 Ab) and mAb1 (Anti-Human LAG-3 Ab)

This experiment was carried out to evaluate the modulation of expression levels of human LAG-3 and PD-1 on T cells in the tumor microenvironment upon treatment with REGN2810 and mAb1 using Regeneron's proprietary PD-$1^{hu/hu}$/LAG-$3^{hu/hu}$ double humanized immune-competent mice. The tumor cell line used in this experiment is a murine colon carcinoma cell line MC38 (obtained from NCI at Frederick, MD, Laboratory of Tumor Immunology and Biology), which has been engineered in house to express full-length chicken ovalbumin fused with eGFP, thus referred here as MC38-cOVA/eGFP. The expression level of human LAG-3 was evaluated ex vivo on both CD4 and CD8 T cells from enzymatically disassociated tumors extracted from tumor bearing double humanized mice. All surface staining was performed with commercially available fluorochrome directly conjugated to antibodies (anti-human LAG-3 antibody: eBioscience, Clone 3DS223H; anti-human PD-1 antibody: BioLegend, Clone EH12.2H7), following standard protocol. Briefly, tumor cells were washed with PBS once, washed with ice cold staining buffer once, stained with commercial available fluorochrome directly conjugated anti-human PD-1 or anti-human LAG-3 antibody in staining buffer for 30 min on ice in the dark, washed with 2 ml of PBS once again. Fixable dye eFluor506 was also included following manufacturer's protocol (eBioscience). Samples were acquired on BD FACSCanto II™ IVD10 equipped with DIVA v8. Data were further analyzed with FlowJo v10.0.6 or the later version.

Results Summary and Conclusions:

Table 12 provides a schematic presentation of the therapeutic dosing regimen in preclinical tumor setting. $1\times10^6$ MC38-cOVA/eGFP cells were implanted s.c. into PD-$1^{hu/hu}$/LAG-$3^{hu/hu}$ double humanized immune-competent mice. At about Day 11, mice were randomized into four groups with average tumor volumes of ~100 $mm^3$ and started treatment as indicated. Tumor samples were collected 3 days after the second dose.

TABLE 12

Therapeutic dosing regimen.

| Group | Treatment | #[ Mice |
|---|---|---|
| Isotype | 25 mg/kg, 2× week, 2 doses, IP | 10 |
| REGN2810(PD-1) | 10 mg/kg, 2× week, 3 doses, IP | 12 |
| mAb1 (anti-human LAG-3) | 25 mg/kg, 2× week, 2 doses, IP | 12 |
| REGN2810 + mAb1 | 10 mg/kg + 25 mg/kg, 2× week, 2 doses, IP | 12 |

As shown in Table 13, the combination of anti-human PD-1 (REGN2810) and anti-human LAG-3 (mAb1) significantly inhibited tumor growth in MC38-cOVA/eGFP syngeneic tumor model in double humanized mice. Tumor-bearing mice (tumor sizes of about 100 $mm^3$) were treated with an hIgG4 isotype control antibody, REGN2810 (anti-human PD-1, hIgG4), mAb1 (anti-human LAG-3, hIgG4s), and combination of REGN2810 and mAb1, twice a week for two doses, and tumor sizes were measured by caliper. Tumor volume was calculated as $V=L\times W^2/2$. In the control group, tumor sizes ranged from 300 to 869 $mm^3$ with median value of 548 $mm^3$. REGN2810 treated group showed reduced tumor sizes (121 to 721 $mm^3$ with median at 466 $mm^3$), but the differences did not reach statistical significance. Whereas mAb1-treated group showed no difference from the isotype control group either (203 to 721 $mm^3$ with median at 592 $mm^3$), the combination treatment significantly delayed tumor growth (113 to 621 $mm^3$ with median at 289 $mm^3$, $p<0.01$).

TABLE 13

Anti-human PD-1 (REGN2810) and anti-Human LAG-3 (mAb1) significantly inhibited tumor growth in MC38-cOVA/GFP syngeneic tumor model in double humanized mice

| | Iso** | αhPD-1 | αhLAG-3** | Combo |
|---|---|---|---|---|
| Mice/group | 10 | 12 | 12 | 12 |
| Minimum | 299.9 | 120.9 | 202.6 | 113.4 |
| 25% Percentile | 437.6 | 321.3 | 426.9 | 192.6 |
| Median | 548.4 | 465.5 | 592.1 | 289.1 |
| 75% Percentile | 617.6 | 597.8 | 631.1 | 349.7 |
| Maximum | 868.7 | 710.6 | 760.7 | 631.4 |

Figure 11:
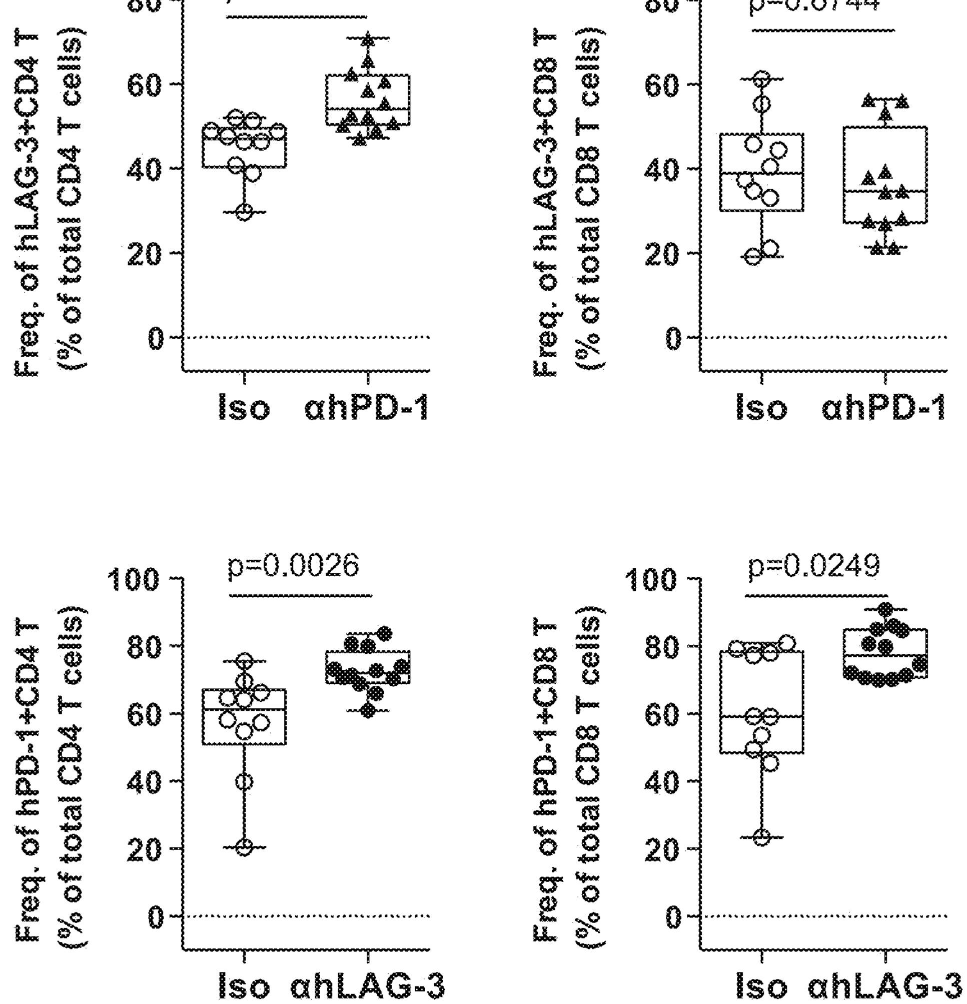
FIG. 11 provides data demonstrating REGN2810 anti-human PD-1 Ab and mAb1 anti-human LAG-3 respectively increase LAG-3+ T cells and PD-1+ T cells in tumor microenvironment.
Figure 13:
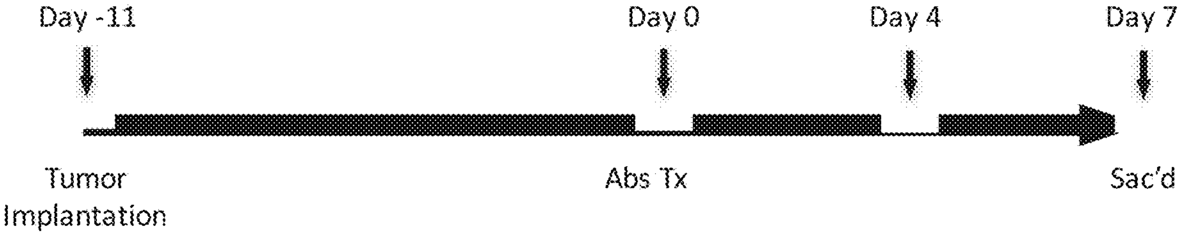
FIG. 13 provides a schematic presentation of the therapeutic dosing regimen used in Example 8.

REGN2810 anti-human PD-1 Ab and mAb1 anti-human LAG-3 respectively increased LAG-3+ T cells and PD-1+ T cells in tumor microenvironment, as can be seen in FIG. 11. Tumors from individual mice were dissociated by GentalMACs (Miltenyi Biotech) according to the Manufacturer's protocol. Samples were stained with a panel of Abs and analyzed by flow cytometer. Data presented were pre-gated on FSC/SSC, viability, singlets, CD45+CD3+ cells, then further gated on CD4 or CD8 T cells. The expression of human LAG-3 and human PD-1 were evaluated between different groups. To eliminate the possible Ab cross-competition, REGN2810—and combination-treated groups were excluded from human PD-1 analysis. Similarly, mAb1—and combination-treated groups were also excluded from human LAG-3 analysis. After two therapeutic doses, REGN2810 significantly increased the frequency of human LAG-3+ CD4 T cells in tumor microenvironment by ~24% (p=0.0006), though it did seem to have a direct modulatory role for LAG-3 expression on CD8 T cells with the dosing regimen tested. Interestingly, mAb1 also increased the frequency of human PD-1+ CD4 (p=0.0026) and CD8 T cells (p=0.0249) in tumor microenvironment by ~28%, respectively. See FIG. 11.

The results from the studies performed here clearly demonstrate that anti-LAG3 antibody labeled with $^{89}$Zr can significantly and specifically localize to tumors. One may envision a scenario where the anti-LAG3 antibody is used in the selection of patients with LAG3 positive tumors for subsequent treatment with LAG3 inhibitors, alone or in combination with other anti-cancer therapeutics including inhibitors of the PD-1/PD-L1 signaling axis.

Example 9: Scaled-Up Manufacturing Process for Producing DFO-Anti-LAG3 Antibody Conjugates This example details the scaled-up manufacturing process for preparing the anti-LAG3 antibody to be suitable for radiolabeling by attaching p-SCN-bn-Deferoxamine (DFO) to the anti-LAG3 antibody (mAb, H4sH15482P) described herein: (1) ultrafiltration and diafiltration (UFDF) processes prior to mAb conjugation removes excipients that inhibit the conjugation process; (2) following the pre-conjugation UFDF, conjugation of the mAb with p-SCN-Bn-deferoxamine is performed to produce DFO-mAb conjugates; and (3) a post-conjugation UFDF to remove residual salts provides a suitable concentration, excipient level, and pH of the conjugated monoclonal antibody. The resulting DFO-mAb conjugates are then provided in a buffered state with improved stability for subsequent formulation.

(1) Pre-Conjugation Ultrafiltration and Diafiltration (UFDF)

100 g mAb was buffer exchanged into a 5 mM acetate buffer solution having a pH of 5.50 using a Sius Prostream (TangenX Technology Corporation) membrane (membrane capacity of ≤500 g/m$^2$) to remove residual salts prior to conjugation. The process volume was reduced to further concentrate the antibody, then the antibody was sterile filtered using a Sartopore 2 (Sartorius) membrane having a 0.45/0.2 μm (heterogeneous PES double layer) or equivalent pore size. The acetate buffer temperature was kept at a target temperature of 20±5° C. The solutions were well mixed.

(2) Conjugation

The concentrated and filtered antibody (20 g) was transferred into a conjugation vessel containing an amine free carbonate buffer system (56 mM Carbonate, 167 mM Sodium Chloride, pH 9.40) resulting in negligible levels of residual acetate. DFO (25 mM p-SCN-Bn-Deferoxamine) was solubilized in DMSO and added to the conjugation vessel, along with additional DMSO such that the DMSO was present in a final amount of 5%. DFO was added in molar excess at a ratio of 4.5:1 DFO to mAb. The total reaction volume equaled 2.0 L. The buffer system was mixed throughout the addition of the reaction ingredients and throughout the reaction time.

The reaction temperature was controlled for specific time by using an equation which relates temperature to reaction time. In this instance, the reaction temperature was held at 20±2° C. for 180 minutes. The reaction was quenched by the addition of 2 M acetic acid (23 mL/L), resulting in the solution having a pH of 6.

(3) Post-Conjugation UFDF

After the conjugation step, the quenched DFO-mAb conjugation solution was buffer exchanged into histidine buffer (10 mM Histidine, pH 5.50 with 0.0005% (w/v) super refined polysorbate 80 added as a shear protectant) to remove residual process salts, DMSO, and unreacted DFO. Once diafiltered, the solution was then concentrated and subsequently formulated. The histidine buffer was selected for long term storage of protein at −80° C. The same Sius Prostream membrane mentioned in step (1) was used in the final UFDF step. The resulting concentrated DFO-mAb conjugate solution was sterile filtered using the Sartopore 2 filter mentioned above.

UV-DAR (target of 1.5) and protein concentration determination was performed as described in Example 2.

TABLE 14

| Molar Extinction Coefficients and Molecular Weight | | | |
|---|---|---|---|
| Antibody | MW (g mol$^{-1}$) | •280 (L g$^{-1}$cm$^{-1}$) | •252 (L g$^{-1}$cm$^{-1}$) |
| H4sH15482P | 145709 | 223400 | 87077 |

Example 10: ImmunoPET Imaging of LAG3 in Tumors Using an $^{89}$Zr-DFO-Anti-LAG3 Antibody Conjugate in Patients with Metastatic Melanoma The primary objective of this study is to determine the safety and tolerability of $^{89}$Zr-DFO-anti-LAG3 antibody conjugate, in which the anti-LAG3 antibody used in the radiolabeled conjugate is H4sH15482P. Outcome measures monitor adverse events and routine laboratory tests for safety.

The Secondary Objectives of the Study are:

Study part A: To qualify $^{89}$Zr-DFO-anti-LAG3 PET as a biomarker for the evaluation of LAG3 expression in tumors. This will be accomplished by evaluating the safety of the $^{89}$Zr-DFO-anti-LAG3 PET tracer, determining optimal tracer mass dose and optimal post-injection imaging time, establishing the relationship of tumor PET signal with LAG3 tissue-based expression, and evaluating dosimetry in patients. Part A comprises a sequential tracer dose escalation design, with tumor biopsy. Imaging and blood draws at days 1, 4, and 7 post tracer injection permit blood poos SUV with subsequent calculation of tumor:blood ratios at the time of imaging; clinical dosimetry based on tissue radiation absorbed dose and effective dose calculated from PET image acquisition data and tracer activity concentration in blood; standardized uptake values (SUVs—decay-corrected activity concentration in target tissue divided by the mean activity concentration in the body at the time of injection) across the tumor regions of interest; maximal SUVs within tumor regions of interest (ROIs) ($SUV_{max}$); and plasma tracer activity concentration, with calculation of area under the curve ($AUC_{0\text{-}7\ days}$).

Study part B: To explore the construct and criterion validity of $^{89}$Zr-DFO-anti-LAG3 PET by correlating the PET signal with tissue-based LAG3 expression and clinical outcome (objective response rate and progression-free survival) after IO therapy. Sequential iPET scanning and tumor biopsies are performed before and after treatment with standard of care immunotherapies selected from the following: nivolumab, ipilimumab, pembrolizumab, and combinations as allowed by label.

The utility of the immune-PET (iPET) tracer can be initially assessed by testing for ability to detect the presence of LAG3 tumors, as well as changes in LAG3 signal induced by an established immunotherapy, and by exploring the correlation of the iPET signal with clinical outcomes (criterion validation: against biologically and clinically meaningful outcomes).

A safe, optimal mass dose of $^{89}$Zr-DFO-anti-LAG3 can be identified that shows adequate tumor uptake by PET, tracer PK, and dosimetry. Selection of three tracer mass dose levels is based on preclinical mouse xenograft imaging and biodistribution studies, and on clinical and preclinical data using unlabeled anti-LAG3 therapeutic antibodies. The planned mass dose escalation is 2 mg, 5 mg, and 10 mg. The approach is to use doses that are sub-therapeutic or pharmacologically inert, so as not to interfere with prospective anti-tumor therapy.

The optimal mass dose will demonstrate tumor SUV, maximal SUV ($SUV_{max}$) within the tumor lesion region of interest (ROI) and tumor:blood ratio all >1 (and ideally a tumor-blood ratio of 3-4) in at least one lesion (ideally in >1 lesion, in patients with several metastases).

Tracer activity in plasma (or serum) and/or blood pool SUV (the activity PK measures for this study) will be detectable throughout the 7-day imaging window, following dosing, suggesting adequate availability of tracer to compartmentalize into tumor lesions. Ratios of tumor and blood signal will be based on SUVs, although other activity concentration units may be used. The same applies to measurements of blood activity concentration, which could be reported in terms of absolute units or normalized units.

LAG3 PET signal intensity in a biopsied lesion will covary with degree of LAG3 expression in the tissue biopsy using semi-quantitative measures.

The autoradiographic LAG3 PET signal will correlate spatially with LAG3 expression in tissue biopsy samples.

LAG3 PET signal intensity will increase following treatment with an immunotherapy.

LAG3 PET signal intensity increase will correlate with response following treatment with an immunotherapy.

Additionally, exploratory objectives and outcome measures include determining expression of LAG3 in tissue biopsies in correlation with tumor $^{89}$Zr-DFO-anti-LAG3 uptake using immunohistochemistry, RNAscope, liquid chromatography mass spectrometry (LC/MS), and autoradiography. For part B only, exploratory objectives include measuring changes in $^{89}$Zr-DFO-anti-LAG3 signal after treatment and correlation of $^{89}$Zr-DFO-anti-LAG3 signal with clinical outcome after treatment. The outcome measures include SUV, SUVmax, tumor:blood ratio, and clinical outcome following immunotherapy treatment (serial CT for the purpose of calculation of responder status using RECIST 1.1 and tumor volume), objective response rate, and progression-free survival.

Patient Target Population

The target population will consist of patients 18 years of age or older with advanced metastatic melanoma, histologically or cytologically confirmed diagnosis, with at least one lesion amendable to biopsy. The patient must have an ECOG performance status of less than or equal to 2, an anticipated life expectancy of at least 3 months, and adequate organ and bone marrow function.

Inclusion of patients with an indication that has a high prevalence of the target will support assessment of LAG3 iPET tumor localization which is a key outcome of the study. Detection and correlation of post-immunotherapy LAG3 expression with clinical outcomes requires a patient population with well characterized clinical response rates to immunotherapies. Metastatic melanoma patients represent a patient population with established response rates to checkpoint inhibitors as well as the high levels of prevalence and expression of LAG3.

Study Design

The study comprises part A (construct validation) and part B (criterion validation). Duration of the study is 9 weeks for Part A (4 weeks screening, 1 week tracer dosing, scans and biopsy, 4 weeks safety follow up), and 18 weeks for Part B (4 weeks screening, 1 week tracer dosing, scans and biopsy, up to 8 weeks on immunotherapy, 1 week second tracer dose and scan, 4 weeks safety follow up).

Part A

Part A is a dose finding study in which patients receive a single tracer dose, followed by serial scans and a biopsy over a 7 day period. Once the scanning sequence and biopsy are completed, subjects can immediately be treated with a standard of care immunotherapy regime (anti-PD-1 alone or in combination with anti-CTLA4 according to labeled indication).

Dose Cohorts in Part A

Part A comprises three sequential dose cohorts, consisting of 3 patients, with potential to expand the cohort to a total of 6 patients (3+3 design). Dose escalation decisions will be informed by a) safety and b) evaluation of iPET positivity. Dose limiting toxicity (DLT) is defined as a Grade 3 or higher (NTCAE) adverse event (AE) related to or possibly related to $^{89}$Zr-DFO-anti-LAG3, one week following tracer administration. For hematologic lab AEs, DLT is defined as Grade 4 or higher. Tumor uptake positivity/tumor localization is defined by a tumor:blood ratio greater than 1. Adequate PK is defined by SUV in blood in the range of 1-5 at optimum imaging time (4 or 7 days post-injection).

Cohort expansion to 6 patients will occur if any of the following conditions are met: (a) exactly 1 patient experiences a DLT or (b) at least 1 patient out of 3 shows tumor localization and adequate PK and no more than 1 patient experiences a DLT.

At the completion of a cohort of either 3 or 6 subjects, dose escalation will occur to a higher available dose if fewer than 3 patients in an expanded cohort experience a DLT.

Part A of study will stop if any of the following conditions are met (Part A stopping rules): more than 1 patient in a cohort experiences a DLT; more than 3 patients show visual tumor localization and adequate PK in each of two consecutive expanded cohorts; or no higher doses are available for escalation.

Upon reaching a Part A stopping rule, Part B dose will be selected as follows: a) if two or three expanded cohorts show more than 3 patients with tumor localization and adequate PK, then the dose cohort with tumor localization in more patients, or the highest tumor:blood ratios, will be chosen. When these are similar between cohorts, the lower dose will be chosen. b) if one cohort shows more than 3 patients with tumor localization and adequate PK, this dose will be chosen. c) if no cohorts show more than 3 patients with tumor localization and adequate PK, the study will terminate without progression to Part B.

Part B

Part B will measure LAG3 iPET signal at the defined tracer dose and post-injection time point (determined in part A), both pre- and post-immunotherapy to assess the hypotheses surrounding the role of LAG3 as an indicator of tumor inflammatory response (exploratory objectives). All patients in Part B will receive the optimal tracer mass dose and post-injection imaging timing as identified in Part A.

Part B patients will receive LAG3 iPET scanning at baseline as well as a biopsy prior to therapy. Patients will then receive a standard of care immunotherapy (currently these are monoclonal antibody-based PD-1 and CTLA-4 pathway blockers), according to the label. Four to eight weeks later an additional iPET scan will be undertaken followed by a second biopsy if feasible.

Patients in Part A who received the optimal tracer mass dose and achieved adequate scan quality may be eligible for Part B and receive a total of two iPET tracer injections. The total number of subjects in Part B (including those that enter from Part A) will not exceed 20.

Biopsy Considerations

Lesions will be selected for biopsy on the basis of accessibility and size (typically at least 20 mm diameter). All patients will undergo a baseline biopsy on the last day of the first set of iPET scans, regardless of whether the iPET study is positive or not. In this way, tissues from patients with a wide range of LAG3 tissue expression will be collected for correlation with LAG3 signal, including negative patients. The biopsy will be scheduled no later than 7 days from date of injection in order to minimize delay of therapy to the patient.

A sequence of assessments that starts with a biopsy followed by the tracer dosing and scans, and then the initiation of therapy may be preferable for practical reasons.

For Part B, a second biopsy after the second scan may be undertaken if feasible and will be optional. Sequential biopsies will be taken from the same site if practicable.

Autoradiography studies will be performed in a subset of biopsied tumors that are positive on iPET scan, with adjacent slices stained against LAG3.

Study Interventions

Part A

Following screening, each subject will receive a dose of $^{89}$Zr-DFO-anti-LAG3 followed by three sequential iPET scans over 6-7 days. Starting dose will be 2 mg, as determined from animal studies and modeling. No later than 1 day after the last iPET scan, the subject will undergo radiology-guided biopsy. If available, archived biopsy tumor tissue will also be analyzed by IHC for LAG3 expression.

For Part A, biopsy is optional, since not all subjects will receive the eventually identified optimal tracer dose.

Decision to progress to Part B will be made on the basis of Part A data and recruitment rate.

Part B

Following screening, each melanoma patient will receive a $^{89}$Zr-DFO-anti-LAG3 at the optimized mass dose (from Part A) followed by PET scanning at the optimal post-injection time point (from Part A). Then, no later than 1 day after iPET imaging, the subject will undergo radiology guided biopsy of a lesion. Subsequently, the patient will be treated, open-label, with available approved immunotherapy regimens (dosed as per label). Subjects will receive a second scan 4-8 weeks after commencement of immunotherapy. A second biopsy after the second scan may be undertaken if feasible and will be optional.

All patients will be screened by an $^{18}$F-FDG PET/CT scan. CT portion of the PET/CT scan must be of diagnostic quality or a diagnostic CT scan acquired during the screening period must be available to assess location and dimension of lesions. These scans will be used to evaluate the lesions for metabolic activity/viability and appropriate dimensions.

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

| SEQ ID NO. | Sequence | Description |
|---|---|---|
| 1. | gaggtgcagc tgttggagtc tgggggaggc ttggtacagc ctggggggtc cctgagactc<br>tcctgtgtgg cctctggatt cacctttagc acctatgcca tgagttgggt ccgccaggct<br>ccagggatgg ggctggagtg ggtctcaagt attagtggta gtggtcgtaa cacatactat<br>gcagactccg tgaagggccg gttcaccatc tccagagaca attccaagaa cacgctgttt<br>cttcaaatga acagcctgag agccgaggac acggccgttt attactgtgc gaaagagtcc<br>gtaactggaa cttcgtccta ctactacggt gtggacgtct ggggccaagg gaccacggtc<br>accgtctcct cg | DNA nucleotide sequence |
| 2. | EVQLLESGGG LVQPGGSLRL SCVASGFTFS<br>TYAMSWVRQA PGMGLEWVSS ISGSGRNTYY<br>ADSVKGRFTI SRDNSKNTLF LQMNSLRAED<br>TAVYYCAKES VTGTSSYYYG VDVWGQGTTV<br>TVSS | AA amino acid sequence |
| 3. | ggattcacct ttagcaccta tgcc | DNA nucleotide sequence |
| 4. | GFTFSTYA | AA amino acid sequence |
| 5. | attagtggta gtggtcgtaa caca | DNA nucleotide sequence |
| 6. | ISGSGRNT | AA amino acid sequence |

-continued

| SEQ ID NO. | Sequence | Description |
|---|---|---|
| 7. | gcgaaagagt ccgtaactgg aacttcgtcc tactactacg gtgtggacgt c | DNA nucleotide sequence |
| 8. | AKESVTGTSS YYYGVDV | AA amino acid sequence |
| 9. | gacatccaga tgacccagtc tccatcctcc ctgtctgcat ctgtaggaga cagagtcacc atcacttgcc gggcaagtca gagcattagc agttatttaa attggtatca tcagaaacca gggaaagccc caaagctcct gatctatgct gcatccagtt tgcaaaatgg ggtcccatca aggttcagtg gcagtggatc tgggacagat ttcactctca ccatcagcag tctgcaacct gaagattttg catcttacta ctgtcaacag agttacagaa ccccgctcac tttcggcgga gggaccaagg tggagatcaa a | DNA nucleotide sequence |
| 10. | DIQMTQSPSS LSASVGDRVT ITCRASQSIS SYLNWYHQKP GKAPKLLIYA ASSLQNGVPS RFSGSGSGTD FTLTISSLQP EDFASYYCQQ SYRTPLTFGG GTKVEIK | AA amino acid sequence |
| 11. | cagagcatta gcagttat | DNA nucleotide sequence |
| 12. | QSISSY | AA amino acid sequence |
| 13. | gctgcatcc | DNA nucleotide sequence |
| 14. | AAS | AA amino acid sequence |
| 15. | caacagagtt acagaacccc gctcact | DNA nucleotide sequence |
| 16. | QQSYRTPLT | AA amino acid sequence |
| 17. | caggtgcagc tggaggagtc tgggggaggc gtggtccagc ctgggaggtc cctgagactc tcctgtgcag cgtctggatt caccttcagt tggtatggca tgcactgggt ccgccaggct ccaggcaagg ggctggagtg ggtggcactt atatggtatg atggaactaa taaaaagtat ggagactccg tgaagggccg attcaccatt tccagagaca attccaagaa cacggtgtat ctgcaaatga acagcctgag agccgaggac acggctgtgt attactgtgc gagagattgt ggacatagtg gcaacgatcg ggggacttac tattactact acggtatgga cgtctggggc caagggacca cggtcaccgt ctcctca | DNA nucleotide sequence |
| 18. | QVQLEESGGG VVQPGRSLRL SCAASGFTFS WYGMHWVRQA PGKGLEWVAL IWYDGTNKKY GDSVKGRFTI SRDNSKNTVY LQMNSLRAED TAVYYCARDC GHSGNDRGTY YYYYGMDVWG QGTTVTVSS | AA amino acid sequence |
| 19. | ggattcacct tcagttggta tggc | DNA nucleotide sequence |
| 20. | GFTFSWYG | AA amino acid sequence |
| 21. | atatggtatg atggaactaa taaa | DNA nucleotide sequence |

-continued

| SEQ ID NO. | Sequence | Description |
|---|---|---|
| 22. | IWYDGTNK | AA amino acid sequence |
| 23. | gcgagagatt gtggacatag tggcaacgat cgggggactt actattacta ctacggtatg gacgtc | DNA nucleotide sequence |
| 24. | ARDCGHSGND RGTYYYYYGM DV | AA amino acid sequence |
| 25. | gacatccaga tgacccagtc tccatcctcc ctgtctgcat ctgtaggaga cagagtcacc atcacttgcc gggcaagtca gagcattagc agctatttaa attggtatca gcagaaacca gggaaagccc ctaagctcct gatctatgct gcatccagtt tgcaaagtgg ggtcccatca aggttcagtg gcagtggatc tgggacagat ttcactctca ccatcagcag tctgcaacct gaagattttg caacttacta ctgtcaacag agttacagta cccctccgat caccttcggc caagggacac gactggagat taaa | DNA nucleotide sequence |
| 26. | DIQMTQSPSS LSASVGDRVT ITCRASQSIS SYLNWYQQKP GKAPKLLIYA ASSLQSGVPS RFSGSGSGTD FTLTISSLQP EDFATYYCQQ SYSTPPITFG QGTRLEIK | AA amino acid sequence |
| 27. | cagagcatta gcagctat | DNA nucleotide sequence |
| 28. | QSISSY | AA amino acid sequence |
| 29. | gctgcatcc | DNA nucleotide sequence |
| 30. | AAS | AA amino acid sequence |
| 31. | caacagagtt acagtacccc tccgatcacc | DNA nucleotide sequence |
| 32. | QQSYSTPPIT | AA amino acid sequence |
| 33. | caggtgcagc tacagcagtg gggcgcagga ctgttgaagc cttcggagac cctgtccctc acctgcgctg tctatggtgg gtccttcagt ggttactact ggaactggat ccgccagccc ccagggaagg ggctggagtg gattggggaa atcagtcata gaggaaccac caactacaac ccgtccctca agagtcgagt caccatatca ctggacacgt ccaagaacca gttctccctg aaactgacct ctgtgaccgc cgcggacacg gctgtgtatt actgttcgag agacgaggaa ctggaattcc gtttctttga ctactggggc cagggaaccc tggtcaccgt ctcctca | DNA nucleotide sequence |
| 34. | QVQLQQWGAG LLKPSETLSL TCAVYGGSFS GYYWNWIRQP PGKGLEWVGE ISHRGTTNYN PSLKSRVTIS LDTSKNQFSL KLTSVTAADT AVYYCSRDEE LEFRFFDYWG QGTLVTVSS | AA amino acid sequence |
| 35. | ggtgggtcct tcagtggtta ctac | DNA nucleotide sequence |

-continued

| SEQ ID NO. | Sequence | Description |
|---|---|---|
| 36. | GGSFSGYY | AA amino acid sequence |
| 37. | atcagtcata gaggaaccac c | DNA nucleotide sequence |
| 38. | ISHRGTT | AA amino acid sequence |
| 39. | tcgagagacg aggaactgga attccgtttc tttgactac | DNA nucleotide sequence |
| 40. | SRDEELEFRF FDY | AA amino acid sequence |
| 41. | gaaattgtgt tgacacagtc tccagccacc ctgtctttgt ctccagggga aagagccacc ctctcctgca gggccagtca gagtgttagc agctatttag cctggtacca acaaaaacct ggccaggctc ccaggctcct cgtctatggt gcatccaaca gggccactgg catcccagcc aggttcagtg gcagtgggtc tgggacagac ttcactctca ccatcagcag cctagagcct gaagattttg cattttatta ctgtcagcag cgtagcaact ggccgctcac tttcggcgga gggaccaagg tggagatcaa a | DNA nucleotide sequence |
| 42. | EIVLTQSPAT LSLSPGERAT LSCRASQSVS SYLAWYQQKP GQAPRLLVYG ASNRATGIPA RFSGSGSGTD FTLTISSLEP EDFAFYYCQQ RSNWPLTFGG GTKVEIK | AA amino acid sequence |
| 43. | cagagtgtta gcagctat | DNA nucleotide sequence |
| 44. | QSVSSY | AA amino acid sequence |
| 45. | ggtgcatcc | DNA nucleotide sequence |
| 46. | GAS | AA amino acid sequence |
| 47. | cagcagcgta gcaactggcc gctcact | DNA nucleotide sequence |
| 48. | QQRSNWPLT | AA amino acid sequence |
| 49. | cagctgcagc tgcaggagtc gggcccagga ctggtgaagc cttcggagac cctgtccctc acctgcactg tctctggtga ctccatcatc agtaatagtt attactgggg ctggatccgc cagcccccag ggaaggggct ggagtggatt ggcaatttct tttatactgg ggccacctac tacaacccgt ccctcaagag tcgagtcacc atatccgctg acacgtccaa gaatcagttc tccctgaagc tgagctctgt gaccgccgca gacacggctc tgtattattg tgcgagttat aataggaatt accggttcga cccctggggc cagggaaccc tggtcaccgt ctcctca | DNA nucleotide sequence |

-continued

| SEQ ID NO. | Sequence | Description |
|---|---|---|
| 50. | QLQLQESGPG LVKPSETLSL TCTVSGDSII SNSYYWGWIR QPPGKGLEWI GNFFYTGATY YNPSLKSRVT ISADTSKNQF SLKLSSVTAA DTALYYCASY NRNYRFDPWG QGTLVTVSS | AA amino acid sequence |
| 51. | ggtgactcca tcatcagtaa tagttattac | DNA nucleotide sequence |
| 52. | GDSIISNSYY | AA amino acid sequence |
| 53. | ttcttttata ctggggccac c | DNA nucleotide sequence |
| 54. | FFYTGAT | AA amino acid sequence |
| 55. | gcgagttata ataggaatta ccggttcgac ccc | DNA nucleotide sequence |
| 56. | ASYNRNYRFD P | AA amino acid sequence |
| 57. | gacatccaga tgacccagtc tccatcctcc ctgtctgcat ctgtaggaga cagagtcacc atcacttgcc gggcaagtca gagcattagc agctatttaa attggtatca gcagaaacca gggaaagccc ctaagctcct gatctatgct gcatccagtt tgcaaagtgg ggtcccatca aggttcagtg gcagtggatc tgggacagat ttcactctca ccatcagcag tctgcaacct gaagattttg caacttactt ctgtcaacag agttacagta cccctccgat caccttcggc caagggacac gactggagat taaa | DNA nucleotide sequence |
| 58. | DIQMTQSPSS LSASVGDRVT ITCRASQSIS SYLNWYQQKP GKAPKLLIYA ASSLQSGVPS RFSGSGSGTD FTLTISSLQP EDFATYFCQQ SYSTPPITFG QGTRLEIK | AA amino acid sequence |
| 59. | cagagcatta gcagctat | DNA nucleotide sequence |
| 60. | QSISSY | AA amino acid sequence |
| 61. | gctgcatcc | DNA nucleotide sequence |
| 62. | AAS | AA amino acid sequence |
| 63. | caacagagtt acagtacccc tccgatcacc | DNA nucleotide sequence |
| 64. | QQSYSTPPIT | AA amino acid sequence |
| 65. | caggtgcagc tacagcagtg gggcgcagga ctgttgaagc cttcggagac cctgtccctc acctgcgctg tctatggtgg gtccttcagt acttactact ggagctggat ccgccagccc ccagggaagg ggctggagtg gattggagag atcaatcata gtggaaacgc cgactacaac | DNA nucleotide sequence |

-continued

| SEQ ID NO. | Sequence | Description |
|---|---|---|
| | ccgtccctca agagtcgagt ctccatatca gtggacacgt ccaagaacca gttctccctg aggctgagct ctgtgaccgc cgcggacacg gctatttatt actgtgcgag agcgggctat tgtagtagtc ccacctgcta ttcctactac tacttcggta tggacgtctg gggccaaggg accacggtca ccgtctcctc a | |
| 66. | QVQLQQWGAG LLKPSETLSL TCAVYGGSFS TYYWSWIRQP PGKGLEWIGE INHSGNADYN PSLKSRVSIS VDTSKNQFSL RLSSVTAADT AIYYCARAGY CSSPTCYSYY YFGMDVWGQG TTVTVSS | AA amino acid sequence |
| 67. | ggtgggtcct tcagtactta ctac | DNA nucleotide sequence |
| 68. | GGSFSTYY | AA amino acid sequence |
| 69. | atcaatcata gtggaaacgc c | DNA nucleotide sequence |
| 70. | INHSGNA | AA amino acid sequence |
| 71. | gcgagagcgg gctattgtag tagtcccacc tgctattcct actactactt cggtatggac gtc | DNA nucleotide sequence |
| 72. | ARAGYCSSPT CYSYYYFGMD V | AA amino acid sequence |
| 73. | gaaattgtgt tgacgcagtc tccaggcacc ctgtctttgt ctctagggga aagagccacc ctctcctgca gggccagtca gagtgttatc agcagcttct tagcctggta ccagcagaaa cctggccagg ctcccaggct cctcatctat ggtgcatcca gcagggccac tggcttccca gacaggttca gtggcagtgg gtctgggaca gacttcactc tcaccatccg cagactggag cctgaagatt ttgcagtgta ttactgtcag cagtatggta actcaccttg gacgttcggc caagggacca aggtggagat caaa | DNA nucleotide sequence |
| 74. | EIVLTQSPGT LSLSLGERAT LSCRASQSVI SSFLAWYQQK PGQAPRLLIY GASSRATGFP 60 DRFSGSGSGT DETLTIRRLE PEDFAVYYCQ QYGNSPWTFG QGTKVEIK | AA amino acid sequence |
| 75. | cagagtgtta tcagcagctt c | DNA nucleotide sequence |
| 76. | QSVISSF | AA amino acid sequence |
| 77. | ggtgcatcc | DNA nucleotide sequence |
| 78. | GAS | AA amino acid sequence |
| 79. | cagcagtatg gtaactcacc ttggacg | DNA nucleotide sequence |

-continued

| SEQ ID NO. | Sequence | Description |
|---|---|---|
| 80. | QQYGNSPWT | AA amino acid sequence |
| 81. | caggtcacct tgaaggagtc tggtcctgtg ctggtgaaac ccacagagac cctcacgctg<br>acctgcaccg tctctgggtt ctcactcagc aatgctggga tgggtgtgag ctgggtccgt<br>cagcccccctg ggaaggccct ggagtggctt gcacacattt tttcgaatga cgagaagtcc<br>tacagcacat ctctgaggac cagactcacc atctccaagg acacctccaa aagccaggtg<br>gtccttaccg tgaccaactt ggaccctgtg gacacagcca catatttctg tgcacggata<br>ccagagttta ccagctcgtc gtgggctctc tactacttct acggtatgga cgtctggggc<br>caagggacca cggtcaccgt ctcctca | DNA nucleotide sequence |
| 82. | QVTLKESGPV LVKPTETLTL TCTVSGFSLS<br>NAGMGVSWVR QPPGKALEWL AHIFSNDEKS<br>YSTSLRTRLT ISKDTSKSQV VLTVTNLDPV<br>DTATYFCARI PEFTSSSWAL YYFYGMDVWG<br>QGTTVTVSS | AA amino acid sequence |
| 83. | gggttctcac tcagcaatgc tgggatgggt | DNA nucleotide sequence |
| 84. | GFSLSNAGMG | AA amino acid sequence |
| 85. | atttttcga atgacgagaa g | DNA nucleotide sequence |
| 86. | IFSNDEK | AA amino acid sequence |
| 87. | gcacggatac cagagtttac cagctcgtcg tgggctctct actacttcta cggtatggac<br>gtc | DNA nucleotide sequence |
| 88. | ARIPEFTSSS WALYYFYGMD V | AA amino acid sequence |
| 89. | gaaattgtgt tgacgcagtc tccaggcacc ctgtctttgt ctccagggga aagcgccacc<br>ctctcctgca gggccagtca gagtattacc agcacctact tcgcctggta ccagcagaaa<br>cctggccagg ctcccaggct cctcatctat gctacatcca gcagggccac tggcgtccca<br>gacaggttca gtggcagtgg gtctgggacg gacttcactc tcaccatcag cagactggag<br>cctgatgatt ttgcagtgta ttactgtcag caatatggta ggtcaccttg gacgttcggc<br>caagggacca aggtggaagt caaa | DNA nucleotide sequence |
| 90. | EIVLTQSPGT LSLSPGESAT LSCRASQSIT STYFAWYQQK<br>PGQAPRLLIY ATSSRATGVP<br>DRFSGSGSGT DFTLTISRLE PDDFAVYYCQ QYGRSPWTFG<br>QGTKVEVK | AA amino acid sequence |
| 91. | cagagtatta ccagcaccta c | DNA nucleotide sequence |
| 92. | QSITSTY | AA amino acid sequence |
| 93. | gctacatcc | DNA nucleotide sequence |

-continued

| SEQ ID NO. | Sequence | Description |
|---|---|---|
| 94. | ATS | AA amino acid sequence |
| 95. | cagcaatatg gtaggtcacc ttggacg | DNA nucleotide sequence |
| 96. | QQYGRSPWT | AA amino acid sequence |
| 97. | caggttcagc tggtgcagtc tggagctgag gtgaagaagc ctggggcctc agtgaaggtc<br>tcctgcaagg cttctggtta cacctttacc agttatggta tcagctgggt gcgacaggcc<br>cctggacaag ggcttgagtg gatgggatgg atcagcgctt acaatgataa cacaaactat<br>gcacagaagc tccagggcag agtcaccatg accgcagaca catccacgaa tacagcctac<br>atggagctaa ggagcctgag atctgacgac acggccattt attactgtgt gcgatggaat<br>tggggttccg tctactggta cttcgatctc tggggccgtg gcaccctggt cactgtctcc<br>tca | DNA nucleotide sequence |
| 98. | QVQLVQSGAE VKKPGASVKV SCKASGYTFT<br>SYGISWVRQA PGQGLEWMGW ISAYNDNTNY<br>AQKLQGRVTM TADTSTNTAY MELRSLRSDD<br>TAIYYCVRWN WGSVYWYFDL WGRGTLVTVS<br>S | AA amino acid sequence |
| 99. | ggttacacct ttaccagtta tggt | DNA nucleotide sequence |
| 100. | GYTFTSYG | AA amino acid sequence |
| 101. | atcagcgctt acaatgataa caca | DNA nucleotide sequence |
| 102. | ISAYNDNT | AA amino acid sequence |
| 103. | gtgcgatgga attggggttc cgtctactgg tacttcgatc tc | DNA nucleotide sequence |
| 104. | VRWNWGSVYW YFDL | AA amino acid sequence |
| 105. | gaaattgtgt tgacgcagtc tccaggcacc ctgtctttgt ctccagggga aagagccacc<br>ctctcctgca gggccagtca gattattagc agcagctact ttgcctggta ccagcagaaa<br>cctggccagg ctcccaggct cctcatctat ggtgcgtcca gcagggccac tggcatccca<br>gacaggttca gtggcagtgt gtctgggaca gacttcactc tcaccatcag cagactggag<br>cctgaagatt ttgcaatgta tttctgtcag cagtatggta actcaccttg gacgttcggc<br>caagggacca aggtggaaat caaa | DNA nucleotide sequence |
| 106. | EIVLTQSPGT LSLSPGERAT LSCRASQIIS SSYFAWYQQK<br>PGQAPRLLIY GASSRATGIP<br>DRFSGSVSGT DFTLTISRLE PEDFAMYFCQ QYGNSPWTFG<br>QGTKVEIK | AA amino acid sequence |

-continued

| SEQ ID NO. | Sequence | Description |
|---|---|---|
| 107. | cagattatta gcagcagcta c | DNA nucleotide sequence |
| 108. | QIISSSY | AA amino acid sequence |
| 109. | ggtgcgtcc | DNA nucleotide sequence |
| 110. | GAS | AA amino acid sequence |
| 111. | cagcagtatg gtaactcacc ttggacg | DNA nucleotide sequence |
| 112. | QQYGNSPWT | AA amino acid sequence |
| 113. | cagatcacct tgaaggagtc tggtcctacg ctggtgaaac ccacacagac cctcacgctg<br>acttgcacct tctctgggtt ctcactcaac actcatagag tgggtgtagg ctggatccgg<br>cagcccccag gaaaggccct ggagtggctt gcactcattt atgggaatga tgttaagaac<br>tacagcccat ctctggagac caggctcacc atcgccaagg acacctccaa aaaccaggtg<br>gtccttacaa tgaccaacat ggaccctgtg gacacagcca catatttctg ttcgtacata<br>acgggggaag gaatgtactg gggccaggga accctggtca ccgtctcctc a | DNA nucleotide sequence |
| 114. | QITLKESGPT LVKPTQTLTL TCTFSGFSLN THRVGVGWIR QPPGKALEWL ALIYGNDVKN<br>YSPSLETRLT IAKDTSKNQV VLTMTNMDPV DTATYFCSYI TGEGMYWGQG TLVTVSS | AA amino acid sequence |
| 115. | gggttctcac tcaacactca tagagtgggt | DNA nucleotide sequence |
| 116. | GFSLNTHRVG | AA amino acid sequence |
| 117. | atttatggga atgatgttaa g | DNA nucleotide sequence |
| 118. | IYGNDVK | AA amino acid sequence |
| 119. | tcgtacataa cgggggaagg aatgtac | DNA nucleotide sequence |
| 120. | SYITGEGMY | AA amino acid sequence |
| 121. | gatgttgtga tgactcagtc tccactctcc ctgtccgtca cccttggaca gccggcctcc<br>atttcctgta ggtctagtca aaacctcatg tacagtgatg gaaacaccta cttgaattgg<br>tttcaccaga ggccaggcca atctccaagg cgtctaattt ataaggtttc taaccgggac<br>tctggggtcc cagacagatt cagcggcagt gggtcaggca ctgatttcac actgaaaatc | DNA nucleotide sequence |

-continued

| SEQ ID NO. | Sequence | Description |
|---|---|---|
| | agcagggtgg aggctgagga tgttggggtt tattactgca tgcaaggtac acactggtac<br>acatttggcc aggggaccaa gctggagatc aaa | |
| 122. | DVVMTQSPLS LSVTLGQPAS ISCRSSQNLM<br>YSDGNTYLNW FHQRPGQSPR RLIYKVSNRD<br>SGVPDRFSGS GSGTDFTLKI SRVEAEDVGV<br>YYCMQGTHWY TFGQGTKLEI K | AA amino acid sequence |
| 123. | caaaacctca tgtacagtga tggaaacacc tac | DNA nucleotide sequence |
| 124. | QNLMYSDGNT Y | AA amino acid sequence |
| 125. | aaggtttct | DNA nucleotide sequence |
| 126. | KVS | AA amino acid sequence |
| 127. | atgcaaggta cacactggta caca | DNA nucleotide sequence |
| 128. | MQGTHWYT | AA amino acid sequence |
| 129. | caggtgcagc tgcagcagtg gggcgcagga ctattgaagc cttcggagac cctgtccctc<br>acctgcgctg tctatggtgg gtctttcagt ggttattact ggagctggat ccgccagccc<br>ccagggaagg gtctggaatg gattggggaa atcaatcata gaggaaacac caactacaac<br>ccgtccctca agagtcgagt caccatatca ctcgacacgt ccaagaaaca gttctccctg<br>aacctgagtt ctgtgaccgc cgcggacacg gctatgtatt actgtacgag agacgaagaa<br>caggaactac gtttccttga ctactggggc cagggaaccc tggtcaccgt ctcctca | DNA nucleotide sequence |
| 130. | QVQLQQWGAG LLKPSETLSL TCAVYGGSFS<br>GYYWSWIRQP PGKGLEWIGE INHRGNTNYN<br>PSLKSRVTIS LDTSKKQFSL NLSSVTAADT<br>AMYYCTRDEE QELRFLDYWG QGTLVTVSS | AA amino acid sequence |
| 131. | ggtgggtctt tcagtggtta ttac | DNA nucleotide sequence |
| 132. | GGSFSGYY | AA amino acid sequence |
| 133. | atcaatcata gaggaaacac c | DNA nucleotide sequence |
| 134. | INHRGNT | AA amino acid sequence |
| 135. | acgagagacg aagaacagga actacgtttc cttgactac | DNA nucleotide sequence |
| 136. | TRDEEQELRF LDY | AA amino acid sequence |

-continued

| SEQ ID NO. | Sequence | Description |
| --- | --- | --- |
| 137. | gagattgtgt tgacacagtc tccagccacc ctgtctttgt ctccagggga aagagccacc ctctcctgca gggccagtca ggatattagc acctacttag cctggtacca acagagagct ggccaggctc ccaggctcct catctatggt gcttccaaca gggccactgg catcccagcc aggttcagtg gcagtgggtc tgggacagac ttcactctca ccatcagcag cctagagcct gaagattttg cattttatta ctgtcaacag cgcagcaact ggccgctcac tttcggcgga gggaccgagg tggagatcaa a | DNA nucleotide sequence |
| 138. | EIVLTQSPAT LSLSPGERAT LSCRASQDIS TYLAWYQQRA GQAPRLLIYG ASNRATGIPA RFSGSGSGTD FTLTISSLEP EDFAFYYCQQ RSNWPLTFGG GTEVEIK | AA amino acid sequence |
| 139. | caggatatta gcacctac | DNA nucleotide sequence |
| 140. | QDISTY | AA amino acid sequence |
| 141. | ggtgcttcc | DNA nucleotide sequence |
| 142. | GAS | AA amino acid sequence |
| 143. | caacagcgca gcaactggcc gctcact | DNA nucleotide sequence |
| 144. | QQRSNWPLT | AA amino acid sequence |
| 145. | caggtgcagc tacagcagtg gggcgcagga ctgttgaagc cttcggagac cctgtccctc acctgcgttg tccatggtgg gtccttcagt ggttactact ggaactggat ccgccagccc ccagggaagg ggctggagtg gattggggaa atcaatcata gaggaaacac caactacaac ccgtccctca agagtcgagt caccgtatca gaagacacgt ccaagaacca gttctccctg aagctgagct ctttgaccgc cgcggacacg gctgtgtatt actgtgtgag aggagaggat tacgattttt ggagtgatta ttataatgac tactggggcc agggaaccct ggtcaccgtc tcctca | DNA nucleotide sequence |
| 146. | QVQLQQWGAG LLKPSETLSL TCVVHGGSFS GYYWNWIRQP PGKGLEWIGE INHRGNTNYN PSLKSRVTVS EDTSKNQFSL KLSSLTAADT AVYYCVRGED YDFWSDYYND YWGQGTLVTV SS | AA amino acid sequence |
| 147. | ggtgggtcct tcagtggtta ctac | DNA nucleotide sequence |
| 148. | GGSFSGYY | AA amino acid sequence |
| 149. | atcaatcata gaggaaacac c | DNA nucleotide sequence |
| 150. | INHRGNT | AA amino acid sequence |

-continued

| SEQ ID NO. | Sequence | Description |
|---|---|---|
| 151. | gtgagaggag aggattacga tttttggagt gattattata atgactac | DNA nucleotide sequence |
| 152. | VRGEDYDFWS DYYNDY | AA amino acid sequence |
| 153. | gaaattgtgt tgacacagtc tccagccacc ctgtctttgt ctccagggga aagagccacc ctctcctgca gggccagtca gactattagc agctacttag cctggcacca acagaaacct ggccaggctc ccaggctcct catctatgat gcatccaaaa gggccacggg catcccagcc aggttcagtg gcagtgggtc tgggacagac ttcactctca ccatcaccag cctagagcct gaagattttg cagtttatta ctgtcagcag cgtagcaact ggcctctcac tttcggcgga gggaccaagg tggagatcaa a | DNA nucleotide sequence |
| 154. | EIVLTQSPAT LSLSPGERAT LSCRASQTIS SYLAWHQQKP GQAPRLLIYD ASKRATGIPA RFSGSGSGTD FTLTITSLEP EDFAVYYCQQ RSNWPLTFGG GTKVEIK | AA amino acid sequence |
| 155. | cagactatta gcagctac | DNA nucleotide sequence |
| 156. | QTISSY | AA amino acid sequence |
| 157. | gatgcatcc | DNA nucleotide sequence |
| 158. | DAS | AA amino acid sequence |
| 159. | cagcagcgta gcaactggcc tctcact | DNA nucleotide sequence |
| 160. | QQRSNWPLT | AA amino acid sequence |
| 161. | caggtgcagc tacagcagtg gggcgcagga ctgttgccgc cttcggagac cctgtccctc atctgcgctg tctatggtgg gtccttcagt ggttactact ggagctggat ccgccagccc ccagggaagg ggctggagtg gattggggaa atcaatcata gaggaagcac caactacaac ccgtccctca agagtcgagc caccatatca gttgacacgt ccaagaacca gttctccctg aagctgagct ctgtgaccgc cgcggacacg gctgtgtatt actgttcgag aggcgaggat tactatgata gtagtggtta ctcgtactac tttgactact ggggccaggg aaccctggtc accgtctcct ca | DNA nucleotide sequence |
| 162. | QVQLQQWGAG LLPPSETLSL ICAVYGGSFS GYYWSWIRQP PGKGLEWIGE INHRGSTNYN PSLKSRATIS VDTSKNQFSL KLSSVTAADT AVYYCSRGED YYDSSGYSYY FDYWGQGTLV TVSS | AA amino acid sequence |
| 163. | ggtgggtcct tcagtggtta ctac | DNA nucleotide sequence |

-continued

| SEQ ID NO. | Sequence | Description |
|---|---|---|
| 164. | GGSFSGYY | AA amino acid sequence |
| 165. | atcaatcata gaggaagcac c | DNA nucleotide sequence |
| 166. | INHRGST | AA amino acid sequence |
| 167. | tcgagaggcg aggattacta tgatagtagt ggttactcgt actactttga ctac | DNA nucleotide sequence |
| 168. | SRGEDYYDSS GYSYYFDY | AA amino acid sequence |
| 169. | gaaattgtgt tgacacagtc tccagccacc ctgtctttgt ctccagggga aagagccacc ctctcctgca gggccagtca gagtgttagc agctacttag cctggtacca acagaaacct ggccaggctc ccaggctcct catctatgat gcatccaaca gggccactgg catcccagcc aggttcagtg gcagtgggtc tgggacagac ttcactctca ccatcagcag cctagagcct gaagattttg cagtttatta ctgtcagcag cgtagcaact ggccgctcac tttcggcgga gggaccaagg tggagatcaa a | DNA nucleotide sequence |
| 170. | EIVLTQSPAT LSLSPGERAT LSCRASQSVS SYLAWYQQKP GQAPRLLIYD ASNRATGIPA RFSGSGSGTD FTLTISSLEP EDFAVYYCQQ RSNWPLTFGG GTKVEIK | AA amino acid sequence |
| 171. | cagagtgtta gcagctac | DNA nucleotide sequence |
| 172. | QSVSSY | AA amino acid sequence |
| 173. | gatgcatcc | DNA nucleotide sequence |
| 174. | DAS | AA amino acid sequence |
| 175. | cagcagcgta gcaactggcc gctcact | DNA nucleotide sequence |
| 176. | QQRSNWPLT | AA amino acid sequence |
| 177. | caggtgcagc tacagcagtg gggcgcagga ctgttgaggc cttcggagac cctgtccctc acctgcgctg tctatggtgg gtccttcagt ggttactact ggaattggat ccgccagtcc ccagggacgg ggctggagtg gattggggaa atcaatcata gagggaacat caacttcaac ccgtccctca agagtcgagt caccatatca gaggacacgt ccaaaaacca attctccctg aggctgaact ctgtgaccgc cgcggacacg gctgtgtatt actgtgcgag aggagaggat tacgatattt ggagtggtta ttatagggag tactggggcc agggaaccct ggtcaccgtc tcctca | DNA nucleotide sequence |

-continued

| SEQ ID NO. | Sequence | Description |
|---|---|---|
| 178. | QVQLQQWGAG LLRPSETLSL TCAVYGGSFS GYYWNWIRQS PGTGLEWIGE INHRGNINFN PSLKSRVTIS EDTSKNQFSL RLNSVTAADT AVYYCARGED YDIWSGYYRE YWGQGTLVTV SS | AA amino acid sequence |
| 179. | ggtgggtcct tcagtggtta ctac | DNA nucleotide sequence |
| 180. | GGSFSGYY | AA amino acid sequence |
| 181. | atcaatcata gagggaacat c | DNA nucleotide sequence |
| 182. | INHRGNI | AA amino acid sequence |
| 183. | gcgagaggag aggattacga tatttggagt ggttattata gggagtac | DNA nucleotide sequence |
| 184. | ARGEDYDIWS GYYREY | AA amino acid sequence |
| 185. | gaaattgtgt tgacacagtc tccagccacc ctgtctttgt ctccagggga aagagccact ctctcctgca gggccagtca gagtgttagc agctacttag cctggtacca gcagaaacct ggccaggctc ccaggctcct catctatgat gcatccaaga gggccactgg catcccagcc aggttcagtg gcagtgggtc tgggacagac ttcactctca ccatcagcag cctagagcct gaagattttg ctgtttatta ctgtcagcag cgtagcaact ggcctctcgc tttcggcgga gggaccaagg tggagatcaa a | DNA nucleotide sequence |
| 186. | EIVLTQSPAT LSLSPGERAT LSCRASQSVS SYLAWYQQKP GQAPRLLIYD ASKRATGIPA RFSGSGSGTD FTLTISSLEP EDFAVYYCQQ RSNWPLAFGG GTKVEIK | AA amino acid sequence |
| 187. | cagagtgtta gcagctac | DNA nucleotide sequence |
| 188. | QSVSSY | AA amino acid sequence |
| 189. | gatgcatcc | DNA nucleotide sequence |
| 190. | DAS | AA amino acid sequence |
| 191. | cagcagcgta gcaactggcc tctcgct | DNA nucleotide sequence |
| 192. | QQRSNWPLA | AA amino acid sequence |
| 193. | caggtgcagc tacagcagtg gggcgcagga ctgttgaagc cttcggagac cctgtccctc acctgcgctg tctatggtgg gtccttcagt gagttctact ggaactggat ccgccagccc | DNA nucleotide sequence |

-continued

| SEQ ID NO. | Sequence | Description |
|---|---|---|
| | ccagagaagg gcctggagtg gattggggaa atcaatcatc gtggaaacac caactacaac ccgtccctca agagtcgagt caccatatca gtagacatgt ccaagaacca gttctccctg cagctgaact ctgtgaccgt cgcggacacg gctctgtatt actgtgcgtt tggctacgat tttcggagtt cttatgagga cgtctggggc caagggacca cggtcaccgt ctcctca | |
| 194. | QVQLQQWGAG LLKPSETLSL TCAVYGGSFS EFYWNWIRQP PEKGLEWIGE INHRGNTNYN 60 PSLKSRVTIS VDMSKNQFSL QLNSVTVADT ALYYCAFGYD FRSSYEDVWG QGTTVTVSS | AA amino acid sequence |
| 195. | ggtgggtcct tcagtgagtt ctac | DNA nucleotide sequence |
| 196. | GGSFSEFY | AA amino acid sequence |
| 197. | atcaatcatc gtggaaacac c | DNA nucleotide sequence |
| 198. | INHRGNT | AA amino acid sequence |
| 199. | gcgtttggct acgattttcg gagttcttat gaggacgtc | DNA nucleotide sequence |
| 200. | AFGYDFRSSY EDV | AA amino acid sequence |
| 201. | gaaattgtgt tgacacagtc tccagccacc ctgtctttgt ctccagggga aagagccacc ctctcctgca gggccagtca ggatattagc acctacttag cctggcacca acagaaacct ggccagcctc ccaggctcct catctatggt tcatccaaca gggccactgg catcccagcc aggttcagtg gcagtgggtc tgggacagac ttcactctca ccatcagcag cctagagcct gaagattttg cagtttatta ctgtcagcag cgtagcaact ggcctctcac tttcggcgga gggaccaagg tggagatcaa a | DNA nucleotide sequence |
| 202. | EIVLTQSPAT LSLSPGERAT LSCRASQDIS TYLAWHQQKP GQPPRLLIYG SSNRATGIPA 60 RFSGSGSGTD FTLTISSLEP EDFAVYYCQQ RSNWPLTFGG GTKVEIK | AA amino acid sequence |
| 203. | caggatatta gcacctac | DNA nucleotide sequence |
| 204. | QDISTY | AA amino acid sequence |
| 205. | ggttcatcc | DNA nucleotide sequence |
| 206. | GSS | AA amino acid sequence |
| 207. | cagcagcgta gcaactggcc tctcact | DNA nucleotide sequence |

-continued

| SEQ ID NO. | Sequence | Description |
|---|---|---|
| 208. | QQRSNWPLT | AA amino acid sequence |
| 209. | gaggtgcagc tgttggagtc tgggggaggc ttggtacagc cggggggtc cctgagactc<br>tcctgtgcag cctctggatt caccttcaga agctatgcca tgagttgggt ccgccaggct<br>ccagggaagg ggctggagtg ggtctcagtt attagtggtg gtggtggtag gacatactac<br>acagactccg tgaagggccg gttcaccatc tccagagaca attccaagag catgctgtat<br>ctgcaaatga acagcctgag agccgaggac acggccattt attactgtgc gaaagagagg<br>gtaactggaa tagaccacta ctactacggt gtggacgtct ggggccaagg gaccacggtc<br>accgtctcct ca | DNA nucleotide sequence |
| 210. | EVQLLESGGG LVQPGGSLRL SCAASGFTFR<br>SYAMSWVRQA PGKGLEWVSV ISGGGGRTYY 60<br>TDSVKGRFTI SRDNSKSMLY LQMNSLRAED<br>TAIYYCAKER VTGIDHYYYG VDVWGQGTTV 120<br>TVSS | AA amino acid sequence |
| 211. | ggattcacct tcagaagcta tgcc | DNA nucleotide sequence |
| 212. | GFTFRSYA | AA amino acid sequence |
| 213. | attagtggtg gtggtggtag gaca | DNA nucleotide sequence |
| 214. | ISGGGGRT | AA amino acid sequence |
| 215. | gcgaaagaga gggtaactgg aatagaccac tactactacg gtgtggacgt<br>c | DNA nucleotide sequence |
| 216. | AKERVTGIDH YYYGVDV | AA amino acid sequence |
| 217. | gacatccaga tgacccagtc tccatcctcc ctgtctgcat ctgtaggaga cagagtcacc<br>atcacttgcc gggcaagtca gagcattagt agctatttaa attggtatca gcagaaacca<br>gggaaagccc ctaagctcct gatctatgct acatccagtt tgcaaagtgg ggtcccatca<br>cggttcagtg gcagtgcatc tggaacagat ttcactctcg ccatcagcag tctgcaacct<br>gaagattttg caacttacta ctgtcaacag agttacacta cccccctcac tttcggcgga<br>gggaccaagg tggagatcaa a | DNA nucleotide sequence |
| 218. | DIQMTQSPSS LSASVGDRVT ITCRASQSIS<br>SYLNWYQQKP GKAPKLLIYA TSSLQSGVPS 60<br>RFSGSASGTD FTLAISSLQP EDFATYYCQQ<br>SYTTPLTFGG GTKVEIK | AA amino acid sequence |
| 219. | cagagcatta gtagctat | DNA nucleotide sequence |
| 220. | QSISSY | AA amino acid sequence |
| 221. | gctacatcc | DNA nucleotide sequence |

-continued

| SEQ ID NO. | Sequence | Description |
|---|---|---|
| 222. | ATS | AA amino acid sequence |
| 223. | caacagagtt acactacccc cctcact | DNA nucleotide sequence |
| 224. | QQSYTTPLT | AA amino acid sequence |
| 225. | gaggtgcagc tggtggagtc tgggggaggc ttggtacaac ctggagggtc cctgagactt tcctgtgcag cctctggatt tacattcagc agttatgaaa tgaactgggt ccgccaggct ccagggaagg ggctggagtg ggtttcatat atcagtagta gtggtaatac caaagactac gcaggctctg tgaagggccg agtcaccatc tccagagaca acgccaagaa cttactgtat ctgcaaatga acagcctgag agccgaggac acggctgttt atcactgtgc gagagatgga gggcattacg atattttgac tggttccatg tcctactact actacgcttt ggacgtctgg ggccaaggga ccacggtcac cgtctcctca | DNA nucleotide sequence |
| 226. | VQLVESGGG LVQPGGSLRL SCAASGFTFS SYEMNWVRQA PGKGLEWVSY ISSSGNTKDY AGSVKGRVTI SRDNAKNLLY LQMNSLRAED TAVYHCARDG GHYDILTGSM SYYYYALDVW GQGTTVTVSS | AA amino acid sequence |
| 227. | ggatttacat tcagcagtta tgaa | DNA nucleotide sequence |
| 228. | GFTFSSYE | AA amino acid sequence |
| 229. | atcagtagta gtggtaatac caaa | DNA nucleotide sequence |
| 230. | ISSSGNTK | AA amino acid sequence |
| 231. | gcgagagatg gagggcatta cgatattttg actggttcca tgtcctacta ctactacgct ttggacgtc | DNA nucleotide sequence |
| 232. | ARDGGHYDIL TGSMSYYYYA LDV | AA amino acid sequence |
| 233. | gacatccaga tgacccagtc tccatcctcc ctgtctgcat ctgtaggaga cagagtcacc atcacttgcc gggcaagtca gagcattagc agctatttaa attggtatca gcagaaacca gggaaagccc ctaagctcct gatctatgct gcatccagtt tgcaaagtgg ggtcccgtca aggttcagtg gcagtggatc tgggacagat ttcactctca ccatcagcag tctgcaacct gaagattttg caacttacta ctgtcaacag agttacagta cccctccgat caccttcggc caagggacac gactggagat taaa | DNA nucleotide sequence |
| 234. | DIQMTQSPSS LSASVGDRVT ITCRASQSIS SYLNWYQQKP GKAPKLLIYA ASSLQSGVPS RFSGSGSGTD FTLTISSLQP EDFATYYCQQ SYSTPPITFG QGTRLEIK | AA amino acid sequence |

-continued

| SEQ ID NO. | Sequence | Description |
|---|---|---|
| 235. | cagagcatta gcagctat | DNA nucleotide sequence |
| 236 | QSISSY | AA amino acid sequence |
| 237. | gctgcatcc | DNA nucleotide sequence |
| 238. | AAS | AA amino acid sequence |
| 239. | caacagagtt acagtacccc tccgatcacc | DNA nucleotide sequence |
| 240. | QQSYSTPPIT | AA amino acid sequence |
| 241. | gaggtgcagc tggtggagtc tgggggaggc ttggtacagc ctggggggtc cctgagactc<br>tcctgtgcag cctctggatt cacctttaaa acctatgcca tgagctgggt ccgccaggct<br>ccagggaggg ggctggagtg ggtctcaggt attagtggta gtggtagtac ctcatactac<br>gcagactccg tgaagggccg gttcaccatc tccagagaca attacaagaa gacgctgtct<br>ctgcaaatga acagtctgag agccgaggac acggccgttt attactgtgc gctggatata<br>atggcaacgg taggaggtct ctttaacaac tggggccagg gaaccctggt caccgtctcc<br>tca | DNA nucleotide sequence |
| 242. | EVQLVESGGG LVQPGGSLRL SCAASGFTFK<br>TYAMSWVRQA PGRGLEWVSG ISGSGSTSYY<br>ADSVKGRFTI SRDNYKKTLS LQMNSLRAED<br>TAVYYCALDI MATVGGLFNN WGQGTLVTVS<br>S | AA amino acid sequence |
| 243. | ggattcacct ttaaaaccta tgcc | DNA nucleotide sequence |
| 244. | GFTFKTYA | AA amino acid sequence |
| 245. | attagtggta gtggtagtac ctca | DNA nucleotide sequence |
| 246. | ISGSGSTS | AA amino acid sequence |
| 247. | gcgctggata taatggcaac ggtaggaggt ctctttaaca ac | DNA nucleotide sequence |
| 248. | ALDIMATVGG LFNN | AA amino acid sequence |
| 249. | aaattgtgt tgacgcagtc tccaggcacc ctgtctttgt ctccagggga aagagccacc<br>ctctcctgca gggccagtca gagtgttagc agcagctact tagcctggta ccagcagaaa<br>cctggccagg ctcccaggct cctcatctat ggtgcatcca gcagggccac tggcatccca | DNA nucleotide sequence |

-continued

| SEQ ID NO. | Sequence | Description |
|---|---|---|
| | gacaggttca gtggcagtgg gtctgggaca gacttcactc tcaccatcag cagactggag cctgaagatt ttgcagtgta ttactgtcag cagtatggta gctcaccttg gacgttcggc caagggacca aggtggaaat caaa | |
| 250. | EIVLTQSPGT LSLSPGERAT LSCRASQSVS SSYLAWYQQK PGQAPRLLIY GASSRATGIP DRFSGSGSGT DETLTISRLE PEDFAVYYCQ QYGSSPWTFG QGTKVEIK | AA amino acid sequence |
| 251. | cagagtgtta gcagcagcta c | DNA nucleotide sequence |
| 252. | QSVSSSY | AA amino acid sequence |
| 253. | ggtgcatcc | DNA nucleotide sequence |
| 254. | GAS | AA amino acid sequence |
| 255. | cagcagtatg gtagctcacc ttggacg | DNA nucleotide sequence |
| 256. | QQYGSSPWT | AA amino acid sequence |
| 257. | aggtgcagc tggtgcagtc tggggctgag gtgaagaagc ctgggtcctc ggtgaaggtc tcctgcaagg cttctggagg caccttcagc agacatacta tcagctgggt gcgacaggcc cctggacaag ggcttgagtg gatgggaggg atcatcccta tctttggtac agcaaactac gcacacaagt tccagggcag agtcacgatt accacggacg aatccacgag cacagcctac atggagctga gcagcctgag atctgaggac acggccgtat attattgtgc gagagcccct tatacccgac aggggtactt cgatctctgg ggccgtggca ccctggtcac cgtctcctca | DNA nucleotide sequence |
| 258. | QVQLVQSGAE VKKPGSSVKV SCKASGGTFS RHTISWVRQA PGQGLEWMGG IIPIFGTANY AHKFQGRVTI TTDESTSTAY MELSSLRSED TAVYYCARAP YTRQGYFDLW GRGTLVTVSS | AA amino acid sequence |
| 259. | ggaggcacct tcagcagaca tact | DNA nucleotide sequence |
| 260 | GGTFSRHT | AA amino acid sequence |
| 261. | atcatcccta tctttggtac agca | DNA nucleotide sequence |
| 262. | IIPIFGTA | AA amino acid sequence |
| 263. | gcgagagccc cttatacccg acaggggtac ttcgatctc | DNA nucleotide sequence |
| 264. | ARAPYTRQGY FDL | AA amino acid sequence |

-continued

| SEQ ID NO. | Sequence | Description |
|---|---|---|
| 265. | gacatcgtga tgacccagtc tccagactcc ctggctgtgt ctctgggcga gagggccacc atcaactgca agtccagcca gagtgtttta tacagctcca acaataagaa ctacttagct tggtaccagc agaaaccagg acagcctcct aagctactca tttactgggc atctacccgg gaatccgggg tccctgaccg attcagtggc agcgggtctg ggacagattt cactctcacc atcagcagcc tgcaggctga agatgtggca gtttattact gtcagcaaga ttatagtact ccgtggacgt tcggccaagg gaccaaggtg gaaatcaaa | DNA nucleotide sequence |
| 266. | DIVMTQSPDS LAVSLGERAT INCKSSQSVL YSSNNKNYLA WYQQKPGQPP KLLIYWASTR ESGVPDRFSG SGSGTDFTLT ISSLQAEDVA VYYCQQDYST PWTFGQGTKV EIK | AA amino acid sequence |
| 267. | cagagtgttt tatacagctc caacaataag aactac | DNA nucleotide sequence |
| 268. | QSVLYSSNNK NY | AA amino acid sequence |
| 269. | tgggcatct | DNA nucleotide sequence |
| 270. | WAS | AA amino acid sequence |
| 271. | cagcaagatt atagtactcc gtggacg | DNA nucleotide sequence |
| 272. | QQDYSTPWT | AA amino acid sequence |
| 273. | caggtgcagc tggtgcagtc tggggctgag gtgaagaagc ctggggcctc agtgaaggtt tcctgcaagg catctggata caccttcacc aactactata tacactgggt gcgacaggcc cctggacaag ggcttgactg gatgggaatt atcaaccctg gtggtggtaa cacaaactac gcacagaagt tcctgggcag agtcaccatg accagggaca cgtccacgac cacagtctac atggagctga gcagcctgag atctgaggac acggccatat attactgtgc gagagaaaac tggaactctt actttgacaa ctggggccag ggaaccctgg tcaccgtctc ctca | DNA nucleotide sequence |
| 274. | QVQLVQSGAE VKKPGASVKV SCKASGYTFT NYYIHWVRQA PGQGLDWMGI INPGGGNTNY 60 AQKFLGRVTM TRDTSTTTVY MELSSLRSED TAIYYCAREN WNSYFDNWGQ GTLVTVSS | AA amino acid sequence |
| 275. | ggatacacct tcaccaacta ctat | DNA nucleotide sequence |
| 276. | GYTFTNYY | AA amino acid sequence |
| 277. | atcaaccctg gtggtggtaa caca | DNA nucleotide sequence |
| 278. | INPGGGNT | AA amino acid sequence |

-continued

| SEQ ID NO. | Sequence | Description |
|---|---|---|
| 279. | gcgagagaaa actggaactc ttactttgac aac | DNA nucleotide sequence |
| 280. | ARENWNSYFD N | AA amino acid sequence |
| 281. | gacatcgtga tgacccagtc tccagactcc ctggctgtgt ctctgggcga gagggccacc atcaactgca agtccagcca gagtgtttta tacagctcca acaataagaa cttcttagct tggtaccagc agaaaccagg acagcctcct aagctgctca tttactgggc atctacccgg gaatccgggg tccctgaccg attcagtggc agcgggtctg ggacagattt cactctcacc atcagcagcc tgcaggctga agatgtggca ctttattact gtcagcaata ttatggtgct ccgtggacgt tcggccaagg gaccaaggtg gaaatcaaa | DNA nucleotide sequence |
| 282. | DIVMTQSPDS LAVSLGERAT INCKSSQSVL YSSNNKNFLA WYQQKPGQPP KLLIYWASTR ESGVPDRFSG SGSGTDFTLT ISSLQAEDVA LYYCQQYYGA PWTFGQGTKV EIK | AA amino acid sequence |
| 283. | cagagtgttt tatacagctc caacaataag aacttc | DNA nucleotide sequence |
| 284. | QSVLYSSNNK NF | AA amino acid sequence |
| 285. | tgggcatct | DNA nucleotide sequence |
| 286. | WAS | AA amino acid sequence |
| 287. | cagcaatatt atggtgctcc gtggacg | DNA nucleotide sequence |
| 288. | QQYYGAPWT | AA amino acid sequence |
| 289. | caggtccagc tggtgcagtc tggggctgag gtgaagaagc ctgggtcctc ggtgaaggtc tcctgcaagg cttctggagg caccttcagc agctatacta tcaactgggt gcgacaggcc cctggacaag ggcttgagtg gatgggaggg atcatcccta tctttggtat agcaaactac gcacagaagt tccagggcag agtcacgatt accacggacg aatccacgaa cacagcctac atggagctga gcagcctgag atctgaggac acggccattt attactgtgc gagagcgaga tatggttcgg ggagttatga ctactggggc cagggaaccc tggtcaccgt ctcctca | DNA nucleotide sequence |
| 290. | QVQLVQSGAE VKKPGSSVKV SCKASGGTFS SYTINWVRQA PGQGLEWMGG IIPIFGIANY AQKFQGRVTI TTDESTNTAY MELSSLRSED TAIYYCARAR YGSGSYDYWG QGTLVTVSS | AA amino acid sequence |
| 291. | ggaggcacct tcagcagcta tact | DNA nucleotide sequence |
| 292. | GGTFSSYT | AA amino acid sequence |

-continued

| SEQ ID NO. | Sequence | Description |
|---|---|---|
| 293. | atcatcccta tctttggtat agca | DNA nucleotide sequence |
| 294. | IIPIFGIA | AA amino acid sequence |
| 295. | gcgagagcga gatatggttc ggggagttat gactac | DNA nucleotide sequence |
| 296. | ARARYGSGSY DY | AA amino acid sequence |
| 297. | gacatcgtga tgacccagtc tccagactcc ctggctgtgt ctctgggcga gagggccacc atcaactgca agtccagcca gagtgtttta tacacctcca acaataagaa ctacttagct tggtaccagc agaaaccagg acagcctcct aagctgctca tttactgggc atctacccgg gaatccgggg tccctgaccg attcagtggc agcgggtctg ggacagattt cactctcacc atcagcagcc tgcaggctga agatgtggca gtttattact gtcagcaata ttataatact ccatggacgt tcggccaagg gaccaaggtg gaaatcaaa | DNA nucleotide sequence |
| 298. | DIVMTQSPDS LAVSLGERAT INCKSSQSVL YTSNNKNYLA WYQQKPGQPP KLLIYWASTR ESGVPDRFSG SGSGTDFTLT ISSLQAEDVA VYYCQQYYNT PWTFGQGTKV EIK | AA amino acid Sequence |
| 299. | cagagtgttt tatacacctc caacaataag aactac | DNA nucleotide sequence |
| 300. | QSVLYTSNNK NY | AA amino acid sequence |
| 301. | tgggcatct | DNA nucleotide sequence |
| 302. | WAS | AA amino acid sequence |
| 303. | cagcaatatt ataatactcc atggacg | DNA nucleotide sequence |
| 304. | QQYYNTPWT | AA amino acid sequence |
| 305. | cagatcacct tgaaggagtc tggtcctacg ctggtgaaac ccacacagac cctcacgctg acctgcacct tctctgggtt ctcactcagc actaatggag tgggtgtggg ctggatccgt cagcccccag gaaaggccct ggagtggctt ggaatcattt attggaatga tgataagcgc tacagcccat ctctgaggag cagactcacc atcaccaagg acacctccaa aaaccaggtg gtccttacaa tgaccaacat ggaccctgtg gacacagcca catattactg tgcacacaga ggcctcttcg gaggttggtt cgacccctgg ggccagggaa ccctggtcac cgtctcctca | DNA nucleotide sequence |
| 306. | QITLKESGPT LVKPTQTLTL TCTFSGFSLS TNGVGVGWIR QPPGKALEWL GIIYWNDDKR YSPSLRSRLT ITKDTSKNQV VLTMTNMDPV DTATYYCAHR GLFGGWFDPW GQGTLVTVSS | AA amino acid sequence |

-continued

| SEQ ID NO. | Sequence | Description |
|---|---|---|
| 307. | gggttctcac tcagcactaa tggagtgggt | DNA nucleotide sequence |
| 308. | GFSLSTNGVG | AA amino acid sequence |
| 309. | atttattgga atgatgataa g | DNA nucleotide sequence |
| 310. | IYWNDDK | AA amino acid sequence |
| 311. | gcacacagag gcctcttcgg aggttggttc gacccc | DNA nucleotide sequence |
| 312. | AHRGLFGGWF DP | AA amino acid sequence |
| 313. | gacatccaga tgacccagtc tccatcctcc ctgtctgcat ctgtaggaga cagagtcacc atcacttgcc gggcaagtca gagcattagc aggtatttaa attggtatca gcagaaacca gggaaagccc ctaacctcct gatctttgct gcatccagtt tgcaaagtgg ggtcccatca aggttcagtg gcagtggatc tgggacagat ttcactctca ccatcagcag tctgcaacct gaagattttg caacttactt ctgtcaacag agttacaata ccccgctcac tttcggcgga gggaccaagg tggagatcaa a | DNA nucleotide sequence |
| 314. | DIQMTQSPSS LSASVGDRVT ITCRASQSIS RYLNWYQQKP GKAPNLLIFA ASSLQSGVPS RFSGSGSGTD FTLTISSLQP EDFATYFCQQ SYNTPLTFGG GTKVEIK | AA amino acid sequence |
| 315. | cagagcatta gcaggtat | DNA nucleotide sequence |
| 316. | QSISRY | AA amino acid sequence |
| 317. | gctgcatcc | DNA nucleotide sequence |
| 318. | AAS | AA amino acid sequence |
| 319. | caacagagtt acaatacccc gctcact | DNA nucleotide sequence |
| 320. | QQSYNTPLT | AA amino acid sequence |
| 321. | gaggtgcagc tggtggagtc tgggggaggc ttggtacagc cggggggtc cctgagactc tcctgtgcaa tctctggatt cacctttagg agttatgcca tgacctgggt ccgccaggct ccagggaagg cgctggagtg ggtctcagtt attagtggta gcggtggtaa cacatactac gcagactccg tgaagggccg gttcaccgtc tccagagaca attccaggaa cacgctgtat | DNA nucleotide sequence |

-continued

| SEQ ID NO. | Sequence | Description |
|---|---|---|
| | ctgcaaatga acagcctgag agccgaggac acggccgtat atttctgttc gaaagttgca gcagctaata attactatta cgctttggac gtctggggcc aagggaccac ggtcaccgtc tcctca | |
| 322. | EVQLVESGGG LVQPGGSLRL SCAISGFTFR SYAMTWVRQA PGKALEWVSV ISGSGGNTYY ADSVKGRFTV SRDNSRNTLY LQMNSLRAED TAVYFCSKVA AANNYYYALD VWGQGTTVTV SS | AA amino acid sequence |
| 323. | ggattcacct ttaggagtta tgcc | DNA nucleotide sequence |
| 324. | GFTFRSYA | AA amino acid sequence |
| 325. | attagtggta gcggtggtaa caca | DNA nucleotide sequence |
| 326. | ISGSGGNT | AA amino acid sequence |
| 327. | tcgaaagttg cagcagctaa taattactat tacgctttgg acgtc | DNA nucleotide sequence |
| 328. | SKVAAANNYY YALDV | AA amino acid sequence |
| 329. | gatattgtga tgactcagtc tccactctcc ctgcccgtca cccctggaga gccggcctcc atctcctgca ggtctagtca gagcctcctg catagtaatg gatacaagta tttggattgg tacctgcaga agccagggca gtctccacaa ctcctgatct atttggtttc taatcgggcc tccggggtcc ctgacaggtt cagtggcagt ggatcaggca cagattttac actgaaaatc agcagagtgg aggctgagga tgttggggtt tattattgca tgcaagctct acaaactccg tacacttttg gccaggggac caagctggag atcaaa | DNA nucleotide sequence |
| 330. | DIVMTQSPLS LPVTPGEPAS ISCRSSQSLL HSNGYKYLDW YLQKPGQSPQ LLIYLVSNRA SGVPDRFSGS GSGTDFTLKI SRVEAEDVGV YYCMQALQTP YTFGQGTKLE IK | AA amino acid sequence |
| 331. | cagagcctcc tgcatagtaa tggatacaag tat | DNA nucleotide sequence |
| 332. | QSLLHSNGYK Y | AA amino acid sequence |
| 333. | ttggtttct | DNA nucleotide sequence |
| 334. | LVS | AA amino acid sequence |
| 335. | atgcaagctc tacaaactcc gtacact | DNA nucleotide sequence |
| 336. | MQALQTPYT | AA amino acid sequence |

-continued

| SEQ ID NO. | Sequence | Description |
|---|---|---|
| 337. | caggtgcagc tggtggagtc tgggggaggc gtggtccagc ctgggaggtc cctgagactc tcctgtgtag cgtctggatt caccttcagt aactatggca tgcactgggt ccgccaggct ccaggcaagg ggctggagtg ggtggcagtt atatggaatg atggaagtaa taaatactat gcagactccg tgaagggccg attcaccatc tccagagaca attccaagaa cacgctgtat ctccaagtga gcagcctgag agccgatgac acggctgtat attactgtgc gagggacgga gaggtcgaat atagcagctc gaattacaac tactacggtc tggatgtctg gggccaaggg accacggtca ccgtctcctc a | DNA nucleotide sequence |
| 338. | QVQLVESGGG VVQPGRSLRL SCVASGFTFS NYGMHWVRQA PGKGLEWVAV IWNDGSNKYY ADSVKGRFTI SRDNSKNTLY LQVSSLRADD TAVYYCARDG EVEYSSSNYN YYGLDVWGQG TTVTVSS | AA amino acid sequence |
| 339. | ggattcacct tcagtaacta tggc | DNA nucleotide sequence |
| 340. | GFTFSNYG | AA amino acid sequence |
| 341. | atatggaatg atggaagtaa taaa | DNA nucleotide sequence |
| 342. | IWNDGSNK | AA amino acid sequence |
| 343. | gcgagggacg gagaggtcga atatagcagc tcgaattaca actactacgg tctggatgtc | DNA nucleotide sequence |
| 344. | ARDGEVEYSS SNYNYYGLDV | AA amino acid sequence |
| 345. | gacatccaga tgacccagtc tccatcctcc ctgtctgcat ctgtaggaga cagagtcacc atcacttgcc aggcgagtca ggacattagc aactatttaa attggtatca gcagaaacca gggaaagccc ctaaactcct gatctacgat gcatccaatt tggaaacagg ggtcccatca aggttcagtg gaagtggatc tgggacagat tttactttca ccatcagcag cctgcagcct gaagatattg taacatatta ctgtcaacag tatgatgatc tcccgatcac cttcggccaa gggacacgac tcgagattaa a | DNA nucleotide sequence |
| 346. | DIQMTQSPSS LSASVGDRVT ITCQASQDIS NYLNWYQQKP GKAPKLLIYD ASNLETGVPS RFSGSGSGTD FTFTISSLQP EDIVTYYCQQ YDDLPITFGQ GTRLEIK | AA amino acid sequence |
| 347. | caggacatta gcaactat | DNA nucleotide sequence |
| 348. | QDISNY | AA amino acid sequence |
| 349. | gatgcatcc | DNA nucleotide sequence |

-continued

| SEQ ID NO. | Sequence | Description |
|---|---|---|
| 350. | DAS | AA amino acid sequence |
| 351. | caacagtatg atgatctccc gatcacc | DNA nucleotide sequence |
| 352. | QQYDDLPIT | AA amino acid sequence |
| 353. | gaggtgcagc tggtggagtc tgggggaggc ttggtacagc ctggggggtc cctgagactc tcctgtgcag cctctggatt ctcctttcat aattttgcca tgaactgggt ccgccaggct ccagggaagg ggctggagtg ggtctcagtt attactggta gtggtactag cacacactac gcagactccg tgaagggccg gttcaccatc tccagagaca attccaagaa aacgctatat ctgcaaatga atagcctgag agccgaggac acggccgtat attactgtgc gaaagatcgg ggctatgatt atagtggttc ttactacaac tggttcgacc cctggggcca gggaaccctg gtcaccgtct cctca | DNA nucleotide sequence |
| 354. | EVQLVESGGG LVQPGGSLRL SCAASGFSFH NFAMNWVRQA PGKGLEWVSV ITGSGTSTHY ADSVKGRFTI SRDNSKKTLY LQMNSLRAED TAVYYCAKDR GYDYSGSYYN WFDPWGQGTL VTVSS | AA amino acid sequence |
| 355. | ggattctcct ttcataattt tgcc | DNA nucleotide sequence |
| 356. | GFSFHNFA | AA amino acid sequence |
| 357. | attactggta gtggtactag caca | DNA nucleotide sequence |
| 358. | ITGSGTST | AA amino acid sequence |
| 359. | gcgaaagatc ggggctatga ttatagtggt tcttactaca actggttcga cccc | DNA nucleotide sequence |
| 360. | AKDRGYDYSG SYYNWFDP | AA amino acid sequence |
| 361. | gacatccaga tgacccagtc tccatcctcc ctgtctgcat ctgtaggaga cagaatcacc atcacttgcc gggcaagtca gagtattagc agctatttaa attggtatca gcagaaacca gggaaagccc ctaaactcct gatctttgct gcatcaaatt tgcaaagtgg ggtcccatca aggttcagtg gcagtggatc tgggacagat ttcactctca ccatcagtag tctgcaacct gaagattttg caacttacta ctgtcaacag agttacagta ccccatcctt attcactttc ggccctggga ccaaagtgga tatcaaa | DNA nucleotide sequence |
| 362. | DIQMTQSPSS LSASVGDRIT ITCRASQSIS SYLNWYQQKP GKAPKLLIFA ASNLQSGVPS RFSGSGSGTD FTLTISSLQP EDFATYYCQQ SYSTPSLFTF GPGTKVDIK | AA amino acid sequence |
| 363. | cagagtatta gcagctat | DNA nucleotide sequence |

-continued

| SEQ ID NO. | Sequence | Description |
|---|---|---|
| 364. | QSISSY | AA amino acid sequence |
| 365. | gctgcatca | DNA nucleotide sequence |
| 366. | AAS | AA amino acid sequence |
| 367. | caacagagtt acagtacccc atccttattc act | DNA nucleotide sequence |
| 368. | QQSYSTPSLF T | AA amino acid sequence |
| 369. | gaggtgcagc tggtggagtc tgggggaggc ttggtacagc ctggagggtc cctgagactc tcctgtgcag tctctggatt caccttcagt agttacgaga tgaactgggt ccgccaggct ccagggaagg ggctggaatg ggtttcacac attagtagta gtggaagtac catatactac gcagactctg tgaagggccg attcaccatg tccagagaca acgccaagaa ctcactgtat ctgcaaatga acagcctgag agccgaggac acggctgttt attactgtgc gagagatggg aatatctgga gtggttatta tgccgcctac tactictacg gtatggacgt ctggggccaa gggaccacgg tcaccgtctc ctca | DNA nucleotide sequence |
| 370. | EVQLVESGGG LVQPGGSLRL SCAVSGFTFS SYEMNWVRQA PGKGLEWVSH ISSSGSTIYY ADSVKGRFTM SRDNAKNSLY LQMNSLRAED TAVYYCARDG NIWSGYYAAY YFYGMDVWGQ GTTVTVSS | AA amino acid sequence |
| 371. | ggattcacct tcagtagtta cgag | DNA nucleotide sequence |
| 372. | GFTFSSYE | AA amino acid sequence |
| 373. | attagtagta gtggaagtac cata | DNA nucleotide sequence |
| 374. | ISSSGSTI | AA amino acid sequence |
| 375. | gcgagagatg ggaatatctg gagtggttat tatgccgcct actacttcta cggtatggac gtc | DNA nucleotide sequence |
| 376. | ARDGNIWSGY YAAYYFYGMD V | AA amino acid sequence |
| 377. | gatattgtga tgacccagac tccactctcc tcacctgtca cccttggaca gccggcctcc atctcctgca ggtctagtca aagcctcgta cacagtgatg gaaaaaccta cttgagttgg cttcagcaga ggccaggcca gcctccaaga ctcctaattt ataagatttc taaccggttc tctggggtcc cagacagaat cagtggcagt ggggcaggga cagatttcac actgaaaatc agcagggtgg aagctgagga tgtcggggtt tattactgca tgcaagctgt acaatttcct cggacgttcg gccaagggac caaggtggaa atcaaa | DNA nucleotide sequence |

-continued

| SEQ ID NO. | Sequence | Description |
|---|---|---|
| 378. | DIVMTQTPLS SPVTLGQPAS ISCRSSQSLV HSDGKTYLSW LQQRPGQPPR LLIYKISNRF SGVPDRISGS GAGTDFTLKI SRVEAEDVGV YYCMQAVQFP RTFGQGTKVE IK | AA amino acid sequence |
| 379. | caaagcctcg tacacagtga tggaaaaacc tac | DNA nucleotide sequence |
| 380. | QSLVHSDGKT Y | AA amino acid sequence |
| 381. | aagatttct | DNA nucleotide sequence |
| 382. | KIS | AA amino acid sequence |
| 383. | atgcaagctg tacaatttcc tcggacg | DNA nucleotide sequence |
| 384. | MQAVQFPRT | AA amino acid sequence |
| 385. | caggtgcagc tacagcagtg gggcgcagga ctgttgaacc cttcggagac cctgtccctc acctgcgctg tctatggtgg ggccttcagt gattactact ggaattggat ccgccagccc ccagggaagg ggctggagtg gattggggaa atcaatcatc gcggaagcac caactacaac ccgtccctca agagtcgtgt caccatttca gttgacacgt ccaagaacca gttctccctg aggatgagct ctgtgaccgc cgcggacgcg gctgtgtatt actgtgcgag aggagaggat tacgatattt ggaatggtta ttatcaggaa aaatggggcc agggaaccct ggtcaccgtc tcctca | DNA nucleotide sequence |
| 386. | QVQLQQWGAG LLNPSETLSL TCAVYGGAFS DYYWNWIRQP PGKGLEWIGE INHRGSTNYN PSLKSRVTIS VDTSKNQFSL RMSSVTAADA AVYYCARGED YDIWNGYYQE KWGQGTLVTV SS | AA amino acid sequence |
| 387. | ggtggggcct tcagtgatta ctac | DNA nucleotide sequence |
| 388. | GGAFSDYY | AA amino acid sequence |
| 389. | atcaatcatc gcggaagcac c | DNA nucleotide sequence |
| 390. | INHRGST | AA amino acid sequence |
| 391. | gcgagaggag aggattacga tatttggaat ggttattatc aggaaaaa | DNA nucleotide sequence |
| 392. | ARGEDYDIWN GYYQEK | AA amino acid sequence |

-continued

| SEQ ID NO. | Sequence | Description |
|---|---|---|
| 393. | gaaattgtgt tgacacagtc tccagccacc ctgtctttgt ctccagggga aagagccacc ctctcctgca gggccagtca gagtattagc acctacttag cctggtacca acagaagcct ggccaggctc ccaggctcct catctatgat gcatccaaga gggccactgg catcccagcc aggttcagtg gcagtgggtc tgggacagac ttcactctca ccatcagcag cctagagcct gaagattttg tagtttatta ctgtcaccag cgtagcaact ggcctctcac tttcggcgga gggaccaagg tggagatcaa a | DNA nucleotide sequence |
| 394. | EIVLTQSPAT LSLSPGERAT LSCRASQSIS TYLAWYQQKP GQAPRLLIYD ASKRATGIPA RFSGSGSGTD FTLTISSLEP EDFVVYYCHQ RSNWPLTFGG GTKVEIK | AA amino acid sequence |
| 395. | cagagtatta gcacctac | DNA nucleotide sequence |
| 396. | QSISTY | AA amino acid sequence |
| 397. | gatgcatcc | DNA nucleotide sequence |
| 398. | DAS | AA amino acid sequence |
| 399. | caccagcgta gcaactggcc tctcact | DNA nucleotide sequence |
| 400. | HQRSNWPLT | AA amino acid sequence |
| 401. | caggtgcagc tgcaggagtc ggggccagga ctggtgaagc cttcggagac cctgtccctc acctgcactg tctctggtgg ttccttcagt agttactact ggagttggct ccggcagccc ccaggaaagg ggctggagtg gattggatat atcttttaca gtgggagtac cgactacaac ccctccctca agagtcgagt caccatttca gtagacacgt ccaagaagca gttctccctg aagctgacct ctgtgaccgc tgcggacacg gccgtctatt actgtgcgcg aacaataagt acgtggtggt tcgcccccctg gggccaggga accctggtca ccgtctcctc a | DNA nucleotide sequence |
| 402. | QVQLQESGPG LVKPSETLSL TCTVSGGSFS SYYWSWLRQP PGKGLEWIGY IFYSGSTDYN PSLKSRVTIS VDTSKKQFSL KLTSVTAADT AVYYCARTIS TWWFAPWGQG TLVTVSS | AA amino acid sequence |
| 403. | ggtggttcct tcagtagtta ctac | DNA nucleotide sequence |
| 404. | GGSFSSYY | AA amino acid sequence |
| 405. | atcttttaca gtgggagtac c | DNA nucleotide sequence |
| 406. | IFYSGST | AA amino acid sequence |

-continued

| SEQ ID NO. | Sequence | Description |
|---|---|---|
| 407. | gcgcgaacaa taagtacgtg gtggttcgcc ccc | DNA nucleotide sequence |
| 408. | ARTISTWWFA P | AA amino acid sequence |
| 409. | gaaatagtga tgacacagtc tccagccacc ctgtctgtgt ctccagggg aagagccacc ctctcctgca gggccagtca gagtgttagc aacaacgtag cctggtacca gcagaaacct ggccaggctc ccaggctcct catctatggt gcatccacca gggccactgg tatcccaggc aggttcagtg gcagtgggtc tggaacagag ttcactctca ccatcagcag cctgcagtct gaagattttg cagtttattc ctgtcagcag tataataact ggctcacttt cggcggaggg accaaggtgg agatcaaa | DNA nucleotide sequence |
| 410. | EIVMTQSPAT LSVSPGGRAT LSCRASQSVS NNVAWYQQKP GQAPRLLIYG ASTRATGIPG RFSGSGSGTE FTLTISSLQS EDFAVYSCQQ YNNWLTFGGG TKVEIK | AA amino acid sequence |
| 411. | cagagtgtta gcaacaac | DNA nucleotide sequence |
| 412. | QSVSNN | AA amino acid sequence |
| 413. | ggtgcatcc | DNA nucleotide sequence |
| 414. | GAS | AA amino acid sequence |
| 415. | cagcagtata ataactggct cact | DNA nucleotide sequence |
| 416. | QQYNNWLT | AA amino acid sequence |
| 417. | caggtgcagc tggtggagtc tgggggaggc gtggtccagc ctgggaggtc cctgagactc tcctgtgtag cgtctggatt cactttcagt agttatggca tgcactgggt ccgccaggct ccaggcaagg ggctggagtg ggtggcaatt atatggtatg atggaagtaa taaatactat gcagactccg tgaagggccg attcaccata tccagagaca attccaagaa cacacagtat ctgcaaatga acagcctgag agccgaggac acggctgtgt attactgtgc gtcagtagct acgtctgggg acttcgacta ctacggtatg gacgtctggg gccaagggac cacggtcacc gtctcctca | DNA nucleotide sequence |
| 418. | QVQLVESGGG VVQPGRSLRL SCVASGFTFS SYGMHWVRQA PGKGLEWVAI IWYDGSNKYY ADSVKGRFTI SRDNSKNTQY LQMNSLRAED TAVYYCASVA TSGDFDYYGM DVWGQGTTVT VSS | AA amino acid sequence |
| 419. | ggattcactt tcagtagtta tggc | DNA nucleotide sequence |
| 420. | GFTFSSYG | AA amino acid sequence |

-continued

| SEQ ID NO. | Sequence | Description |
|---|---|---|
| 421. | atatggtatg atggaagtaa taaa | DNA nucleotide sequence |
| 422. | IWYDGSNK | AA amino acid sequence |
| 423. | gcgtcagtag ctacgtctgg ggacttcgac tactacggta tggacgtc | DNA nucleotide sequence |
| 424. | ASVATSGDFD YYGMDV | AA amino acid sequence |
| 425. | gaaattgtgt tgacacagtc tccagccacc ctgtctttgt ctccagggga aagaaccacc ctctcctgca gggccagtca gagaattagc acctacttag cctggtatca acagaaacct ggccaggctc ccaggctcct catctatgat gcatccaaaa gggccactgg catcccagcc aggttcagtg gtagtgggtc tgggacaggc ttcactctca ccatcagcag cctagagcct gaagattttg cagtttatta ctgtcagcag cgtagtaact ggcctctcac tttcggcgga gggaccaagg tggagatcaa a | DNA nucleotide sequence |
| 426. | EIVLTQSPAT LSLSPGERTT LSCRASQRIS TYLAWYQQKP GQAPRLLIYD ASKRATGIPA RFSGSGSGTG FTLTISSLEP EDFAVYYCQQ RSNWPLTFGG GTKVEIK | AA amino acid sequence |
| 427. | cagagaatta gcacctac | DNA nucleotide sequence |
| 428. | QRISTY | AA amino acid sequence |
| 429. | gatgcatcc | DNA nucleotide sequence |
| 430. | DAS | AA amino acid sequence |
| 431. | cagcagcgta gtaactggcc tctcact | DNA nucleotide sequence |
| 432. | QQRSNWPLT | AA amino acid sequence |
| 433. | gaggtgcagc tggtgcagtc tggagcagag gtgagaaagc ccggggagtc tctgaagatc tcctgtaagg gttctggata cagctttact aactactgga tcgtctgggt gcgccagatg cccgggaaag gcctggagtg gatggggatc atctatcctg gtgactctga taccagatac agcccgtcct tccaaggcca ggtcaccatc tcagccgaca agtccatcag caccgcctac ctgcagtgga gcagcctgaa ggcctcggac accgccatgt attactgtgc gagacgggat acgatttcc cttcctatcc cctctggggc cagggaaccc tggtcaccgt ctcctca | DNA nucleotide sequence |
| 434. | EVQLVQSGAE VRKPGESLKI SCKGSGYSFT NYWIVWVRQM PGKGLEWMGI IYPGDSDTRY SPSFQGQVTI SADKSISTAY LQWSSLKASD TAMYYCARRD TIFPSYPLWG QGTLVTVSS | AA amino acid sequence |

-continued

| SEQ ID NO. | Sequence | Description |
|---|---|---|
| 435. | ggatacagct ttactaacta ctgg | DNA nucleotide sequence |
| 436. | GYSFTNYW | AA amino acid sequence |
| 437. | atctatcctg gtgactctga tacc | DNA nucleotide sequence |
| 438. | IYPGDSDT | AA amino acid sequence |
| 439. | gcgagacggg atacgatttt cccttcctat cccctc | DNA nucleotide sequence |
| 440. | ARRDTIFPSY PL | AA amino acid sequence |
| 441. | gatattgtga tgactcagtc tcctctctcc ctgcccgtca cccctggaga gccggcctcc atctcctgca ggtctagtca gagcctcctg aatagtaatg gatacaactt tttggattgg tacctgcaga agccagggca gtctccacaa ctcctgatct atttggtttc taatcgggcc tccggggtcc ctgacaggtt cagtggcagt ggatcaggca cagattttac actgaaaatc agcagagtgg aggctgagga tattggggtt tattactgca tgcaagctct ccaaactccg atcaccttcg gccaagggac acgactggag attaaa | DNA nucleotide sequence |
| 442. | DIVMTQSPLS LPVTPGEPAS ISCRSSQSLL NSNGYNFLDW YLQKPGQSPQ LLIYLVSNRA SGVPDRFSGS GSGTDFTLKI SRVEAEDIGV YYCMQALQTP ITFGQGTRLE IK | AA amino acid sequence |
| 443. | cagagcctcc tgaatagtaa tggatacaac ttt | DNA nucleotide sequence |
| 444. | QSLLNSNGYN F | AA amino acid sequence |
| 445. | ttggtttct | DNA nucleotide sequence |
| 446. | LVS | AA amino acid sequence |
| 447. | atgcaagctc tccaaactcc gatcacc | DNA nucleotide sequence |
| 448. | MQALQTPIT | AA amino acid sequence |
| 449. | cagatcacct tgaaggagtc tggtcctacg ctggtgaaac ccacacagac cctcacgctg acctgcacct tctctgggtt ctcactcagc actaatggag tgggtgtggg ctggatccgt cagcccccag gaaaggccct ggagtggctt acactcattt attggaatga aaataagcac tacagcccat ctctgaaaaa caggatcacc atcaccaagg acacctccaa aaaccaggtg gtccttacaa tgaccaactt ggaccctgtg gacacagcca cttattactg tgtacacagg | DNA nucleotide sequence |

-continued

| SEQ ID NO. | Sequence | Description |
|---|---|---|
| | ggatggttgg gagcaatctt tgcctactgg ggccagggaa ccctggtcac cgtctcctca | |
| 450. | QITLKESGPT LVKPTQTLTL TCTFSGFSLS TNGVGVGWIR QPPGKALEWL TLIYWNENKH YSPSLKNRIT ITKDTSKNQV VLTMTNLDPV DTATYYCVHR GWLGAIFAYW GQGTLVTVSS | AA amino acid sequence |
| 451. | gggttctcac tcagcactaa tggagtgggt | DNA nucleotide sequence |
| 452. | GFSLSTNGVG | AA amino acid sequence |
| 453. | atttattgga atgaaaataa g | DNA nucleotide sequence |
| 454. | IYWNENK | AA amino acid sequence |
| 455. | gtacacaggg gatggttggg agcaatcttt gcctac | DNA nucleotide sequence |
| 456. | VHRGWLGAIF AY | AA amino acid sequence |
| 457. | gaggtgcagc tggtggagtc tgggggaggc ttggtacagc ctggggggtc cctgagactc tcctgtgcag cctctggatt cacctttact agttatgcca tgacctgggt ccgccaggct ccagggaagg ggctggagtg ggtctcagat attagtggta gtggtggtag aacatattac gcagactccg tgaagggccg gttcaccatc tccagagaca attccaagaa tatgctgtat ctgcaaatga acatcctgag agccgaagac acggccgtat atcattgtgc gaagggaaca ggccagcagg tggaccttta caactactac tatgctttgg acgtctgggg ccaagggacc acggtcaccg tctcctca | DNA nucleotide sequence |
| 458. | EVQLVESGGG LVQPGGSLRL SCAASGFTFT SYAMTWVRQA PGKGLEWVSD ISGSGGRTYY ADSVKGRFTI SRDNSKNMLY LQMNILRAED TAVYHCAKGT GQQVDLYNYY YALDVWGQGT TVTVSS | AA amino acid sequence |
| 459. | ggattcacct ttactagtta tgcc | DNA nucleotide sequence |
| 460. | GFTFTSYA | AA amino acid sequence |
| 461. | attagtggta gtggtggtag aaca | DNA nucleotide sequence |
| 462. | ISGSGGRT | AA amino acid sequence |
| 463. | gcgaagggaa caggccagca ggtggacctt tacaactact actatgcttt ggacgtc | DNA nucleotide sequence |
| 464. | AKGTGQQVDL YNYYYALDV | AA amino acid sequence |

-continued

| SEQ ID NO. | Sequence | Description |
|---|---|---|
| 465. | caggtgcagc tggtggagtc tgggggaggc gtggtccagc ctgggaggtc cctgagactc<br>tcctgtgcag cgtctggatt caccttcagt tactatggca tgcactgggt ccgccaggct<br>ccaggcaagg ggctggagtg ggtggcagtt atatggtatg atggaagtaa taaacactat<br>gcagactccg tgaagggccg attcaccatc tccagagaca attccaagaa cacgctgtat<br>ctgcaaatga acagcctgag agccgacgac acggctgtct attactgtgc gagagataag<br>ggtataagtg gaattaaggg gggttcttac tactactact atgccatgga cgtctggggc<br>caagggacca cggtcaccgt ctcctca | DNA nucleotide sequence |
| 466. | QVQLVESGGG VVQPGRSLRL SCAASGFTFS<br>YYGMHWVRQA PGKGLEWVAV IWYDGSNKHY<br>ADSVKGRFTI SRDNSKNTLY LQMNSLRADD<br>TAVYYCARDK GISGIKGGSY YYYYAMDVWG<br>QGTTVTVSS | AA amino acid sequence |
| 467. | ggattcacct tcagttacta tggc | DNA nucleotide sequence |
| 468. | GFTFSYYG | AA amino acid sequence |
| 469. | atatggtatg atggaagtaa taaa | DNA nucleotide sequence |
| 470. | IWYDGSNK | AA amino acid sequence |
| 471. | gcgagagata agggtataag tggaattaag gggggttctt actactacta ctatgccatg<br>gacgtc | DNA nucleotide sequence |
| 472. | ARDKGISGIK GGSYYYYYAM DV | AA amino acid sequence |
| 473. | gaggtgcagc tggtggagtc tgggggaggc ttggtaaagc ctggggggtc ccttagactc<br>tcctgtgcag cctctggatt cactttcagt aacgcctgga tgacctgggt ccgccaggct<br>ccagggaagg ggctggagtg ggttggccgt attaaaaaca aaattgatgg tcggacaaca<br>gactacgctg cacccgtgaa aggcagattc accatctcaa gagatgattc aaaaaacacg<br>gtttatctgc aaatgaacag cctgaaaacc gaggacacag ccgtttatta ctgttccacg<br>gtggactaca attggtactt cgatttctgg ggccgtggca ccctggtcac tgtctcctca | DNA nucleotide sequence |
| 474. | EVQLVESGGG LVKPGGSLRL SCAASGFTFS<br>NAWMTWVRQA PGKGLEWVGR IKNKIDGGTT<br>DYAAPVKGRF TISRDDSKNT VYLQMNSLKT<br>EDTAVYYCST VDYNWYFDFW GRGTLVTVSS | AA amino acid sequence |
| 475. | ggattcactt tcagtaacgc ctgg | DNA nucleotide sequence |
| 476. | GFTFSNAW | AA amino acid sequence |
| 477. | attaaaaaca aaattgatgg tgggacaaca | DNA nucleotide sequence |

-continued

| SEQ ID NO. | Sequence | Description |
|---|---|---|
| 478. | IKNKIDGGTT | AA amino acid sequence |
| 479. | tccacggtgg actacaattg gtacttcgat ttc | DNA nucleotide sequence |
| 480. | STVDYNWYFD F | AA amino acid sequence |
| 481. | caggtgcagc tggtggagtc tgggggaggc gtggtccagc ctgggaggtc cctgagactc tcctgtgcag cgtctggatt caccttcagt ttctttggca tgcactgggt ccgccaggct ccaggcaagg ggctggagtg ggtggcactt atatggtatg atggaactaa tgaaaactat gcagactccg tgaagggccg attcaccatc tccagagaca attccaagtc cacgctgtat ctgcaaatga acagtctgag agccgaggac acggctgttt actactgtgc gagagatagg ggagtggcga catttacgag gggggaattac tactacaact acggtatgga cgtctggggc caagggacca cggtcaccgt ctcctca | DNA nucleotide sequence |
| 482. | QVQLVESGGG VVQPGRSLRL SCAASGFTFS FFGMHWVRQA PGKGLEWVAL IWYDGTNENY ADSVKGRFTI SRDNSKSTLY LQMNSLRAED TAVYYCARDR GVATFTRGNY YYNYGMDVWG QGTTVTVSS | AA amino acid sequence |
| 483. | ggattcacct tcagtttctt tggc | DNA nucleotide sequence |
| 484. | GFTFSFFG | AA amino acid sequence |
| 485. | atatggtatg atggaactaa tgaa | DNA nucleotide sequence |
| 486. | IWYDGTNE | AA amino acid sequence |
| 487. | gcgagagata ggggagtggc gacatttacg agggggaatt actactacaa ctacggtatg gacgtc | DNA nucleotide sequence |
| 488. | ARDRGVATFT RGNYYYNYGM DV | AA amino acid sequence |
| 489. | caggtgcagc tggtggagtc tgggggaggc gtggtccagc ctgggaggtc cctgagactc tcctgtgcag cgtctggatt caccttcagt ttctatggca tgcactgggt ccgccaggct ccaggcaagg ggctggaggg ggtggcagtt atatggtatg atggaagtaa taaatactat gcagactccg tgaagggccg attcaccata tccagagaca attccaagaa catgctgtat ctacaaatga ccagcctgag agccgaggac acggctgtgt attactgtgc gagagattcg ggtaaaactg gaactgggat aactgggtac tcctactact acggtatgga cgtctggggc caagggacca cggtcaccgt ctcctca | DNA nucleotide sequence |
| 490. | QVQLVESGGG VVQPGRSLRL SCAASGFTFS FYGMHWWRQA PGKGLEGVAV IWYDGSNKYY ADSVKGRFTI SRDNSKNMLY LQMTSLRAED TAVYYCARDS GKTGTGITGY SYYYGMDVWG QGTTVTVSS | AA amino acid sequence |

-continued

| SEQ ID NO. | Sequence | Description |
|---|---|---|
| 491. | ggattcacct tcagtttcta tggc | DNA nucleotide sequence |
| 492. | GFTFSFYG | AA amino acid sequence |
| 493. | atatggtatg atggaagtaa taaa | DNA nucleotide sequence |
| 494. | IWYDGSNK | AA amino acid sequence |
| 495. | gcgagagatt cgggtaaaac tggaactggg ataactgggt actcctacta ctacggtatg gacgtc | DNA nucleotide sequence |
| 496. | ARDSGKTGTG ITGYSYYYGM DV | AA amino acid sequence |
| 497. | cagctgcagc tgcaggagtc gggcccagga ctggtgaagc cttcggagac cctgtccctc acctgcactg tctctggtgg ctccatcatc actaatagtt attactgggg ctggatccgc cagcccccag ggaagggtct ggagtggatt ggtagtatct attatagtgg gaggacctac tacaacccgt ccctcgagag tcgagtcacc atatccgtgg acacgtccaa gaaccagttc tccctgaagt tgacctctgt gaccgccgca gacacggcta tatattactg tgcgagggaa ggggatccgt cgctcgaccc ctggggccag ggaaccctgg tcaccgtctc ctca | DNA nucleotide sequence |
| 498. | QLQLQESGPG LVKPSETLSL TCTVSGGSII TNSYYWGWIR QPPGKGLEWI GSIYYSGRTY YNPSLESRVT ISVDTSKNQF SLKLTSVTAA DTAIYYCARE GDPSLDPWGQ GTLVTVSS | AA amino acid sequence |
| 499. | ggtggctcca tcatcactaa tagttattac | DNA nucleotide sequence |
| 500. | GGSIITNSYY | AA amino acid sequence |
| 501. | atctattata gtgggaggac c | DNA nucleotide sequence |
| 502. | IYYSGRT | AA amino acid sequence |
| 503. | gcgagggaag gggatccgtc gctcgacccc | DNA nucleotide sequence |
| 504. | AREGDPSLDP | AA amino acid sequence |
| 505. | gaggtgcagc tggtggagtc tgggggagac ttggtacagc ctggggggtc cctgagactc tcctgtgcag cctctggatt cacctttagc acctatgcca tgaactgggt ccgccaggct ccagggaagg ggctggagtg ggtctcacat attagtggta gtggtggtaa ttcatactcc gcagactccg tgaagggccg gttcaccatc tccagagaca attccaagaa cacgctatat | DNA nucleotide sequence |

-continued

| SEQ ID NO. | Sequence | Description |
|---|---|---|
| | ctgcaaatga acagcctgcg agccgaggac acggccatat attactgttc gctggatata<br>atggctacag taggcggtct ctttgcctac tggggccagg gaaccctggt caccgtctcc<br>tca | |
| 506. | EVQLVESGGD LVQPGGSLRL SCAASGFTFS<br>TYAMNWVRQA PGKGLEWVSH ISGSGGNSYS<br>ADSVKGRFTI SRDNSKNTLY LQMNSLRAED<br>TAIYYCSLDI MATVGGLFAY WGQGTLVTVS<br>S | AA amino acid sequence |
| 507. | ggattcacct ttagcaccta tgcc | DNA nucleotide sequence |
| 508. | GFTFSTYA | AA amino acid sequence |
| 509. | attagtggta gtggtggtaa ttca | DNA nucleotide sequence |
| 510. | ISGSGGNS | AA amino acid sequence |
| 511. | tcgctggata taatggctac agtaggcggt ctctttgcct ac | DNA nucleotide sequence |
| 512. | SLDIMATVGG LFAY | AA amino acid sequence |
| 513. | caggtgcagc tggtggagtc tgggggaggc gtggtccagc ctgggaggtc cctgagactc<br>tcctgtgtag cgtctggatt catcttcagt ttctatggca tgcactgggt ccgccaggct<br>ccagacaagg ggctggagtg ggtggcagtt atatggtatg atggaagtaa tgaatactat<br>gcagactccg tgaagggccg attcaccatc tccagagaca attccaagaa cacgctgtat<br>ctgcaaatga acagcctgag agccgaggac acggctgtgt attactgtgg gagagatcaa<br>ggtatttcgt attacgatat tttgactggt aattataact attactacgg tgtggacgtc<br>tggggccaag ggaccacggt caccgtctcc tca | DNA nucleotide sequence |
| 514. | QVQLVESGGG VVQPGRSLRL SCVASGFIFS<br>FYGMHWVRQA PDKGLEWVAV IWYDGSNEYY<br>ADSVKGRFTI SRDNSKNTLY LQMNSLRAED<br>TAVYYCGRDQ GISYYDILTG NYNYYYGVDV<br>WGQGTTVTVS S | AA amino acid sequence |
| 515. | ggattcatct tcagtttcta tggc | DNA nucleotide sequence |
| 516. | GFIFSFYG | AA amino acid sequence |
| 517. | atatggtatg atggaagtaa tgaa | DNA nucleotide sequence |
| 518. | IWYDGSNE | AA amino acid sequence |
| 519. | gggagagatc aaggtatttc gtattacgat attttgactg gtaattataa ctattactac<br>ggtgtggacg tc | DNA nucleotide sequence |

-continued

| SEQ ID NO. | Sequence | Description |
|---|---|---|
| 520. | GRDQGISYYD ILTGNYNYYY GVDV | AA amino acid sequence |
| 521. | gacatccaga tgacccagtc tccatcctcc ctgtctgcat ctgtaggaga cagagtcacc atcacttgcc gggcaagtca gagcattagc agctatttaa attggtatca gcagaaacca gggaaagccc ctaagctcct gatctatgct gcatccagtt tgcaaagtgg ggtcccgtca aggttcagtg gcagtggatc tgggacagat ttcactctca ccatcagcag tctgcaacct gaagattttg caacttacta ctgtcaacag agttacagta cccctccgat caccttcggc caagggacac gactggagat taaa | DNA nucleotide sequence |
| 522. | DIQMTQSPSS LSASVGDRVT ITCRASQSIS SYLNWYQQKP GKAPKLLIYA ASSLQSGVPS RFSGSGSGTD FTLTISSLQP EDFATYYCQQ SYSTPPITFG QGTRLEIK | AA amino acid sequence |
| 523. | cagagcatta gcagctat | DNA nucleotide sequence |
| 524. | QSISSY | AA amino acid sequence |
| 525. | gctgcatcc | DNA nucleotide sequence |
| 526. | AAS | AA amino acid sequence |
| 527. | caacagagtt acagtacccc tccgatcacc | DNA nucleotide sequence |
| 528. | QQSYSTPPIT | AA amino acid sequence |
| 529. | gaaattgtgt tgacgcagtc tccaggcacc ctgtctttgt ctccagggga aagagccacc ctctcctgca gggccagtca gagtgttagc agcagctact tagcctggta ccagcagaaa cctggccagg ctcccaggct cctcatctat ggtgcatcca gcagggccac tggcatccca gacaggttca gtggcagtgg gtctgggaca gacttcactc tcaccatcag cagactggag cctgaagatt ttgcagtgta ttactgtcag cagtatggta gctcaccttg gacgttcggc caagggacca aggtggaaat caaa | DNA nucleotide sequence |
| 530. | EIVLTQSPGT LSLSPGERAT LSCRASQSVS SSYLAWYQQK PGQAPRLLIY GASSRATGIP DRFSGSGSGT DFTLTISRLE PEDFAVYYCQ QYGSSPWTFG QGTKVEIK | AA amino acid sequence |
| 531. | cagagtgtta gcagcagcta c | DNA nucleotide sequence |
| 532. | QSVSSSY | AA amino acid sequence |
| 533. | ggtgcatcc | DNA nucleotide sequence |

-continued

| SEQ ID NO. | Sequence | Description |
|---|---|---|
| 534. | GAS | AA amino acid sequence |
| 535. | cagcagtatg gtagctcacc ttggacg | DNA nucleotide sequence |
| 536. | QQYGSSPWT | AA amino acid sequence |
| 537. | caggtgcagc tacagcagtg gggcgcagga ctgttgaagc cttcggagac cctgtccctc<br>acctgcgctg tctatggtgg gtccttcagt ggttactact ggaactggat ccgccagccc<br>ccagggaagg ggctggagtg ggttggggaa atcagtcata gaggaagcac caactacaac<br>ccgtccctca agagtcgagt caccatatca ctggacacgt ccaagaacca gttctccctg<br>aagctgacct ctgtgaccgc cgcggacacg gctgtgtatt actgttcgag agacgaggaa<br>ctggaattcc gtttctttga ctactggggc cagggaaccc tggtcaccgt ctcctca | DNA nucleotide sequence |
| 538. | QVQLQQWGAG LLKPSETLSL TCAVYGGSFS<br>GYYWNWIRQP PGKGLEWVGE ISHRGSTNYN<br>PSLKSRVTIS LDTSKNQFSL KLTSVTAADT<br>AVYYCSRDEE LEFRFFDYWG QGTLVTVSS | AA amino acid sequence |
| 539. | ggtgggtcct tcagtggtta ctac | DNA nucleotide sequence |
| 540. | GGSFSGYY | AA amino acid sequence |
| 541. | atcagtcata gaggaagcac c | DNA nucleotide sequence |
| 542. | ISHRGST | AA amino acid sequence |
| 543. | tcgagagacg aggaactgga attccgtttc tttgactac | DNA nucleotide sequence |
| 544. | SRDEELEFRF FDY | AA amino acid sequence |
| 545. | gaaattgtgt tgacacagtc tccagccacc ctgtctttgt ctccagggga aagagccacc<br>ctctcctgca gggccagtca gagtgttagc agctatttag cctggtacca acaaaaacct<br>ggccaggctc ccaggctcct cgtctatggt gcatccaaca gggccactgg catcccagcc<br>aggttcagtg gcagtgggtc tgggacagac ttcactctca ccatcagcag cctagagcct<br>gaagattttg cattttatta ctgtcagcag cgtagcaact ggccgctcac tttcggcgga<br>gggaccaagg tggagatcaa a | DNA nucleotide sequence |
| 546. | EIVLTQSPAT LSLSPGERAT LSCRASQSVS<br>SYLAWYQQKP GQAPRLLVYG ASNRATGIPA<br>RFSGSGSGTD FTLTISSLEP EDFAFYYCQQ<br>RSNWPLTFGG GTKVEIK | AA amino acid Sequence |
| 547. | cagagtgtta gcagctat | DNA nucleotide sequence |

-continued

| SEQ ID NO. | Sequence | Description |
|---|---|---|
| 548. | QSVSSY | AA amino acid sequence |
| 549. | ggtgcatcc | DNA nucleotide sequence |
| 550. | GAS | AA amino acid sequence |
| 551. | cagcagcgta gcaactggcc gctcact | DNA nucleotide sequence |
| 552. | QQRSNWPLT | AA amino acid sequence |
| 553. | gaggtgcagc tggtggagtc tgggggaggc ttggtacagc ctggggggtc cctgagactc<br>tcctgtgtag cctctggatt cacctttagc ctctatgcca tgacctgggt ccgccaggtt<br>ccagggaagg ggctggaatg ggtctcaact attagtggta gtggtggtgg cacatactac<br>acagactccg ttaagggccg gttcaccatc tccagagaca attccaagaa cacactgtat<br>ctgcaaatga acagcctgag agccgacgac acggccgttt tttactgtac gaaagagagt<br>acaactggaa cttactccta cttctacggt atggacgtct ggggccaagg gaccacggtc<br>accgtctcct ca | DNA nucleotide sequence |
| 554. | EVQLVESGGG LVQPGGSLRL SCVASGFTFS<br>LYAMTWVRQV PGKGLEWVST ISGSGGGTYY<br>TDSVKGRFTI SRDNSKNTLY LQMNSLRADD<br>TAVFYCTKES TTGTYSYFYG MDVWGQGTTV<br>TVSS | AA amino acid sequence |
| 555. | ggattcacct ttagcctcta tgcc | DNA nucleotide sequence |
| 556. | GFTFSLYA | AA amino acid sequence |
| 557. | attagtggta gtggtggtgg caca | DNA nucleotide sequence |
| 558. | ISGSGGGT | AA amino acid sequence |
| 559. | acgaaagaga gtacaactgg aacttactcc tacttctacg gtatggacgt c | DNA nucleotide sequence |
| 560. | TKESTIGTYS YFYGMDV | AA amino acid sequence |
| 561. | gacatccaga tgacccagtc tccatcctcc ctgtctgcat ctgtaggaga cagagtcacc<br>atcacttgcc gggcaagtca gaccattagc agctatttaa attggtatca gcagaaacca<br>gggaaagccc ctaagctcct gatctatgct gcatccagtt tgcaaagtgg ggtcccatca<br>aggttcagtg gcagtggatc tgggacagat ttcactctca ccctcagcgg tctccaacct<br>gaagattttg caacttacta ctgtcaacag agttacagta ccccgctcac tttcggcgga<br>gggaccaagg tggagatcaa a | DNA nucleotide sequence |

-continued

| SEQ ID NO. | Sequence | Description |
|---|---|---|
| 562. | DIQMTQSPSS LSASVGDRVT ITCRASQTIS SYLNWYQQKP GKAPKLLIYA ASSLQSGVPS RFSGSGSGTD FTLTLSGLQP EDFATYYCQQ SYSTPLTFGG GTKVEIK | AA amino acid sequence |
| 563. | cagaccatta gcagctat | DNA nucleotide sequence |
| 564. | QTISSY | AA amino acid sequence |
| 565. | gctgcatcc | DNA nucleotide sequence |
| 566. | AAS | AA amino acid sequence |
| 567. | caacagagtt acagtacccc gctcact | DNA nucleotide sequence |
| 568. | QQSYSTPLT | AA amino acid sequence |
| 569. | ASTKGPSVFP LAPCSRSTSE STAALGCLVK DYFPEPVTVS WNSGALTSGV HTFPAVLQSS GLYSLSSVVT VPSSSLGTKT YTCNVDHKPS NTKVDKRVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCSVMHE ALHNHYTQKS LSLSLGK | AA amino acid sequence |
| 570. | ASTKGPSVFP LAPCSRSTSE STAALGQLVK DYFPEPVTVS WNSGALTSGV HTFPAVLQSS GLYSLSSVVT VPSSSLGTKT YTCNVDHKPS NTKVDKRVES KYGPPCPPCP APPVAGPSVF LFPPKPKDTL MISRTPEVTC VVVDVSQEDP EVQFNWYVDG VEVHNAKTKP REEQFNSTYR VVSVLTVLHQ DWLNGKEYKC KVSNKGLPSS IEKTISKAKG QPREPQVYTL PPSQEEMTKN QVSLTCLVKG FYPSDIAVEW ESNGQPENNY KTTPPVLDSD GSFFLYSRLT VDKSRWQEGN VFSCSVMHEA LHNHYTQKSL SLSLGK | AA amino acid sequence |
| 571. | ASTKGPSVFP LAPCSRSTSE STAALGQLVK DYFPEPVTVS WNSGALTSGV HTFPAVLQSS GLYSLSSVVT VPSSSLGTKT YTCNVDHKPS NTKVDKRVES KYGPPCPPCP APPVAGPSVF LFPPKPKDTL MISRTPEVTC VVVDVSQEDP EVQFNWYVDG VEVHNAKTKP REEQFNSTYR VVSVLTVLHQ DWLNGKEYKQ KVSNKGLPSS IEKTISKAKG QPREPQVYTL PPSQEEMTKN QVSLTCLVKG FYPSDIAVEW ESNGQPENNY KTTPPVLDSD GSFFLYSRLT VDKSRWQEGN VFSCSVMHEA LHNRFTQKSL SLSPGK | AA amino acid sequence |
| 572. | ASTKGPSVFP LAPCSRSTSE STAALGQLVK DYFPEPVTVS WNSGALTSGV HTFPAVLQSS GLYSLSSVVT VPSSSLGTKT YTCNVDHKPS NTKVDKRVES KYGPPCPPCP APGGGGPSVF LFPPKPKDTL MISRTPEVTC VVVDVSQEDP EVQFNWYVDG VEVHNAKTKP REEQFNSTYR VVSVLTVLHQ DWLNGKEYKC KVSNKGLPSS IEKTISKAKG QPREPQVYTL PPSQEEMTKN QVSLTCLVKG FYPSDIAVEW ESNGQPENNY KTTPPVLDSD GSFFLYSRLT VDKSRWQEGN VFSCSVMHEA LHNHYTQKSL SLSLGK | AA amino acid sequence |

-continued

| SEQ ID NO. | Sequence | Description |
|---|---|---|
| 573. | ASTKGPSVFP LAPCSRSTSE STAALGQLVK DYFPEPVTVS WNSGALTSGV HTFPAVLQSS GLYSLSSVVT VPSSSLGTKT YTCNVDHKPS NTKVDKRVES KYGPPCPPCP APGGGGPSVF LFPPKPKDTL MISRTPEVTC VVVDVSQEDP EVQFNWYVDG VEVHNAKTKP REEQFNSTYR VVSVLTVLHQ DWLNGKEYKC KVSNKGLPSS IEKTISKAKG QPREPQVYTL PPSQEEMTKN QVSLTCLVKG FYPSDIAVEW ESNGQPENNY KTTPPVLDSD GSFFLYSRLT VDKSRWQEGN VFSCSVMHEA LHNRFTQKSL SLSPGK | AA amino acid sequence |
| 574. | VPVVWAQEGA PAQLPCSPTI PLQDLSLLRR AGVTWQHQPD SGPPAAAPGH PLAPGPHPAA PSSWGPRPRR YTVLSVGPGG LRSGRLPLQP RVQLDERGRQ RGDFSLWLRP ARRADAGEYR AAVHLRDRAL SCRLRLRLGQ ASMTASPPGS LRASDWVILN CSFSRPDRPA SVHWFRNRGQ GRVPVRESPH HHLAESFLFL PQVSPMDSGP WGCILTYRDG FNVSIMYNLT VLGLEPPTPL TVYAGAGSRV GLPCRLPAGV GTRSFLTAKW TPPGGGPDLL VTGDNGDFTL RLEDVSQAQA GTYTCHIHLQ EQQLNATVTL AIITVTPKSF GSPGSLGKLL CEVTPVSGQE RFVWSSLDTP SQRSFSGPWL EAQEAQLLSQ PWQCQLYQGE RLLGAAVYFT ELSSPGAQRS GRAPGALPAG HLEQKLISEE DLGGEQKLIS EEDLHHHHHH | AA amino acid sequence |
| 575. | VPVVWAQEGA PAQLPCSPTI PLQDLSLLRR AGVTWQHQPD SGPPAAAPGH PLAPGPHPAA PSSWGPRPRR YTVLSVGPGG LRSGRLPLQP RVQLDERGRQ RGDFSLWLRP ARRADAGEYR AAVHLRDRAL SCRLRLRLGQ ASMTASPPGS LRASDWVILN CSFSRPDRPA SVHWFRNRGQ GRVPVRESPH HHLAESFLFL PQVSPMDSGP WGCILTYRDG FNVSIMYNLT VLGLEPPTPL TVYAGAGSRV GLPCRLPAGV GTRSFLTAKW TPPGGGPDLL VTGDNGDFTL RLEDVSQAQA GTYTCHIHLQ EQQLNATVTL AIITVTPKSF GSPGSLGKLL CEVTPVSGQE RFVWSSLDTP SQRSFSGPWL EAQEAQLLSQ PWQCQLYQGE RLLGAAVYFT ELSSPGAQRS GRAPGALPAG HLEPRGPTIK PCPPCKCPAP NLLGGPSVFI FPPKIKDVLM ISLSPIVTCV VVDVSEDDPD VQISWFVNNV EVHTAQTQTH REDYNSTLRV VSALPIQHQD WMSGKEFKCK VNNKDLPAPI ERTISKPKGS VRAPQVYVLP PPEEEMTKKQ VTLTCMVTDF MPEDIYVEWT NNGKTELNYK NTEPVLDSDG SYFMYSKLRV EKKNWVERNS YSCSVVHEGL HNHHTTKSFS RTPGK | AA amino acid sequence |
| 576. | APVKPPQPGA EISVVWAQEG APAQLPCSPT IPLQDLSLLR RAGVTWQHQP DSGPPAPAPG HPPVPGHRPA APYSWGPRPR RYTVLSVGPG GLRSGRLPLQ PRVQLDERGR QRGDFSLWLR PARRADAGEY RATVHLRDRA LSCRLRLRVG QASMTASPPG SLRTSDWVIL NCSFSRPDRP ASVHWFRSRG QGRVPVQGSP HHHLAESFLF LPHVGPMDSG LWGCILTYRD GFNVSIMYNL TVLGLEPATP LTVYAGAGSR VELPCRLPPA VGTQSFLTAK WAPPGGGPDL LVAGDNGDFT LRLEDVSQAQ AGTYICHIRL QGQQLNATVT LAIITVTPKS FGSPGSLGKL LCEVTPASGQ EHFVWSPLNT PSQRSFSGPW LEAQEAQLLS QPWQCQLHQG ERLLGAAVYF TELSSPGAQR SGRAPGALRA GHLPLFLILG VLFLLLLVTG AFGFHLWRRQ WRPRRFSALE QGIHPPQAQS KIEELEQEPE LEPEPELERE LGPEPEPGPE PEPEQL | AA amino acid sequence |
| 577. | QVQLVESGGG VVQPGRSLRL SCVASGFTFS SYGMHWRQA PGKGLEWWVAI IWYDGSNKYY ADSVKGRFTI SRDNSKNTQY LQMNSLRAED TAVYYCASVA TSGDFDYYGM DVWGQGTTVT VSSASTKGPS VFPLAPCSRS TSESTAALGQ | AA amino acid sequence |

-continued

| SEQ ID NO. | Sequence | Description |
|---|---|---|
| | LVKDYFPEPV TVSWNSGALT SGVHTFPAVL<br>QSSGLYSLSS VVTVPSSSLG TKTYTQNVDH<br>KPSNTKVDKR VESKYGPPCP PCPAPPVAGP<br>SVFLFPPKPK DTLMISRTPE VTCVVVDVSQ<br>EDPEVQFNWY VDGVEVHNAK TKPREEQFNS<br>TYRVVSVLTV LHQDWLNGKE YKCKVSNKGL<br>PSSIEKTISK AKGQPREPQV YTLPPSQEEM<br>TKNQVSLTCL VKGFYPSDIA VEWESNGQPE<br>NNYKTTPPVL DSDGSFFLYS RLTVDKSRWQ<br>EGNVFSCSVM HEALHNHYTQ KSLSLSLGK | |
| 578. | EIVLTQSPAT LSLSPGERTT LSCRASQRIS<br>TYLAWYQQKP GQAPRLLIYD ASKRATGIPA<br>RFSGSGSGTG FTLTISSLEP EDFAVYYCQQ<br>RSNWPLTFGG GTKVEIKRTV AAPSVFIFPP<br>SDEQLKSGTA SVVCLLNNFY PREAKVQWKV<br>DNALQSGNSQ ESVTEQDSKD STYSLSSTLT<br>LSKADYEKHK VYACEVTHQG LSSPVTKSEN<br>RGEC | AA amino acid sequence |
| 579. | QVQLVESGGG VVQPGRSLRL SCVASGFTFS<br>SYGMHWVRQA PGKGLEWVAI IWYDGSNKYY<br>ADSVKGRFTI SRDNSKNTQY LQMNSLRAED<br>TAVYYCASVA TSGDFDYYGM DVWGQGTTVT<br>VSSASTKGPS VFPLAPCSRS TSESTAALGC<br>LVKDYFPEPV TVSWNSGALT SGVHTFPAVL<br>QSSGLYSLSS VVTVPSSSLG TKTYTCNVDH<br>KPSNTKVDKR VESKYGPPCP PCPAPEFLGG<br>PSVFLFPPKP KDTLMISRTP EVTCVVVDVS<br>QEDPEVQFNW YVDGVEVHNA KTKPREEQFN<br>STYRVVSVLT VLHQDWLNGK EYKCKVSNKG<br>LPSSIEKTIS KAKGQPREPQ VYTLPPSQEE<br>MTKNQVSLTC LVKGFYPSDI AVEWESNGQP<br>ENNYKTTPPV LDSDGSFFLY SRLTVDKSRW<br>QEGNVFSCSV MHEALHNHYT QKSLSLSLGK | AA amino acid sequence |
| 580. | QVQLQQWGAG LLKPSETLSL TCAVYGGSFS<br>GYYWNWIRQP PGKGLEWVGE ISHRGSTNYN<br>PSLKSRVTIS LDTSKNQFSL KLTSVTAADT<br>AVYYCSRDEE LEFRFFDYWG QGTLVTVSSA<br>STKGPSVFPL APCSRSTSES TAALGQLVKD<br>YFPEPVTVSW NSGALTSGVH TFPAVLQSSG<br>LYSLSSVVTV PSSSLGTKTY TCNVDHKPSN<br>TKVDKRVESK YGPPCPPCPA PPVAGPSVFL<br>FPPKPKDTLM ISRTPEVTCV VVDVSQEDPE<br>VQFNWYVDGV EVHNAKTKPR EEQFNSTYRV<br>VSVLTVLHQD WLNGKEYKCK VSNKGLPSSI<br>EKTISKAKGQ PREPQVYTLP PSQEEMTKNQ<br>VSLTCLVKGF YPSDIAVEWE SNGQPENNYK<br>TTPPVLDSDG SFFLYSRLTV DKSRWQEGNV<br>FSCSVMHEAL HNHYTQKSLS LSLGK | AA amino acid sequence |
| 581. | EIVLTQSPAT LSLSPGERAT LSCRASQSVS<br>SYLAWYQQKP GQAPRLLVYG ASNRATGIPA<br>RFSGSGSGTD FTLTISSLEP EDFAFYYCQQ<br>RSNWPLTFGG GTKVEIKRTV AAPSVFIFPP<br>SDEQLKSGTA SVVCLLNNFY PREAKVQWKV<br>DNALQSGNSQ ESVTEQDSKD STYSLSSTLT<br>LSKADYEKHK VYACEVTHQG LSSPVTKSFN<br>RGEC | AA amino acid sequence |
| 582. | MWEAQFLGLL FLQPLWVAPV KPLQPGAEVP<br>VVWAQEGAPA QLPCSPTIPL QDLSLLRRAG<br>VTWQHQPDSG PPAAAPGHPL APGPHPAAPS<br>SWGPRPRRYT VLSVGPGGLR SGRLPLQPRV<br>QLDERGRQRG DFSLWLRPAR RADAGEYRAA<br>VHLRDRALSC RLRLRLGQAS MTASPPGSLR<br>ASDWVILNCS FSRPDRPASV HWFRNRGQGR<br>VPVRESPHHH LAESFLFLPQ VSPMDSGPWG<br>CILTYRDGEN VSIMYNLTVL GLEPPTPLTV<br>YAGAGSRVGL PCRLPAGVGT RSFLTAKWTP<br>PGGGPDLLVT GDNGDFTLRL EDVSQAQAGT<br>YTCHIHLQEQ QLNATVTLAI ITVTPKSFGS<br>PGSLGKLLCE VTPVSGQERF VWSSLDTPSQ<br>RSFSGPWLEA QEAQLLSQPW QCQLYQGERL | AA amino acid sequence |

-continued

| SEQ ID NO. | Sequence | Description |
|---|---|---|
| | LGAAVYFTEL SSPGAQRSGR APGALPAGHL LLFLILGVLS LLLLVTGAFG FHLWRRQWRP RRFSALEQGI HPPQAQSKIE ELEQEPEPEP EPEPEPEPEP EPEQL | |
| 583. | ENPVVHFFKN IVTPR | AA amino acid sequence |
| 584. | agcagctctg ccctcat | DNA nucleotide sequence |
| 585. | gctctggctg gtcttcagta tg | DNA nucleotide sequence |
| 586. | ttgccgtatg gttggtttga ac | DNA nucleotide sequence |
| 587. | LQPGAEVPVV WAQEGAPAQL PCSPTIPLQD LSLLRRAGVT WQHQPDSGPP AAAPGHPLAP GPHPAAPSSW GPRPRRYTVL SVGPGGLRSG RLPLQPRVQL DERGRQRGDF SLWLRPARRA DAGEYRAAVH LRDRALSCRL RLRLGQASMT ASPPGSLRAS DWVILNCSFS RPDRPASVHW FRNRGQGRVP VRESPHHHLA ESFLFLPQVS PMDSGPWGCI LTYRDGFNVS IMYNLTVLGL EPPTPLTVYA GAGSRVGLPC RLPAGVGTRS FLTAKWTPPG GGPDLLVTGD NGDFTLRLED VSQAQAGTYT CHIHLQEQQL NATVTLAIIT VTPKSFGSPG SLGKLLCEVT PVSGQERFVW SSLDTPSQRS FSGPWLEAQE AQLLSQPWQC QLYQGERLLG AAVYFTELSS PGAQRSGRAP GALPAGHLIE GRMDPKSCDK THTCPPCPAP ELLGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSRDELTKNQ VSLTCLVKGF YPSDIAVEWE SNGQPENNYK TTPPVLDSDG SFFLYSKLTV DKSRWQQGNV FSCSVMHEAL HNHYTQKSLS LSPGK | AA amino acid sequence |
| 588. | VPVVWAQEGA PAQLPCSPTI PLQDLSLLRR AGVTWQHQPD SGPPAAAPGH PLAPGPHPAA PSSWGPRPRR YTVLSVGPGG LRSGRLPLQP RVQLDERGRQ RGDFSLWLRP ARRADAGEYR AAVHLRDRAL SCRLRLRLGQ ASMTASPPGS LRASDWVILN CSFSRPDRPA SVHWFRNRGQ GRVPVRESPH HHLAESFLFL PQVSPMDSGP WGCILTYRDG FNVSIMYNLT VLGLEPPTPL TVYAGAGSRV GLPCRLPAGV GTRSFLTAKW TPPGGGPDLL VTGDNGDFTL RLEDVSQAQA GTYTCHIHLQ EQQLNATVTL AIITVTPKSF GSPGSLGKLL CEVTPVSGQE RFVWSSLDTP SQRSFSGPWL EAQEAQLLSQ PWQCQLYQGE RLLGAAVYFT ELSSPGAQRS GRAPGALPAG HL | AA amino acid sequence |
| 589. | LRRAGVTWQH QPDSGPPAAA PGHPLAPGPH PAAPSSWGPR PRRY | AA amino acid sequence |

What is claimed is:

1. A method for identifying a candidate for anti-tumor therapy, the method comprising:

(i) administering a radiolabeled anti-LAG3 antibody conjugate to a patient with a solid tumor, wherein the radiolabeled anti-LAG3 antibody conjugate comprises an anti-LAG3 antibody or antigen-binding fragment thereof comprising:

three heavy chain complementarity determining regions (HCDRs) in a heavy chain variable region (HCVR), wherein the HCVR has an amino acid sequence selected from the group consisting of SEQ ID NOs: 2, 18, 34, 50, 66, 82, 98, 130, 146, 162, 178, 194, 210, 226, 242, 258, 274, 290, 322, 338, 354, 370, 386, 402, 418, 434, 458, 466, 474, 482, 490, 498, 506, 514, 538, and 554; and three light chain complementarity determining regions (LCDRs) in a light chain variable region (LCVR), wherein the LCVR has an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 378, 394, 410, 426, 442, 522, 530, 546, and 562;

(ii) visualizing LAG3 expression by positron emission tomography (PET) imaging, wherein presence of the radiolabeled antibody conjugate in the tumor identifies the patient as a candidate for anti-tumor therapy.

2. The method of claim 1, wherein the radiolabeled anti-LAG3 antibody conjugate comprises an anti-LAG3 antibody or antigen-binding fragment thereof, a chelating moiety, and a positron emitter.

3. The method of claim 2, wherein the antibody or antigen-binding fragment thereof is covalently bonded to one or more moieties of Formula (A):

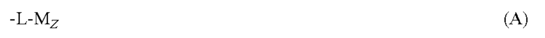

$$-L-M_Z \qquad (A)$$

wherein L is the chelating moiety; M is the positron emitter; and z, independently at each occurrence, is 0 or 1; and wherein at least one of z is 1.

4. The method of claim 2, wherein the chelating moiety comprises desferrioxamine.

5. The method of claim 2, wherein the positron emitter is $^{89}Zr$.

6. The method of claim 3, wherein-L-Mis

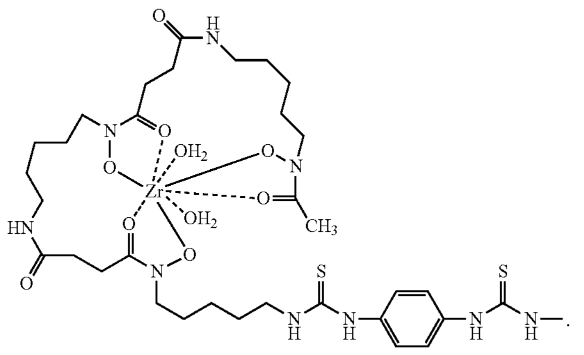

wherein Zr is the positron emitter, $^{89}Zr$.

7. The method of claim 3, wherein the antibody or antigen-binding fragment thereof is covalently bonded to one, two, or three moieties of Formula (A).

8. The method of claim 2, wherein the radiolabeled anti-LAG3 antibody conjugate comprises an antibody or antigen-binding fragment thereof having three heavy chain complementarity determining regions (HCDRs) and three light chain complementarity determining regions (LCDRs) within the heavy chain variable region (HCVR)/light chain variable region (LCVR) amino acid sequence pair selected from the group consisting of SEQ ID NOs: 2/10, 18/26, 34/42, 50/58, 66/74, 82/90, 98/106, 130/138, 146/154, 162/170, 178/186, 194/202, 210/218, 226/234, 242/250, 258/266, 274/282, 290/298, 322/330, 338/346, 354/362, 370/378, 386/394, 402/410, 418/426, 434/442, 458/522, 466/522, 474/522, 482/522, 490/522, 498/530, 506/530, 514/530, 538/546, and 554/562.

9. The method of claim 8, wherein the radiolabeled anti-LAG3 antibody conjugate comprises an antibody or antigen-binding fragment thereof comprising a set of three HCDRs and three LCDRs, wherein the set of CDRs is selected from the group consisting of SEQ ID NOs: 4/6/8/12/14/16, 20/22/24/28/30/32, 36/38/40/44/46/48, 52/54/56/60/62/64, 68/70/72/76/78/80, 84/86/88/92/94/96, 100/102/104/108/110/112, 132/134/136/140/142/144, 148/150/152/156/158/160, 164/166/168/172/174/176, 180/182/184/188/190/192, 196/198/200/204/206/208, 212/214/216/220/222/224, 228/230/232/236/238/240, 244/246/248/252/254/256, 260/262/264/268/270/272, 276/278/280/284/286/288, 292/294/296/300/302/304, 324/326/328/332/334/336, 340/342/344/348/350/352, 356/358/360/364/366/368, 372/374/376/380/382/384, 388/390/392/396/398/400, 404/406/408/412/414/416, 420/422/424/428/430/432, 436/438/440/444/446/448, 460/462/464/524/526/528, 468/470/472/524/526/528, 476/478/480/524/526/528, 484/486/488/524/526/528, 492/494/496/524/526/528, 500/502/504/532/534/536, 508/510/512/532/534/536, 516/518/520/532/534/536, 540/542/544/548/550/552, and 556/558/560/564/566/568, respectively.

10. The method of claim 2, wherein the radiolabeled anti-LAG3 antibody conjugate comprises an antibody or antigen-binding fragment thereof having three HCDRs in an HCVR of SEQ ID NO: 418; and three LCDRs in an LCVR of SEQ ID NO: 426.

11. The method of claim 2, wherein the radiolabeled anti-LAG3 antibody conjugate comprises an antibody or antigen-binding fragment thereof having an HCDR1 amino acid sequence comprising SEQ ID NO: 420; an HCDR2 amino acid sequence comprising SEQ ID NO: 422; and an HCDR3 amino acid sequence comprising SEQ ID NO: 424; an LCDR1 amino acid sequence comprising SEQ ID NO: 428; an LCDR2 amino acid sequence comprising SEQ ID NO: 430; and an LCDR3 amino acid sequence comprising SEQ ID NO: 432.

12. The method of claim 1, wherein the radiolabeled anti-LAG3 antibody conjugate is administered at a dose of about 20 mg or less.

13. The method of claim 1, wherein the anti-tumor therapy is selected from nivolumab, ipilimumab, pembrolizumab, and combinations thereof.

14. The method of claim 1, wherein the anti-tumor therapy is a LAG3 inhibitor.

15. The method of claim 1, wherein the anti-tumor therapy is an anti-LAG3 antibody.

16. The method of claim 15, wherein the anti-tumor therapy is an anti-LAG3 antibody or antigen-binding fragment thereof that binds specifically to LAG3 and comprises three heavy chain complementarity determining regions (HCDRs) and three light chain complementarity determining regions (LCDRs) within the heavy chain variable region (HCVR)/light chain variable region (LCVR) amino acid sequence pair, wherein the HCVR/LCVR amino acid sequence pair is selected from the group consisting of SEQ ID NOS: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/394, 402/410, 418/426, 434/442, 450/522, 458/522, 466/522, 474/522, 482/522, 490/522, 498/530, 506/530, 514/530, 538/546, and 554/562.

* * * * *

SEQUENCE LISTING

Sequence total quantity: 589
SEQ ID NO: 1 moltype = DNA length = 372
FEATURE Location/Qualifiers
misc_feature 1..372
note = synthetic -continued

```
source                  1..372
                        mol_type = other DNA
                        organism = synthetic construct
SEQUENCE: 1
gaggtgcagc tgttggagtc tgggggaggc ttggtacagc ctgggggggtc cctgagactc  60
tcctgtgtgg cctctggatt cacctttagc acctatgcca tgagttgggt ccgccaggct  120
ccagggatgg ggctggagtg ggtctcaagt attagtggta gtggtcgtaa cacatactat  180
gcagactccg tgaagggccg gttcaccatc tccagagaca attccaagaa cacgctgttt  240
cttcaaatga acagcctgag agccgaggac acggccgttt attactgtgc gaaagagtcc  300
gtaactggaa cttcgtccta ctactacggt gtggacgtct ggggccaagg gaccacggtc  360
accgtctcct cg                                                       372

SEQ ID NO: 2            moltype = AA  length = 124
FEATURE                 Location/Qualifiers
REGION                  1..124
                        note = synthetic
source                  1..124
                        mol_type = protein
                        organism = synthetic construct
SEQUENCE: 2
EVQLLESGGG LVQPGGSLRL SCVASGFTFS TYAMSWVRQA PGMGLEWVSS ISGSGRNTYY  60
ADSVKGRFTI SRDNSKNTLF LQMNSLRAED TAVYYCAKES VTGTSSYYYG VDVWGQGTTV  120
TVSS                                                                124

SEQ ID NO: 3            moltype = DNA  length = 24
FEATURE                 Location/Qualifiers
misc_feature            1..24
                        note = synthetic
source                  1..24
                        mol_type = other DNA
                        organism = synthetic construct
SEQUENCE: 3
ggattcacct ttagcaccta tgcc                                          24

SEQ ID NO: 4            moltype = AA  length = 8
FEATURE                 Location/Qualifiers
REGION                  1..8
                        note = synthetic
source                  1..8
                        mol_type = protein
                        organism = synthetic construct
SEQUENCE: 4
GFTFSTYA                                                            8

SEQ ID NO: 5            moltype = DNA  length = 24
FEATURE                 Location/Qualifiers
misc_feature            1..24
                        note = synthetic
source                  1..24
                        mol_type = other DNA
                        organism = synthetic construct
SEQUENCE: 5
attagtggta gtggtcgtaa caca                                          24

SEQ ID NO: 6            moltype = AA  length = 8
FEATURE                 Location/Qualifiers
REGION                  1..8
                        note = synthetic
source                  1..8
                        mol_type = protein
                        organism = synthetic construct
SEQUENCE: 6
ISGSGRNT                                                            8

SEQ ID NO: 7            moltype = DNA  length = 51
FEATURE                 Location/Qualifiers
misc_feature            1..51
                        note = synthetic
source                  1..51
                        mol_type = other DNA
                        organism = synthetic construct
SEQUENCE: 7
gcgaaagagt ccgtaactgg aacttcgtcc tactactacg gtgtggacgt c            51

SEQ ID NO: 8            moltype = AA  length = 17
FEATURE                 Location/Qualifiers
REGION                  1..17
                        note = synthetic
source                  1..17
```

```
                         mol_type = protein
                         organism = synthetic construct
SEQUENCE: 8
AKESVTGTSS YYYGVDV                                                  17

SEQ ID NO: 9             moltype = DNA  length = 321
FEATURE                  Location/Qualifiers
misc_feature             1..321
                         note = synthetic
source                   1..321
                         mol_type = other DNA
                         organism = synthetic construct
SEQUENCE: 9
gacatccaga tgacccagtc tccatcctcc ctgtctgcat ctgtaggaga cagagtcacc  60
atcacttgcc gggcaagtca gagcattagc agttatttaa attggtatca tcagaaacca  120
gggaaagccc caaagctcct gatctatgct gcatccagtt tgcaaaatgg ggtcccatca  180
aggttcagtg gcagtggatc tgggacagat ttcactctca ccatcagcag tctgcaacct  240
gaagattttg catcttacta ctgtcaacag agttacagaa ccccgctcac tttcggcgga  300
gggaccaagg tggagatcaa a                                             321

SEQ ID NO: 10            moltype = AA  length = 107
FEATURE                  Location/Qualifiers
REGION                   1..107
                         note = synthetic
source                   1..107
                         mol_type = protein
                         organism = synthetic construct
SEQUENCE: 10
DIQMTQSPSS LSASVGDRVT ITCRASQSIS SYLNWYHQKP GKAPKLLIYA ASSLQNGVPS  60
RFSGSGSGTD FTLTISSLQP EDFASYYCQQ SYRTPLTFGG GTKVEIK                 107

SEQ ID NO: 11            moltype = DNA  length = 18
FEATURE                  Location/Qualifiers
misc_feature             1..18
                         note = synthetic
source                   1..18
                         mol_type = other DNA
                         organism = synthetic construct
SEQUENCE: 11
cagagcatta gcagttat                                                 18

SEQ ID NO: 12            moltype = AA  length = 6
FEATURE                  Location/Qualifiers
REGION                   1..6
                         note = synthetic
source                   1..6
                         mol_type = protein
                         organism = synthetic construct
SEQUENCE: 12
QSISSY                                                              6

SEQ ID NO: 13            moltype =   length =
SEQUENCE: 13
000

SEQ ID NO: 14            moltype =   length =
SEQUENCE: 14
000

SEQ ID NO: 15            moltype = DNA  length = 27
FEATURE                  Location/Qualifiers
misc_feature             1..27
                         note = synthetic
source                   1..27
                         mol_type = other DNA
                         organism = synthetic construct
SEQUENCE: 15
caacagagtt acagaacccc gctcact                                       27

SEQ ID NO: 16            moltype = AA  length = 9
FEATURE                  Location/Qualifiers
REGION                   1..9
                         note = synthetic
source                   1..9
                         mol_type = protein
                         organism = synthetic construct
SEQUENCE: 16
QQSYRTPLT                                                           9
```

```
SEQ ID NO: 17           moltype = DNA  length = 387
FEATURE                 Location/Qualifiers
misc_feature            1..387
                        note = synthetic
source                  1..387
                        mol_type = other DNA
                        organism = synthetic construct
SEQUENCE: 17
caggtgcagc tggaggagtc tgggggaggc gtggtccagc ctgggaggtc cctgagactc  60
tcctgtgcag cgtctggatt caccttcagt tggtatggca tgcactgggt ccgccaggct  120
ccaggcaagg ggctggagtg ggtggcactt atatggtatg atggaactaa taaaaagtat  180
ggagactccg tgaagggccg attcaccatt tccagagaca attccaagaa cacggtgtat  240
ctgcaaatga acagcctgag agccgaggac acggctgtgt attactgtgc gagagattgt  300
ggacatagtg gcaacgatcg gggggacttac tattactact acggtatgga cgtctggggc  360
caagggacca cggtcaccgt ctcctca                                      387

SEQ ID NO: 18           moltype = AA  length = 129
FEATURE                 Location/Qualifiers
REGION                  1..129
                        note = synthetic
source                  1..129
                        mol_type = protein
                        organism = synthetic construct
SEQUENCE: 18
QVQLEESGGG VVQPGRSLRL SCAASGFTFS WYGMHWVRQA PGKGLEWVAL IWYDGTNKKY  60
GDSVKGRFTI SRDNSKNTVY LQMNSLRAED TAVYYCARDC GHSGNDRGTY YYYYGMDVWG  120
QGTTVTVSS                                                          129

SEQ ID NO: 19           moltype = DNA  length = 24
FEATURE                 Location/Qualifiers
misc_feature            1..24
                        note = synthetic
source                  1..24
                        mol_type = other DNA
                        organism = synthetic construct
SEQUENCE: 19
ggattcacct tcagttggta tggc                                         24

SEQ ID NO: 20           moltype = AA  length = 8
FEATURE                 Location/Qualifiers
REGION                  1..8
                        note = synthetic
source                  1..8
                        mol_type = protein
                        organism = synthetic construct
SEQUENCE: 20
GFTFSWYG                                                           8

SEQ ID NO: 21           moltype = DNA  length = 24
FEATURE                 Location/Qualifiers
misc_feature            1..24
                        note = synthetic
source                  1..24
                        mol_type = other DNA
                        organism = synthetic construct
SEQUENCE: 21
atatggtatg atggaactaa taaa                                         24

SEQ ID NO: 22           moltype = AA  length = 8
FEATURE                 Location/Qualifiers
REGION                  1..8
                        note = synthetic
source                  1..8
                        mol_type = protein
                        organism = synthetic construct
SEQUENCE: 22
IWYDGTNK                                                           8

SEQ ID NO: 23           moltype = DNA  length = 66
FEATURE                 Location/Qualifiers
misc_feature            1..66
                        note = synthetic
source                  1..66
                        mol_type = other DNA
                        organism = synthetic construct
SEQUENCE: 23
gcgagagatt gtggacatag tggcaacgat cgggggactt actattacta ctacggtatg  60
gacgtc                                                             66
```

-continued

```
SEQ ID NO: 24          moltype = AA  length = 22
FEATURE                Location/Qualifiers
REGION                 1..22
                       note = synthetic
source                 1..22
                       mol_type = protein
                       organism = synthetic construct
SEQUENCE: 24
ARDCGHSGND RGTYYYYYGM DV                                           22

SEQ ID NO: 25          moltype = DNA  length = 324
FEATURE                Location/Qualifiers
misc_feature           1..324
                       note = synthetic
source                 1..324
                       mol_type = other DNA
                       organism = synthetic construct
SEQUENCE: 25
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                         324

SEQ ID NO: 26          moltype = AA  length = 108
FEATURE                Location/Qualifiers
REGION                 1..108
                       note = synthetic
source                 1..108
                       mol_type = protein
                       organism = synthetic construct
SEQUENCE: 26
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIK               108

SEQ ID NO: 27          moltype = DNA  length = 18
FEATURE                Location/Qualifiers
misc_feature           1..18
                       note = synthetic
source                 1..18
                       mol_type = other DNA
                       organism = synthetic construct
SEQUENCE: 27
cagagcatta gcagctat                                                18

SEQ ID NO: 28          moltype = AA  length = 6
FEATURE                Location/Qualifiers
REGION                 1..6
                       note = synthetic
source                 1..6
                       mol_type = protein
                       organism = synthetic construct
SEQUENCE: 28
QSISSY                                                             6

SEQ ID NO: 29          moltype =   length =
SEQUENCE: 29
000

SEQ ID NO: 30          moltype =   length =
SEQUENCE: 30
000

SEQ ID NO: 31          moltype = DNA  length = 30
FEATURE                Location/Qualifiers
misc_feature           1..30
                       note = synthetic
source                 1..30
                       mol_type = other DNA
                       organism = synthetic construct
SEQUENCE: 31
caacagagtt acagtacccc tccgatcacc                                   30

SEQ ID NO: 32          moltype = AA  length = 10
FEATURE                Location/Qualifiers
REGION                 1..10
                       note = synthetic
source                 1..10
```

```
                        mol_type = protein
                        organism = synthetic construct
SEQUENCE: 32
QQSYSTPPIT                                                      10

SEQ ID NO: 33           moltype = DNA  length = 357
FEATURE                 Location/Qualifiers
misc_feature            1..357
                        note = synthetic
source                  1..357
                        mol_type = other DNA
                        organism = synthetic construct
SEQUENCE: 33
caggtgcagc tacagcagtg gggcgcagga ctgttgaagc cttcggagac cctgtccctc  60
acctgcgctg tctatggtgg gtccttcagt ggttactact ggaactggat ccgccagccc  120
ccagggaagg ggctggagtg ggttggggaa atcagtcata gaggaaccac caactacaac  180
ccgtccctca agagtcgagt caccatatca ctggacacgt ccaagaacca gttctccctg  240
aaactgacct ctgtgaccgc cgcggacacg gctgtgtatt actgttcgag agacgaggaa  300
ctggaattcc gtttctttga ctactggggc cagggaaccc tggtcaccgt ctcctca     357

SEQ ID NO: 34           moltype = AA  length = 119
FEATURE                 Location/Qualifiers
REGION                  1..119
                        note = synthetic
source                  1..119
                        mol_type = protein
                        organism = synthetic construct
SEQUENCE: 34
QVQLQQWGAG LLKPSETLSL TCAVYGGSFS GYYWNWIRQP PGKGLEWVGE ISHRGTTNYN  60
PSLKSRVTIS LDTSKNQFSL KLTSVTAADT AVYYCSRDEE LEFRFFDYWG QGTLVTVSS   119

SEQ ID NO: 35           moltype = DNA  length = 24
FEATURE                 Location/Qualifiers
misc_feature            1..24
                        note = synthetic
source                  1..24
                        mol_type = other DNA
                        organism = synthetic construct
SEQUENCE: 35
ggtgggtcct tcagtggtta ctac                                      24

SEQ ID NO: 36           moltype = AA  length = 8
FEATURE                 Location/Qualifiers
REGION                  1..8
                        note = synthetic
source                  1..8
                        mol_type = protein
                        organism = synthetic construct
SEQUENCE: 36
GGSFSGYY                                                        8

SEQ ID NO: 37           moltype = DNA  length = 21
FEATURE                 Location/Qualifiers
misc_feature            1..21
                        note = synthetic
source                  1..21
                        mol_type = other DNA
                        organism = synthetic construct
SEQUENCE: 37
atcagtcata gaggaaccac c                                         21

SEQ ID NO: 38           moltype = AA  length = 7
FEATURE                 Location/Qualifiers
REGION                  1..7
                        note = synthetic
source                  1..7
                        mol_type = protein
                        organism = synthetic construct
SEQUENCE: 38
ISHRGTT                                                         7

SEQ ID NO: 39           moltype = DNA  length = 39
FEATURE                 Location/Qualifiers
misc_feature            1..39
                        note = synthetic
source                  1..39
                        mol_type = other DNA
                        organism = synthetic construct
SEQUENCE: 39
```

```
tcgagagacg aggaactgga attccgtttc tttgactac                    39

SEQ ID NO: 40          moltype = AA  length = 13
FEATURE                Location/Qualifiers
REGION                 1..13
                       note = synthetic
source                 1..13
                       mol_type = protein
                       organism = synthetic construct
SEQUENCE: 40
SRDEELEFRF FDY                                                13

SEQ ID NO: 41          moltype = DNA  length = 321
FEATURE                Location/Qualifiers
misc_feature           1..321
                       note = synthetic
source                 1..321
                       mol_type = other DNA
                       organism = synthetic construct
SEQUENCE: 41
gaaattgtgt tgacacagtc tccagccacc ctgtctttgt ctccagggga aagagccacc  60
ctctcctgca gggccagtca gagtgttagc agctatttag cctggtacca acaaaaacct  120
ggccaggctc ccaggctcct cgtctatggt gcatccaaca gggccactgg catcccagcc  180
aggttcagtg gcagtgggtc tgggacagac ttcactctca ccatcagcag cctagagcct  240
gaagattttg cattttatta ctgtcagcag cgtagcaact ggccgctcac tttcggcgga  300
gggaccaagg tggagatcaa a                                       321

SEQ ID NO: 42          moltype = AA  length = 107
FEATURE                Location/Qualifiers
REGION                 1..107
                       note = synthetic
source                 1..107
                       mol_type = protein
                       organism = synthetic construct
SEQUENCE: 42
EIVLTQSPAT LSLSPGERAT LSCRASQSVS SYLAWYQQKP GQAPRLLVYG ASNRATGIPA  60
RFSGSGSGTD FTLTISSLEP EDFAFYYCQQ RSNWPLTFGG GTKVEIK             107

SEQ ID NO: 43          moltype = DNA  length = 18
FEATURE                Location/Qualifiers
misc_feature           1..18
                       note = synthetic
source                 1..18
                       mol_type = other DNA
                       organism = synthetic construct
SEQUENCE: 43
cagagtgtta gcagctat                                           18

SEQ ID NO: 44          moltype = AA  length = 6
FEATURE                Location/Qualifiers
REGION                 1..6
                       note = synthetic
source                 1..6
                       mol_type = protein
                       organism = synthetic construct
SEQUENCE: 44
QSVSSY                                                        6

SEQ ID NO: 45          moltype =   length =
SEQUENCE: 45
000

SEQ ID NO: 46          moltype =   length =
SEQUENCE: 46
000

SEQ ID NO: 47          moltype = DNA  length = 27
FEATURE                Location/Qualifiers
misc_feature           1..27
                       note = synthetic
source                 1..27
                       mol_type = other DNA
                       organism = synthetic construct
SEQUENCE: 47
cagcagcgta gcaactggcc gctcact                                 27

SEQ ID NO: 48          moltype = AA  length = 9
FEATURE                Location/Qualifiers
REGION                 1..9
```

```
                       note = synthetic
source                 1..9
                       mol_type = protein
                       organism = synthetic construct
SEQUENCE: 48
QQRSNWPLT                                                        9

SEQ ID NO: 49          moltype = DNA  length = 357
FEATURE                Location/Qualifiers
misc_feature           1..357
                       note = synthetic
source                 1..357
                       mol_type = other DNA
                       organism = synthetic construct
SEQUENCE: 49
cagctgcagc tgcaggagtc gggcccagga ctggtgaagc cttcggagac cctgtccctc  60
acctgcactg tctctggtga ctccatcatc agtaatagtt attactgggg ctggatccgc  120
cagcccccag ggaaggggct ggagtggatt ggcaatttct tttatactgg ggccacctac  180
tacaacccgt ccctcaagag tcgagtcacc atatccgctg acacgtccaa gaatcagttc  240
tccctgaagc tgagctctgt gaccgccgca gacacggctc tgtattattg tgcgagttat  300
aataggaatt accggttcga cccctggggc cagggaaccc tggtcaccgt ctcctca     357

SEQ ID NO: 50          moltype = AA  length = 119
FEATURE                Location/Qualifiers
REGION                 1..119
                       note = synthetic
source                 1..119
                       mol_type = protein
                       organism = synthetic construct
SEQUENCE: 50
QLQLQESGPG LVKPSETLSL TCTVSGDSII SNSYYWGWIR QPPGKGLEWI GNFFYTGATY  60
YNPSLKSRVT ISADTSKNQF SLKLSSVTAA DTALYYCASY NRNYRFDPWG QGTLVTVSS   119

SEQ ID NO: 51          moltype = DNA  length = 30
FEATURE                Location/Qualifiers
misc_feature           1..30
                       note = synthetic
source                 1..30
                       mol_type = other DNA
                       organism = synthetic construct
SEQUENCE: 51
ggtgactcca tcatcagtaa tagttattac                                 30

SEQ ID NO: 52          moltype = AA  length = 10
FEATURE                Location/Qualifiers
REGION                 1..10
                       note = synthetic
source                 1..10
                       mol_type = protein
                       organism = synthetic construct
SEQUENCE: 52
GDSIISNSYY                                                       10

SEQ ID NO: 53          moltype = DNA  length = 21
FEATURE                Location/Qualifiers
misc_feature           1..21
                       note = synthetic
source                 1..21
                       mol_type = other DNA
                       organism = synthetic construct
SEQUENCE: 53
ttcttttata ctggggccac c                                          21

SEQ ID NO: 54          moltype = AA  length = 7
FEATURE                Location/Qualifiers
REGION                 1..7
                       note = synthetic
source                 1..7
                       mol_type = protein
                       organism = synthetic construct
SEQUENCE: 54
FFYTGAT                                                          7

SEQ ID NO: 55          moltype = DNA  length = 33
FEATURE                Location/Qualifiers
misc_feature           1..33
                       note = synthetic
source                 1..33
                       mol_type = other DNA
```

```
                         organism = synthetic construct
SEQUENCE: 55
gcgagttata ataggaatta ccggttcgac ccc                          33

SEQ ID NO: 56            moltype = AA  length = 11
FEATURE                  Location/Qualifiers
REGION                   1..11
                         note = synthetic
source                   1..11
                         mol_type = protein
                         organism = synthetic construct
SEQUENCE: 56
ASYNRNYRFD P                                                  11

SEQ ID NO: 57            moltype = DNA  length = 324
FEATURE                  Location/Qualifiers
misc_feature             1..324
                         note = synthetic
source                   1..324
                         mol_type = other DNA
                         organism = synthetic construct
SEQUENCE: 57
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttactt ctgtcaacag agttacagta cccctccgat caccttcggc  300
caagggacac gactggagat taaa                                    324

SEQ ID NO: 58            moltype = AA  length = 108
FEATURE                  Location/Qualifiers
REGION                   1..108
                         note = synthetic
source                   1..108
                         mol_type = protein
                         organism = synthetic construct
SEQUENCE: 58
DIQMTQSPSS LSASVGDRVT ITCRASQSIS SYLNWYQQKP GKAPKLLIYA ASSLQSGVPS  60
RFSGSGSGTD FTLTISSLQP EDFATYFCQQ SYSTPPITFG QGTRLEIK          108

SEQ ID NO: 59            moltype = DNA  length = 18
FEATURE                  Location/Qualifiers
misc_feature             1..18
                         note = synthetic
source                   1..18
                         mol_type = other DNA
                         organism = synthetic construct
SEQUENCE: 59
cagagcatta gcagctat                                           18

SEQ ID NO: 60            moltype = AA  length = 6
FEATURE                  Location/Qualifiers
REGION                   1..6
                         note = synthetic
source                   1..6
                         mol_type = protein
                         organism = synthetic construct
SEQUENCE: 60
QSISSY                                                        6

SEQ ID NO: 61            moltype =   length =
SEQUENCE: 61
000

SEQ ID NO: 62            moltype =   length =
SEQUENCE: 62
000

SEQ ID NO: 63            moltype = DNA  length = 30
FEATURE                  Location/Qualifiers
misc_feature             1..30
                         note = synthetic
source                   1..30
                         mol_type = other DNA
                         organism = synthetic construct
SEQUENCE: 63
caacagagtt acagtacccc tccgatcacc                              30

SEQ ID NO: 64            moltype = AA  length = 10
```

-continued

```
FEATURE                Location/Qualifiers
REGION                 1..10
                       note = synthetic
source                 1..10
                       mol_type = protein
                       organism = synthetic construct
SEQUENCE: 64
QQSYSTPPIT                                                        10

SEQ ID NO: 65          moltype = DNA  length = 381
FEATURE                Location/Qualifiers
misc_feature           1..381
                       note = synthetic
source                 1..381
                       mol_type = other DNA
                       organism = synthetic construct
SEQUENCE: 65
caggtgcagc tacagcagtg ggcgcagga ctgttgaagc cttcggagac cctgtccctc  60
acctgcgctg tctatggtgg gtccttcagt acttactact ggagctggat ccgccagccc  120
ccagggaagg ggctggagtg gattggagag atcaatcata gtggaaacgc cgactacaac  180
ccgtccctca agagtcgagt ctccatatca gtggacacgt ccaagaacca gttctccctg  240
aggctgagct ctgtgaccgc cgcggacacg gctatttatt actgtgcgag agcgggctat  300
tgtagtagtc ccacctgcta ttcctactac tacttcggta tggacgtctg gggccaaggg  360
accacggtca ccgtctcctc a                                           381

SEQ ID NO: 66          moltype = AA  length = 127
FEATURE                Location/Qualifiers
REGION                 1..127
                       note = synthetic
source                 1..127
                       mol_type = protein
                       organism = synthetic construct
SEQUENCE: 66
QVQLQQWGAG LLKPSETLSL TCAVYGGSFS TYYWSWIRQP PGKGLEWIGE INHSGNADYN  60
PSLKSRVSIS VDTSKNQFSL RLSSVTAADT AIYYCARAGY CSSPTCYSYY YFGMDVWGQG  120
TTVTVSS                                                           127

SEQ ID NO: 67          moltype = DNA  length = 24
FEATURE                Location/Qualifiers
misc_feature           1..24
                       note = synthetic
source                 1..24
                       mol_type = other DNA
                       organism = synthetic construct
SEQUENCE: 67
ggtgggtcct tcagtactta ctac                                        24

SEQ ID NO: 68          moltype = AA  length = 8
FEATURE                Location/Qualifiers
REGION                 1..8
                       note = synthetic
source                 1..8
                       mol_type = protein
                       organism = synthetic construct
SEQUENCE: 68
GGSFSTYY                                                          8

SEQ ID NO: 69          moltype = DNA  length = 21
FEATURE                Location/Qualifiers
misc_feature           1..21
                       note = synthetic
source                 1..21
                       mol_type = other DNA
                       organism = synthetic construct
SEQUENCE: 69
atcaatcata gtggaaacgc c                                           21

SEQ ID NO: 70          moltype = AA  length = 7
FEATURE                Location/Qualifiers
REGION                 1..7
                       note = synthetic
source                 1..7
                       mol_type = protein
                       organism = synthetic construct
SEQUENCE: 70
INHSGNA                                                           7

SEQ ID NO: 71          moltype = DNA  length = 63
FEATURE                Location/Qualifiers
```

```
misc_feature          1..63
                      note = synthetic
source                1..63
                      mol_type = other DNA
                      organism = synthetic construct
SEQUENCE: 71
gcgagagcgg gctattgtag tagtcccacc tgctattcct actactactt cggtatggac  60
gtc                                                                63

SEQ ID NO: 72         moltype = AA  length = 21
FEATURE               Location/Qualifiers
REGION                1..21
                      note = synthetic
source                1..21
                      mol_type = protein
                      organism = synthetic construct
SEQUENCE: 72
ARAGYCSSPT CYSYYYFGMD V                                            21

SEQ ID NO: 73         moltype = DNA  length = 324
FEATURE               Location/Qualifiers
misc_feature          1..324
                      note = synthetic
source                1..324
                      mol_type = other DNA
                      organism = synthetic construct
SEQUENCE: 73
gaaattgtgt tgacgcagtc tccaggcacc ctgtctttgt ctctagggga aagagccacc  60
ctctcctgca gggccagtca gagtgttatc agcagcttct tagcctggta ccagcagaaa  120
cctggccagg ctcccaggct cctcatctat ggtgcatcca gcagggccac tggcttccca  180
gacaggttca gtggcagtgg gtctgggaca gacttcactc tcaccatccg cagactggag  240
cctgaagatt ttgcagtgta ttactgtcag cagtatggta actcaccttg gacgttcggc  300
caagggacca aggtggagat caaa                                         324

SEQ ID NO: 74         moltype = AA  length = 108
FEATURE               Location/Qualifiers
REGION                1..108
                      note = synthetic
source                1..108
                      mol_type = protein
                      organism = synthetic construct
SEQUENCE: 74
EIVLTQSPGT LSLSLGERAT LSCRASQSVI SSFLAWYQQK PGQAPRLLIY GASSRATGFP  60
DRFSGSGSGT DFTLTIRRLE PEDFAVYYCQ QYGNSPWTFG QGTKVEIK               108

SEQ ID NO: 75         moltype = DNA  length = 21
FEATURE               Location/Qualifiers
misc_feature          1..21
                      note = synthetic
source                1..21
                      mol_type = other DNA
                      organism = synthetic construct
SEQUENCE: 75
cagagtgtta tcagcagctt c                                            21

SEQ ID NO: 76         moltype = AA  length = 7
FEATURE               Location/Qualifiers
REGION                1..7
                      note = synthetic
source                1..7
                      mol_type = protein
                      organism = synthetic construct
SEQUENCE: 76
QSVISSF                                                            7

SEQ ID NO: 77         moltype =   length =
SEQUENCE: 77
000

SEQ ID NO: 78         moltype =   length =
SEQUENCE: 78
000

SEQ ID NO: 79         moltype = DNA  length = 27
FEATURE               Location/Qualifiers
misc_feature          1..27
                      note = synthetic
source                1..27
                      mol_type = other DNA
```

```
                          organism = synthetic construct
SEQUENCE: 79
cagcagtatg gtaactcacc ttggacg                                      27

SEQ ID NO: 80             moltype = AA  length = 9
FEATURE                   Location/Qualifiers
REGION                    1..9
                          note = synthetic
source                    1..9
                          mol_type = protein
                          organism = synthetic construct
SEQUENCE: 80
QQYGNSPWT                                                          9

SEQ ID NO: 81             moltype = DNA  length = 387
FEATURE                   Location/Qualifiers
misc_feature              1..387
                          note = synthetic
source                    1..387
                          mol_type = other DNA
                          organism = synthetic construct
SEQUENCE: 81
caggtcacct tgaaggagtc tggtcctgtg ctggtgaaac ccacagagac cctcacgctg  60
acctgcaccg tctctgggtt ctcactcagc aatgctggga tgggtgtgag ctgggtccgt  120
cagcccccctg ggaaggccct ggagtggctt gcacacattt tttcgaatga cgagaagtcc  180
tacagcacat ctctgaggac cagactcacc atctccaagg acacctccaa aagccaggtg  240
gtccttaccg tgaccaactt ggaccctgtg gacacagcca catatttctg tgcacggata  300
ccagagttta ccagctcgtc gtgggctctc tactacttct acggtatgga cgtctggggc  360
caagggacca cggtcaccgt ctcctca                                      387

SEQ ID NO: 82             moltype = AA  length = 129
FEATURE                   Location/Qualifiers
REGION                    1..129
                          note = synthetic
source                    1..129
                          mol_type = protein
                          organism = synthetic construct
SEQUENCE: 82
QVTLKESGPV LVKPTETLTL TCTVSGFSLS NAGMGVSWVR QPPGKALEWL AHIFSNDEKS  60
YSTSLRTRLT ISKDTSKSQV VLTVTNLDPV DTATYFCARI PEFTSSSWAL YYFYGMDVWG  120
QGTTVTVSS                                                          129

SEQ ID NO: 83             moltype = DNA  length = 30
FEATURE                   Location/Qualifiers
misc_feature              1..30
                          note = synthetic
source                    1..30
                          mol_type = other DNA
                          organism = synthetic construct
SEQUENCE: 83
gggttctcac tcagcaatgc tgggatgggt                                   30

SEQ ID NO: 84             moltype = AA  length = 10
FEATURE                   Location/Qualifiers
REGION                    1..10
                          note = synthetic
source                    1..10
                          mol_type = protein
                          organism = synthetic construct
SEQUENCE: 84
GFSLSNAGMG                                                         10

SEQ ID NO: 85             moltype = DNA  length = 21
FEATURE                   Location/Qualifiers
misc_feature              1..21
                          note = synthetic
source                    1..21
                          mol_type = other DNA
                          organism = synthetic construct
SEQUENCE: 85
atttttcga atgacgagaa g                                             21

SEQ ID NO: 86             moltype = AA  length = 7
FEATURE                   Location/Qualifiers
REGION                    1..7
                          note = synthetic
source                    1..7
                          mol_type = protein
                          organism = synthetic construct
```

```
SEQUENCE: 86
IFSNDEK                                                            7

SEQ ID NO: 87          moltype = DNA  length = 63
FEATURE                Location/Qualifiers
misc_feature           1..63
                       note = synthetic
source                 1..63
                       mol_type = other DNA
                       organism = synthetic construct
SEQUENCE: 87
gcacggatac cagagtttac cagctcgtcg tgggctctct actacttcta cggtatggac  60
gtc                                                                63

SEQ ID NO: 88          moltype = AA  length = 21
FEATURE                Location/Qualifiers
REGION                 1..21
                       note = synthetic
source                 1..21
                       mol_type = protein
                       organism = synthetic construct
SEQUENCE: 88
ARIPEFTSSS WALYYFYGMD V                                            21

SEQ ID NO: 89          moltype = DNA  length = 324
FEATURE                Location/Qualifiers
misc_feature           1..324
                       note = synthetic
source                 1..324
                       mol_type = other DNA
                       organism = synthetic construct
SEQUENCE: 89
gaaattgtgt tgacgcagtc tccaggcacc ctgtctttgt ctccagggga aagcgccacc  60
ctctcctgca gggccagtca gagtattacc agcacctact tcgcctggta ccagcagaaa  120
cctggccagg ctcccaggct cctcatctat gctacatcca gcagggccac tggcgtccca  180
gacaggttca gtggcagtgg gtctgggacg gacttcactc tcaccatcag cagactggag  240
cctgatgatt ttgcagtgta ttactgtcag caatatggta ggtcaccttg gacgttcggc  300
caagggacca aggtggaagt caaa                                         324

SEQ ID NO: 90          moltype = AA  length = 108
FEATURE                Location/Qualifiers
REGION                 1..108
                       note = synthetic
source                 1..108
                       mol_type = protein
                       organism = synthetic construct
SEQUENCE: 90
EIVLTQSPGT LSLSPGESAT LSCRASQSIT STYFAWYQQK PGQAPRLLIY ATSSRATGVP  60
DRFSGSGSGT DFTLTISRLE PDDFAVYYCQ QYGRSPWTFG QGTKVEVK                108

SEQ ID NO: 91          moltype = DNA  length = 21
FEATURE                Location/Qualifiers
misc_feature           1..21
                       note = synthetic
source                 1..21
                       mol_type = other DNA
                       organism = synthetic construct
SEQUENCE: 91
cagagtatta ccagcaccta c                                            21

SEQ ID NO: 92          moltype = AA  length = 7
FEATURE                Location/Qualifiers
REGION                 1..7
                       note = synthetic
source                 1..7
                       mol_type = protein
                       organism = synthetic construct
SEQUENCE: 92
QSITSTY                                                            7

SEQ ID NO: 93          moltype =   length =
SEQUENCE: 93
000

SEQ ID NO: 94          moltype =   length =
SEQUENCE: 94
000

SEQ ID NO: 95          moltype = DNA  length = 27
```

```
FEATURE                Location/Qualifiers
misc_feature           1..27
                       note = synthetic
source                 1..27
                       mol_type = other DNA
                       organism = synthetic construct
SEQUENCE: 95
cagcaatatg gtaggtcacc ttggacg                                    27

SEQ ID NO: 96          moltype = AA  length = 9
FEATURE                Location/Qualifiers
REGION                 1..9
                       note = synthetic
source                 1..9
                       mol_type = protein
                       organism = synthetic construct
SEQUENCE: 96
QQYGRSPWT                                                        9

SEQ ID NO: 97          moltype = DNA  length = 363
FEATURE                Location/Qualifiers
misc_feature           1..363
                       note = synthetic
source                 1..363
                       mol_type = other DNA
                       organism = synthetic construct
SEQUENCE: 97
caggttcagc tggtgcagtc tggagctgag gtgaagaagc ctggggcctc agtgaaggtc  60
tcctgcaagg cttctggtta cacctttacc agttatggta tcagctgggt gcgacaggcc  120
cctggacaag ggcttgagtg gatgggatgg atcagcgctt acaatgataa cacaaactat  180
gcacagaagc tccagggcag agtcaccatg accgcagaca catccacgaa tacagcctac  240
atggagctaa ggagcctgag atctgacgac acggccattt attactgtgt gcgatggaat  300
tggggttccg tctactggta cttcgatctc tggggccgtg gcaccctggt cactgtctcc  360
tca                                                              363

SEQ ID NO: 98          moltype = AA  length = 121
FEATURE                Location/Qualifiers
REGION                 1..121
                       note = synthetic
source                 1..121
                       mol_type = protein
                       organism = synthetic construct
SEQUENCE: 98
QVQLVQSGAE VKKPGASVKV SCKASGYTFT SYGISWVRQA PGQGLEWMGW ISAYNDNTNY  60
AQKLQGRVTM TADTSTNTAY MELRSLRSDD TAIYYCVRWN WGSVYWYFDL WGRGTLVTVS  120
S                                                                121

SEQ ID NO: 99          moltype = DNA  length = 24
FEATURE                Location/Qualifiers
misc_feature           1..24
                       note = synthetic
source                 1..24
                       mol_type = other DNA
                       organism = synthetic construct
SEQUENCE: 99
ggttacacct ttaccagtta tggt                                       24

SEQ ID NO: 100         moltype = AA  length = 8
FEATURE                Location/Qualifiers
REGION                 1..8
                       note = synthetic
source                 1..8
                       mol_type = protein
                       organism = synthetic construct
SEQUENCE: 100
GYTFTSYG                                                         8

SEQ ID NO: 101         moltype = DNA  length = 24
FEATURE                Location/Qualifiers
misc_feature           1..24
                       note = synthetic
source                 1..24
                       mol_type = other DNA
                       organism = synthetic construct
SEQUENCE: 101
atcagcgctt acaatgataa caca                                       24

SEQ ID NO: 102         moltype = AA  length = 8
FEATURE                Location/Qualifiers
```

```
REGION                  1..8
                        note = synthetic
source                  1..8
                        mol_type = protein
                        organism = synthetic construct
SEQUENCE: 102
ISAYNDNT                                                            8

SEQ ID NO: 103          moltype = DNA  length = 42
FEATURE                 Location/Qualifiers
misc_feature            1..42
                        note = synthetic
source                  1..42
                        mol_type = other DNA
                        organism = synthetic construct
SEQUENCE: 103
gtgcgatgga attggggttc cgtctactgg tacttcgatc tc                      42

SEQ ID NO: 104          moltype = AA  length = 14
FEATURE                 Location/Qualifiers
REGION                  1..14
                        note = synthetic
source                  1..14
                        mol_type = protein
                        organism = synthetic construct
SEQUENCE: 104
VRWNWGSVYW YFDL                                                     14

SEQ ID NO: 105          moltype = DNA  length = 324
FEATURE                 Location/Qualifiers
misc_feature            1..324
                        note = synthetic
source                  1..324
                        mol_type = other DNA
                        organism = synthetic construct
SEQUENCE: 105
gaaattgtgt tgacgcagtc tccaggcacc ctgtctttgt ctccagggga aagagccacc  60
ctctcctgca gggccagtca gattattagc agcagctact ttgcctggta ccagcagaaa  120
cctggccagg ctcccaggct cctcatctat ggtgcgtcca gcagggccac tggcatccca  180
gacaggttca gtggcagtgt gtctgggaca gacttcactc tcaccatcag cagactggag  240
cctgaagatt ttgcaatgta tttctgtcag cagtatggta actcaccttg gacgttcggc  300
caagggacca aggtggaaat caaa                                          324

SEQ ID NO: 106          moltype = AA  length = 108
FEATURE                 Location/Qualifiers
REGION                  1..108
                        note = synthetic
source                  1..108
                        mol_type = protein
                        organism = synthetic construct
SEQUENCE: 106
EIVLTQSPGT LSLSPGERAT LSCRASQIIS SSYFAWYQQK PGQAPRLLIY GASSRATGIP  60
DRFSGSVSGT DFTLTISRLE PEDFAMYFCQ QYGNSPWTFG QGTKVEIK                108

SEQ ID NO: 107          moltype = DNA  length = 21
FEATURE                 Location/Qualifiers
misc_feature            1..21
                        note = synthetic
source                  1..21
                        mol_type = other DNA
                        organism = synthetic construct
SEQUENCE: 107
cagattatta gcagcagcta c                                             21

SEQ ID NO: 108          moltype = AA  length = 7
FEATURE                 Location/Qualifiers
REGION                  1..7
                        note = synthetic
source                  1..7
                        mol_type = protein
                        organism = synthetic construct
SEQUENCE: 108
QIISSSY                                                             7

SEQ ID NO: 109          moltype =   length =
SEQUENCE: 109
000

SEQ ID NO: 110          moltype =   length =
```

```
SEQUENCE: 110
000

SEQ ID NO: 111          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 111
cagcagtatg gtaactcacc ttggacg                                     27

SEQ ID NO: 112          moltype = AA  length = 9
FEATURE                 Location/Qualifiers
REGION                  1..9
                        note = synthetic
source                  1..9
                        mol_type = protein
                        organism = synthetic construct
SEQUENCE: 112
QQYGNSPWT                                                         9

SEQ ID NO: 113          moltype = DNA  length = 351
FEATURE                 Location/Qualifiers
misc_feature            1..351
                        note = synthetic
source                  1..351
                        mol_type = other DNA
                        organism = synthetic construct
SEQUENCE: 113
cagatcacct tgaaggagtc tggtcctacg ctggtgaaac ccacacagac cctcacgctg  60
acttgcacct tctctgggtt ctcactcaac actcatagag tgggtgtagg ctggatccgg  120
cagcccccag gaaaggccct ggagtggctt gcactcattt atgggaatga tgttaagaac  180
tacagcccat ctctggagac caggctcacc atcgccaagg acacctccaa aaaccaggtg  240
gtccttacaa tgaccaacat ggaccctgtg gacacagcca catatttctg ttcgtacata  300
acgggggaag gaatgtactg gggccaggga accctggtca ccgtctcctc a          351

SEQ ID NO: 114          moltype = AA  length = 117
FEATURE                 Location/Qualifiers
REGION                  1..117
                        note = synthetic
source                  1..117
                        mol_type = protein
                        organism = synthetic construct
SEQUENCE: 114
QITLKESGPT LVKPTQTLTL TCTFSGFSLN THRVGVGWIR QPPGKALEWL ALIYGNDVKN  60
YSPSLETRLT IAKDTSKNQV VLTMTNMDPV DTATYFCSYI TGEGMYWGQG TLVTVSS     117

SEQ ID NO: 115          moltype = DNA  length = 30
FEATURE                 Location/Qualifiers
misc_feature            1..30
                        note = synthetic
source                  1..30
                        mol_type = other DNA
                        organism = synthetic construct
SEQUENCE: 115
gggttctcac tcaacactca tagagtgggt                                  30

SEQ ID NO: 116          moltype = AA  length = 10
FEATURE                 Location/Qualifiers
REGION                  1..10
                        note = synthetic
source                  1..10
                        mol_type = protein
                        organism = synthetic construct
SEQUENCE: 116
GFSLNTHRVG                                                        10

SEQ ID NO: 117          moltype = DNA  length = 21
FEATURE                 Location/Qualifiers
misc_feature            1..21
                        note = synthetic
source                  1..21
                        mol_type = other DNA
                        organism = synthetic construct
SEQUENCE: 117
atttatggga atgatgttaa g                                           21
```

-continued

```
SEQ ID NO: 118          moltype = AA  length = 7
FEATURE                 Location/Qualifiers
REGION                  1..7
                        note = synthetic
source                  1..7
                        mol_type = protein
                        organism = synthetic construct
SEQUENCE: 118
IYGNDVK                                                             7

SEQ ID NO: 119          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 119
tcgtacataa cgggggaagg aatgtac                                       27

SEQ ID NO: 120          moltype = AA  length = 9
FEATURE                 Location/Qualifiers
REGION                  1..9
                        note = synthetic
source                  1..9
                        mol_type = protein
                        organism = synthetic construct
SEQUENCE: 120
SYITGEGMY                                                           9

SEQ ID NO: 121          moltype = DNA  length = 333
FEATURE                 Location/Qualifiers
misc_feature            1..333
                        note = synthetic
source                  1..333
                        mol_type = other DNA
                        organism = synthetic construct
SEQUENCE: 121
gatgttgtga tgactcagtc tccactctcc ctgtccgtca cccttggaca gccggcctcc  60
atttcctgta ggtctagtca aaacctcatg tacagtgatg gaaacaccta cttgaattgg  120
tttcaccaga ggccaggcca atctccaagg cgtctaattt ataaggtttc taaccgggac  180
tctggggtcc cagacagatt cagcggcagt gggtcaggca ctgatttcac actgaaaatc  240
agcagggtgg aggctgagga tgttggggtt tattactgca tgcaaggtac acactggtac  300
acatttggcc aggggaccaa gctggagatc aaa                                333

SEQ ID NO: 122          moltype = AA  length = 111
FEATURE                 Location/Qualifiers
REGION                  1..111
                        note = synthetic
source                  1..111
                        mol_type = protein
                        organism = synthetic construct
SEQUENCE: 122
DVVMTQSPLS LSVTLGQPAS ISCRSSQNLM YSDGNTYLNW FHQRPGQSPR RLIYKVSNRD  60
SGVPDRFSGS GSGTDFTLKI SRVEAEDVGV YYCMQGTHWY TFGQGTKLEI K            111

SEQ ID NO: 123          moltype = DNA  length = 33
FEATURE                 Location/Qualifiers
misc_feature            1..33
                        note = synthetic
source                  1..33
                        mol_type = other DNA
                        organism = synthetic construct
SEQUENCE: 123
caaaacctca tgtacagtga tggaaacacc tac                                33

SEQ ID NO: 124          moltype = AA  length = 11
FEATURE                 Location/Qualifiers
REGION                  1..11
                        note = synthetic
source                  1..11
                        mol_type = protein
                        organism = synthetic construct
SEQUENCE: 124
QNLMYSDGNT Y                                                        11

SEQ ID NO: 125          moltype =   length =
SEQUENCE: 125
000
```

```
SEQ ID NO: 126          moltype =   length =
SEQUENCE: 126
000

SEQ ID NO: 127          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 127
atgcaaggta cacactggta caca                                        24

SEQ ID NO: 128          moltype = AA  length = 8
FEATURE                 Location/Qualifiers
REGION                  1..8
                        note = synthetic
source                  1..8
                        mol_type = protein
                        organism = synthetic construct
SEQUENCE: 128
MQGTHWYT                                                          8

SEQ ID NO: 129          moltype = DNA  length = 357
FEATURE                 Location/Qualifiers
misc_feature            1..357
                        note = synthetic
source                  1..357
                        mol_type = other DNA
                        organism = synthetic construct
SEQUENCE: 129
caggtgcagc tgcagcagtg gggcgcagga ctattgaagc cttcggagac cctgtccctc  60
acctgcgctg tctatggtgg gtctttcagt ggttattact ggagctggat ccgccagccc  120
ccagggaagg gtctggaatg gattggggaa atcaatcata gaggaaacac caactacaac  180
ccgtccctca agagtcgagt caccatatca ctcgacacgt ccaagaaaca gttctccctg  240
aacctgagtt ctgtgaccgc cgcggacacg gctatgtatt actgtacgag agacgaagaa  300
caggaactac gtttccttga ctactggggc cagggaaccc tggtcaccgt ctcctca     357

SEQ ID NO: 130          moltype = AA  length = 119
FEATURE                 Location/Qualifiers
REGION                  1..119
                        note = synthetic
source                  1..119
                        mol_type = protein
                        organism = synthetic construct
SEQUENCE: 130
QVQLQQWGAG LLKPSETLSL TCAVYGGSFS GYYWSWIRQP PGKGLEWIGE INHRGNTNYN  60
PSLKSRVTIS LDTSKKQFSL NLSSVTAADT AMYYCTRDEE QELRFLDYWG QGTLVTVSS   119

SEQ ID NO: 131          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 131
ggtgggtctt tcagtggtta ttac                                        24

SEQ ID NO: 132          moltype = AA  length = 8
FEATURE                 Location/Qualifiers
REGION                  1..8
                        note = synthetic
source                  1..8
                        mol_type = protein
                        organism = synthetic construct
SEQUENCE: 132
GGSFSGYY                                                          8

SEQ ID NO: 133          moltype = DNA  length = 21
FEATURE                 Location/Qualifiers
misc_feature            1..21
                        note = synthetic
source                  1..21
                        mol_type = other DNA
                        organism = synthetic construct
SEQUENCE: 133
```

```
atcaatcata gaggaaacac c                                            21

SEQ ID NO: 134         moltype = AA  length = 7
FEATURE                Location/Qualifiers
REGION                 1..7
                       note = synthetic
source                 1..7
                       mol_type = protein
                       organism = synthetic construct
SEQUENCE: 134
INHRGNT                                                            7

SEQ ID NO: 135         moltype = DNA  length = 39
FEATURE                Location/Qualifiers
misc_feature           1..39
                       note = synthetic
source                 1..39
                       mol_type = other DNA
                       organism = synthetic construct
SEQUENCE: 135
acgagagacg aagaacagga actacgtttc cttgactac                         39

SEQ ID NO: 136         moltype = AA  length = 13
FEATURE                Location/Qualifiers
REGION                 1..13
                       note = synthetic
source                 1..13
                       mol_type = protein
                       organism = synthetic construct
SEQUENCE: 136
TRDEEQELRF LDY                                                     13

SEQ ID NO: 137         moltype = DNA  length = 321
FEATURE                Location/Qualifiers
misc_feature           1..321
                       note = synthetic
source                 1..321
                       mol_type = other DNA
                       organism = synthetic construct
SEQUENCE: 137
gagattgtgt tgacacagtc tccagccacc ctgtctttgt ctccagggga aagagccacc  60
ctctcctgca gggccagtca ggatattagc acctacttag cctggtacca acagagagct  120
ggccaggctc ccaggctcct catctatggt gcttccaaca gggccactgg catcccagcc  180
aggttcagtg gcagtgggtc tgggacagac ttcactctca ccatcagcag cctagagcct  240
gaagattttg cattttatta ctgtcaacag cgcagcaact ggccgctcac tttcggcgga  300
gggaccgagg tggagatcaa a                                            321

SEQ ID NO: 138         moltype = AA  length = 107
FEATURE                Location/Qualifiers
REGION                 1..107
                       note = synthetic
source                 1..107
                       mol_type = protein
                       organism = synthetic construct
SEQUENCE: 138
EIVLTQSPAT LSLSPGERAT LSCRASQDIS TYLAWYQQRA GQAPRLLIYG ASNRATGIPA  60
RFSGSGSGTD FTLTISSLEP EDFAFYYCQQ RSNWPLTFGG GTEVEIK                107

SEQ ID NO: 139         moltype = DNA  length = 18
FEATURE                Location/Qualifiers
misc_feature           1..18
                       note = synthetic
source                 1..18
                       mol_type = other DNA
                       organism = synthetic construct
SEQUENCE: 139
caggatatta gcacctac                                                18

SEQ ID NO: 140         moltype = AA  length = 6
FEATURE                Location/Qualifiers
REGION                 1..6
                       note = synthetic
source                 1..6
                       mol_type = protein
                       organism = synthetic construct
SEQUENCE: 140
QDISTY                                                             6

SEQ ID NO: 141         moltype =   length =
```

```
SEQUENCE: 141
000

SEQ ID NO: 142          moltype =   length =
SEQUENCE: 142
000

SEQ ID NO: 143          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 143
caacagcgca gcaactggcc gctcact                                       27

SEQ ID NO: 144          moltype = AA  length = 9
FEATURE                 Location/Qualifiers
REGION                  1..9
                        note = synthetic
source                  1..9
                        mol_type = protein
                        organism = synthetic construct
SEQUENCE: 144
QQRSNWPLT                                                           9

SEQ ID NO: 145          moltype = DNA  length = 366
FEATURE                 Location/Qualifiers
misc_feature            1..366
                        note = synthetic
source                  1..366
                        mol_type = other DNA
                        organism = synthetic construct
SEQUENCE: 145
caggtgcagc tacagcagtg gggcgcagga ctgttgaagc cttcggagac cctgtccctc  60
acctgcgttg tccatggtgg gtccttcagt ggttactact ggaactggat ccgccagccc  120
ccagggaagg ggctggagtg gattggggaa atcaatcata gaggaaacac caactacaac  180
ccgtccctca agagtcgagt caccgtatca gaagacacgt ccaagaacca gttctccctg  240
aagctgagct ctttgaccgc cgcggacacg gctgtgtatt actgtgtgag aggagaggat  300
tacgattttt ggagtgatta ttataatgac tactggggcc agggaaccct ggtcaccgtc  360
tcctca                                                              366

SEQ ID NO: 146          moltype = AA  length = 122
FEATURE                 Location/Qualifiers
REGION                  1..122
                        note = synthetic
source                  1..122
                        mol_type = protein
                        organism = synthetic construct
SEQUENCE: 146
QVQLQQWGAG LLKPSETLSL TCVVHGGSFS GYYWNWIRQP PGKGLEWIGE INHRGNTNYN  60
PSLKSRVTVS EDTSKNQFSL KLSSLTAADT AVYYCVRGED YDFWSDYYND YWGQGTLVTV  120
SS                                                                  122

SEQ ID NO: 147          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 147
ggtgggtcct tcagtggtta ctac                                          24

SEQ ID NO: 148          moltype = AA  length = 8
FEATURE                 Location/Qualifiers
REGION                  1..8
                        note = synthetic
source                  1..8
                        mol_type = protein
                        organism = synthetic construct
SEQUENCE: 148
GGSFSGYY                                                            8

SEQ ID NO: 149          moltype = DNA  length = 21
FEATURE                 Location/Qualifiers
misc_feature            1..21
                        note = synthetic
```

```
source                  1..21
                        mol_type = other DNA
                        organism = synthetic construct
SEQUENCE: 149
atcaatcata gaggaaacac c                                                21

SEQ ID NO: 150          moltype = AA  length = 7
FEATURE                 Location/Qualifiers
REGION                  1..7
                        note = synthetic
source                  1..7
                        mol_type = protein
                        organism = synthetic construct
SEQUENCE: 150
INHRGNT                                                                7

SEQ ID NO: 151          moltype = DNA  length = 48
FEATURE                 Location/Qualifiers
misc_feature            1..48
                        note = synthetic
source                  1..48
                        mol_type = other DNA
                        organism = synthetic construct
SEQUENCE: 151
gtgagaggag aggattacga tttttggagt gattattata atgactac                   48

SEQ ID NO: 152          moltype = AA  length = 16
FEATURE                 Location/Qualifiers
REGION                  1..16
                        note = synthetic
source                  1..16
                        mol_type = protein
                        organism = synthetic construct
SEQUENCE: 152
VRGEDYDFWS DYYNDY                                                      16

SEQ ID NO: 153          moltype = DNA  length = 321
FEATURE                 Location/Qualifiers
misc_feature            1..321
                        note = synthetic
source                  1..321
                        mol_type = other DNA
                        organism = synthetic construct
SEQUENCE: 153
gaaattgtgt tgacacagtc tccagccacc ctgtctttgt ctccagggga aagagccacc  60
ctctcctgca gggccagtca gactattagc agctacttag cctggcacca acagaaacct  120
ggccaggctc ccaggctcct catctatgat gcatccaaaa gggccacggg catcccagcc  180
aggttcagtg gcagtgggtc tgggacagac ttcactctca ccatcaccag cctagagcct  240
gaagattttg cagtttatta ctgtcagcag cgtagcaact ggcctctcac tttcggcgga  300
gggaccaagg tggagatcaa a                                                321

SEQ ID NO: 154          moltype = AA  length = 107
FEATURE                 Location/Qualifiers
REGION                  1..107
                        note = synthetic
source                  1..107
                        mol_type = protein
                        organism = synthetic construct
SEQUENCE: 154
EIVLTQSPAT LSLSPGERAT LSCRASQTIS SYLAWHQQKP GQAPRLLIYD ASKRATGIPA  60
RFSGSGSGTD FTLTITSLEP EDFAVYYCQQ RSNWPLTFGG GTKVEIK                107

SEQ ID NO: 155          moltype = DNA  length = 18
FEATURE                 Location/Qualifiers
misc_feature            1..18
                        note = synthetic
source                  1..18
                        mol_type = other DNA
                        organism = synthetic construct
SEQUENCE: 155
cagactatta gcagctac                                                    18

SEQ ID NO: 156          moltype = AA  length = 6
FEATURE                 Location/Qualifiers
REGION                  1..6
                        note = synthetic
source                  1..6
                        mol_type = protein
                        organism = synthetic construct
```

```
SEQUENCE: 156
QTISSY                                                      6

SEQ ID NO: 157         moltype =   length =
SEQUENCE: 157
000

SEQ ID NO: 158         moltype =   length =
SEQUENCE: 158
000

SEQ ID NO: 159         moltype = DNA  length = 27
FEATURE                Location/Qualifiers
misc_feature           1..27
                       note = synthetic
source                 1..27
                       mol_type = other DNA
                       organism = synthetic construct
SEQUENCE: 159
cagcagcgta gcaactggcc tctcact                               27

SEQ ID NO: 160         moltype = AA  length = 9
FEATURE                Location/Qualifiers
REGION                 1..9
                       note = synthetic
source                 1..9
                       mol_type = protein
                       organism = synthetic construct
SEQUENCE: 160
QQRSNWPLT                                                   9

SEQ ID NO: 161         moltype = DNA  length = 372
FEATURE                Location/Qualifiers
misc_feature           1..372
                       note = synthetic
source                 1..372
                       mol_type = other DNA
                       organism = synthetic construct
SEQUENCE: 161
caggtgcagc tacagcagtg gggcgcagga ctgttgccgc cttcggagac cctgtccctc  60
atctgcgctg tctatggtgg gtccttcagt ggttactact ggagctggat ccgccagccc  120
ccagggaagg ggctggagtg gattggggaa atcaatcata gaggaagcac caactacaac  180
ccgtccctca agagtcgagc caccatatca gttgacacgt ccaagaacca gttctccctg  240
aagctgagct ctgtgaccgc cgcggacacg gctgtgtatt actgttcgag aggcgaggat  300
tactatgata gtagtggtta ctcgtactac tttgactact ggggccaggg aaccctggtc  360
accgtctcct ca                                               372

SEQ ID NO: 162         moltype = AA  length = 124
FEATURE                Location/Qualifiers
REGION                 1..124
                       note = synthetic
source                 1..124
                       mol_type = protein
                       organism = synthetic construct
SEQUENCE: 162
QVQLQQWGAG LLPPSETLSL ICAVYGGSFS GYYWSWIRQP PGKGLEWIGE INHRGSTNYN  60
PSLKSRATIS VDTSKNQFSL KLSSVTAADT AVYYCSRGED YYDSSGYSYY FDYWGQGTLV  120
TVSS                                                        124

SEQ ID NO: 163         moltype = DNA  length = 24
FEATURE                Location/Qualifiers
misc_feature           1..24
                       note = synthetic
source                 1..24
                       mol_type = other DNA
                       organism = synthetic construct
SEQUENCE: 163
ggtgggtcct tcagtggtta ctac                                  24

SEQ ID NO: 164         moltype = AA  length = 8
FEATURE                Location/Qualifiers
REGION                 1..8
                       note = synthetic
source                 1..8
                       mol_type = protein
                       organism = synthetic construct
SEQUENCE: 164
GGSFSGYY                                                    8
```

```
SEQ ID NO: 165          moltype = DNA  length = 21
FEATURE                 Location/Qualifiers
misc_feature            1..21
                        note = synthetic
source                  1..21
                        mol_type = other DNA
                        organism = synthetic construct
SEQUENCE: 165
atcaatcata gaggaagcac c                                            21

SEQ ID NO: 166          moltype = AA  length = 7
FEATURE                 Location/Qualifiers
REGION                  1..7
                        note = synthetic
source                  1..7
                        mol_type = protein
                        organism = synthetic construct
SEQUENCE: 166
INHRGST                                                            7

SEQ ID NO: 167          moltype = DNA  length = 54
FEATURE                 Location/Qualifiers
misc_feature            1..54
                        note = synthetic
source                  1..54
                        mol_type = other DNA
                        organism = synthetic construct
SEQUENCE: 167
tcgagaggcg aggattacta tgatagtagt ggttactcgt actactttga ctac        54

SEQ ID NO: 168          moltype = AA  length = 18
FEATURE                 Location/Qualifiers
REGION                  1..18
                        note = synthetic
source                  1..18
                        mol_type = protein
                        organism = synthetic construct
SEQUENCE: 168
SRGEDYYDSS GYSYYFDY                                                18

SEQ ID NO: 169          moltype = DNA  length = 321
FEATURE                 Location/Qualifiers
misc_feature            1..321
                        note = synthetic
source                  1..321
                        mol_type = other DNA
                        organism = synthetic construct
SEQUENCE: 169
gaaattgtgt tgacacagtc tccagccacc ctgtctttgt ctccagggga aagagccacc  60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtagcaact ggccgctcac tttcggcgga  300
gggaccaagg tggagatcaa a                                            321

SEQ ID NO: 170          moltype = AA  length = 107
FEATURE                 Location/Qualifiers
REGION                  1..107
                        note = synthetic
source                  1..107
                        mol_type = protein
                        organism = synthetic construct
SEQUENCE: 170
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPLTFGG GTKVEIK                107

SEQ ID NO: 171          moltype = DNA  length = 18
FEATURE                 Location/Qualifiers
misc_feature            1..18
                        note = synthetic
source                  1..18
                        mol_type = other DNA
                        organism = synthetic construct
SEQUENCE: 171
cagagtgtta gcagctac                                                18

SEQ ID NO: 172          moltype = AA  length = 6
FEATURE                 Location/Qualifiers
REGION                  1..6
```

```
                        note = synthetic
source                  1..6
                        mol_type = protein
                        organism = synthetic construct
SEQUENCE: 172
QSVSSY                                                          6

SEQ ID NO: 173          moltype =   length =
SEQUENCE: 173
000

SEQ ID NO: 174          moltype =   length =
SEQUENCE: 174
000

SEQ ID NO: 175          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 175
cagcagcgta gcaactggcc gctcact                                   27

SEQ ID NO: 176          moltype = AA  length = 9
FEATURE                 Location/Qualifiers
REGION                  1..9
                        note = synthetic
source                  1..9
                        mol_type = protein
                        organism = synthetic construct
SEQUENCE: 176
QQRSNWPLT                                                       9

SEQ ID NO: 177          moltype = DNA  length = 366
FEATURE                 Location/Qualifiers
misc_feature            1..366
                        note = synthetic
source                  1..366
                        mol_type = other DNA
                        organism = synthetic construct
SEQUENCE: 177
caggtgcagc tacagcagtg gggcgcagga ctgttgaggc cttcggagac cctgtccctc  60
acctgcgctg tctatggtgg gtccttcagt ggttactact ggaattggat ccgccagtcc  120
ccagggacgg ggctggagtg gattggggaa atcaatcata gagggaacat caacttcaac  180
ccgtccctca agagtcgagt caccatatca gaggacacgt ccaaaaacca attctccctg  240
aggctgaact ctgtgaccgc cgcggacacg gctgtgtatt actgtgcgag aggagaggat  300
tacgatattt ggagtggtta ttatagggag tactggggcc agggaaccct ggtcaccgtc  360
tcctca                                                          366

SEQ ID NO: 178          moltype = AA  length = 122
FEATURE                 Location/Qualifiers
REGION                  1..122
                        note = synthetic
source                  1..122
                        mol_type = protein
                        organism = synthetic construct
SEQUENCE: 178
QVQLQQWGAG LLRPSETLSL TCAVYGGSFS GYYWNWIRQS PGTGLEWIGE INHRGNINFN  60
PSLKSRVTIS EDTSKNQFSL RLNSVTAADT AVYYCARGED YDIWSGYYRE YWGQGTLVTV  120
SS                                                              122

SEQ ID NO: 179          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 179
ggtgggtcct tcagtggtta ctac                                      24

SEQ ID NO: 180          moltype = AA  length = 8
FEATURE                 Location/Qualifiers
REGION                  1..8
                        note = synthetic
source                  1..8
                        mol_type = protein
```

```
                        organism = synthetic construct
SEQUENCE: 180
GGSFSGYY                                                            8

SEQ ID NO: 181          moltype = DNA  length = 21
FEATURE                 Location/Qualifiers
misc_feature            1..21
                        note = synthetic
source                  1..21
                        mol_type = other DNA
                        organism = synthetic construct
SEQUENCE: 181
atcaatcata gagggaacat c                                             21

SEQ ID NO: 182          moltype = AA  length = 7
FEATURE                 Location/Qualifiers
REGION                  1..7
                        note = synthetic
source                  1..7
                        mol_type = protein
                        organism = synthetic construct
SEQUENCE: 182
INHRGNI                                                             7

SEQ ID NO: 183          moltype = DNA  length = 48
FEATURE                 Location/Qualifiers
misc_feature            1..48
                        note = synthetic
source                  1..48
                        mol_type = other DNA
                        organism = synthetic construct
SEQUENCE: 183
gcgagaggag aggattacga tatttggagt ggttattata gggagtac                48

SEQ ID NO: 184          moltype = AA  length = 16
FEATURE                 Location/Qualifiers
REGION                  1..16
                        note = synthetic
source                  1..16
                        mol_type = protein
                        organism = synthetic construct
SEQUENCE: 184
ARGEDYDIWS GYYREY                                                   16

SEQ ID NO: 185          moltype = DNA  length = 321
FEATURE                 Location/Qualifiers
misc_feature            1..321
                        note = synthetic
source                  1..321
                        mol_type = other DNA
                        organism = synthetic construct
SEQUENCE: 185
gaaattgtgt tgacacagtc tccagccacc ctgtctttgt ctccagggga aagagccact  60
ctctcctgca gggccagtca gagtgttagc agctacttag cctggtacca gcagaaacct  120
ggccaggctc ccaggctcct catctatgat gcatccaaga gggccactgg catcccagcc  180
aggttcagtg gcagtgggtc tgggacagac ttcactctca ccatcagcag cctagagcct  240
gaagattttg ctgtttatta ctgtcagcag cgtagcaact ggcctctcgc tttcggcgga  300
gggaccaagg tggagatcaa a                                             321

SEQ ID NO: 186          moltype = AA  length = 107
FEATURE                 Location/Qualifiers
REGION                  1..107
                        note = synthetic
source                  1..107
                        mol_type = protein
                        organism = synthetic construct
SEQUENCE: 186
EIVLTQSPAT LSLSPGERAT LSCRASQSVS SYLAWYQQKP GQAPRLLIYD ASKRATGIPA  60
RFSGSGSGTD FTLTISSLEP EDFAVYYCQQ RSNWPLAFGG GTKVEIK                 107

SEQ ID NO: 187          moltype = DNA  length = 18
FEATURE                 Location/Qualifiers
misc_feature            1..18
                        note = synthetic
source                  1..18
                        mol_type = other DNA
                        organism = synthetic construct
SEQUENCE: 187
cagagtgtta gcagctac                                                 18
```

```
SEQ ID NO: 188          moltype = AA  length = 6
FEATURE                 Location/Qualifiers
REGION                  1..6
                        note = synthetic
source                  1..6
                        mol_type = protein
                        organism = synthetic construct
SEQUENCE: 188
QSVSSY                                                          6

SEQ ID NO: 189          moltype =   length =
SEQUENCE: 189
000

SEQ ID NO: 190          moltype =   length =
SEQUENCE: 190
000

SEQ ID NO: 191          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 191
cagcagcgta gcaactggcc tctcgct                                   27

SEQ ID NO: 192          moltype = AA  length = 9
FEATURE                 Location/Qualifiers
REGION                  1..9
                        note = synthetic
source                  1..9
                        mol_type = protein
                        organism = synthetic construct
SEQUENCE: 192
QQRSNWPLA                                                       9

SEQ ID NO: 193          moltype = DNA  length = 357
FEATURE                 Location/Qualifiers
misc_feature            1..357
                        note = synthetic
source                  1..357
                        mol_type = other DNA
                        organism = synthetic construct
SEQUENCE: 193
caggtgcagc tacagcagtg gggcgcagga ctgttgaagc cttcggagac cctgtccctc  60
acctgcgctg tctatggtgg gtccttcagt gagttctact ggaactggat ccgccagccc  120
ccagagaagg gcctggagtg gattggggaa atcaatcatc gtggaaacac caactacaac  180
ccgtccctca agagtcgagt caccatatca gtagacatgt ccaagaacca gttctccctg  240
cagctgaact ctgtgaccgt cgcggacacg gctctgtatt actgtgcgtt tggctacgat  300
tttcggagtt cttatgagga cgtctggggc caagggacca cggtcaccgt ctcctca     357

SEQ ID NO: 194          moltype = AA  length = 119
FEATURE                 Location/Qualifiers
REGION                  1..119
                        note = synthetic
source                  1..119
                        mol_type = protein
                        organism = synthetic construct
SEQUENCE: 194
QVQLQQWGAG LLKPSETLSL TCAVYGGSFS EFYWNWIRQP PEKGLEWIGE INHRGNTNYN  60
PSLKSRVTIS VDMSKNQFSL QLNSVTVADT ALYYCAFGYD FRSSYEDVWG QGTTVTVSS   119

SEQ ID NO: 195          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 195
ggtgggtcct tcagtgagtt ctac                                      24

SEQ ID NO: 196          moltype = AA  length = 8
FEATURE                 Location/Qualifiers
REGION                  1..8
                        note = synthetic
```

```
source                  1..8
                        mol_type = protein
                        organism = synthetic construct
SEQUENCE: 196
GGSFSEFY                                                                8

SEQ ID NO: 197          moltype = DNA  length = 21
FEATURE                 Location/Qualifiers
misc_feature            1..21
                        note = synthetic
source                  1..21
                        mol_type = other DNA
                        organism = synthetic construct
SEQUENCE: 197
atcaatcatc gtggaaacac c                                                 21

SEQ ID NO: 198          moltype = AA  length = 7
FEATURE                 Location/Qualifiers
REGION                  1..7
                        note = synthetic
source                  1..7
                        mol_type = protein
                        organism = synthetic construct
SEQUENCE: 198
INHRGNT                                                                 7

SEQ ID NO: 199          moltype = DNA  length = 39
FEATURE                 Location/Qualifiers
misc_feature            1..39
                        note = synthetic
source                  1..39
                        mol_type = other DNA
                        organism = synthetic construct
SEQUENCE: 199
gcgtttggct acgattttcg gagttcttat gaggacgtc                              39

SEQ ID NO: 200          moltype = AA  length = 13
FEATURE                 Location/Qualifiers
REGION                  1..13
                        note = synthetic
source                  1..13
                        mol_type = protein
                        organism = synthetic construct
SEQUENCE: 200
AFGYDFRSSY EDV                                                          13

SEQ ID NO: 201          moltype = DNA  length = 321
FEATURE                 Location/Qualifiers
misc_feature            1..321
                        note = synthetic
source                  1..321
                        mol_type = other DNA
                        organism = synthetic construct
SEQUENCE: 201
gaaattgtgt tgacacagtc tccagccacc ctgtctttgt ctccagggga aagagccacc  60
ctctcctgca gggccagtca ggatattagc acctacttag cctggcacca acagaaacct  120
ggccagcctc ccaggctcct catctatggt tcatccaaca gggccactgg catcccagcc  180
aggttcagtg gcagtgggtc tgggacagac ttcactctca ccatcagcag cctagagcct  240
gaagattttg cagtttatta ctgtcagcag cgtagcaact ggcctctcac tttcggcgga  300
gggaccaagg tggagatcaa a                                                 321

SEQ ID NO: 202          moltype = AA  length = 107
FEATURE                 Location/Qualifiers
REGION                  1..107
                        note = synthetic
source                  1..107
                        mol_type = protein
                        organism = synthetic construct
SEQUENCE: 202
EIVLTQSPAT LSLSPGERAT LSCRASQDIS TYLAWHQQKP GQPPRLLIYG SSNRATGIPA  60
RFSGSGSGTD FTLTISSLEP EDFAVYYCQQ RSNWPLTFGG GTKVEIK                 107

SEQ ID NO: 203          moltype = DNA  length = 18
FEATURE                 Location/Qualifiers
misc_feature            1..18
                        note = synthetic
source                  1..18
                        mol_type = other DNA
                        organism = synthetic construct
```

```
SEQUENCE: 203
caggatatta gcacctac                                           18

SEQ ID NO: 204         moltype = AA  length = 6
FEATURE                Location/Qualifiers
REGION                 1..6
                       note = synthetic
source                 1..6
                       mol_type = protein
                       organism = synthetic construct
SEQUENCE: 204
QDISTY                                                        6

SEQ ID NO: 205         moltype =   length =
SEQUENCE: 205
000

SEQ ID NO: 206         moltype =   length =
SEQUENCE: 206
000

SEQ ID NO: 207         moltype = DNA  length = 27
FEATURE                Location/Qualifiers
misc_feature           1..27
                       note = synthetic
source                 1..27
                       mol_type = other DNA
                       organism = synthetic construct
SEQUENCE: 207
cagcagcgta gcaactggcc tctcact                                 27

SEQ ID NO: 208         moltype = AA  length = 9
FEATURE                Location/Qualifiers
REGION                 1..9
                       note = synthetic
source                 1..9
                       mol_type = protein
                       organism = synthetic construct
SEQUENCE: 208
QQRSNWPLT                                                     9

SEQ ID NO: 209         moltype = DNA  length = 372
FEATURE                Location/Qualifiers
misc_feature           1..372
                       note = synthetic
source                 1..372
                       mol_type = other DNA
                       organism = synthetic construct
SEQUENCE: 209
gaggtgcagc tgttggagtc tgggggaggc ttggtacagc cggggggtc cctgagactc  60
tcctgtgcag cctctggatt caccttcaga agctatgcca tgagttgggt ccgccaggct  120
ccagggaagg ggctggagtg ggtctcagtt attagtggtg gtggtggtag gacatactac  180
acagactccg tgaagggccg gttcaccatc tccagagaca attccaagag catgctgtat  240
ctgcaaatga acagcctgag agccgaggac acggccattt attactgtgc gaaagagagg  300
gtaactggaa tagaccacta ctactacggt gtggacgtct ggggccaagg gaccacggtc  360
accgtctcct ca                                                 372

SEQ ID NO: 210         moltype = AA  length = 124
FEATURE                Location/Qualifiers
REGION                 1..124
                       note = synthetic
source                 1..124
                       mol_type = protein
                       organism = synthetic construct
SEQUENCE: 210
EVQLLESGGG LVQPGGSLRL SCAASGFTFR SYAMSWVRQA PGKGLEWVSV ISGGGGRTYY  60
TDSVKGRFTI SRDNSKSMLY LQMNSLRAED TAIYYCAKER VTGIDHYYYG VDVWGQGTTV  120
TVSS                                                          124

SEQ ID NO: 211         moltype = DNA  length = 24
FEATURE                Location/Qualifiers
misc_feature           1..24
                       note = synthetic
source                 1..24
                       mol_type = other DNA
                       organism = synthetic construct
SEQUENCE: 211
ggattcacct tcagaagcta tgcc                                    24
```

```
SEQ ID NO: 212          moltype = AA  length = 8
FEATURE                 Location/Qualifiers
REGION                  1..8
                        note = synthetic
source                  1..8
                        mol_type = protein
                        organism = synthetic construct
SEQUENCE: 212
GFTFRSYA                                                                    8

SEQ ID NO: 213          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 213
attagtggtg gtggtggtag gaca                                                  24

SEQ ID NO: 214          moltype = AA  length = 8
FEATURE                 Location/Qualifiers
REGION                  1..8
                        note = synthetic
source                  1..8
                        mol_type = protein
                        organism = synthetic construct
SEQUENCE: 214
ISGGGGRT                                                                    8

SEQ ID NO: 215          moltype = DNA  length = 51
FEATURE                 Location/Qualifiers
misc_feature            1..51
                        note = synthetic
source                  1..51
                        mol_type = other DNA
                        organism = synthetic construct
SEQUENCE: 215
gcgaaagaga gggtaactgg aatagaccac tactactacg gtgtggacgt c                    51

SEQ ID NO: 216          moltype = AA  length = 17
FEATURE                 Location/Qualifiers
REGION                  1..17
                        note = synthetic
source                  1..17
                        mol_type = protein
                        organism = synthetic construct
SEQUENCE: 216
AKERVTGIDH YYYGVDV                                                          17

SEQ ID NO: 217          moltype = DNA  length = 321
FEATURE                 Location/Qualifiers
misc_feature            1..321
                        note = synthetic
source                  1..321
                        mol_type = other DNA
                        organism = synthetic construct
SEQUENCE: 217
gacatccaga tgacccagtc tccatcctcc ctgtctgcat ctgtaggaga cagagtcacc  60
atcacttgcc gggcaagtca gagcattagt agctatttaa attggtatca gcagaaacca  120
gggaaagccc ctaagctcct gatctatgct acatccagtt tgcaaagtgg ggtcccatca  180
cggttcagtg gcagtgcatc tggaacagat ttcactctcg ccatcagcag tctgcaacct  240
gaagattttg caacttacta ctgtcaacag agttacacta cccccctcac tttcggcgga  300
gggaccaagg tggagatcaa a                                             321

SEQ ID NO: 218          moltype = AA  length = 107
FEATURE                 Location/Qualifiers
REGION                  1..107
                        note = synthetic
source                  1..107
                        mol_type = protein
                        organism = synthetic construct
SEQUENCE: 218
DIQMTQSPSS LSASVGDRVT ITCRASQSIS SYLNWYQQKP GKAPKLLIYA TSSLQSGVPS  60
RFSGSASGTD FTLAISSLQP EDFATYYCQQ SYTTPLTFGG GTKVEIK                 107

SEQ ID NO: 219          moltype = DNA  length = 18
FEATURE                 Location/Qualifiers
misc_feature            1..18
```

```
                        note = synthetic
source                  1..18
                        mol_type = other DNA
                        organism = synthetic construct
SEQUENCE: 219
cagagcatta gtagctat                                            18

SEQ ID NO: 220          moltype = AA  length = 6
FEATURE                 Location/Qualifiers
REGION                  1..6
                        note = synthetic
source                  1..6
                        mol_type = protein
                        organism = synthetic construct
SEQUENCE: 220
QSISSY                                                         6

SEQ ID NO: 221          moltype =   length =
SEQUENCE: 221
000

SEQ ID NO: 222          moltype =   length =
SEQUENCE: 222
000

SEQ ID NO: 223          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 223
caacagagtt acactacccc cctcact                                  27

SEQ ID NO: 224          moltype = AA  length = 9
FEATURE                 Location/Qualifiers
REGION                  1..9
                        note = synthetic
source                  1..9
                        mol_type = protein
                        organism = synthetic construct
SEQUENCE: 224
QQSYTTPLT                                                      9

SEQ ID NO: 225          moltype = DNA  length = 390
FEATURE                 Location/Qualifiers
misc_feature            1..390
                        note = synthetic
source                  1..390
                        mol_type = other DNA
                        organism = synthetic construct
SEQUENCE: 225
gaggtgcagc tggtggagtc tgggggaggc ttggtacaac ctggagggtc cctgagactt  60
tcctgtgcag cctctggatt tacattcagc agttatgaaa tgaactgggt ccgccaggct  120
ccagggaagg ggctggagtg ggtttcatat atcagtagta gtggtaatac caaagactac  180
gcaggctctg tgaagggccg agtcaccatc tccagagaca acgccaagaa cttactgtat  240
ctgcaaatga acagcctgag agccgaggac acggctgttt atcactgtgc gagagatgga  300
gggcattacg atattttgac tggttccatg tcctactact actacgcttt ggacgtctgg  360
ggccaaggga ccacggtcac cgtctcctca                               390

SEQ ID NO: 226          moltype = AA  length = 130
FEATURE                 Location/Qualifiers
REGION                  1..130
                        note = synthetic
source                  1..130
                        mol_type = protein
                        organism = synthetic construct
SEQUENCE: 226
EVQLVESGGG LVQPGGSLRL SCAASGFTFS SYEMNWVRQA PGKGLEWVSY ISSSGNTKDY  60
AGSVKGRVTI SRDNAKNLLY LQMNSLRAED TAVYHCARDG GHYDILTGSM SYYYYALDVW  120
GQGTTVTVSS                                                     130

SEQ ID NO: 227          moltype = DNA  length = 24
FEATURE                 Location/Qualifiers
misc_feature            1..24
                        note = synthetic
source                  1..24
                        mol_type = other DNA
```

```
                         organism = synthetic construct
SEQUENCE: 227
ggatttacat tcagcagtta tgaa                                       24

SEQ ID NO: 228           moltype = AA  length = 8
FEATURE                  Location/Qualifiers
REGION                   1..8
                         note = synthetic
source                   1..8
                         mol_type = protein
                         organism = synthetic construct
SEQUENCE: 228
GFTFSSYE                                                         8

SEQ ID NO: 229           moltype = DNA  length = 24
FEATURE                  Location/Qualifiers
misc_feature             1..24
                         note = synthetic
source                   1..24
                         mol_type = other DNA
                         organism = synthetic construct
SEQUENCE: 229
atcagtagta gtggtaatac caaa                                       24

SEQ ID NO: 230           moltype = AA  length = 8
FEATURE                  Location/Qualifiers
REGION                   1..8
                         note = synthetic
source                   1..8
                         mol_type = protein
                         organism = synthetic construct
SEQUENCE: 230
ISSSGNTK                                                         8

SEQ ID NO: 231           moltype = DNA  length = 69
FEATURE                  Location/Qualifiers
misc_feature             1..69
                         note = synthetic
source                   1..69
                         mol_type = other DNA
                         organism = synthetic construct
SEQUENCE: 231
gcgagagatg gagggcatta cgatattttg actggttcca tgtcctacta ctactacgct  60
ttggacgtc                                                        69

SEQ ID NO: 232           moltype = AA  length = 23
FEATURE                  Location/Qualifiers
REGION                   1..23
                         note = synthetic
source                   1..23
                         mol_type = protein
                         organism = synthetic construct
SEQUENCE: 232
ARDGGHYDIL TGSMSYYYYA LDV                                        23

SEQ ID NO: 233           moltype = DNA  length = 324
FEATURE                  Location/Qualifiers
misc_feature             1..324
                         note = synthetic
source                   1..324
                         mol_type = other DNA
                         organism = synthetic construct
SEQUENCE: 233
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                       324

SEQ ID NO: 234           moltype = AA  length = 108
FEATURE                  Location/Qualifiers
REGION                   1..108
                         note = synthetic
source                   1..108
                         mol_type = protein
                         organism = synthetic construct
SEQUENCE: 234
DIQMTQSPSS LSASVGDRVT ITCRASQSIS SYLNWYQQKP GKAPKLLIYA ASSLQSGVPS  60
```

```
RFSGSGSGTD FTLTISSLQP EDFATYYCQQ SYSTPPITFG QGTRLEIK            108

SEQ ID NO: 235          moltype = DNA  length = 18
FEATURE                 Location/Qualifiers
misc_feature            1..18
                        note = synthetic
source                  1..18
                        mol_type = other DNA
                        organism = synthetic construct
SEQUENCE: 235
cagagcatta gcagctat                                             18

SEQ ID NO: 236          moltype = AA  length = 6
FEATURE                 Location/Qualifiers
REGION                  1..6
                        note = synthetic
source                  1..6
                        mol_type = protein
                        organism = synthetic construct
SEQUENCE: 236
QSISSY                                                          6

SEQ ID NO: 237          moltype =   length =
SEQUENCE: 237
000

SEQ ID NO: 238          moltype =   length =
SEQUENCE: 238
000

SEQ ID NO: 239          moltype = DNA  length = 30
FEATURE                 Location/Qualifiers
misc_feature            1..30
                        note = synthetic
source                  1..30
                        mol_type = other DNA
                        organism = synthetic construct
SEQUENCE: 239
caacagagtt acagtacccc tccgatcacc                                30

SEQ ID NO: 240          moltype = AA  length = 10
FEATURE                 Location/Qualifiers
REGION                  1..10
                        note = synthetic
source                  1..10
                        mol_type = protein
                        organism = synthetic construct
SEQUENCE: 240
QQSYSTPPIT                                                      10

SEQ ID NO: 241          moltype = DNA  length = 363
FEATURE                 Location/Qualifiers
misc_feature            1..363
                        note = synthetic
source                  1..363
                        mol_type = other DNA
                        organism = synthetic construct
SEQUENCE: 241
gaggtgcagc tggtggagtc tgggggaggc ttggtacagc ctgggggtc cctgagactc  60
tcctgtgcag cctctggatt cacctttaaa acctatgcca tgagctgggt ccgccaggct  120
ccagggaggg ggctggagtg ggtctcaggt attagtggta gtggtagtac ctcatactac  180
gcagactccg tgaagggccg gttcaccatc tccagagaca attacaagaa gacgctgtct  240
ctgcaaatga acagtctgag agccgaggac acggccgttt attactgtgc gctggatata  300
atggcaacgg taggaggtct ctttaacaac tggggccagg gaaccctggt caccgtctcc  360
tca                                                             363

SEQ ID NO: 242          moltype = AA  length = 121
FEATURE                 Location/Qualifiers
REGION                  1..121
                        note = synthetic
source                  1..121
                        mol_type = protein
                        organism = synthetic construct
SEQUENCE: 242
EVQLVESGGG LVQPGGSLRL SCAASGFTFK TYAMSWVRQA PGRGLEWVSG ISGSGSTSYY  60
ADSVKGRFTI SRDNYKKTLS LQMNSLRAED TAVYYCALDI MATVGGLFNN WGQGTLVTVS  120
S                                                               121

SEQ ID NO: 243          moltype = DNA  length = 24
```

```
FEATURE                Location/Qualifiers
misc_feature           1..24
                       note = synthetic
source                 1..24
                       mol_type = other DNA
                       organism = synthetic construct
SEQUENCE: 243
ggattcacct ttaaaaccta tgcc                                        24

SEQ ID NO: 244         moltype = AA  length = 8
FEATURE                Location/Qualifiers
REGION                 1..8
                       note = synthetic
source                 1..8
                       mol_type = protein
                       organism = synthetic construct
SEQUENCE: 244
GFTFKTYA                                                          8

SEQ ID NO: 245         moltype = DNA  length = 24
FEATURE                Location/Qualifiers
misc_feature           1..24
                       note = synthetic
source                 1..24
                       mol_type = other DNA
                       organism = synthetic construct
SEQUENCE: 245
attagtggta gtggtagtac ctca                                        24

SEQ ID NO: 246         moltype = AA  length = 8
FEATURE                Location/Qualifiers
REGION                 1..8
                       note = synthetic
source                 1..8
                       mol_type = protein
                       organism = synthetic construct
SEQUENCE: 246
ISGSGSTS                                                          8

SEQ ID NO: 247         moltype = DNA  length = 42
FEATURE                Location/Qualifiers
misc_feature           1..42
                       note = synthetic
source                 1..42
                       mol_type = other DNA
                       organism = synthetic construct
SEQUENCE: 247
gcgctggata taatggcaac ggtaggaggt ctctttaaca ac                    42

SEQ ID NO: 248         moltype = AA  length = 14
FEATURE                Location/Qualifiers
REGION                 1..14
                       note = synthetic
source                 1..14
                       mol_type = protein
                       organism = synthetic construct
SEQUENCE: 248
ALDIMATVGG LFNN                                                   14

SEQ ID NO: 249         moltype = DNA  length = 324
FEATURE                Location/Qualifiers
misc_feature           1..324
                       note = synthetic
source                 1..324
                       mol_type = other DNA
                       organism = synthetic construct
SEQUENCE: 249
gaaattgtgt tgacgcagtc tccaggcacc ctgtctttgt ctccagggga aagagccacc  60
ctctcctgca gggccagtca gagtgttagc agcagctact tagcctggta ccagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag cagtatggta gctcaccttg gacgttcggc  300
caagggacca aggtggaaat caaa                                        324

SEQ ID NO: 250         moltype = AA  length = 108
FEATURE                Location/Qualifiers
REGION                 1..108
                       note = synthetic
source                 1..108
```

```
                        mol_type = protein
                        organism = synthetic construct
SEQUENCE: 250
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPWTFG QGTKVEIK              108

SEQ ID NO: 251          moltype = DNA  length = 21
FEATURE                 Location/Qualifiers
misc_feature            1..21
                        note = synthetic
source                  1..21
                        mol_type = other DNA
                        organism = synthetic construct
SEQUENCE: 251
cagagtgtta gcagcagcta c                                           21

SEQ ID NO: 252          moltype = AA  length = 7
FEATURE                 Location/Qualifiers
REGION                  1..7
                        note = synthetic
source                  1..7
                        mol_type = protein
                        organism = synthetic construct
SEQUENCE: 252
QSVSSSY                                                           7

SEQ ID NO: 253          moltype =   length =
SEQUENCE: 253
000

SEQ ID NO: 254          moltype =   length =
SEQUENCE: 254
000

SEQ ID NO: 255          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 255
cagcagtatg gtagctcacc ttggacg                                     27

SEQ ID NO: 256          moltype = AA  length = 9
FEATURE                 Location/Qualifiers
REGION                  1..9
                        note = synthetic
source                  1..9
                        mol_type = protein
                        organism = synthetic construct
SEQUENCE: 256
QQYGSSPWT                                                         9

SEQ ID NO: 257          moltype = DNA  length = 360
FEATURE                 Location/Qualifiers
misc_feature            1..360
                        note = synthetic
source                  1..360
                        mol_type = other DNA
                        organism = synthetic construct
SEQUENCE: 257
caggtgcagc tggtgcagtc tggggctgag gtgaagaagc ctgggtcctc ggtgaaggtc  60
tcctgcaagg cttctggagg caccttcagc agacatacta tcagctgggt gcgacaggcc  120
cctggacaag ggcttgagtg gatgggaggg atcatcccta tctttggtac agcaaactac  180
gcacacaagt tccagggcag agtcacgatt accacggacg aatccacgag cacagcctac  240
atggagctga gcagcctgag atctgaggac acggccgtat attattgtgc gagagcccct  300
tatacccgac aggggtactt cgatctctgg ggccgtggca ccctggtcac cgtctcctca  360

SEQ ID NO: 258          moltype = AA  length = 120
FEATURE                 Location/Qualifiers
REGION                  1..120
                        note = synthetic
source                  1..120
                        mol_type = protein
                        organism = synthetic construct
SEQUENCE: 258
QVQLVQSGAE VKKPGSSVKV SCKASGGTFS RHTISWVRQA PGQGLEWMGG IIPIFGTANY  60
AHKFQGRVTI TTDESTSTAY MELSSLRSED TAVYYCARAP YTRQGYFDLW GRGTLVTVSS  120
```

```
SEQ ID NO: 259          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 259
ggaggcacct tcagcagaca tact                                        24

SEQ ID NO: 260          moltype = AA  length = 8
FEATURE                 Location/Qualifiers
REGION                  1..8
                        note = synthetic
source                  1..8
                        mol_type = protein
                        organism = synthetic construct
SEQUENCE: 260
GGTFSRHT                                                          8

SEQ ID NO: 261          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 261
atcatcccta tctttggtac agca                                        24

SEQ ID NO: 262          moltype = AA  length = 8
FEATURE                 Location/Qualifiers
REGION                  1..8
                        note = synthetic
source                  1..8
                        mol_type = protein
                        organism = synthetic construct
SEQUENCE: 262
IIPIFGTA                                                          8

SEQ ID NO: 263          moltype = DNA  length = 39
FEATURE                 Location/Qualifiers
misc_feature            1..39
                        note = synthetic
source                  1..39
                        mol_type = other DNA
                        organism = synthetic construct
SEQUENCE: 263
gcgagagccc cttatacccg acaggggtac ttcgatctc                        39

SEQ ID NO: 264          moltype = AA  length = 13
FEATURE                 Location/Qualifiers
REGION                  1..13
                        note = synthetic
source                  1..13
                        mol_type = protein
                        organism = synthetic construct
SEQUENCE: 264
ARAPYTRQGY FDL                                                    13

SEQ ID NO: 265          moltype = DNA  length = 339
FEATURE                 Location/Qualifiers
misc_feature            1..339
                        note = synthetic
source                  1..339
                        mol_type = other DNA
                        organism = synthetic construct
SEQUENCE: 265
gacatcgtga tgacccagtc tccagactcc ctggctgtgt ctctgggcga gagggccacc  60
atcaactgca agtccagcca gagtgtttta tacagctcca acaataagaa ctacttagct  120
tggtaccagc agaaaccagg acagcctcct aagctactca tttactgggc atctacccgg  180
gaatccgggg tccctgaccg attcagtggc agcgggtctg ggacagattt cactctcacc  240
atcagcagcc tgcaggctga agatgtggca gtttattact gtcagcaaga ttatagtact  300
ccgtggacgt tcggccaagg gaccaaggtg gaaatcaaa                        339

SEQ ID NO: 266          moltype = AA  length = 113
FEATURE                 Location/Qualifiers
REGION                  1..113
```

```
                        note = synthetic
source                  1..113
                        mol_type = protein
                        organism = synthetic construct
SEQUENCE: 266
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQDYST PWTFGQGTKV EIK        113

SEQ ID NO: 267          moltype = DNA  length = 36
FEATURE                 Location/Qualifiers
misc_feature            1..36
                        note = synthetic
source                  1..36
                        mol_type = other DNA
                        organism = synthetic construct
SEQUENCE: 267
cagagtgttt tatacagctc caacaataag aactac                           36

SEQ ID NO: 268          moltype = AA  length = 12
FEATURE                 Location/Qualifiers
REGION                  1..12
                        note = synthetic
source                  1..12
                        mol_type = protein
                        organism = synthetic construct
SEQUENCE: 268
QSVLYSSNNK NY                                                     12

SEQ ID NO: 269          moltype =   length =
SEQUENCE: 269
000

SEQ ID NO: 270          moltype =   length =
SEQUENCE: 270
000

SEQ ID NO: 271          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 271
cagcaagatt atagtactcc gtggacg                                     27

SEQ ID NO: 272          moltype = AA  length = 9
FEATURE                 Location/Qualifiers
REGION                  1..9
                        note = synthetic
source                  1..9
                        mol_type = protein
                        organism = synthetic construct
SEQUENCE: 272
QQDYSTPWT                                                         9

SEQ ID NO: 273          moltype = DNA  length = 354
FEATURE                 Location/Qualifiers
misc_feature            1..354
                        note = synthetic
source                  1..354
                        mol_type = other DNA
                        organism = synthetic construct
SEQUENCE: 273
caggtgcagc tggtgcagtc tggggctgag gtgaagaagc ctggggcctc agtgaaggtt  60
tcctgcaagg catctggata caccttcacc aactactata tacactgggt gcgacaggcc  120
cctggacaag ggcttgactg gatgggaatt atcaaccctg gtggtggtaa cacaaactac  180
gcacagaagt tcctgggcag agtcaccatg accagggaca cgtccacgac cacagtctac  240
atggagctga gcagcctgag atctgaggac acggccatat attactgtgc gagagaaaac  300
tggaactctt actttgacaa ctggggccag ggaaccctgg tcaccgtctc ctca        354

SEQ ID NO: 274          moltype = AA  length = 118
FEATURE                 Location/Qualifiers
REGION                  1..118
                        note = synthetic
source                  1..118
                        mol_type = protein
                        organism = synthetic construct
SEQUENCE: 274
```

```
QVQLVQSGAE VKKPGASVKV SCKASGYTFT NYYIHWVRQA PGQGLDWMGI INPGGGNTNY  60
AQKFLGRVTM TRDTSTTTVY MELSSLRSED TAIYYCAREN WNSYFDNWGQ GTLVTVSS    118

SEQ ID NO: 275          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 275
ggatacacct tcaccaacta ctat                                         24

SEQ ID NO: 276          moltype = AA  length = 8
FEATURE                 Location/Qualifiers
REGION                  1..8
                        note = synthetic
source                  1..8
                        mol_type = protein
                        organism = synthetic construct
SEQUENCE: 276
GYTFTNYY                                                           8

SEQ ID NO: 277          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 277
atcaaccctg gtggtggtaa caca                                         24

SEQ ID NO: 278          moltype = AA  length = 8
FEATURE                 Location/Qualifiers
REGION                  1..8
                        note = synthetic
source                  1..8
                        mol_type = protein
                        organism = synthetic construct
SEQUENCE: 278
INPGGGNT                                                           8

SEQ ID NO: 279          moltype = DNA  length = 33
FEATURE                 Location/Qualifiers
misc_feature            1..33
                        note = synthetic
source                  1..33
                        mol_type = other DNA
                        organism = synthetic construct
SEQUENCE: 279
gcgagagaaa actggaactc ttactttgac aac                               33

SEQ ID NO: 280          moltype = AA  length = 11
FEATURE                 Location/Qualifiers
REGION                  1..11
                        note = synthetic
source                  1..11
                        mol_type = protein
                        organism = synthetic construct
SEQUENCE: 280
ARENWNSYFD N                                                       11

SEQ ID NO: 281          moltype = DNA  length = 339
FEATURE                 Location/Qualifiers
misc_feature            1..339
                        note = synthetic
source                  1..339
                        mol_type = other DNA
                        organism = synthetic construct
SEQUENCE: 281
gacatcgtga tgacccagtc tccagactcc ctggctgtgt ctctgggcga gagggccacc  60
atcaactgca agtccagcca gagtgtttta tacagctcca acaataagaa cttcttagct  120
tggtaccagc agaaaccagg acagcctcct aagctgctca tttactgggc atctacccgg  180
gaatccgggg tccctgaccg attcagtggc agcgggtctg ggacagattt cactctcacc  240
atcagcagcc tgcaggctga agatgtggca ctttattact gtcagcaata ttatggtgct  300
ccgtggacgt tcggccaagg gaccaaggtg gaaatcaaa                         339

SEQ ID NO: 282          moltype = AA  length = 113
```

```
FEATURE                Location/Qualifiers
REGION                 1..113
                       note = synthetic
source                 1..113
                       mol_type = protein
                       organism = synthetic construct
SEQUENCE: 282
DIVMTQSPDS LAVSLGERAT INCKSSQSVL YSSNNKNFLA WYQQKPGQPP KLLIYWASTR  60
ESGVPDRFSG SGSGTDFTLT ISSLQAEDVA LYYCQQYYGA PWTFGQGTKV EIK         113

SEQ ID NO: 283         moltype = DNA  length = 36
FEATURE                Location/Qualifiers
misc_feature           1..36
                       note = synthetic
source                 1..36
                       mol_type = other DNA
                       organism = synthetic construct
SEQUENCE: 283
cagagtgttt tatacagctc caacaataag aacttc                            36

SEQ ID NO: 284         moltype = AA  length = 12
FEATURE                Location/Qualifiers
REGION                 1..12
                       note = synthetic
source                 1..12
                       mol_type = protein
                       organism = synthetic construct
SEQUENCE: 284
QSVLYSSNNK NF                                                      12

SEQ ID NO: 285         moltype =   length =
SEQUENCE: 285
000

SEQ ID NO: 286         moltype =   length =
SEQUENCE: 286
000

SEQ ID NO: 287         moltype = DNA  length = 27
FEATURE                Location/Qualifiers
misc_feature           1..27
                       note = synthetic
source                 1..27
                       mol_type = other DNA
                       organism = synthetic construct
SEQUENCE: 287
cagcaatatt atggtgctcc gtggacg                                      27

SEQ ID NO: 288         moltype = AA  length = 9
FEATURE                Location/Qualifiers
REGION                 1..9
                       note = synthetic
source                 1..9
                       mol_type = protein
                       organism = synthetic construct
SEQUENCE: 288
QQYYGAPWT                                                          9

SEQ ID NO: 289         moltype = DNA  length = 357
FEATURE                Location/Qualifiers
misc_feature           1..357
                       note = synthetic
source                 1..357
                       mol_type = other DNA
                       organism = synthetic construct
SEQUENCE: 289
caggtccagc tggtgcagtc tggggctgag gtgaagaagc ctgggtcctc ggtgaaggtc  60
tcctgcaagg cttctggagg caccttcagc agctatacta tcaactgggt gcgacaggcc  120
cctggacaag ggcttgagtg gatgggaggg atcatcccta tctttggtat agcaaactac  180
gcacagaagt tccagggcag agtcacgatt accacggacg aatccacgaa cacagcctac  240
atggagctga gcagcctgag atctgaggac acggccattt attactgtgc gagagcgaga  300
tatggttcgg ggagttatga ctactggggc cagggaaccc tggtcaccgt ctcctca     357

SEQ ID NO: 290         moltype = AA  length = 119
FEATURE                Location/Qualifiers
REGION                 1..119
                       note = synthetic
source                 1..119
                       mol_type = protein
```

```
                        organism = synthetic construct
SEQUENCE: 290
QVQLVQSGAE VKKPGSSVKV SCKASGGTFS SYTINWVRQA PGQGLEWMGG IIPIFGIANY  60
AQKFQGRVTI TTDESTNTAY MELSSLRSED TAIYYCARAR YGSGSYDYWG QGTLVTVSS   119

SEQ ID NO: 291          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 291
ggaggcacct tcagcagcta tact                                        24

SEQ ID NO: 292          moltype = AA  length = 8
FEATURE                 Location/Qualifiers
REGION                  1..8
                        note = synthetic
source                  1..8
                        mol_type = protein
                        organism = synthetic construct
SEQUENCE: 292
GGTFSSYT                                                          8

SEQ ID NO: 293          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 293
atcatcccta tctttggtat agca                                        24

SEQ ID NO: 294          moltype = AA  length = 8
FEATURE                 Location/Qualifiers
REGION                  1..8
                        note = synthetic
source                  1..8
                        mol_type = protein
                        organism = synthetic construct
SEQUENCE: 294
IIPIFGIA                                                          8

SEQ ID NO: 295          moltype = DNA  length = 36
FEATURE                 Location/Qualifiers
misc_feature            1..36
                        note = synthetic
source                  1..36
                        mol_type = other DNA
                        organism = synthetic construct
SEQUENCE: 295
gcgagagcga gatatggttc ggggagttat gactac                           36

SEQ ID NO: 296          moltype = AA  length = 12
FEATURE                 Location/Qualifiers
REGION                  1..12
                        note = synthetic
source                  1..12
                        mol_type = protein
                        organism = synthetic construct
SEQUENCE: 296
ARARYGSGSY DY                                                     12

SEQ ID NO: 297          moltype = DNA  length = 339
FEATURE                 Location/Qualifiers
misc_feature            1..339
                        note = synthetic
source                  1..339
                        mol_type = other DNA
                        organism = synthetic construct
SEQUENCE: 297
gacatcgtga tgacccagtc tccagactcc ctggctgtgt ctctgggcga gagggccacc  60
atcaactgca agtccagcca gagtgtttta tacacctcca acaataagaa ctacttagct  120
tggtaccagc agaaaccagg acagcctcct aagctgctca tttactgggc atctacccgg  180
gaatccgggg tccctgaccg attcagtggc agcgggtctg ggacagattt cactctcacc  240
atcagcagcc tgcaggctga agatgtggca gtttattact gtcagcaata ttataatact  300
ccatggacgt tcggccaagg gaccaaggtg gaaatcaaa                        339
```

```
SEQ ID NO: 298         moltype = AA  length = 113
FEATURE                Location/Qualifiers
REGION                 1..113
                       note = synthetic
source                 1..113
                       mol_type = protein
                       organism = synthetic construct
SEQUENCE: 298
DIVMTQSPDS LAVSLGERAT INCKSSQSVL YTSNNKNYLA WYQQKPGQPP KLLIYWASTR  60
ESGVPDRFSG SGSGTDFTLT ISSLQAEDVA VYYCQQYYNT PWTFGQGTKV EIK         113

SEQ ID NO: 299         moltype = DNA  length = 36
FEATURE                Location/Qualifiers
misc_feature           1..36
                       note = synthetic
source                 1..36
                       mol_type = other DNA
                       organism = synthetic construct
SEQUENCE: 299
cagagtgttt tatacacctc caacaataag aactac                            36

SEQ ID NO: 300         moltype = AA  length = 12
FEATURE                Location/Qualifiers
REGION                 1..12
                       note = synthetic
source                 1..12
                       mol_type = protein
                       organism = synthetic construct
SEQUENCE: 300
QSVLYTSNNK NY                                                      12

SEQ ID NO: 301         moltype =   length =
SEQUENCE: 301
000

SEQ ID NO: 302         moltype =   length =
SEQUENCE: 302
000

SEQ ID NO: 303         moltype = DNA  length = 27
FEATURE                Location/Qualifiers
misc_feature           1..27
                       note = synthetic
source                 1..27
                       mol_type = other DNA
                       organism = synthetic construct
SEQUENCE: 303
cagcaatatt ataatactcc atggacg                                      27

SEQ ID NO: 304         moltype = AA  length = 9
FEATURE                Location/Qualifiers
REGION                 1..9
                       note = synthetic
source                 1..9
                       mol_type = protein
                       organism = synthetic construct
SEQUENCE: 304
QQYYNTPWT                                                          9

SEQ ID NO: 305         moltype = DNA  length = 360
FEATURE                Location/Qualifiers
misc_feature           1..360
                       note = synthetic
source                 1..360
                       mol_type = other DNA
                       organism = synthetic construct
SEQUENCE: 305
cagatcacct tgaaggagtc tggtcctacg ctggtgaaac ccacacagac cctcacgctg  60
acctgcacct tctctgggtt ctcactcagc actaatggag tgggtgtggg ctggatccgt  120
cagcccccag gaaaggccct ggagtggctt ggaatcattt attggaatga tgataagcgc  180
tacagcccat ctctgaggag cagactcacc atcaccaagg acacctccaa aaaccaggtg  240
gtccttacaa tgaccaacat ggaccctgtg gacacagcca catattactg tgcacacaga  300
ggcctcttcg gaggttggtt cgacccctgg ggccagggaa ccctggtcac cgtctcctca  360

SEQ ID NO: 306         moltype = AA  length = 120
FEATURE                Location/Qualifiers
REGION                 1..120
                       note = synthetic
```

```
source                  1..120
                        mol_type = protein
                        organism = synthetic construct
SEQUENCE: 306
QITLKESGPT LVKPTQTLTL TCTFSGFSLS TNGVGVGWIR QPPGKALEWL GIIYWNDDKR  60
YSPSLRSRLT ITKDTSKNQV VLTMTNMDPV DTATYYCAHR GLFGGWFDPW GQGTLVTVSS  120

SEQ ID NO: 307          moltype = DNA  length = 30
FEATURE                 Location/Qualifiers
misc_feature            1..30
                        note = synthetic
source                  1..30
                        mol_type = other DNA
                        organism = synthetic construct
SEQUENCE: 307
gggttctcac tcagcactaa tggagtgggt                                  30

SEQ ID NO: 308          moltype = AA  length = 10
FEATURE                 Location/Qualifiers
REGION                  1..10
                        note = synthetic
source                  1..10
                        mol_type = protein
                        organism = synthetic construct
SEQUENCE: 308
GFSLSTNGVG                                                        10

SEQ ID NO: 309          moltype = DNA  length = 21
FEATURE                 Location/Qualifiers
misc_feature            1..21
                        note = synthetic
source                  1..21
                        mol_type = other DNA
                        organism = synthetic construct
SEQUENCE: 309
atttattgga atgatgataa g                                           21

SEQ ID NO: 310          moltype = AA  length = 7
FEATURE                 Location/Qualifiers
REGION                  1..7
                        note = synthetic
source                  1..7
                        mol_type = protein
                        organism = synthetic construct
SEQUENCE: 310
IYWNDDK                                                           7

SEQ ID NO: 311          moltype = DNA  length = 36
FEATURE                 Location/Qualifiers
misc_feature            1..36
                        note = synthetic
source                  1..36
                        mol_type = other DNA
                        organism = synthetic construct
SEQUENCE: 311
gcacacagag gcctcttcgg aggttggttc gacccc                           36

SEQ ID NO: 312          moltype = AA  length = 12
FEATURE                 Location/Qualifiers
REGION                  1..12
                        note = synthetic
source                  1..12
                        mol_type = protein
                        organism = synthetic construct
SEQUENCE: 312
AHRGLFGGWF DP                                                     12

SEQ ID NO: 313          moltype = DNA  length = 321
FEATURE                 Location/Qualifiers
misc_feature            1..321
                        note = synthetic
source                  1..321
                        mol_type = other DNA
                        organism = synthetic construct
SEQUENCE: 313
gacatccaga tgacccagtc tccatcctcc ctgtctgcat ctgtaggaga cagagtcacc  60
atcacttgcc gggcaagtca gagcattagc aggtatttaa attggtatca gcagaaacca  120
gggaaagccc ctaacctcct gatctttgct gcatccagtt tgcaaagtgg ggtcccatca  180
aggttcagtg gcagtggatc tgggacagat ttcactctca ccatcagcag tctgcaacct  240
```

```
gaagattttg caacttactt ctgtcaacag agttacaata ccccgctcac tttcggcgga  300
gggaccaagg tggagatcaa a                                            321

SEQ ID NO: 314         moltype = AA  length = 107
FEATURE                Location/Qualifiers
REGION                 1..107
                       note = synthetic
source                 1..107
                       mol_type = protein
                       organism = synthetic construct
SEQUENCE: 314
DIQMTQSPSS LSASVGDRVT ITCRASQSIS RYLNWYQQKP GKAPNLLIFA ASSLQSGVPS  60
RFSGSGSGTD FTLTISSLQP EDFATYFCQQ SYNTPLTFGG GTKVEIK                107

SEQ ID NO: 315         moltype = DNA  length = 18
FEATURE                Location/Qualifiers
misc_feature           1..18
                       note = synthetic
source                 1..18
                       mol_type = other DNA
                       organism = synthetic construct
SEQUENCE: 315
cagagcatta gcaggtat                                                18

SEQ ID NO: 316         moltype = AA  length = 6
FEATURE                Location/Qualifiers
REGION                 1..6
                       note = synthetic
source                 1..6
                       mol_type = protein
                       organism = synthetic construct
SEQUENCE: 316
QSISRY                                                             6

SEQ ID NO: 317         moltype =   length =
SEQUENCE: 317
000

SEQ ID NO: 318         moltype =   length =
SEQUENCE: 318
000

SEQ ID NO: 319         moltype = DNA  length = 27
FEATURE                Location/Qualifiers
misc_feature           1..27
                       note = synthetic
source                 1..27
                       mol_type = other DNA
                       organism = synthetic construct
SEQUENCE: 319
caacagagtt acaatacccc gctcact                                      27

SEQ ID NO: 320         moltype = AA  length = 9
FEATURE                Location/Qualifiers
REGION                 1..9
                       note = synthetic
source                 1..9
                       mol_type = protein
                       organism = synthetic construct
SEQUENCE: 320
QQSYNTPLT                                                          9

SEQ ID NO: 321         moltype = DNA  length = 366
FEATURE                Location/Qualifiers
misc_feature           1..366
                       note = synthetic
source                 1..366
                       mol_type = other DNA
                       organism = synthetic construct
SEQUENCE: 321
gaggtgcagc tggtggagtc tgggggaggc ttggtacagc cggggggggtc cctgagactc  60
tcctgtgcaa tctctggatt cacctttagg agttatgcca tgacctgggt ccgccaggct  120
ccagggaagg cgctggagtg ggtctcagtt attagtggta gcggtggtaa cacatactac  180
gcagactccg tgaagggccg gttcaccgtc tccagagaca attccaggaa cacgctgtat  240
ctgcaaatga acagcctgag agccgaggac acggccgtat atttctgttc gaaagttgca  300
gcagctaata attactatta cgctttggac gtctggggcc aagggaccac ggtcaccgtc  360
tcctca                                                             366

SEQ ID NO: 322         moltype = AA  length = 122
```

```
FEATURE                Location/Qualifiers
REGION                 1..122
                       note = synthetic
source                 1..122
                       mol_type = protein
                       organism = synthetic construct
SEQUENCE: 322
EVQLVESGGG LVQPGGSLRL SCAISGFTFR SYAMTWVRQA PGKALEWVSV ISGSGGNTYY  60
ADSVKGRFTV SRDNSRNTLY LQMNSLRAED TAVYFCSKVA AANNYYYALD VWGQGTTVTV  120
SS                                                                122

SEQ ID NO: 323         moltype = DNA  length = 24
FEATURE                Location/Qualifiers
misc_feature           1..24
                       note = synthetic
source                 1..24
                       mol_type = other DNA
                       organism = synthetic construct
SEQUENCE: 323
ggattcacct ttaggagtta tgcc                                        24

SEQ ID NO: 324         moltype = AA  length = 8
FEATURE                Location/Qualifiers
REGION                 1..8
                       note = synthetic
source                 1..8
                       mol_type = protein
                       organism = synthetic construct
SEQUENCE: 324
GFTFRSYA                                                          8

SEQ ID NO: 325         moltype = DNA  length = 24
FEATURE                Location/Qualifiers
misc_feature           1..24
                       note = synthetic
source                 1..24
                       mol_type = other DNA
                       organism = synthetic construct
SEQUENCE: 325
attagtggta gcggtggtaa caca                                        24

SEQ ID NO: 326         moltype = AA  length = 8
FEATURE                Location/Qualifiers
REGION                 1..8
                       note = synthetic
source                 1..8
                       mol_type = protein
                       organism = synthetic construct
SEQUENCE: 326
ISGSGGNT                                                          8

SEQ ID NO: 327         moltype = DNA  length = 45
FEATURE                Location/Qualifiers
misc_feature           1..45
                       note = synthetic
source                 1..45
                       mol_type = other DNA
                       organism = synthetic construct
SEQUENCE: 327
tcgaaagttg cagcagctaa taattactat tacgctttgg acgtc                 45

SEQ ID NO: 328         moltype = AA  length = 15
FEATURE                Location/Qualifiers
REGION                 1..15
                       note = synthetic
source                 1..15
                       mol_type = protein
                       organism = synthetic construct
SEQUENCE: 328
SKVAAANNYY YALDV                                                  15

SEQ ID NO: 329         moltype = DNA  length = 336
FEATURE                Location/Qualifiers
misc_feature           1..336
                       note = synthetic
source                 1..336
                       mol_type = other DNA
                       organism = synthetic construct
SEQUENCE: 329
```

```
gatattgtga tgactcagtc tccactctcc ctgcccgtca cccctggaga gccggcctcc  60
atctcctgca ggtctagtca gagcctcctg catagtaatg gatacaagta tttggattgg  120
tacctgcaga agccagggca gtctccacaa ctcctgatct atttggtttc taatcgggcc  180
tccggggtcc ctgacaggtt cagtggcagt ggatcaggca cagattttac actgaaaatc  240
agcagagtgg aggctgagga tgttggggtt tattattgca tgcaagctct acaaactccg  300
tacacttttg gccaggggac caagctggag atcaaa                            336

SEQ ID NO: 330         moltype = AA  length = 112
FEATURE                Location/Qualifiers
REGION                 1..112
                       note = synthetic
source                 1..112
                       mol_type = protein
                       organism = synthetic construct
SEQUENCE: 330
DIVMTQSPLS LPVTPGEPAS ISCRSSQSLL HSNGYKYLDW YLQKPGQSPQ LLIYLVSNRA  60
SGVPDRFSGS GSGTDFTLKI SRVEAEDVGV YYCMQALQTP YTFGQGTKLE IK          112

SEQ ID NO: 331         moltype = DNA  length = 33
FEATURE                Location/Qualifiers
misc_feature           1..33
                       note = synthetic
source                 1..33
                       mol_type = other DNA
                       organism = synthetic construct
SEQUENCE: 331
cagagcctcc tgcatagtaa tggatacaag tat                               33

SEQ ID NO: 332         moltype = AA  length = 11
FEATURE                Location/Qualifiers
REGION                 1..11
                       note = synthetic
source                 1..11
                       mol_type = protein
                       organism = synthetic construct
SEQUENCE: 332
QSLLHSNGYK Y                                                       11

SEQ ID NO: 333         moltype =   length =
SEQUENCE: 333
000

SEQ ID NO: 334         moltype =   length =
SEQUENCE: 334
000

SEQ ID NO: 335         moltype = DNA  length = 27
FEATURE                Location/Qualifiers
misc_feature           1..27
                       note = synthetic
source                 1..27
                       mol_type = other DNA
                       organism = synthetic construct
SEQUENCE: 335
atgcaagctc tacaaactcc gtacact                                      27

SEQ ID NO: 336         moltype = AA  length = 9
FEATURE                Location/Qualifiers
REGION                 1..9
                       note = synthetic
source                 1..9
                       mol_type = protein
                       organism = synthetic construct
SEQUENCE: 336
MQALQTPYT                                                          9

SEQ ID NO: 337         moltype = DNA  length = 381
FEATURE                Location/Qualifiers
misc_feature           1..381
                       note = synthetic
source                 1..381
                       mol_type = other DNA
                       organism = synthetic construct
SEQUENCE: 337
caggtgcagc tggtggagtc tgggggaggc gtggtccagc ctgggaggtc cctgagactc  60
tcctgtgtag cgtctggatt caccttcagt aactatggca tgcactgggt ccgccaggct  120
ccaggcaagg ggctggagtg ggtggcagtt atatggaatg atggaagtaa taaatactat  180
gcagactccg tgaagggccg attcaccatc tccagagaca attccaagaa cacgctgtat  240
ctccaagtga gcagcctgag agccgatgac acggctgtat attactgtgc gagggacgga  300
```

```
gaggtcgaat atagcagctc gaattacaac tactacggtc tggatgtctg gggccaaggg  360
accacggtca ccgtctcctc a                                           381

SEQ ID NO: 338         moltype = AA  length = 127
FEATURE                Location/Qualifiers
REGION                 1..127
                       note = synthetic
source                 1..127
                       mol_type = protein
                       organism = synthetic construct
SEQUENCE: 338
QVQLVESGGG VVQPGRSLRL SCVASGFTFS NYGMHWVRQA PGKGLEWVAV IWNDGSNKYY  60
ADSVKGRFTI SRDNSKNTLY LQVSSLRADD TAVYYCARDG EVEYSSSNYN YYGLDVWGQG  120
TTVTVSS                                                           127

SEQ ID NO: 339         moltype = DNA  length = 24
FEATURE                Location/Qualifiers
misc_feature           1..24
                       note = synthetic
source                 1..24
                       mol_type = other DNA
                       organism = synthetic construct
SEQUENCE: 339
ggattcacct tcagtaacta tggc                                        24

SEQ ID NO: 340         moltype = AA  length = 8
FEATURE                Location/Qualifiers
REGION                 1..8
                       note = synthetic
source                 1..8
                       mol_type = protein
                       organism = synthetic construct
SEQUENCE: 340
GFTFSNYG                                                          8

SEQ ID NO: 341         moltype = DNA  length = 24
FEATURE                Location/Qualifiers
misc_feature           1..24
                       note = synthetic
source                 1..24
                       mol_type = other DNA
                       organism = synthetic construct
SEQUENCE: 341
atatggaatg atggaagtaa taaa                                        24

SEQ ID NO: 342         moltype = AA  length = 8
FEATURE                Location/Qualifiers
REGION                 1..8
                       note = synthetic
source                 1..8
                       mol_type = protein
                       organism = synthetic construct
SEQUENCE: 342
IWNDGSNK                                                          8

SEQ ID NO: 343         moltype = DNA  length = 60
FEATURE                Location/Qualifiers
misc_feature           1..60
                       note = synthetic
source                 1..60
                       mol_type = other DNA
                       organism = synthetic construct
SEQUENCE: 343
gcgagggacg gagaggtcga atatagcagc tcgaattaca actactacgg tctggatgtc  60

SEQ ID NO: 344         moltype = AA  length = 20
FEATURE                Location/Qualifiers
REGION                 1..20
                       note = synthetic
source                 1..20
                       mol_type = protein
                       organism = synthetic construct
SEQUENCE: 344
ARDGEVEYSS SNYNYYGLDV                                             20

SEQ ID NO: 345         moltype = DNA  length = 321
FEATURE                Location/Qualifiers
misc_feature           1..321
                       note = synthetic
```

```
source                  1..321
                        mol_type = other DNA
                        organism = synthetic construct
SEQUENCE: 345
gacatccaga tgacccagtc tccatcctcc ctgtctgcat ctgtaggaga cagagtcacc  60
atcacttgcc aggcgagtca ggacattagc aactatttaa attggtatca gcagaaacca  120
gggaaagccc ctaaactcct gatctacgat gcatccaatt tggaaacagg ggtcccatca  180
aggttcagtg gaagtggatc tgggacagat tttactttca ccatcagcag cctgcagcct  240
gaagatattg taacatatta ctgtcaacag tatgatgatc tcccgatcac cttcggccaa  300
gggacacgac tggagattaa a                                              321

SEQ ID NO: 346          moltype = AA  length = 107
FEATURE                 Location/Qualifiers
REGION                  1..107
                        note = synthetic
source                  1..107
                        mol_type = protein
                        organism = synthetic construct
SEQUENCE: 346
DIQMTQSPSS LSASVGDRVT ITCQASQDIS NYLNWYQQKP GKAPKLLIYD ASNLETGVPS  60
RFSGSGSGTD FTFTISSLQP EDIVTYYCQQ YDDLPITFGQ GTRLEIK                107

SEQ ID NO: 347          moltype = DNA  length = 18
FEATURE                 Location/Qualifiers
misc_feature            1..18
                        note = synthetic
source                  1..18
                        mol_type = other DNA
                        organism = synthetic construct
SEQUENCE: 347
caggacatta gcaactat                                                  18

SEQ ID NO: 348          moltype = AA  length = 6
FEATURE                 Location/Qualifiers
REGION                  1..6
                        note = synthetic
source                  1..6
                        mol_type = protein
                        organism = synthetic construct
SEQUENCE: 348
QDISNY                                                               6

SEQ ID NO: 349          moltype =   length =
SEQUENCE: 349
000

SEQ ID NO: 350          moltype =   length =
SEQUENCE: 350
000

SEQ ID NO: 351          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 351
caacagtatg atgatctccc gatcacc                                        27

SEQ ID NO: 352          moltype = AA  length = 9
FEATURE                 Location/Qualifiers
REGION                  1..9
                        note = synthetic
source                  1..9
                        mol_type = protein
                        organism = synthetic construct
SEQUENCE: 352
QQYDDLPIT                                                            9

SEQ ID NO: 353          moltype = DNA  length = 375
FEATURE                 Location/Qualifiers
misc_feature            1..375
                        note = synthetic
source                  1..375
                        mol_type = other DNA
                        organism = synthetic construct
SEQUENCE: 353
gaggtgcagc tggtggagtc tgggggaggc ttggtacagc ctggggggtc cctgagactc  60
```

```
tcctgtgcag cctctggatt ctcctttcat aattttgcca tgaactgggt ccgccaggct  120
ccagggaagg ggctggagtg ggtctcagtt attactggta gtggtactag cacacactac  180
gcagactccg tgaagggccg gttcaccatc tccagagaca attccaagaa aacgctatat  240
ctgcaaatga atagcctgag agccgaggac acggccgtat attactgtgc gaaagatcgg  300
ggctatgatt atagtggttc ttactacaac tggttcgacc cctggggcca gggaaccctg  360
gtcaccgtct cctca                                                   375

SEQ ID NO: 354          moltype = AA  length = 125
FEATURE                 Location/Qualifiers
REGION                  1..125
                        note = synthetic
source                  1..125
                        mol_type = protein
                        organism = synthetic construct
SEQUENCE: 354
EVQLVESGGG LVQPGGSLRL SCAASGFSFH NFAMNWVRQA PGKGLEWVSV ITGSGTSTHY  60
ADSVKGRFTI SRDNSKKTLY LQMNSLRAED TAVYYCAKDR GYDYSGSYYN WFDPWGQGTL  120
VTVSS                                                              125

SEQ ID NO: 355          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 355
ggattctcct ttcataattt tgcc                                         24

SEQ ID NO: 356          moltype = AA  length = 8
FEATURE                 Location/Qualifiers
REGION                  1..8
                        note = synthetic
source                  1..8
                        mol_type = protein
                        organism = synthetic construct
SEQUENCE: 356
GFSFHNFA                                                           8

SEQ ID NO: 357          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 357
attactggta gtggtactag caca                                         24

SEQ ID NO: 358          moltype = AA  length = 8
FEATURE                 Location/Qualifiers
REGION                  1..8
                        note = synthetic
source                  1..8
                        mol_type = protein
                        organism = synthetic construct
SEQUENCE: 358
ITGSGTST                                                           8

SEQ ID NO: 359          moltype = DNA  length = 54
FEATURE                 Location/Qualifiers
misc_feature            1..54
                        note = synthetic
source                  1..54
                        mol_type = other DNA
                        organism = synthetic construct
SEQUENCE: 359
gcgaaagatc ggggctatga ttatagtggt tcttactaca actggttcga cccc        54

SEQ ID NO: 360          moltype = AA  length = 18
FEATURE                 Location/Qualifiers
REGION                  1..18
                        note = synthetic
source                  1..18
                        mol_type = protein
                        organism = synthetic construct
SEQUENCE: 360
AKDRGYDYSG SYYNWFDP                                                18
```

```
SEQ ID NO: 361          moltype = DNA  length = 327
FEATURE                 Location/Qualifiers
misc_feature            1..327
                        note = synthetic
source                  1..327
                        mol_type = other DNA
                        organism = synthetic construct
SEQUENCE: 361
gacatccaga tgacccagtc tccatcctcc ctgtctgcat ctgtaggaga cagaatcacc  60
atcacttgcc gggcaagtca gagtattagc agctatttaa attggtatca gcagaaacca  120
gggaaagccc ctaaactcct gatctttgct gcatcaaatt tgcaaagtgg ggtcccatca  180
aggttcagtg gcagtggatc tgggacagat ttcactctca ccatcagtag tctgcaacct  240
gaagattttg caacttacta ctgtcaacag agttacagta ccccatcctt attcactttc  300
ggccctggga ccaaagtgga tatcaaa                                      327

SEQ ID NO: 362          moltype = AA  length = 109
FEATURE                 Location/Qualifiers
REGION                  1..109
                        note = synthetic
source                  1..109
                        mol_type = protein
                        organism = synthetic construct
SEQUENCE: 362
DIQMTQSPSS LSASVGDRIT ITCRASQSIS SYLNWYQQKP GKAPKLLIFA ASNLQSGVPS  60
RFSGSGSGTD FTLTISSLQP EDFATYYCQQ SYSTPSLFTF GPGTKVDIK              109

SEQ ID NO: 363          moltype = DNA  length = 18
FEATURE                 Location/Qualifiers
misc_feature            1..18
                        note = synthetic
source                  1..18
                        mol_type = other DNA
                        organism = synthetic construct
SEQUENCE: 363
cagagtatta gcagctat                                                18

SEQ ID NO: 364          moltype = AA  length = 6
FEATURE                 Location/Qualifiers
REGION                  1..6
                        note = synthetic
source                  1..6
                        mol_type = protein
                        organism = synthetic construct
SEQUENCE: 364
QSISSY                                                             6

SEQ ID NO: 365          moltype =   length =
SEQUENCE: 365
000

SEQ ID NO: 366          moltype =   length =
SEQUENCE: 366
000

SEQ ID NO: 367          moltype = DNA  length = 33
FEATURE                 Location/Qualifiers
misc_feature            1..33
                        note = synthetic
source                  1..33
                        mol_type = other DNA
                        organism = synthetic construct
SEQUENCE: 367
caacagagtt acagtacccc atccttattc act                               33

SEQ ID NO: 368          moltype = AA  length = 11
FEATURE                 Location/Qualifiers
REGION                  1..11
                        note = synthetic
source                  1..11
                        mol_type = protein
                        organism = synthetic construct
SEQUENCE: 368
QQSYSTPSLF T                                                       11

SEQ ID NO: 369          moltype = DNA  length = 384
FEATURE                 Location/Qualifiers
misc_feature            1..384
                        note = synthetic
source                  1..384
```

```
                        mol_type = other DNA
                        organism = synthetic construct
SEQUENCE: 369
gaggtgcagc tggtggagtc tgggggaggc ttggtacagc ctggagggtc cctgagactc  60
tcctgtgcag tctctggatt caccttcagt agttacgaga tgaactgggt ccgccaggct  120
ccagggaagg ggctggaatg ggtttcacac attagtagta gtggaagtac catatactac  180
gcagactctg tgaagggccg attcaccatg tccagagaca acgccaagaa ctcactgtat  240
ctgcaaatga acagcctgag agccgaggac acggctgttt attactgtgc gagagatggg  300
aatatctgga gtggttatta tgccgcctac tacttctacg gtatggacgt ctggggccaa  360
gggaccacgg tcaccgtctc ctca                                          384

SEQ ID NO: 370          moltype = AA  length = 128
FEATURE                 Location/Qualifiers
REGION                  1..128
                        note = synthetic
source                  1..128
                        mol_type = protein
                        organism = synthetic construct
SEQUENCE: 370
EVQLVESGGG LVQPGGSLRL SCAVSGFTFS SYEMNWVRQA PGKGLEWVSH ISSSGSTIYY  60
ADSVKGRFTM SRDNAKNSLY LQMNSLRAED TAVYYCARDG NIWSGYYAAY YFYGMDVWGQ  120
GTTVTVSS                                                            128

SEQ ID NO: 371          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 371
ggattcacct tcagtagtta cgag                                          24

SEQ ID NO: 372          moltype = AA  length = 8
FEATURE                 Location/Qualifiers
REGION                  1..8
                        note = synthetic
source                  1..8
                        mol_type = protein
                        organism = synthetic construct
SEQUENCE: 372
GFTFSSYE                                                            8

SEQ ID NO: 373          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 373
attagtagta gtggaagtac cata                                          24

SEQ ID NO: 374          moltype = AA  length = 8
FEATURE                 Location/Qualifiers
REGION                  1..8
                        note = synthetic
source                  1..8
                        mol_type = protein
                        organism = synthetic construct
SEQUENCE: 374
ISSSGSTI                                                            8

SEQ ID NO: 375          moltype = DNA  length = 63
FEATURE                 Location/Qualifiers
misc_feature            1..63
                        note = synthetic
source                  1..63
                        mol_type = other DNA
                        organism = synthetic construct
SEQUENCE: 375
gcgagagatg ggaatatctg gagtggttat tatgccgcct actacttcta cggtatggac  60
gtc                                                                 63

SEQ ID NO: 376          moltype = AA  length = 21
FEATURE                 Location/Qualifiers
REGION                  1..21
                        note = synthetic
source                  1..21
```

```
                        mol_type = protein
                        organism = synthetic construct
SEQUENCE: 376
ARDGNIWSGY YAAYYFYGMD V                                             21

SEQ ID NO: 377          moltype = DNA  length = 336
FEATURE                 Location/Qualifiers
misc_feature            1..336
                        note = synthetic
source                  1..336
                        mol_type = other DNA
                        organism = synthetic construct
SEQUENCE: 377
gatattgtga tgacccagac tccactctcc tcacctgtca cccttggaca gccggcctcc  60
atctcctgca ggtctagtca aagcctcgta cacagtgatg gaaaaaccta cttgagttgg  120
cttcagcaga ggccaggcca gcctccaaga ctcctaattt ataagatttc taaccggttc  180
tctggggtcc cagacagaat cagtggcagt ggggcaggga cagatttcac actgaaaatc  240
agcagggtgg aagctgagga tgtcggggtt tattactgca tgcaagctgt acaatttcct  300
cggacgttcg gccaagggac caaggtggaa atcaaa                             336

SEQ ID NO: 378          moltype = AA  length = 112
FEATURE                 Location/Qualifiers
REGION                  1..112
                        note = synthetic
source                  1..112
                        mol_type = protein
                        organism = synthetic construct
SEQUENCE: 378
DIVMTQTPLS SPVTLGQPAS ISCRSSQSLV HSDGKTYLSW LQQRPGQPPR LLIYKISNRF  60
SGVPDRISGS GAGTDFTLKI SRVEAEDVGV YYCMQAVQFP RTFGQGTKVE IK          112

SEQ ID NO: 379          moltype = DNA  length = 33
FEATURE                 Location/Qualifiers
misc_feature            1..33
                        note = synthetic
source                  1..33
                        mol_type = other DNA
                        organism = synthetic construct
SEQUENCE: 379
caaagcctcg tacacagtga tggaaaaacc tac                                33

SEQ ID NO: 380          moltype = AA  length = 11
FEATURE                 Location/Qualifiers
REGION                  1..11
                        note = synthetic
source                  1..11
                        mol_type = protein
                        organism = synthetic construct
SEQUENCE: 380
QSLVHSDGKT Y                                                        11

SEQ ID NO: 381          moltype =   length =
SEQUENCE: 381
000

SEQ ID NO: 382          moltype =   length =
SEQUENCE: 382
000

SEQ ID NO: 383          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 383
atgcaagctg tacaatttcc tcggacg                                       27

SEQ ID NO: 384          moltype = AA  length = 9
FEATURE                 Location/Qualifiers
REGION                  1..9
                        note = synthetic
source                  1..9
                        mol_type = protein
                        organism = synthetic construct
SEQUENCE: 384
MQAVQFPRT                                                           9
```

```
SEQ ID NO: 385         moltype = DNA  length = 366
FEATURE                Location/Qualifiers
misc_feature           1..366
                       note = synthetic
source                 1..366
                       mol_type = other DNA
                       organism = synthetic construct
SEQUENCE: 385
caggtgcagc tacagcagtg gggcgcagga ctgttgaacc cttcggagac cctgtccctc  60
acctgcgctg tctatggtgg ggccttcagt gattactact ggaattggat ccgccagccc  120
ccagggaagg ggctggagtg gattggggaa atcaatcatc gcggaagcac caactacaac  180
ccgtccctca agagtcgtgt caccatttca gttgacacgt ccaagaacca gttctccctg  240
aggatgagct ctgtgaccgc cgcggacgcg gctgtgtatt actgtgcgag aggagaggat  300
tacgatattt ggaatggtta ttatcaggaa aaatggggcc agggaaccct ggtcaccgtc  360
tcctca                                                             366

SEQ ID NO: 386         moltype = AA  length = 122
FEATURE                Location/Qualifiers
REGION                 1..122
                       note = synthetic
source                 1..122
                       mol_type = protein
                       organism = synthetic construct
SEQUENCE: 386
QVQLQQWGAG LLNPSETLSL TCAVYGGAFS DYYWNWIRQP PGKGLEWIGE INHRGSTNYN  60
PSLKSRVTIS VDTSKNQFSL RMSSVTAADA AVYYCARGED YDIWNGYYQE KWGQGTLVTV  120
SS                                                                 122

SEQ ID NO: 387         moltype = DNA  length = 24
FEATURE                Location/Qualifiers
misc_feature           1..24
                       note = synthetic
source                 1..24
                       mol_type = other DNA
                       organism = synthetic construct
SEQUENCE: 387
ggtggggcct tcagtgatta ctac                                         24

SEQ ID NO: 388         moltype = AA  length = 8
FEATURE                Location/Qualifiers
REGION                 1..8
                       note = synthetic
source                 1..8
                       mol_type = protein
                       organism = synthetic construct
SEQUENCE: 388
GGAFSDYY                                                           8

SEQ ID NO: 389         moltype = DNA  length = 21
FEATURE                Location/Qualifiers
misc_feature           1..21
                       note = synthetic
source                 1..21
                       mol_type = other DNA
                       organism = synthetic construct
SEQUENCE: 389
atcaatcatc gcggaagcac c                                            21

SEQ ID NO: 390         moltype = AA  length = 7
FEATURE                Location/Qualifiers
REGION                 1..7
                       note = synthetic
source                 1..7
                       mol_type = protein
                       organism = synthetic construct
SEQUENCE: 390
INHRGST                                                            7

SEQ ID NO: 391         moltype = DNA  length = 48
FEATURE                Location/Qualifiers
misc_feature           1..48
                       note = synthetic
source                 1..48
                       mol_type = other DNA
                       organism = synthetic construct
SEQUENCE: 391
gcgagaggag aggattacga tatttggaat ggttattatc aggaaaaa               48

SEQ ID NO: 392         moltype = AA  length = 16
```

```
FEATURE                Location/Qualifiers
REGION                 1..16
                       note = synthetic
source                 1..16
                       mol_type = protein
                       organism = synthetic construct
SEQUENCE: 392
ARGEDYDIWN GYYQEK                                                16

SEQ ID NO: 393         moltype = DNA  length = 321
FEATURE                Location/Qualifiers
misc_feature           1..321
                       note = synthetic
source                 1..321
                       mol_type = other DNA
                       organism = synthetic construct
SEQUENCE: 393
gaaattgtgt tgacacagtc tccagccacc ctgtctttgt ctccagggga aagagccacc  60
ctctcctgca gggccagtca gagtattagc acctacttag cctggtacca acagaagcct  120
ggccaggctc ccaggctcct catctatgat gcatccaaga gggccactgg catcccagcc  180
aggttcagtg gcagtgggtc tgggacagac ttcactctca ccatcagcag cctagagcct  240
gaagattttg tagtttatta ctgtcaccag cgtagcaact ggcctctcac tttcggcgga  300
gggaccaagg tggagatcaa a                                          321

SEQ ID NO: 394         moltype = AA  length = 107
FEATURE                Location/Qualifiers
REGION                 1..107
                       note = synthetic
source                 1..107
                       mol_type = protein
                       organism = synthetic construct
SEQUENCE: 394
EIVLTQSPAT LSLSPGERAT LSCRASQSIS TYLAWYQQKP GQAPRLLIYD ASKRATGIPA  60
RFSGSGSGTD FTLTISSLEP EDFVVYYCHQ RSNWPLTFGG GTKVEIK              107

SEQ ID NO: 395         moltype = DNA  length = 18
FEATURE                Location/Qualifiers
misc_feature           1..18
                       note = synthetic
source                 1..18
                       mol_type = other DNA
                       organism = synthetic construct
SEQUENCE: 395
cagagtatta gcacctac                                              18

SEQ ID NO: 396         moltype = AA  length = 6
FEATURE                Location/Qualifiers
REGION                 1..6
                       note = synthetic
source                 1..6
                       mol_type = protein
                       organism = synthetic construct
SEQUENCE: 396
QSISTY                                                           6

SEQ ID NO: 397         moltype =   length =
SEQUENCE: 397
000

SEQ ID NO: 398         moltype =   length =
SEQUENCE: 398
000

SEQ ID NO: 399         moltype = DNA  length = 27
FEATURE                Location/Qualifiers
misc_feature           1..27
                       note = synthetic
source                 1..27
                       mol_type = other DNA
                       organism = synthetic construct
SEQUENCE: 399
caccagcgta gcaactggcc tctcact                                    27

SEQ ID NO: 400         moltype = AA  length = 9
FEATURE                Location/Qualifiers
REGION                 1..9
                       note = synthetic
source                 1..9
                       mol_type = protein
```

```
                         organism = synthetic construct
SEQUENCE: 400
HQRSNWPLT                                                        9

SEQ ID NO: 401           moltype = DNA  length = 351
FEATURE                  Location/Qualifiers
misc_feature             1..351
                         note = synthetic
source                   1..351
                         mol_type = other DNA
                         organism = synthetic construct
SEQUENCE: 401
caggtgcagc tgcaggagtc ggggccagga ctggtgaagc cttcggagac cctgtccctc  60
acctgcactg tctctggtgg ttccttcagt agttactact ggagttggct ccggcagccc  120
ccaggaaagg ggctggagtg gattggatat atcttttaca gtgggagtac cgactacaac  180
ccctccctca agagtcgagt caccatttca gtagacacgt ccaagaagca gttctccctg  240
aagctgacct ctgtgaccgc tgcggacacg gccgtctatt actgtgcgcg aacaataagt  300
acgtggtggt tcgcccccctg gggccaggga accctggtca ccgtctcctc a          351

SEQ ID NO: 402           moltype = AA  length = 117
FEATURE                  Location/Qualifiers
REGION                   1..117
                         note = synthetic
source                   1..117
                         mol_type = protein
                         organism = synthetic construct
SEQUENCE: 402
QVQLQESGPG LVKPSETLSL TCTVSGGSFS SYYWSWLRQP PGKGLEWIGY IFYSGSTDYN  60
PSLKSRVTIS VDTSKKQFSL KLTSVTAADT AVYYCARTIS TWWFAPWGQG TLVTVSS     117

SEQ ID NO: 403           moltype = DNA  length = 24
FEATURE                  Location/Qualifiers
misc_feature             1..24
                         note = synthetic
source                   1..24
                         mol_type = other DNA
                         organism = synthetic construct
SEQUENCE: 403
ggtggttcct tcagtagtta ctac                                       24

SEQ ID NO: 404           moltype = AA  length = 8
FEATURE                  Location/Qualifiers
REGION                   1..8
                         note = synthetic
source                   1..8
                         mol_type = protein
                         organism = synthetic construct
SEQUENCE: 404
GGSFSSYY                                                         8

SEQ ID NO: 405           moltype = DNA  length = 21
FEATURE                  Location/Qualifiers
misc_feature             1..21
                         note = synthetic
source                   1..21
                         mol_type = other DNA
                         organism = synthetic construct
SEQUENCE: 405
atcttttaca gtgggagtac c                                          21

SEQ ID NO: 406           moltype = AA  length = 7
FEATURE                  Location/Qualifiers
REGION                   1..7
                         note = synthetic
source                   1..7
                         mol_type = protein
                         organism = synthetic construct
SEQUENCE: 406
IFYSGST                                                          7

SEQ ID NO: 407           moltype = DNA  length = 33
FEATURE                  Location/Qualifiers
misc_feature             1..33
                         note = synthetic
source                   1..33
                         mol_type = other DNA
                         organism = synthetic construct
SEQUENCE: 407
gcgcgaacaa taagtacgtg gtggttcgcc ccc                             33
```

```
SEQ ID NO: 408          moltype = AA  length = 11
FEATURE                 Location/Qualifiers
REGION                  1..11
                        note = synthetic
source                  1..11
                        mol_type = protein
                        organism = synthetic construct
SEQUENCE: 408
ARTISTWWFA P                                                       11

SEQ ID NO: 409          moltype = DNA  length = 318
FEATURE                 Location/Qualifiers
misc_feature            1..318
                        note = synthetic
source                  1..318
                        mol_type = other DNA
                        organism = synthetic construct
SEQUENCE: 409
gaaatagtga tgacacagtc tccagccacc ctgtctgtgt ctccaggggg aagagccacc  60
ctctcctgca gggccagtca gagtgttagc aacaacgtag cctggtacca gcagaaacct  120
ggccaggctc ccaggctcct catctatggt gcatccacca gggccactgg tatcccaggc  180
aggttcagtg gcagtgggtc tggaacagag ttcactctca ccatcagcag cctgcagtct  240
gaagattttg cagtttattc ctgtcagcag tataataact ggctcacttt cggcggaggg  300
accaaggtgg agatcaaa                                                318

SEQ ID NO: 410          moltype = AA  length = 106
FEATURE                 Location/Qualifiers
REGION                  1..106
                        note = synthetic
source                  1..106
                        mol_type = protein
                        organism = synthetic construct
SEQUENCE: 410
EIVMTQSPAT LSVSPGGRAT LSCRASQSVS NNVAWYQQKP GQAPRLLIYG ASTRATGIPG  60
RFSGSGSGTE FTLTISSLQS EDFAVYSCQQ YNNWLTFGGG TKVEIK                 106

SEQ ID NO: 411          moltype = DNA  length = 18
FEATURE                 Location/Qualifiers
misc_feature            1..18
                        note = synthetic
source                  1..18
                        mol_type = other DNA
                        organism = synthetic construct
SEQUENCE: 411
cagagtgtta gcaacaac                                                18

SEQ ID NO: 412          moltype = AA  length = 6
FEATURE                 Location/Qualifiers
REGION                  1..6
                        note = synthetic
source                  1..6
                        mol_type = protein
                        organism = synthetic construct
SEQUENCE: 412
QSVSNN                                                             6

SEQ ID NO: 413          moltype =   length =
SEQUENCE: 413
000

SEQ ID NO: 414          moltype =   length =
SEQUENCE: 414
000

SEQ ID NO: 415          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 415
cagcagtata ataactggct cact                                         24

SEQ ID NO: 416          moltype = AA  length = 8
FEATURE                 Location/Qualifiers
REGION                  1..8
                        note = synthetic
```

```
source                  1..8
                        mol_type = protein
                        organism = synthetic construct
SEQUENCE: 416
QQYNNWLT                                                               8

SEQ ID NO: 417          moltype = DNA  length = 369
FEATURE                 Location/Qualifiers
misc_feature            1..369
                        note = synthetic
source                  1..369
                        mol_type = other DNA
                        organism = synthetic construct
SEQUENCE: 417
caggtgcagc tggtggagtc tgggggaggc gtggtccagc ctgggaggtc cctgagactc  60
tcctgtgtag cgtctggatt cactttcagt agttatggca tgcactgggt ccgccaggct  120
ccaggcaagg ggctggagtg ggtggcaatt atatggtatg atggaagtaa taaatactat  180
gcagactccg tgaagggccg attcaccata tccagagaca attccaagaa cacacagtat  240
ctgcaaatga acagcctgag agccgaggac acggctgtgt attactgtgc gtcagtagct  300
acgtctgggg acttcgacta ctacggtatg gacgtctggg gccaagggac cacggtcacc  360
gtctcctca                                                              369

SEQ ID NO: 418          moltype = AA  length = 123
FEATURE                 Location/Qualifiers
REGION                  1..123
                        note = synthetic
source                  1..123
                        mol_type = protein
                        organism = synthetic construct
SEQUENCE: 418
QVQLVESGGG VVQPGRSLRL SCVASGFTFS SYGMHWVRQA PGKGLEWVAI IWYDGSNKYY  60
ADSVKGRFTI SRDNSKNTQY LQMNSLRAED TAVYYCASVA TSGDFDYYGM DVWGQGTTVT  120
VSS                                                                    123

SEQ ID NO: 419          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 419
ggattcactt tcagtagtta tggc                                             24

SEQ ID NO: 420          moltype = AA  length = 8
FEATURE                 Location/Qualifiers
REGION                  1..8
                        note = synthetic
source                  1..8
                        mol_type = protein
                        organism = synthetic construct
SEQUENCE: 420
GFTFSSYG                                                               8

SEQ ID NO: 421          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 421
atatggtatg atggaagtaa taaa                                             24

SEQ ID NO: 422          moltype = AA  length = 8
FEATURE                 Location/Qualifiers
REGION                  1..8
                        note = synthetic
source                  1..8
                        mol_type = protein
                        organism = synthetic construct
SEQUENCE: 422
IWYDGSNK                                                               8

SEQ ID NO: 423          moltype = DNA  length = 48
FEATURE                 Location/Qualifiers
misc_feature            1..48
                        note = synthetic
source                  1..48
```

```
                        mol_type = other DNA
                        organism = synthetic construct
SEQUENCE: 423
gcgtcagtag ctacgtctgg ggacttcgac tactacggta tggacgtc              48

SEQ ID NO: 424          moltype = AA  length = 16
FEATURE                 Location/Qualifiers
REGION                  1..16
                        note = synthetic
source                  1..16
                        mol_type = protein
                        organism = synthetic construct
SEQUENCE: 424
ASVATSGDFD YYGMDV                                                 16

SEQ ID NO: 425          moltype = DNA  length = 321
FEATURE                 Location/Qualifiers
misc_feature            1..321
                        note = synthetic
source                  1..321
                        mol_type = other DNA
                        organism = synthetic construct
SEQUENCE: 425
gaaattgtgt tgacacagtc tccagccacc ctgtctttgt ctccagggga aagaaccacc  60
ctctcctgca gggccagtca gagaattagc acctacttag cctggtatca acagaaacct  120
ggccaggctc ccaggctcct catctatgat gcatccaaaa gggccactgg catcccagcc  180
aggttcagtg gtagtgggtc tgggacaggc ttcactctca ccatcagcag cctagagcct  240
gaagattttg cagtttatta ctgtcagcag cgtagtaact ggcctctcac tttcggcgga  300
gggaccaagg tggagatcaa a                                           321

SEQ ID NO: 426          moltype = AA  length = 107
FEATURE                 Location/Qualifiers
REGION                  1..107
                        note = synthetic
source                  1..107
                        mol_type = protein
                        organism = synthetic construct
SEQUENCE: 426
EIVLTQSPAT LSLSPGERTT LSCRASQRIS TYLAWYQQKP GQAPRLLIYD ASKRATGIPA  60
RFSGSGSGTG FTLTISSLEP EDFAVYYCQQ RSNWPLTFGG GTKVEIK               107

SEQ ID NO: 427          moltype = DNA  length = 18
FEATURE                 Location/Qualifiers
misc_feature            1..18
                        note = synthetic
source                  1..18
                        mol_type = other DNA
                        organism = synthetic construct
SEQUENCE: 427
cagagaatta gcacctac                                               18

SEQ ID NO: 428          moltype = AA  length = 6
FEATURE                 Location/Qualifiers
REGION                  1..6
                        note = synthetic
source                  1..6
                        mol_type = protein
                        organism = synthetic construct
SEQUENCE: 428
QRISTY                                                            6

SEQ ID NO: 429          moltype =   length =
SEQUENCE: 429
000

SEQ ID NO: 430          moltype =   length =
SEQUENCE: 430
000

SEQ ID NO: 431          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 431
cagcagcgta gtaactggcc tctcact                                     27
```

```
SEQ ID NO: 432          moltype = AA  length = 9
FEATURE                 Location/Qualifiers
REGION                  1..9
                        note = synthetic
source                  1..9
                        mol_type = protein
                        organism = synthetic construct
SEQUENCE: 432
QQRSNWPLT                                                         9

SEQ ID NO: 433          moltype = DNA  length = 357
FEATURE                 Location/Qualifiers
misc_feature            1..357
                        note = synthetic
source                  1..357
                        mol_type = other DNA
                        organism = synthetic construct
SEQUENCE: 433
gaggtgcagc tggtgcagtc tggagcagag gtgagaaagc ccggggagtc tctgaagatc  60
tcctgtaagg gttctggata cagctttact aactactgga tcgtctgggt gcgccagatg  120
cccgggaaag gcctggagtg gatggggatc atctatcctg gtgactctga taccagatac  180
agcccgtcct tccaaggcca ggtcaccatc tcagccgaca agtccatcag caccgcctac  240
ctgcagtgga gcagcctgaa ggcctcggac accgccatgt attactgtgc gagacgggat  300
acgattttcc cttcctatcc cctctggggc cagggaaccc tggtcaccgt ctcctca     357

SEQ ID NO: 434          moltype = AA  length = 119
FEATURE                 Location/Qualifiers
REGION                  1..119
                        note = synthetic
source                  1..119
                        mol_type = protein
                        organism = synthetic construct
SEQUENCE: 434
EVQLVQSGAE VRKPGESLKI SCKGSGYSFT NYWIVWVRQM PGKGLEWMGI IYPGDSDTRY  60
SPSFQGQVTI SADKSISTAY LQWSSLKASD TAMYYCARRD TIFPSYPLWG QGTLVTVSS   119

SEQ ID NO: 435          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 435
ggatacagct ttactaacta ctgg                                         24

SEQ ID NO: 436          moltype = AA  length = 8
FEATURE                 Location/Qualifiers
REGION                  1..8
                        note = synthetic
source                  1..8
                        mol_type = protein
                        organism = synthetic construct
SEQUENCE: 436
GYSFTNYW                                                          8

SEQ ID NO: 437          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 437
atctatcctg gtgactctga tacc                                         24

SEQ ID NO: 438          moltype = AA  length = 8
FEATURE                 Location/Qualifiers
REGION                  1..8
                        note = synthetic
source                  1..8
                        mol_type = protein
                        organism = synthetic construct
SEQUENCE: 438
IYPGDSDT                                                          8

SEQ ID NO: 439          moltype = DNA  length = 36
FEATURE                 Location/Qualifiers
misc_feature            1..36
```

```
                       note = synthetic
source                 1..36
                       mol_type = other DNA
                       organism = synthetic construct
SEQUENCE: 439
gcgagacggg atacgatttt cccttcctat cccctc                         36

SEQ ID NO: 440         moltype = AA  length = 12
FEATURE                Location/Qualifiers
REGION                 1..12
                       note = synthetic
source                 1..12
                       mol_type = protein
                       organism = synthetic construct
SEQUENCE: 440
ARRDTIFPSY PL                                                   12

SEQ ID NO: 441         moltype = DNA  length = 336
FEATURE                Location/Qualifiers
misc_feature           1..336
                       note = synthetic
source                 1..336
                       mol_type = other DNA
                       organism = synthetic construct
SEQUENCE: 441
gatattgtga tgactcagtc tcctctctcc ctgcccgtca cccctggaga gccggcctcc  60
atctcctgca ggtctagtca gagcctcctg aatagtaatg gatacaactt tttggattgg  120
tacctgcaga agccagggca gtctccacaa ctcctgatct atttggtttc taatcgggcc  180
tccggggtcc ctgacaggtt cagtggcagt ggatcaggca cagattttac actgaaaatc  240
agcagagtgg aggctgagga tattggggtt tattactgca tgcaagctct ccaaactccg  300
atcaccttcg gccaagggac acgactggag attaaa                         336

SEQ ID NO: 442         moltype = AA  length = 112
FEATURE                Location/Qualifiers
REGION                 1..112
                       note = synthetic
source                 1..112
                       mol_type = protein
                       organism = synthetic construct
SEQUENCE: 442
DIVMTQSPLS LPVTPGEPAS ISCRSSQSLL NSNGYNFLDW YLQKPGQSPQ LLIYLVSNRA  60
SGVPDRFSGS GSGTDFTLKI SRVEAEDIGV YYCMQALQTP ITFGQGTRLE IK          112

SEQ ID NO: 443         moltype = DNA  length = 33
FEATURE                Location/Qualifiers
misc_feature           1..33
                       note = synthetic
source                 1..33
                       mol_type = other DNA
                       organism = synthetic construct
SEQUENCE: 443
cagagcctcc tgaatagtaa tggatacaac ttt                            33

SEQ ID NO: 444         moltype = AA  length = 11
FEATURE                Location/Qualifiers
REGION                 1..11
                       note = synthetic
source                 1..11
                       mol_type = protein
                       organism = synthetic construct
SEQUENCE: 444
QSLLNSNGYN F                                                    11

SEQ ID NO: 445         moltype =   length =
SEQUENCE: 445
000

SEQ ID NO: 446         moltype =   length =
SEQUENCE: 446
000

SEQ ID NO: 447         moltype = DNA  length = 27
FEATURE                Location/Qualifiers
misc_feature           1..27
                       note = synthetic
source                 1..27
                       mol_type = other DNA
                       organism = synthetic construct
SEQUENCE: 447
```

```
atgcaagctc tccaaactcc gatcacc                                   27

SEQ ID NO: 448         moltype = AA  length = 9
FEATURE                Location/Qualifiers
REGION                 1..9
                       note = synthetic
source                 1..9
                       mol_type = protein
                       organism = synthetic construct
SEQUENCE: 448
MQALQTPIT                                                       9

SEQ ID NO: 449         moltype = DNA  length = 360
FEATURE                Location/Qualifiers
misc_feature           1..360
                       note = synthetic
source                 1..360
                       mol_type = other DNA
                       organism = synthetic construct
SEQUENCE: 449
cagatcacct tgaaggagtc tggtcctacg ctggtgaaac ccacacagac cctcacgctg  60
acctgcacct tctctgggtt ctcactcagc actaatggag tgggtgtggg ctggatccgt  120
cagcccccag gaaaggccct ggagtggctt acactcattt attggaatga aaataagcac  180
tacagcccat ctctgaaaaa caggatcacc atcaccaagg acacctccaa aaaccaggtg  240
gtccttacaa tgaccaactt ggaccctgtg gacacagcca cttattactg tgtacacagg  300
ggatggttgg gagcaatctt tgcctactgg ggccagggaa ccctggtcac cgtctcctca  360

SEQ ID NO: 450         moltype = AA  length = 120
FEATURE                Location/Qualifiers
REGION                 1..120
                       note = synthetic
source                 1..120
                       mol_type = protein
                       organism = synthetic construct
SEQUENCE: 450
QITLKESGPT LVKPTQTLTL TCTFSGFSLS TNGVGVGWIR QPPGKALEWL TLIYWNENKH  60
YSPSLKNRIT ITKDTSKNQV VLTMTNLDPV DTATYYCVHR GWLGAIFAYW GQGTLVTVSS  120

SEQ ID NO: 451         moltype = DNA  length = 30
FEATURE                Location/Qualifiers
misc_feature           1..30
                       note = synthetic
source                 1..30
                       mol_type = other DNA
                       organism = synthetic construct
SEQUENCE: 451
gggttctcac tcagcactaa tggagtgggt                                30

SEQ ID NO: 452         moltype = AA  length = 10
FEATURE                Location/Qualifiers
REGION                 1..10
                       note = synthetic
source                 1..10
                       mol_type = protein
                       organism = synthetic construct
SEQUENCE: 452
GFSLSTNGVG                                                      10

SEQ ID NO: 453         moltype = DNA  length = 21
FEATURE                Location/Qualifiers
misc_feature           1..21
                       note = synthetic
source                 1..21
                       mol_type = other DNA
                       organism = synthetic construct
SEQUENCE: 453
atttattgga atgaaaataa g                                         21

SEQ ID NO: 454         moltype = AA  length = 7
FEATURE                Location/Qualifiers
REGION                 1..7
                       note = synthetic
source                 1..7
                       mol_type = protein
                       organism = synthetic construct
SEQUENCE: 454
IYWNENK                                                         7

SEQ ID NO: 455         moltype = DNA  length = 36
```

-continued

```
FEATURE                Location/Qualifiers
misc_feature           1..36
                       note = synthetic
source                 1..36
                       mol_type = other DNA
                       organism = synthetic construct
SEQUENCE: 455
gtacacaggg gatggttggg agcaatcttt gcctac                             36

SEQ ID NO: 456         moltype = AA  length = 12
FEATURE                Location/Qualifiers
REGION                 1..12
                       note = synthetic
source                 1..12
                       mol_type = protein
                       organism = synthetic construct
SEQUENCE: 456
VHRGWLGAIF AY                                                       12

SEQ ID NO: 457         moltype = DNA  length = 378
FEATURE                Location/Qualifiers
misc_feature           1..378
                       note = synthetic
source                 1..378
                       mol_type = other DNA
                       organism = synthetic construct
SEQUENCE: 457
gaggtgcagc tggtggagtc tgggggaggc ttggtacagc ctggggggtc cctgagactc  60
tcctgtgcag cctctggatt cacctttact agttatgcca tgacctgggt ccgccaggct  120
ccagggaagg ggctggagtg ggtctcagat attagtggta gtggtggtag aacatattac  180
gcagactccg tgaagggccg gttcaccatc tccagagaca attccaagaa tatgctgtat  240
ctgcaaatga acatcctgag agccgaagac acggccgtat atcattgtgc gaagggaaca  300
ggccagcagg tggaccttta caactactac tatgctttgg acgtctgggg ccaagggacc  360
acggtcaccg tctcctca                                                 378

SEQ ID NO: 458         moltype = AA  length = 126
FEATURE                Location/Qualifiers
REGION                 1..126
                       note = synthetic
source                 1..126
                       mol_type = protein
                       organism = synthetic construct
SEQUENCE: 458
EVQLVESGGG LVQPGGSLRL SCAASGFTFT SYAMTWVRQA PGKGLEWVSD ISGSGGRTYY  60
ADSVKGRFTI SRDNSKNMLY LQMNILRAED TAVYHCAKGT GQQVDLYNYY YALDVWGQGT  120
TVTVSS                                                              126

SEQ ID NO: 459         moltype = DNA  length = 24
FEATURE                Location/Qualifiers
misc_feature           1..24
                       note = synthetic
source                 1..24
                       mol_type = other DNA
                       organism = synthetic construct
SEQUENCE: 459
ggattcacct ttactagtta tgcc                                          24

SEQ ID NO: 460         moltype = AA  length = 8
FEATURE                Location/Qualifiers
REGION                 1..8
                       note = synthetic
source                 1..8
                       mol_type = protein
                       organism = synthetic construct
SEQUENCE: 460
GFTFTSYA                                                            8

SEQ ID NO: 461         moltype = DNA  length = 24
FEATURE                Location/Qualifiers
misc_feature           1..24
                       note = synthetic
source                 1..24
                       mol_type = other DNA
                       organism = synthetic construct
SEQUENCE: 461
attagtggta gtggtggtag aaca                                          24

SEQ ID NO: 462         moltype = AA  length = 8
FEATURE                Location/Qualifiers
```

```
REGION                1..8
                      note = synthetic
source                1..8
                      mol_type = protein
                      organism = synthetic construct
SEQUENCE: 462
ISGSGGRT                                                        8

SEQ ID NO: 463        moltype = DNA  length = 57
FEATURE               Location/Qualifiers
misc_feature          1..57
                      note = synthetic
source                1..57
                      mol_type = other DNA
                      organism = synthetic construct
SEQUENCE: 463
gcgaagggaa caggccagca ggtggacctt tacaactact actatgcttt ggacgtc     57

SEQ ID NO: 464        moltype = AA  length = 19
FEATURE               Location/Qualifiers
REGION                1..19
                      note = synthetic
source                1..19
                      mol_type = protein
                      organism = synthetic construct
SEQUENCE: 464
AKGTGQQVDL YNYYYALDV                                             19

SEQ ID NO: 465        moltype = DNA  length = 387
FEATURE               Location/Qualifiers
misc_feature          1..387
                      note = synthetic
source                1..387
                      mol_type = other DNA
                      organism = synthetic construct
SEQUENCE: 465
caggtgcagc tggtggagtc tgggggaggc gtggtccagc ctgggaggtc cctgagactc  60
tcctgtgcag cgtctggatt caccttcagt tactatggca tgcactgggt ccgccaggct  120
ccaggcaagg ggctggagtg ggtggcagtt atatggtatg atggaagtaa taaacactat  180
gcagactccg tgaagggccg attcaccatc tccagagaca attccaagaa cacgctgtat  240
ctgcaaatga acagcctgag agccgacgac acggctgtct attactgtgc gagagataag  300
ggtataagtg gaattaaggg gggttcttac tactactact atgccatgga cgtctggggc  360
caagggacca cggtcaccgt ctcctca                                      387

SEQ ID NO: 466        moltype = AA  length = 129
FEATURE               Location/Qualifiers
REGION                1..129
                      note = synthetic
source                1..129
                      mol_type = protein
                      organism = synthetic construct
SEQUENCE: 466
QVQLVESGGG VVQPGRSLRL SCAASGFTFS YYGMHWVRQA PGKGLEWVAV IWYDGSNKHY  60
ADSVKGRFTI SRDNSKNTLY LQMNSLRADD TAVYYCARDK GISGIKGGSY YYYYAMDVWG  120
QGTTVTVSS                                                          129

SEQ ID NO: 467        moltype = DNA  length = 24
FEATURE               Location/Qualifiers
misc_feature          1..24
                      note = synthetic
source                1..24
                      mol_type = other DNA
                      organism = synthetic construct
SEQUENCE: 467
ggattcacct tcagttacta tggc                                         24

SEQ ID NO: 468        moltype = AA  length = 8
FEATURE               Location/Qualifiers
REGION                1..8
                      note = synthetic
source                1..8
                      mol_type = protein
                      organism = synthetic construct
SEQUENCE: 468
GFTFSYYG                                                           8

SEQ ID NO: 469        moltype = DNA  length = 24
FEATURE               Location/Qualifiers
misc_feature          1..24
```

```
                      note = synthetic
source                1..24
                      mol_type = other DNA
                      organism = synthetic construct
SEQUENCE: 469
atatggtatg atggaagtaa taaa                                        24

SEQ ID NO: 470        moltype = AA  length = 8
FEATURE               Location/Qualifiers
REGION                1..8
                      note = synthetic
source                1..8
                      mol_type = protein
                      organism = synthetic construct
SEQUENCE: 470
IWYDGSNK                                                          8

SEQ ID NO: 471        moltype = DNA  length = 66
FEATURE               Location/Qualifiers
misc_feature          1..66
                      note = synthetic
source                1..66
                      mol_type = other DNA
                      organism = synthetic construct
SEQUENCE: 471
gcgagagata agggtataag tggaattaag gggggttctt actactacta ctatgccatg  60
gacgtc                                                            66

SEQ ID NO: 472        moltype = AA  length = 22
FEATURE               Location/Qualifiers
REGION                1..22
                      note = synthetic
source                1..22
                      mol_type = protein
                      organism = synthetic construct
SEQUENCE: 472
ARDKGISGIK GGSYYYYYAM DV                                          22

SEQ ID NO: 473        moltype = DNA  length = 360
FEATURE               Location/Qualifiers
misc_feature          1..360
                      note = synthetic
source                1..360
                      mol_type = other DNA
                      organism = synthetic construct
SEQUENCE: 473
gaggtgcagc tggtggagtc tgggggaggc ttggtaaagc ctggggggtc ccttagactc  60
tcctgtgcag cctctggatt cactttcagt aacgcctgga tgacctgggt ccgccaggct  120
ccagggaagg ggctggagtg ggttggccgt attaaaaaca aaattgatgg tgggacaaca  180
gactacgctg cacccgtgaa aggcagattc accatctcaa gagatgattc aaaaaacacg  240
gtttatctgc aaatgaacag cctgaaaacc gaggacacag ccgtttatta ctgttccacg  300
gtggactaca attggtactt cgatttctgg ggccgtggca ccctggtcac tgtctcctca  360

SEQ ID NO: 474        moltype = AA  length = 120
FEATURE               Location/Qualifiers
REGION                1..120
                      note = synthetic
source                1..120
                      mol_type = protein
                      organism = synthetic construct
SEQUENCE: 474
EVQLVESGGG LVKPGGSLRL SCAASGFTFS NAWMTWVRQA PGKGLEWVGR IKNKIDGGTT  60
DYAAPVKGRF TISRDDSKNT VYLQMNSLKT EDTAVYYCST VDYNWYFDFW GRGTLVTVSS  120

SEQ ID NO: 475        moltype = DNA  length = 24
FEATURE               Location/Qualifiers
misc_feature          1..24
                      note = synthetic
source                1..24
                      mol_type = other DNA
                      organism = synthetic construct
SEQUENCE: 475
ggattcactt tcagtaacgc ctgg                                        24

SEQ ID NO: 476        moltype = AA  length = 8
FEATURE               Location/Qualifiers
REGION                1..8
                      note = synthetic
source                1..8
```

```
                        mol_type = protein
                        organism = synthetic construct
SEQUENCE: 476
GFTFSNAW                                                              8

SEQ ID NO: 477          moltype = DNA  length = 30
FEATURE                 Location/Qualifiers
misc_feature            1..30
                        note = synthetic
source                  1..30
                        mol_type = other DNA
                        organism = synthetic construct
SEQUENCE: 477
attaaaaaca aaattgatgg tgggacaaca                                      30

SEQ ID NO: 478          moltype = AA  length = 10
FEATURE                 Location/Qualifiers
REGION                  1..10
                        note = synthetic
source                  1..10
                        mol_type = protein
                        organism = synthetic construct
SEQUENCE: 478
IKNKIDGGTT                                                            10

SEQ ID NO: 479          moltype = DNA  length = 33
FEATURE                 Location/Qualifiers
misc_feature            1..33
                        note = synthetic
source                  1..33
                        mol_type = other DNA
                        organism = synthetic construct
SEQUENCE: 479
tccacggtgg actacaattg gtacttcgat ttc                                  33

SEQ ID NO: 480          moltype = AA  length = 11
FEATURE                 Location/Qualifiers
REGION                  1..11
                        note = synthetic
source                  1..11
                        mol_type = protein
                        organism = synthetic construct
SEQUENCE: 480
STVDYNWYFD F                                                          11

SEQ ID NO: 481          moltype = DNA  length = 387
FEATURE                 Location/Qualifiers
misc_feature            1..387
                        note = synthetic
source                  1..387
                        mol_type = other DNA
                        organism = synthetic construct
SEQUENCE: 481
caggtgcagc tggtggagtc tgggggaggc gtggtccagc ctgggaggtc cctgagactc  60
tcctgtgcag cgtctggatt caccttcagt ttctttggca tgcactgggt ccgccaggct  120
ccaggcaagg ggctggagtg ggtggcactt atatggtatg atggaactaa tgaaaactat  180
gcagactccg tgaagggccg attcaccatc tccagagaca attccaagtc cacgctgtat  240
ctgcaaatga acagtctgag agccgaggac acggctgttt actactgtgc gagagatagg  300
ggagtggcga catttacgag ggggaattac tactacaact acggtatgga cgtctggggc  360
caagggacca cggtcaccgt ctcctca                                         387

SEQ ID NO: 482          moltype = AA  length = 129
FEATURE                 Location/Qualifiers
REGION                  1..129
                        note = synthetic
source                  1..129
                        mol_type = protein
                        organism = synthetic construct
SEQUENCE: 482
QVQLVESGGG VVQPGRSLRL SCAASGFTFS FFGMHWVRQA PGKGLEWVAL IWYDGTNENY  60
ADSVKGRFTI SRDNSKSTLY LQMNSLRAED TAVYYCARDR GVATFTRGNY YYNYGMDVWG  120
QGTTVTVSS                                                             129

SEQ ID NO: 483          moltype = DNA  length = 24
FEATURE                 Location/Qualifiers
misc_feature            1..24
                        note = synthetic
source                  1..24
                        mol_type = other DNA
```

```
                        organism = synthetic construct
SEQUENCE: 483
ggattcacct tcagtttctt tggc                                          24

SEQ ID NO: 484          moltype = AA  length = 8
FEATURE                 Location/Qualifiers
REGION                  1..8
                        note = synthetic
source                  1..8
                        mol_type = protein
                        organism = synthetic construct
SEQUENCE: 484
GFTFSFFG                                                            8

SEQ ID NO: 485          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 485
atatggtatg atggaactaa tgaa                                          24

SEQ ID NO: 486          moltype = AA  length = 8
FEATURE                 Location/Qualifiers
REGION                  1..8
                        note = synthetic
source                  1..8
                        mol_type = protein
                        organism = synthetic construct
SEQUENCE: 486
IWYDGTNE                                                            8

SEQ ID NO: 487          moltype = DNA  length = 66
FEATURE                 Location/Qualifiers
misc_feature            1..66
                        note = synthetic
source                  1..66
                        mol_type = other DNA
                        organism = synthetic construct
SEQUENCE: 487
gcgagagata ggggagtggc gacatttacg agggggaatt actactacaa ctacggtatg  60
gacgtc                                                              66

SEQ ID NO: 488          moltype = AA  length = 22
FEATURE                 Location/Qualifiers
REGION                  1..22
                        note = synthetic
source                  1..22
                        mol_type = protein
                        organism = synthetic construct
SEQUENCE: 488
ARDRGVATFT RGNYYYNYGM DV                                            22

SEQ ID NO: 489          moltype = DNA  length = 387
FEATURE                 Location/Qualifiers
misc_feature            1..387
                        note = synthetic
source                  1..387
                        mol_type = other DNA
                        organism = synthetic construct
SEQUENCE: 489
caggtgcagc tggtggagtc tgggggaggc gtggtccagc ctgggaggtc cctgagactc  60
tcctgtgcag cgtctggatt caccttcagt ttctatggca tgcactgggt ccgccaggct  120
ccaggcaagg ggctggaggg ggtggcagtt atatggtatg atggaagtaa taaatactat  180
gcagactccg tgaagggccg attcaccata tccagagaca attccaagaa catgctgtat  240
ctacaaatga ccagcctgag agccgaggac acggctgtgt attactgtgc gagagattcg  300
ggtaaaactg gaactgggat aactgggtac tcctactact acggtatgga cgtctggggc  360
caagggacca cggtcaccgt ctcctca                                       387

SEQ ID NO: 490          moltype = AA  length = 129
FEATURE                 Location/Qualifiers
REGION                  1..129
                        note = synthetic
source                  1..129
                        mol_type = protein
                        organism = synthetic construct
SEQUENCE: 490
```

```
QVQLVESGGG VVQPGRSLRL SCAASGFTFS FYGMHWVRQA PGKGLEGVAV IWYDGSNKYY  60
ADSVKGRFTI SRDNSKNMLY LQMTSLRAED TAVYYCARDS GKTGTGITGY SYYYGMDVWG  120
QGTTVTVSS                                                          129

SEQ ID NO: 491          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 491
ggattcacct tcagtttcta tggc                                         24

SEQ ID NO: 492          moltype = AA  length = 8
FEATURE                 Location/Qualifiers
REGION                  1..8
                        note = synthetic
source                  1..8
                        mol_type = protein
                        organism = synthetic construct
SEQUENCE: 492
GFTFSFYG                                                           8

SEQ ID NO: 493          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 493
atatggtatg atggaagtaa taaa                                         24

SEQ ID NO: 494          moltype = AA  length = 8
FEATURE                 Location/Qualifiers
REGION                  1..8
                        note = synthetic
source                  1..8
                        mol_type = protein
                        organism = synthetic construct
SEQUENCE: 494
IWYDGSNK                                                           8

SEQ ID NO: 495          moltype = DNA  length = 66
FEATURE                 Location/Qualifiers
misc_feature            1..66
                        note = synthetic
source                  1..66
                        mol_type = other DNA
                        organism = synthetic construct
SEQUENCE: 495
gcgagagatt cgggtaaaac tggaactggg ataactgggt actcctacta ctacggtatg  60
gacgtc                                                             66

SEQ ID NO: 496          moltype = AA  length = 22
FEATURE                 Location/Qualifiers
REGION                  1..22
                        note = synthetic
source                  1..22
                        mol_type = protein
                        organism = synthetic construct
SEQUENCE: 496
ARDSGKTGTG ITGYSYYYGM DV                                           22

SEQ ID NO: 497          moltype = DNA  length = 354
FEATURE                 Location/Qualifiers
misc_feature            1..354
                        note = synthetic
source                  1..354
                        mol_type = other DNA
                        organism = synthetic construct
SEQUENCE: 497
cagctgcagc tgcaggagtc gggcccagga ctggtgaagc cttcggagac cctgtccctc  60
acctgcactg tctctggtgg ctccatcatc actaatagtt attactgggg ctggatccgc  120
cagcccccag ggaagggtct ggagtggatt ggtagtatct attatagtgg gaggacctac  180
tacaacccgt ccctcgagag tcgagtcacc atatccgtgg acacgtccaa gaaccagttc  240
tccctgaagt tgacctctgt gaccgccgca gacacggcta tatattactg tgcgagggaa  300
ggggatccgt cgctcgaccc ctggggccag ggaaccctgg tcaccgtctc ctca        354
```

```
SEQ ID NO: 498          moltype = AA  length = 118
FEATURE                 Location/Qualifiers
REGION                  1..118
                        note = synthetic
source                  1..118
                        mol_type = protein
                        organism = synthetic construct
SEQUENCE: 498
QLQLQESGPG LVKPSETLSL TCTVSGGSII TNSYYWGWIR QPPGKGLEWI GSIYYSGRTY  60
YNPSLESRVT ISVDTSKNQF SLKLTSVTAA DTAIYYCARE GDPSLDPWGQ GTLVTVSS    118

SEQ ID NO: 499          moltype = DNA  length = 30
FEATURE                 Location/Qualifiers
misc_feature            1..30
                        note = synthetic
source                  1..30
                        mol_type = other DNA
                        organism = synthetic construct
SEQUENCE: 499
ggtggctcca tcatcactaa tagttattac                                   30

SEQ ID NO: 500          moltype = AA  length = 10
FEATURE                 Location/Qualifiers
REGION                  1..10
                        note = synthetic
source                  1..10
                        mol_type = protein
                        organism = synthetic construct
SEQUENCE: 500
GGSIITNSYY                                                         10

SEQ ID NO: 501          moltype = DNA  length = 21
FEATURE                 Location/Qualifiers
misc_feature            1..21
                        note = synthetic
source                  1..21
                        mol_type = other DNA
                        organism = synthetic construct
SEQUENCE: 501
atctattata gtgggaggac c                                            21

SEQ ID NO: 502          moltype = AA  length = 7
FEATURE                 Location/Qualifiers
REGION                  1..7
                        note = synthetic
source                  1..7
                        mol_type = protein
                        organism = synthetic construct
SEQUENCE: 502
IYYSGRT                                                            7

SEQ ID NO: 503          moltype = DNA  length = 30
FEATURE                 Location/Qualifiers
misc_feature            1..30
                        note = synthetic
source                  1..30
                        mol_type = other DNA
                        organism = synthetic construct
SEQUENCE: 503
gcgagggaag gggatccgtc gctcgacccc                                   30

SEQ ID NO: 504          moltype = AA  length = 10
FEATURE                 Location/Qualifiers
REGION                  1..10
                        note = synthetic
source                  1..10
                        mol_type = protein
                        organism = synthetic construct
SEQUENCE: 504
AREGDPSLDP                                                         10

SEQ ID NO: 505          moltype = DNA  length = 363
FEATURE                 Location/Qualifiers
misc_feature            1..363
                        note = synthetic
source                  1..363
                        mol_type = other DNA
                        organism = synthetic construct
```

```
SEQUENCE: 505
gaggtgcagc tggtggagtc tgggggagac ttggtacagc ctggggggtc cctgagactc  60
tcctgtgcag cctctggatt cacctttagc acctatgcca tgaactgggt ccgccaggct  120
ccagggaagg ggctggagtg ggtctcacat attagtggta gtggtggtaa ttcatactcc  180
gcagactccg tgaagggccg gttcaccatc tccagagaca attccaagaa cacgctatat  240
ctgcaaatga acagcctgcg agccgaggac acggccatat attactgttc gctggatata  300
atggctacag taggcggtct ctttgcctac tggggccagg gaaccctggt caccgtctcc  360
tca                                                               363

SEQ ID NO: 506         moltype = AA  length = 121
FEATURE                Location/Qualifiers
REGION                 1..121
                       note = synthetic
source                 1..121
                       mol_type = protein
                       organism = synthetic construct
SEQUENCE: 506
EVQLVESGGD LVQPGGSLRL SCAASGFTFS TYAMNWVRQA PGKGLEWVSH ISGSGGNSYS  60
ADSVKGRFTI SRDNSKNTLY LQMNSLRAED TAIYYCSLDI MATVGGLFAY WGQGTLVTVS  120
S                                                                 121

SEQ ID NO: 507         moltype = DNA  length = 24
FEATURE                Location/Qualifiers
misc_feature           1..24
                       note = synthetic
source                 1..24
                       mol_type = other DNA
                       organism = synthetic construct
SEQUENCE: 507
ggattcacct ttagcaccta tgcc                                        24

SEQ ID NO: 508         moltype = AA  length = 8
FEATURE                Location/Qualifiers
REGION                 1..8
                       note = synthetic
source                 1..8
                       mol_type = protein
                       organism = synthetic construct
SEQUENCE: 508
GFTFSTYA                                                          8

SEQ ID NO: 509         moltype = DNA  length = 24
FEATURE                Location/Qualifiers
misc_feature           1..24
                       note = synthetic
source                 1..24
                       mol_type = other DNA
                       organism = synthetic construct
SEQUENCE: 509
attagtggta gtggtggtaa ttca                                        24

SEQ ID NO: 510         moltype = AA  length = 8
FEATURE                Location/Qualifiers
REGION                 1..8
                       note = synthetic
source                 1..8
                       mol_type = protein
                       organism = synthetic construct
SEQUENCE: 510
ISGSGGNS                                                          8

SEQ ID NO: 511         moltype = DNA  length = 42
FEATURE                Location/Qualifiers
misc_feature           1..42
                       note = synthetic
source                 1..42
                       mol_type = other DNA
                       organism = synthetic construct
SEQUENCE: 511
tcgctggata taatggctac agtaggcggt ctctttgcct ac                    42

SEQ ID NO: 512         moltype = AA  length = 14
FEATURE                Location/Qualifiers
REGION                 1..14
                       note = synthetic
source                 1..14
                       mol_type = protein
                       organism = synthetic construct
SEQUENCE: 512
```

```
SLDIMATVGG LFAY                                                14

SEQ ID NO: 513          moltype = DNA  length = 393
FEATURE                 Location/Qualifiers
misc_feature            1..393
                        note = synthetic
source                  1..393
                        mol_type = other DNA
                        organism = synthetic construct
SEQUENCE: 513
caggtgcagc tggtggagtc tgggggaggc gtggtccagc ctgggaggtc cctgagactc  60
tcctgtgtag cgtctggatt catcttcagt ttctatggca tgcactgggt ccgccaggct  120
ccagacaagg ggctggagtg ggtggcagtt atatggtatg atggaagtaa tgaatactat  180
gcagactccg tgaagggccg attcaccatc tccagagaca attccaagaa cacgctgtat  240
ctgcaaatga acagcctgag agccgaggac acggctgtgt attactgtgg gagagatcaa  300
ggtatttcgt attacgatat tttgactggt aattataact attactacgg tgtggacgtc  360
tggggccaag ggaccacggt caccgtctcc tca                           393

SEQ ID NO: 514          moltype = AA  length = 131
FEATURE                 Location/Qualifiers
REGION                  1..131
                        note = synthetic
source                  1..131
                        mol_type = protein
                        organism = synthetic construct
SEQUENCE: 514
QVQLVESGGG VVQPGRSLRL SCVASGFIFS FYGMHWVRQA PDKGLEWVAV IWYDGSNEYY  60
ADSVKGRFTI SRDNSKNTLY LQMNSLRAED TAVYYCGRDQ GISYYDILTG NYNYYYGVDV  120
WGQGTTVTVS S                                                   131

SEQ ID NO: 515          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 515
ggattcatct tcagtttcta tggc                                     24

SEQ ID NO: 516          moltype = AA  length = 8
FEATURE                 Location/Qualifiers
REGION                  1..8
                        note = synthetic
source                  1..8
                        mol_type = protein
                        organism = synthetic construct
SEQUENCE: 516
GFIFSFYG                                                       8

SEQ ID NO: 517          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 517
atatggtatg atggaagtaa tgaa                                     24

SEQ ID NO: 518          moltype = AA  length = 8
FEATURE                 Location/Qualifiers
REGION                  1..8
                        note = synthetic
source                  1..8
                        mol_type = protein
                        organism = synthetic construct
SEQUENCE: 518
IWYDGSNE                                                       8

SEQ ID NO: 519          moltype = DNA  length = 72
FEATURE                 Location/Qualifiers
misc_feature            1..72
                        note = synthetic
source                  1..72
                        mol_type = other DNA
                        organism = synthetic construct
SEQUENCE: 519
gggagagatc aaggtatttc gtattacgat attttgactg gtaattataa ctattactac  60
```

```
ggtgtggacg tc                                                    72

SEQ ID NO: 520          moltype = AA  length = 24
FEATURE                 Location/Qualifiers
REGION                  1..24
                        note = synthetic
source                  1..24
                        mol_type = protein
                        organism = synthetic construct
SEQUENCE: 520
GRDQGISYYD ILTGNYNYYY GVDV                                       24

SEQ ID NO: 521          moltype = DNA  length = 324
FEATURE                 Location/Qualifiers
misc_feature            1..324
                        note = synthetic
source                  1..324
                        mol_type = other DNA
                        organism = synthetic construct
SEQUENCE: 521
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                       324

SEQ ID NO: 522          moltype = AA  length = 108
FEATURE                 Location/Qualifiers
REGION                  1..108
                        note = synthetic
source                  1..108
                        mol_type = protein
                        organism = synthetic construct
SEQUENCE: 522
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIK              108

SEQ ID NO: 523          moltype = DNA  length = 18
FEATURE                 Location/Qualifiers
misc_feature            1..18
                        note = synthetic
source                  1..18
                        mol_type = other DNA
                        organism = synthetic construct
SEQUENCE: 523
cagagcatta gcagctat                                              18

SEQ ID NO: 524          moltype = AA  length = 6
FEATURE                 Location/Qualifiers
REGION                  1..6
                        note = synthetic
source                  1..6
                        mol_type = protein
                        organism = synthetic construct
SEQUENCE: 524
QSISSY                                                           6

SEQ ID NO: 525          moltype =   length =
SEQUENCE: 525
000

SEQ ID NO: 526          moltype =   length =
SEQUENCE: 526
000

SEQ ID NO: 527          moltype = DNA  length = 30
FEATURE                 Location/Qualifiers
misc_feature            1..30
                        note = synthetic
source                  1..30
                        mol_type = other DNA
                        organism = synthetic construct
SEQUENCE: 527
caacagagtt acagtacccc tccgatcacc                                 30

SEQ ID NO: 528          moltype = AA  length = 10
FEATURE                 Location/Qualifiers
REGION                  1..10
```

```
                       note = synthetic
source                 1..10
                       mol_type = protein
                       organism = synthetic construct
SEQUENCE: 528
QQSYSTPPIT                                                        10

SEQ ID NO: 529         moltype = DNA  length = 324
FEATURE                Location/Qualifiers
misc_feature           1..324
                       note = synthetic
source                 1..324
                       mol_type = other DNA
                       organism = synthetic construct
SEQUENCE: 529
gaaattgtgt tgacgcagtc tccaggcacc ctgtctttgt ctccagggga aagagccacc  60
ctctcctgca gggccagtca gagtgttagc agcagctact tagcctggta ccagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag cagtatggta gctcaccttg gacgttcggc  300
caagggacca aggtggaaat caaa                                         324

SEQ ID NO: 530         moltype = AA  length = 108
FEATURE                Location/Qualifiers
REGION                 1..108
                       note = synthetic
source                 1..108
                       mol_type = protein
                       organism = synthetic construct
SEQUENCE: 530
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPWTFG QGTKVEIK               108

SEQ ID NO: 531         moltype = DNA  length = 21
FEATURE                Location/Qualifiers
misc_feature           1..21
                       note = synthetic
source                 1..21
                       mol_type = other DNA
                       organism = synthetic construct
SEQUENCE: 531
cagagtgtta gcagcagcta c                                           21

SEQ ID NO: 532         moltype = AA  length = 7
FEATURE                Location/Qualifiers
REGION                 1..7
                       note = synthetic
source                 1..7
                       mol_type = protein
                       organism = synthetic construct
SEQUENCE: 532
QSVSSSY                                                           7

SEQ ID NO: 533         moltype =   length =
SEQUENCE: 533
000

SEQ ID NO: 534         moltype =   length =
SEQUENCE: 534
000

SEQ ID NO: 535         moltype = DNA  length = 27
FEATURE                Location/Qualifiers
misc_feature           1..27
                       note = synthetic
source                 1..27
                       mol_type = other DNA
                       organism = synthetic construct
SEQUENCE: 535
cagcagtatg gtagctcacc ttggacg                                     27

SEQ ID NO: 536         moltype = AA  length = 9
FEATURE                Location/Qualifiers
REGION                 1..9
                       note = synthetic
source                 1..9
                       mol_type = protein
                       organism = synthetic construct
SEQUENCE: 536
```

```
QQYGSSPWT                                                          9

SEQ ID NO: 537          moltype = DNA  length = 357
FEATURE                 Location/Qualifiers
misc_feature            1..357
                        note = synthetic
source                  1..357
                        mol_type = other DNA
                        organism = synthetic construct
SEQUENCE: 537
caggtgcagc tacagcagtg gggcgcagga ctgttgaagc cttcggagac cctgtccctc  60
acctgcgctg tctatggtgg gtccttcagt ggttactact ggaactggat ccgccagccc  120
ccagggaagg ggctggagtg ggttggggaa atcagtcata gaggaagcac caactacaac  180
ccgtccctca agagtcgagt caccatatca ctggacacgt ccaagaacca gttctccctg  240
aagctgacct ctgtgaccgc cgcggacacg gctgtgtatt actgttcgag agacgaggaa  300
ctggaattcc gtttctttga ctactggggc cagggaaccc tggtcaccgt ctcctca     357

SEQ ID NO: 538          moltype = AA  length = 119
FEATURE                 Location/Qualifiers
REGION                  1..119
                        note = synthetic
source                  1..119
                        mol_type = protein
                        organism = synthetic construct
SEQUENCE: 538
QVQLQQWGAG LLKPSETLSL TCAVYGGSFS GYYWNWIRQP PGKGLEWVGE ISHRGSTNYN  60
PSLKSRVTIS LDTSKNQFSL KLTSVTAADT AVYYCSRDEE LEFRFFDYWG QGTLVTVSS   119

SEQ ID NO: 539          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 539
ggtgggtcct tcagtggtta ctac                                         24

SEQ ID NO: 540          moltype = AA  length = 8
FEATURE                 Location/Qualifiers
REGION                  1..8
                        note = synthetic
source                  1..8
                        mol_type = protein
                        organism = synthetic construct
SEQUENCE: 540
GGSFSGYY                                                           8

SEQ ID NO: 541          moltype = DNA  length = 21
FEATURE                 Location/Qualifiers
misc_feature            1..21
                        note = synthetic
source                  1..21
                        mol_type = other DNA
                        organism = synthetic construct
SEQUENCE: 541
atcagtcata gaggaagcac c                                            21

SEQ ID NO: 542          moltype = AA  length = 7
FEATURE                 Location/Qualifiers
REGION                  1..7
                        note = synthetic
source                  1..7
                        mol_type = protein
                        organism = synthetic construct
SEQUENCE: 542
ISHRGST                                                            7

SEQ ID NO: 543          moltype = DNA  length = 39
FEATURE                 Location/Qualifiers
misc_feature            1..39
                        note = synthetic
source                  1..39
                        mol_type = other DNA
                        organism = synthetic construct
SEQUENCE: 543
tcgagagacg aggaactgga attccgtttc tttgactac                         39

SEQ ID NO: 544          moltype = AA  length = 13
```

```
FEATURE                Location/Qualifiers
REGION                 1..13
                       note = synthetic
source                 1..13
                       mol_type = protein
                       organism = synthetic construct
SEQUENCE: 544
SRDEELEFRF FDY                                                   13

SEQ ID NO: 545         moltype = DNA  length = 321
FEATURE                Location/Qualifiers
misc_feature           1..321
                       note = synthetic
source                 1..321
                       mol_type = other DNA
                       organism = synthetic construct
SEQUENCE: 545
gaaattgtgt tgacacagtc tccagccacc ctgtctttgt ctccagggga aagagccacc  60
ctctcctgca gggccagtca gagtgttagc agctatttag cctggtacca acaaaaacct  120
ggccaggctc ccaggctcct cgtctatggt gcatccaaca gggccactgg catcccagcc  180
aggttcagtg gcagtgggtc tgggacagac ttcactctca ccatcagcag cctagagcct  240
gaagattttg cattttatta ctgtcagcag cgtagcaact ggccgctcac tttcggcgga  300
gggaccaagg tggagatcaa a                                          321

SEQ ID NO: 546         moltype = AA  length = 107
FEATURE                Location/Qualifiers
REGION                 1..107
                       note = synthetic
source                 1..107
                       mol_type = protein
                       organism = synthetic construct
SEQUENCE: 546
EIVLTQSPAT LSLSPGERAT LSCRASQSVS SYLAWYQQKP GQAPRLLVYG ASNRATGIPA  60
RFSGSGSGTD FTLTISSLEP EDFAFYYCQQ RSNWPLTFGG GTKVEIK              107

SEQ ID NO: 547         moltype = DNA  length = 18
FEATURE                Location/Qualifiers
misc_feature           1..18
                       note = synthetic
source                 1..18
                       mol_type = other DNA
                       organism = synthetic construct
SEQUENCE: 547
cagagtgtta gcagctat                                              18

SEQ ID NO: 548         moltype = AA  length = 6
FEATURE                Location/Qualifiers
REGION                 1..6
                       note = synthetic
source                 1..6
                       mol_type = protein
                       organism = synthetic construct
SEQUENCE: 548
QSVSSY                                                           6

SEQ ID NO: 549         moltype =   length =
SEQUENCE: 549
000

SEQ ID NO: 550         moltype =   length =
SEQUENCE: 550
000

SEQ ID NO: 551         moltype = DNA  length = 27
FEATURE                Location/Qualifiers
misc_feature           1..27
                       note = synthetic
source                 1..27
                       mol_type = other DNA
                       organism = synthetic construct
SEQUENCE: 551
cagcagcgta gcaactggcc gctcact                                    27

SEQ ID NO: 552         moltype = AA  length = 9
FEATURE                Location/Qualifiers
REGION                 1..9
                       note = synthetic
source                 1..9
                       mol_type = protein
```

```
                        organism = synthetic construct
SEQUENCE: 552
QQRSNWPLT                                                         9

SEQ ID NO: 553          moltype = DNA  length = 372
FEATURE                 Location/Qualifiers
misc_feature            1..372
                        note = synthetic
source                  1..372
                        mol_type = other DNA
                        organism = synthetic construct
SEQUENCE: 553
gaggtgcagc tggtggagtc tgggggaggc ttggtacagc ctgggggtc cctgagactc  60
tcctgtgtag cctctggatt cacctttagc ctctatgcca tgacctgggt ccgccaggtt  120
ccagggaagg ggctggaatg ggtctcaact attagtggta gtggtggtgg cacatactac  180
acagactccg ttaagggccg gttcaccatc tccagagaca attccaagaa cacactgtat  240
ctgcaaatga acagcctgag agccgacgac acggccgttt tttactgtac gaaagagagt  300
acaactggaa cttactccta cttctacggt atggacgtct ggggccaagg gaccacggtc  360
accgtctcct ca                                                     372

SEQ ID NO: 554          moltype = AA  length = 124
FEATURE                 Location/Qualifiers
REGION                  1..124
                        note = synthetic
source                  1..124
                        mol_type = protein
                        organism = synthetic construct
SEQUENCE: 554
EVQLVESGGG LVQPGGSLRL SCVASGFTFS LYAMTWVRQV PGKGLEWVST ISGSGGGTYY  60
TDSVKGRFTI SRDNSKNTLY LQMNSLRADD TAVFYCTKES TTGTYSYFYG MDVWGQGTTV  120
TVSS                                                              124

SEQ ID NO: 555          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 555
ggattcacct ttagcctcta tgcc                                        24

SEQ ID NO: 556          moltype = AA  length = 8
FEATURE                 Location/Qualifiers
REGION                  1..8
                        note = synthetic
source                  1..8
                        mol_type = protein
                        organism = synthetic construct
SEQUENCE: 556
GFTFSLYA                                                          8

SEQ ID NO: 557          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 557
attagtggta gtggtggtgg caca                                        24

SEQ ID NO: 558          moltype = AA  length = 8
FEATURE                 Location/Qualifiers
REGION                  1..8
                        note = synthetic
source                  1..8
                        mol_type = protein
                        organism = synthetic construct
SEQUENCE: 558
ISGSGGGT                                                          8

SEQ ID NO: 559          moltype = DNA  length = 51
FEATURE                 Location/Qualifiers
misc_feature            1..51
                        note = synthetic
source                  1..51
                        mol_type = other DNA
                        organism = synthetic construct
```

```
SEQUENCE: 559
acgaaagaga gtacaactgg aacttactcc tacttctacg gtatggacgt c          51

SEQ ID NO: 560         moltype = AA  length = 17
FEATURE                Location/Qualifiers
REGION                 1..17
                       note = synthetic
source                 1..17
                       mol_type = protein
                       organism = synthetic construct
SEQUENCE: 560
TKESTTGTYS YFYGMDV                                                17

SEQ ID NO: 561         moltype = DNA  length = 321
FEATURE                Location/Qualifiers
misc_feature           1..321
                       note = synthetic
source                 1..321
                       mol_type = other DNA
                       organism = synthetic construct
SEQUENCE: 561
gacatccaga tgacccagtc tccatcctcc ctgtctgcat ctgtaggaga cagagtcacc  60
atcacttgcc gggcaagtca gaccattagc agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccctcagcgg tctccaacct  240
gaagattttg caacttacta ctgtcaacag agttacagta ccccgctcac tttcggcgga  300
gggaccaagg tggagatcaa a                                            321

SEQ ID NO: 562         moltype = AA  length = 107
FEATURE                Location/Qualifiers
REGION                 1..107
                       note = synthetic
source                 1..107
                       mol_type = protein
                       organism = synthetic construct
SEQUENCE: 562
DIQMTQSPSS LSASVGDRVT ITCRASQTIS SYLNWYQQKP GKAPKLLIYA ASSLQSGVPS  60
RFSGSGSGTD FTLTLSGLQP EDFATYYCQQ SYSTPLTFGG GTKVEIK                107

SEQ ID NO: 563         moltype = DNA  length = 18
FEATURE                Location/Qualifiers
misc_feature           1..18
                       note = synthetic
source                 1..18
                       mol_type = other DNA
                       organism = synthetic construct
SEQUENCE: 563
cagaccatta gcagctat                                               18

SEQ ID NO: 564         moltype = AA  length = 6
FEATURE                Location/Qualifiers
REGION                 1..6
                       note = synthetic
source                 1..6
                       mol_type = protein
                       organism = synthetic construct
SEQUENCE: 564
QTISSY                                                            6

SEQ ID NO: 565         moltype =   length =
SEQUENCE: 565
000

SEQ ID NO: 566         moltype =   length =
SEQUENCE: 566
000

SEQ ID NO: 567         moltype = DNA  length = 27
FEATURE                Location/Qualifiers
misc_feature           1..27
                       note = synthetic
source                 1..27
                       mol_type = other DNA
                       organism = synthetic construct
SEQUENCE: 567
caacagagtt acagtacccc gctcact                                     27

SEQ ID NO: 568         moltype = AA  length = 9
FEATURE                Location/Qualifiers
```

```
REGION                 1..9
                       note = synthetic
source                 1..9
                       mol_type = protein
                       organism = synthetic construct
SEQUENCE: 568
QQSYSTPLT                                                        9

SEQ ID NO: 569         moltype = AA  length = 327
FEATURE                Location/Qualifiers
REGION                 1..327
                       note = synthetic
source                 1..327
                       mol_type = protein
                       organism = synthetic construct
SEQUENCE: 569
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                    327

SEQ ID NO: 570         moltype = AA  length = 326
FEATURE                Location/Qualifiers
REGION                 1..326
                       note = synthetic
source                 1..326
                       mol_type = protein
                       organism = synthetic construct
SEQUENCE: 570
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APPVAGPSVF  120
LFPPKPKDTL MISRTPEVTC VVVDVSQEDP EVQFNWYVDG VEVHNAKTKP REEQFNSTYR  180
VVSVLTVLHQ DWLNGKEYKC KVSNKGLPSS IEKTISKAKG QPREPQVYTL PPSQEEMTKN  240
QVSLTCLVKG FYPSDIAVEW ESNGQPENNY KTTPPVLDSD GSFFLYSRLT VDKSRWQEGN  300
VFSCSVMHEA LHNHYTQKSL SLSLGK                                     326

SEQ ID NO: 571         moltype = AA  length = 326
FEATURE                Location/Qualifiers
REGION                 1..326
                       note = synthetic
source                 1..326
                       mol_type = protein
                       organism = synthetic construct
SEQUENCE: 571
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APPVAGPSVF  120
LFPPKPKDTL MISRTPEVTC VVVDVSQEDP EVQFNWYVDG VEVHNAKTKP REEQFNSTYR  180
VVSVLTVLHQ DWLNGKEYKC KVSNKGLPSS IEKTISKAKG QPREPQVYTL PPSQEEMTKN  240
QVSLTCLVKG FYPSDIAVEW ESNGQPENNY KTTPPVLDSD GSFFLYSRLT VDKSRWQEGN  300
VFSCSVMHEA LHNRFTQKSL SLSPGK                                     326

SEQ ID NO: 572         moltype = AA  length = 326
FEATURE                Location/Qualifiers
REGION                 1..326
                       note = synthetic
source                 1..326
                       mol_type = protein
                       organism = synthetic construct
SEQUENCE: 572
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APGGGGPSVF  120
LFPPKPKDTL MISRTPEVTC VVVDVSQEDP EVQFNWYVDG VEVHNAKTKP REEQFNSTYR  180
VVSVLTVLHQ DWLNGKEYKC KVSNKGLPSS IEKTISKAKG QPREPQVYTL PPSQEEMTKN  240
QVSLTCLVKG FYPSDIAVEW ESNGQPENNY KTTPPVLDSD GSFFLYSRLT VDKSRWQEGN  300
VFSCSVMHEA LHNHYTQKSL SLSLGK                                     326

SEQ ID NO: 573         moltype = AA  length = 326
FEATURE                Location/Qualifiers
REGION                 1..326
                       note = synthetic
source                 1..326
                       mol_type = protein
                       organism = synthetic construct
SEQUENCE: 573
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APGGGGPSVF  120
LFPPKPKDTL MISRTPEVTC VVVDVSQEDP EVQFNWYVDG VEVHNAKTKP REEQFNSTYR  180
```

-continued

```
VVSVLTVLHQ DWLNGKEYKC KVSNKGLPSS IEKTISKAKG QPREPQVYTL PPSQEEMTKN  240
QVSLTCLVKG FYPSDIAVEW ESNGQPENNY KTTPPVLDSD GSFFLYSRLT VDKSRWQEGN  300
VFSCSVMHEA LHNRFTQKSL SLSPGK                                      326

SEQ ID NO: 574         moltype = AA  length = 450
FEATURE                Location/Qualifiers
REGION                 1..450
                       note = aa 1-478: Human Lag3 (aa 29 through 450 of
                        NP_002277.4) aa 451-478: myc-myc-hexahistidine tag
source                 1..450
                       mol_type = protein
                       organism = synthetic construct
SEQUENCE: 574
VPVVWAQEGA PAQLPCSPTI PLQDLSLLRR AGVTWQHQPD SGPPAAAPGH PLAPGPHPAA  60
PSSWGPRPRR YTVLSVGPGG LRSGRLPLQP RVQLDERGRQ RGDFSLWLRP ARRADAGEYR  120
AAVHLRDRAL SCRLRLRLGQ ASMTASPPGS LRASDWVILN CSFSRPDRPA SVHWFRNRGQ  180
GRVPVRESPH HHLAESFLFL PQVSPMDSGP WGCILTYRDG FNVSIMYNLT VLGLEPPTPL  240
TVYAGAGSRV GLPCRLPAGV GTRSFLTAKW TPPGGGPDLL VTGDNGDFTL RLEDVSQAQA  300
GTYTCHIHLQ EQQLNATVTL AIITVTPKSF GSPGSLGKLL CEVTPVSGQE RFVWSSLDTP  360
SQRSFSGPWL EAQEAQLLSQ PWQCQLYQGE RLLGAAVYFT ELSSPGAQRS GRAPGALPAG  420
HLEQKLISEE DLGGEQKLIS EEDLHHHHHH                                  450

SEQ ID NO: 575         moltype = AA  length = 655
FEATURE                Location/Qualifiers
REGION                 1..655
                       note = aa 1-683: Human Lag3 (aa 29 through 450 of
                        NP_002277.4) aa 451-683: mIgG2aFc
source                 1..655
                       mol_type = protein
                       organism = synthetic construct
SEQUENCE: 575
VPVVWAQEGA PAQLPCSPTI PLQDLSLLRR AGVTWQHQPD SGPPAAAPGH PLAPGPHPAA  60
PSSWGPRPRR YTVLSVGPGG LRSGRLPLQP RVQLDERGRQ RGDFSLWLRP ARRADAGEYR  120
AAVHLRDRAL SCRLRLRLGQ ASMTASPPGS LRASDWVILN CSFSRPDRPA SVHWFRNRGQ  180
GRVPVRESPH HHLAESFLFL PQVSPMDSGP WGCILTYRDG FNVSIMYNLT VLGLEPPTPL  240
TVYAGAGSRV GLPCRLPAGV GTRSFLTAKW TPPGGGPDLL VTGDNGDFTL RLEDVSQAQA  300
GTYTCHIHLQ EQQLNATVTL AIITVTPKSF GSPGSLGKLL CEVTPVSGQE RFVWSSLDTP  360
SQRSFSGPWL EAQEAQLLSQ PWQCQLYQGE RLLGAAVYFT ELSSPGAQRS GRAPGALPAG  420
HLEPRGPTIK PCPPCKCPAP NLLGGPSVFI FPPKIKDVLM ISLSPIVTCV VVDVSEDDPD  480
VQISWFVNNV EVHTAQTQTH REDYNSTLRV VSALPIQHQD WMSGKEFKCK VNNKDLPAPI  540
ERTISKPKGS VRAPQVYVLP PPEEEMTKKQ VTLTCMVTDF MPEDIYVEWT NNGKTELNYK  600
NTEPVLDSDG SYFMYSKLRV EKKNWVERNS YSCSVVHEGL HNHHTTKSFS RTPGK       655

SEQ ID NO: 576         moltype = AA  length = 516
FEATURE                Location/Qualifiers
REGION                 1..516
                       note = aa 1-533 (aa 18 through 533 of cynomolgus
                        XP_005570011.1 modified to replace amino acid at position
                        74 with a P based on Rhesus macaque XP_001108923.1
source                 1..516
                       mol_type = protein
                       organism = synthetic construct
SEQUENCE: 576
APVKPPQPGA EISVVWAQEG APAQLPCSPT IPLQDLSLLR RAGVTWQHQP DSGPPAPAPG  60
HPPVPGHRPA APYSWGPRPR RYTVLSVGPG GLRSGRLPLQ PRVQLDERGR QRGDFSLWLR  120
PARRADAGEY RATVHLRDRA LSCRLRLRVG QASMTASPPG SLRTSDWVIL NCSFSRPDRP  180
ASVHWFRSRG QGRVPVQGSP HHHLAESFLF LPHVGPMDSG LWGCILTYRD GFNVSIMYNL  240
TVLGLEPATP LTVYAGAGSR VELPCRLPPA VGTQSFLTAK WAPPGGGPDL LVAGDNGDFT  300
LRLEDVSQAQ AGTYICHIRL QGQQLNATVT LAIITVTPKS FGSPGSLGKL LCEVTPASGQ  360
EHFVWSPLNT PSQRSFSGPW LEAQEAQLLS QPWQCQLHQG ERLLGAAVYF TELSSPGAQR  420
SGRAPGALRA GHLPLFLILG VLFLLLLVTG AFGFHLWRRQ WRPRRFSALE QGIHPPQAQS  480
KIEELEQEPE LEPEPELERE LGPEPEPGPE PEPEQL                           516

SEQ ID NO: 577         moltype = AA  length = 449
FEATURE                Location/Qualifiers
REGION                 1..449
                       note = synthetic
source                 1..449
                       mol_type = protein
                       organism = synthetic construct
SEQUENCE: 577
QVQLVESGGG VVQPGRSLRL SCVASGFTFS SYGMHWVRQA PGKGLEWVAI IWYDGSNKYY  60
ADSVKGRFTI SRDNSKNTQY LQMNSLRAED TAVYYCASVA TSGDFDYYGM DVWGQGTTVT  120
VSSASTKGPS VFPLAPCSRS TSESTAALGC LVKDYFPEPV TVSWNSGALT SGVHTFPAVL  180
QSSGLYSLSS VVTVPSSSLG TKTYTCNVDH KPSNTKVDKR VESKYGPPCP PCPAPPVAGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGK                                   449
```

```
SEQ ID NO: 578          moltype = AA  length = 214
FEATURE                 Location/Qualifiers
REGION                  1..214
                        note = synthetic
source                  1..214
                        mol_type = protein
                        organism = synthetic construct
SEQUENCE: 578
EIVLTQSPAT LSLSPGERTT LSCRASQRIS TYLAWYQQKP GQAPRLLIYD ASKRATGIPA  60
RFSGSGSGTG FTLTISSLEP EDFAVYYCQQ RSNWPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 579          moltype = AA  length = 450
FEATURE                 Location/Qualifiers
REGION                  1..450
                        note = synthetic
source                  1..450
                        mol_type = protein
                        organism = synthetic construct
SEQUENCE: 579
QVQLVESGGG VVQPGRSLRL SCVASGFTFS SYGMHWVRQA PGKGLEWVAI IWYDGSNKYY  60
ADSVKGRFTI SRDNSKNTQY LQMNSLRAED TAVYYCASVA TSGDFDYYGM DVWGQGTTVT  120
VSSASTKGPS VFPLAPCSRS TSESTAALGC LVKDYFPEPV TVSWNSGALT SGVHTFPAVL  180
QSSGLYSLSS VVTVPSSSLG TKTYTCNVDH KPSNTKVDKR VESKYGPPCP PCPAPEFLGG  240
PSVFLFPPKP KDTLMISRTP EVTCVVVDVS QEDPEVQFNW YVDGVEVHNA KTKPREEQFN  300
STYRVVSVLT VLHQDWLNGK EYKCKVSNKG LPSSIEKTIS KAKGQPREPQ VYTLPPSQEE  360
MTKNQVSLTC LVKGFYPSDI AVEWESNGQP ENNYKTTPPV LDSDGSFFLY SRLTVDKSRW  420
QEGNVFSCSV MHEALHNHYT QKSLSLSLGK                                  450

SEQ ID NO: 580          moltype = AA  length = 445
FEATURE                 Location/Qualifiers
REGION                  1..445
                        note = synthetic
source                  1..445
                        mol_type = protein
                        organism = synthetic construct
SEQUENCE: 580
QVQLQQWGAG LLKPSETLSL TCAVYGGSFS GYYWNWIRQP PGKGLEWVGE ISHRGSTNYN  60
PSLKSRVTIS LDTSKNQFSL KLTSVTAADT AVYYCSRDEE LEFRFFDYWG QGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PPVAGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLGK                                       445

SEQ ID NO: 581          moltype = AA  length = 214
FEATURE                 Location/Qualifiers
REGION                  1..214
                        note = synthetic
source                  1..214
                        mol_type = protein
                        organism = synthetic construct
SEQUENCE: 581
EIVLTQSPAT LSLSPGERAT LSCRASQSVS SYLAWYQQKP GQAPRLLVYG ASNRATGIPA  60
RFSGSGSGTD FTLTISSLEP EDFAFYYCQQ RSNWPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 582          moltype = AA  length = 525
FEATURE                 Location/Qualifiers
REGION                  1..525
                        note = synthetic
source                  1..525
                        mol_type = protein
                        organism = synthetic construct
SEQUENCE: 582
MWEAQFLGLL FLQPLWVAPV KPLQPGAEVP VVWAQEGAPA QLPCSPTIPL QDLSLLRRAG  60
VTWQHQPDSG PPAAAPGHPL APGPHPAAPS SWGPRPRRYT VLSVGPGGLR SGRLPLQPRV  120
QLDERGRQRG DFSLWLRPAR RADAGEYRAA VHLRDRALSC RLRLRLGQAS MTASPPGSLR  180
ASDWVILNCS FSRPDRPASV HWFRNRGQGR VPVRESPHHH LAESFLFLPQ VSPMDSGPWG  240
CILTYRDGFN VSIMYNLTVL GLEPPTPLTV YAGAGSRVGL PCRLPAGVGT RSFLTAKWTP  300
PGGGPDLLVT GDNGDFTLRL EDVSQAQAGT YTCHIHLQEQ QLNATVTLAI ITVTPKSFGS  360
PGSLGKLLCE VTPVSGQERF VWSSLDTPSQ RSFSGPWLEA QEAQLLSQPW QCQLYQGERL  420
LGAAVYFTEL SSPGAQRSGR APGALPAGHL LLFLILGVLS LLLLVTGAFG FHLWRRQWRP  480
RRFSALEQGI HPPQAQSKIE ELEQEPEPEP EPEPEPEPEP EPEQL                 525
```

```
SEQ ID NO: 583          moltype = AA  length = 15
FEATURE                 Location/Qualifiers
REGION                  1..15
                        note = synthetic
source                  1..15
                        mol_type = protein
                        organism = synthetic construct
SEQUENCE: 583
ENPVVHFFKN IVTPR                                                   15

SEQ ID NO: 584          moltype = DNA  length = 17
FEATURE                 Location/Qualifiers
misc_feature            1..17
                        note = synthetic
source                  1..17
                        mol_type = other DNA
                        organism = synthetic construct
SEQUENCE: 584
agcagctctg ccctcat                                                 17

SEQ ID NO: 585          moltype = DNA  length = 22
FEATURE                 Location/Qualifiers
misc_feature            1..22
                        note = synthetic
source                  1..22
                        mol_type = other DNA
                        organism = synthetic construct
SEQUENCE: 585
gctctggctg gtcttcagta tg                                           22

SEQ ID NO: 586          moltype = DNA  length = 22
FEATURE                 Location/Qualifiers
misc_feature            1..22
                        note = synthetic
source                  1..22
                        mol_type = other DNA
                        organism = synthetic construct
SEQUENCE: 586
ttgccgtatg gttggtttga ac                                           22

SEQ ID NO: 587          moltype = AA  length = 665
FEATURE                 Location/Qualifiers
REGION                  1..665
                        note = hLAG3.Fc
source                  1..665
                        mol_type = protein
                        organism = synthetic construct
SEQUENCE: 587
LQPGAEVPVV WAQEGAPAQL PCSPTIPLQD LSLLRRAGVT WQHQPDSGPP AAAPGHPLAP  60
GPHPAAPSSW GPRPRRYTVL SVGPGGLRSG RLPLQPRVQL DERGRQRGDF SLWLRPARRA  120
DAGEYRAAVH LRDRALSCRL RLRLGQASMT ASPPGSLRAS DWVILNCSFS RPDRPASVHW  180
FRNRGQGRVP VRESPHHHLA ESFLFLPQVS PMDSGPWGCI LTYRDGFNVS IMYNLTVLGL  240
EPPTPLTVYA GAGSRVGLPC RLPAGVGTRS FLTAKWTPPG GGPDLLVTGD NGDFTLRLED  300
VSQAQAGTYT CHIHLQEQQL NATVTLAIIT VTPKSFGSPG SLGKLLCEVT PVSGQERFVW  360
SSLDTPSQRS FSGPWLEAQE AQLLSQPWQC QLYQGERLLG AAVYFTELSS PGAQRSGRAP  420
GALPAGHLIE GRMDPKSCDK THTCPPCPAP ELLGGPSVFL FPPKPKDTLM ISRTPEVTCV  480
VVDVSHEDPE VKFNWYVDGV EVHNAKTKPR EEQYNSTYRV VSVLTVLHQD WLNGKEYKCK  540
VSNKALPAPI EKTISKAKGQ PREPQVYTLP PSRDELTKNQ VSLTCLVKGF YPSDIAVEWE  600
SNGQPENNYK TTPPVLDSDG SFFLYSKLTV DKSRWQQGNV FSCSVMHEAL HNHYTQKSLS  660
LSPGK                                                              665

SEQ ID NO: 588          moltype = AA  length = 422
FEATURE                 Location/Qualifiers
REGION                  1..422
                        note = hLAG3 extracellular domain P18627
source                  1..422
                        mol_type = protein
                        organism = synthetic construct
SEQUENCE: 588
VPVVWAQEGA PAQLPCSPTI PLQDLSLLRR AGVTWQHQPD SGPPAAAPGH PLAPGPHPAA  60
PSSWGPRPRR YTVLSVGPGG LRSGRLPLQP RVQLDERGRQ RGDFSLWLRP ARRADAGEYR  120
AAVHLRDRAL SCRLRLRLGQ ASMTASPPGS LRASDWVILN CSFSRPDRPA SVHWFRNRGQ  180
GRVPVRESPH HHLAESFLFL PQVSPMDSGP WGCILTYRDG FNVSIMYNLT VLGLEPPTPL  240
TVYAGAGSRV GLPCRLPAGV GTRSFLTAKW TPPGGGPDLL VTGDNGDFTL RLEDVSQAQA  300
GTYTCHIHLQ EQQLNATVTL AIITVTPKSF GSPGSLGKLL CEVTPVSGQE RFVWSSLDTP  360
SQRSFSGPWL EAQEAQLLSQ PWQCQLYQGE RLLGAAVYFT ELSSPGAQRS GRAPGALPAG  420
HL                                                                 422

SEQ ID NO: 589          moltype = AA  length = 44
```

-continued

```
FEATURE                 Location/Qualifiers
REGION                  1..44
                        note = hLAG3 epitope
source                  1..44
                        mol_type = protein
                        organism = synthetic construct
SEQUENCE: 589
LRRAGVTWQH QPDSGPPAAA PGHPLAPGPH PAAPSSWGPR PRRY                  44
```